United States Patent
Ohtsuka et al.

(10) Patent No.: US 9,856,321 B2
(45) Date of Patent: *Jan. 2, 2018

(54) ANTI-DR5 ANTIBODIES, POLYNUCLEOTIDES AND METHODS

(71) Applicant: Daiichi Sankyo Company, Limited, Chuo-ku, Tokyo (JP)

(72) Inventors: Toshiaki Ohtsuka, Saitama (JP); Takeshi Takizawa, Tokyo (JP); Akiko Oguni, Tokyo (JP); Tatsuji Matsuoka, Tokyo (JP); Hiroko Yoshida, Tokyo (JP); Yumi Matsui, Tokyo (JP)

(73) Assignee: Daiichi Sankyo Company, Limited, Chuo-ku, Tokyo (JP)

( * ) Notice: Subject to any disclaimer, the term of this patent is extended or adjusted under 35 U.S.C. 154(b) by 57 days.

This patent is subject to a terminal disclaimer.

(21) Appl. No.: 14/845,755

(22) Filed: Sep. 4, 2015

(65) Prior Publication Data

US 2016/0068603 A1    Mar. 10, 2016

Related U.S. Application Data

(63) Continuation of application No. 13/881,645, filed as application No. PCT/JP2011/074866 on Oct. 27, 2011, now Pat. No. 9,127,070.

(30) Foreign Application Priority Data

Oct. 29, 2010   (JP) ................................ 2010-243549

(51) Int. Cl.
*C12P 21/08* (2006.01)
*C07K 16/28* (2006.01)
(Continued)

(52) U.S. Cl.
CPC ........ *C07K 16/2878* (2013.01); *A61K 31/337* (2013.01); *A61K 31/439* (2013.01);
(Continued)

(58) Field of Classification Search
None
See application file for complete search history.

(56) References Cited

U.S. PATENT DOCUMENTS 5,859,205 A    1/1999  Adair
7,115,717 B2   10/2006 Mori
(Continued)

FOREIGN PATENT DOCUMENTS

EP      0 870 827 B1    3/2004
JP      2004-502409 A   1/2004
(Continued)

OTHER PUBLICATIONS

Ashkenazi, A., et al., "Ligand-Based Targeting of Apoptosis in Cancer: the Potential of Recombinant Human Apoptosis Ligand 2/Tumor Necrosis Factor—Related Apoptosis-Inducing Ligand (rhApo2L/TRAIL)," Journal of Clinical Oncology 26(21):3621-3630, Jul. 2008.
(Continued)

*Primary Examiner* — Claire Kaufman
(74) *Attorney, Agent, or Firm* — Christensen O'Connor Johnson Kindness PLLC

(57) ABSTRACT

The present invention relates to an antibody which has a therapeutic effect on cancer, an autoimmune disease, or an inflammatory disease. That is, the present invention relates to an antibody which exhibits a cytotoxic activity against death domain-containing receptor-expressing cells through apoptosis.
[Object]
An object of the invention is to provide a pharmaceutical having a therapeutic effect on cancer.
(Continued)

[Means for Resolution]
A novel anti-DR5 antibody capable of inducing apoptosis in cells has more potent cytotoxic activity than currently available anti-DR5 antibodies.

29 Claims, 51 Drawing Sheets

(51) Int. Cl.
| | |
|---|---|
| A61K 39/395 | (2006.01) |
| C07K 14/705 | (2006.01) |
| A61K 31/337 | (2006.01) |
| A61K 31/4745 | (2006.01) |
| A61K 31/475 | (2006.01) |
| A61K 31/555 | (2006.01) |
| A61K 31/439 | (2006.01) |
| A61K 31/4545 | (2006.01) |
| A61K 31/513 | (2006.01) |
| C07K 16/30 | (2006.01) |
| A61K 45/06 | (2006.01) |
| A61K 39/00 | (2006.01) |

(52) U.S. Cl.
CPC ........ *A61K 31/4545* (2013.01); *A61K 31/475* (2013.01); *A61K 31/4745* (2013.01); *A61K 31/513* (2013.01); *A61K 31/555* (2013.01); *A61K 39/3955* (2013.01); *A61K 39/39558* (2013.01); *A61K 45/06* (2013.01); *C07K 14/70578* (2013.01); *C07K 16/30* (2013.01); *A61K 2039/505* (2013.01); *C07K 2299/00* (2013.01); *C07K 2317/24* (2013.01); *C07K 2317/34* (2013.01); *C07K 2317/51* (2013.01); *C07K 2317/515* (2013.01); *C07K 2317/55* (2013.01); *C07K 2317/73* (2013.01); *C07K 2317/92* (2013.01); *C07K 2319/30* (2013.01)

(56) References Cited

U.S. PATENT DOCUMENTS

| | | |
|---|---|---|
| 2003/0190687 A1 | 10/2003 | Zhou |
| 2005/0171339 A1 | 8/2005 | Sugo |
| 2006/0287508 A1 | 12/2006 | Sugo |

FOREIGN PATENT DOCUMENTS

| | | |
|---|---|---|
| WO | 98/35986 A1 | 8/1998 |
| WO | 98/41629 A2 | 9/1998 |
| WO | 98/46643 A1 | 10/1998 |
| WO | 98/51793 A1 | 11/1998 |
| WO | 99/02653 A1 | 1/1999 |
| WO | 99/09165 A1 | 2/1999 |
| WO | 99/11791 A2 | 3/1999 |
| WO | 99/12963 A2 | 3/1999 |
| WO | 0075191 A2 | 12/2000 |
| WO | 01/83560 A1 | 11/2001 |
| WO | 02/094880 A1 | 11/2002 |
| WO | 03/037913 A2 | 5/2003 |
| WO | 03/038043 A2 | 5/2003 |
| WO | 03/054216 A2 | 7/2003 |
| WO | 03/057881 A1 | 7/2003 |
| WO | 2004/050895 A2 | 6/2004 |
| WO | 2006/083937 A2 | 8/2006 |
| WO | 2006/083971 A2 | 8/2006 |
| WO | 2007/022157 A2 | 2/2007 |
| WO | 2007/027713 A2 | 3/2007 |
| WO | 2008/073581 A2 | 6/2008 |
| WO | 2011/031835 A1 | 3/2011 |
| WO | 2011/039126 A1 | 4/2011 |
| WO | 2011/057099 A2 | 5/2011 |
| WO | 2011/098520 A1 | 8/2011 |

OTHER PUBLICATIONS

Borysenko, C.W., et al., "Death Receptor-3 Mediates Apoptosis in Human Osteoblasts Under Narrowly Regulated Conditions," Journal of Cellular Physiology 209(3):1021-1028, Dec. 2006.
Chari, R.V.J., et al., "Immunoconjugates Containing Novel Maytansinoids: Promising Anticancer Drugs," Cancer Research 52(1):127-131, Jan. 1992.
Chaudhary, P.M., et al., "Death Receptor 5, a New Member of the Tnfr Family, and DR4 Induce FADD-Dependent Apoptosis and Activate the NF-κB Pathway," Immunity 7(6):821-830, Dec. 1997.
Choy, E.H.S., et al., "Chinmeric Anti-CD4 Monoclonal Antibody Cross-Linked by Monocyte Fcγ Receptor Mediates Apoptosis of Human CD4 Lymphocytes," European Journal of Immunology 23(10):2676-2681, Oct. 1993.
De Oliveira Pinto, L.M., et al., "Increased Sensitivity of T Lymphocytes to Tumor Necrosis Factor Receptor 1 (TNFR1)-and TNFR2-Mediated Apoptosis in HIV Infection: Relation to Expression of Bcl-2 and Active Caspase-8 and Caspase-3," Blood 99(5):1666-1675, Mar. 2002.
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," Journal of Immunology 169(6):3076-3084, Sep. 2002.
Dhein, J., et al., "Induction of Apoptosis by Monoclonal Antibody Anti-APO-1 Class Switch Variants Is Dependent on Cross-Linking of APO-1 Cell Surface Antigens," Journal of Immunology 149(10):3166-3173, Nov. 1992.
Doronina, S.O., et al., "Novel Peptide Linkers for Highly Potent Antibody-Auristatin Conjugate," Bioconjugate Chemistry 19(10):1960-1963, Oct. 2008.
Extended European Search Report dated Mar. 12, 2014, issued in corresponding European Application No. 11836421.5, filed Apr. 23, 2013, 10 pages.
Communication Pursuant to Article 94(3) EPC dated Nov. 26, 2014, issued in corresponding European Application No. 11836421.5, filed Apr. 23, 2013, 7 pages.
Fujisawa, K., et al., "Therapeutic Effect of the Anti-Fas Antibody on Arthritis in HTLV-1 tax Transgenic Mice," Journal of Clinical Investigation 98(2):271-278, Jul. 1996.
Further Examination Report dated May 16, 2014, issued in related New Zealand Application No. 610153, filed Oct. 27, 2011, 2 pages.
Golstein, P., et al., "Homology Between Reaper and the Cell Death Domains of Fas and TNFR1," Cell 81(2):185-186, Apr. 1995.
Griffith, T.S., et al., "Functional Analysis of Trail Receptors Using Monoclonal Antibodies," Journal of Immunology 162(5):2597-2605, Mar. 1999.
Hasunuma, T., et al., "Induction of Fas-Dependent Apoptosis in Synovial Infiltrating Cells in Rheumatoid Arthritis," International Immunology 8(10):1595-1602, Oct. 1996.
Ichikawa, K., et al., "Tumoricidal Activity of a Novel Anti-Human DR5 Monoclonal Antibody Without Hepatocyte Cytotoxicity," Nature Medicine 7(8):954-960, Aug. 2001.
International Search Report dated Jan. 10, 2012, issued in corresponding International Application No. PCT/JP2011/074866, filed Oct. 27, 2011, 3 pages.
International Preliminary Report on Patentability and Written Opinion dated May 14, 2013, issued in corresponding International Application No. PCT/JP2011/074866, filed Oct. 27, 2011, 7 pages.
LeBlanc, H.N., and A. Ashkenazi, "Apo2L/TRAIL and Its Death and Decoy Receptors," Cell Death and Differentiation 10(1):66-75, Jan. 2003.
Locklin, R.M., et al., "Agonists of TRAIL Death Receptors Induce Myeloma Cell Apoptosis That Is Not Prevented by Cells of the Bone Marrow Microenvironment," Leukemia 21(4):805-812, Feb. 2007.
MacCallum, R.M., et al., "Antibody-Antigen Interactions: Contact Analysis and Binding Site Topography," Journal of Molecular Biology 262(5):732-745, Oct. 1996.
Office Action dated Jul. 3, 2015, issued in corresponding Russian Application No. 2013124808110(036458), filed Oct. 9, 2011, 9 pages.

(56) References Cited

OTHER PUBLICATIONS

Office Action dated Oct. 29, 2014, issued in corresponding Colombian Application No. 13-131.563, filed Oct. 27, 2011, 14 pages.

Schneider, P., et al., "TRAIL Receptors 1 (DR4) and 2 (DR5) Signal FADD-Dependent Apoptosis and Activate NF-κB," Immunity 7(6):831-836, Dec. 1997.

Sela-Culang, I., et al., "The Structural Basis of Antibody-Antigen Recognition," Frontiers in Immunology, vol. 4, Article 302, pp. 1-13, Oct. 2013.

Sumimoto, S.-I., et al., "Anti-Fas Antibody Induces Different Types of Cell Death in the Human Histiocytic Cell Line, U937, and the Human B Cell Line, B104: The Role of Single-Strand DNA Breaks and Poly(ADP-Ribosyl)ation in Cell Death," Cellular Immunology 153(1):184-193, Jan. 1994.

White, K., et al., "Genetic Control of Programmed Cell Death in *Drosophila*," Science 264(5159):677-683, Apr. 1994.

Wiley, S.R., et al., "Identification and Characterization of a New Member of the TNF Family That Induces Apoptosis," Immunity 3(6):673-682, Dec. 1995.

Search Report dated Jun. 21, 2017, issued in RU Application No. 2016122187, filed Oct. 27, 2011, 2 pages.

Fig. 2
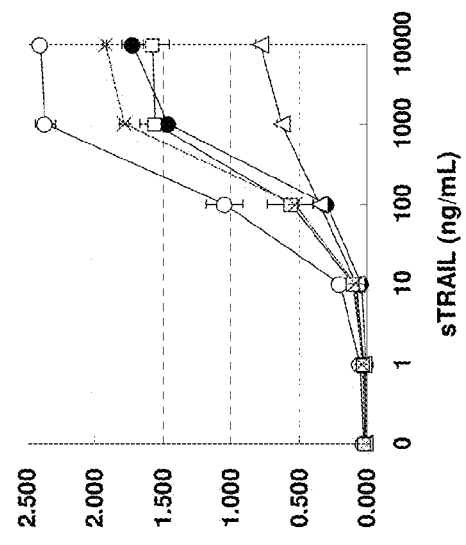
A)
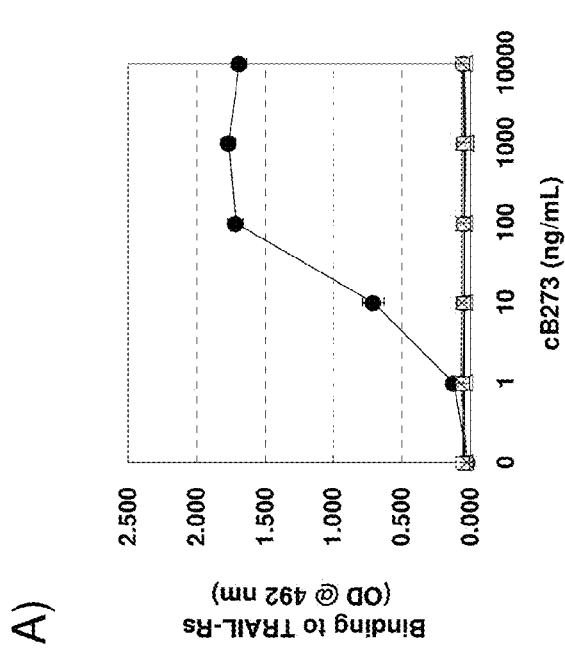
B)

A) Human ovarian cancer cell line
B) Human colon cancer cell line
C) Human lung cancer cell line
D) Human breast cancer cell line

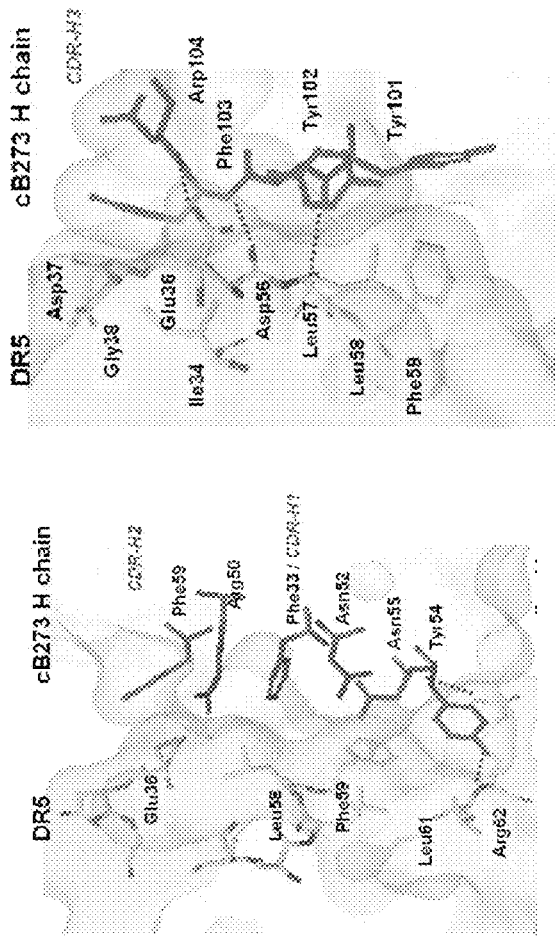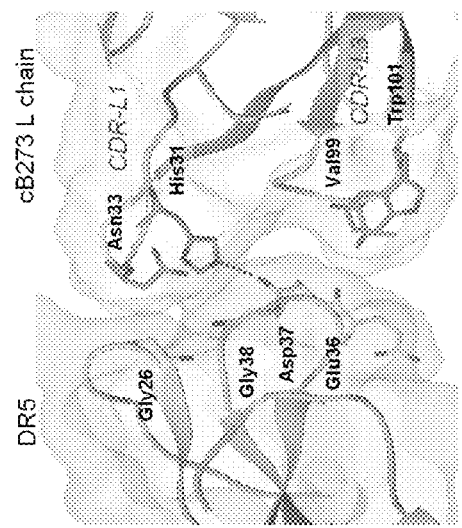
Fig. 7 A) B)

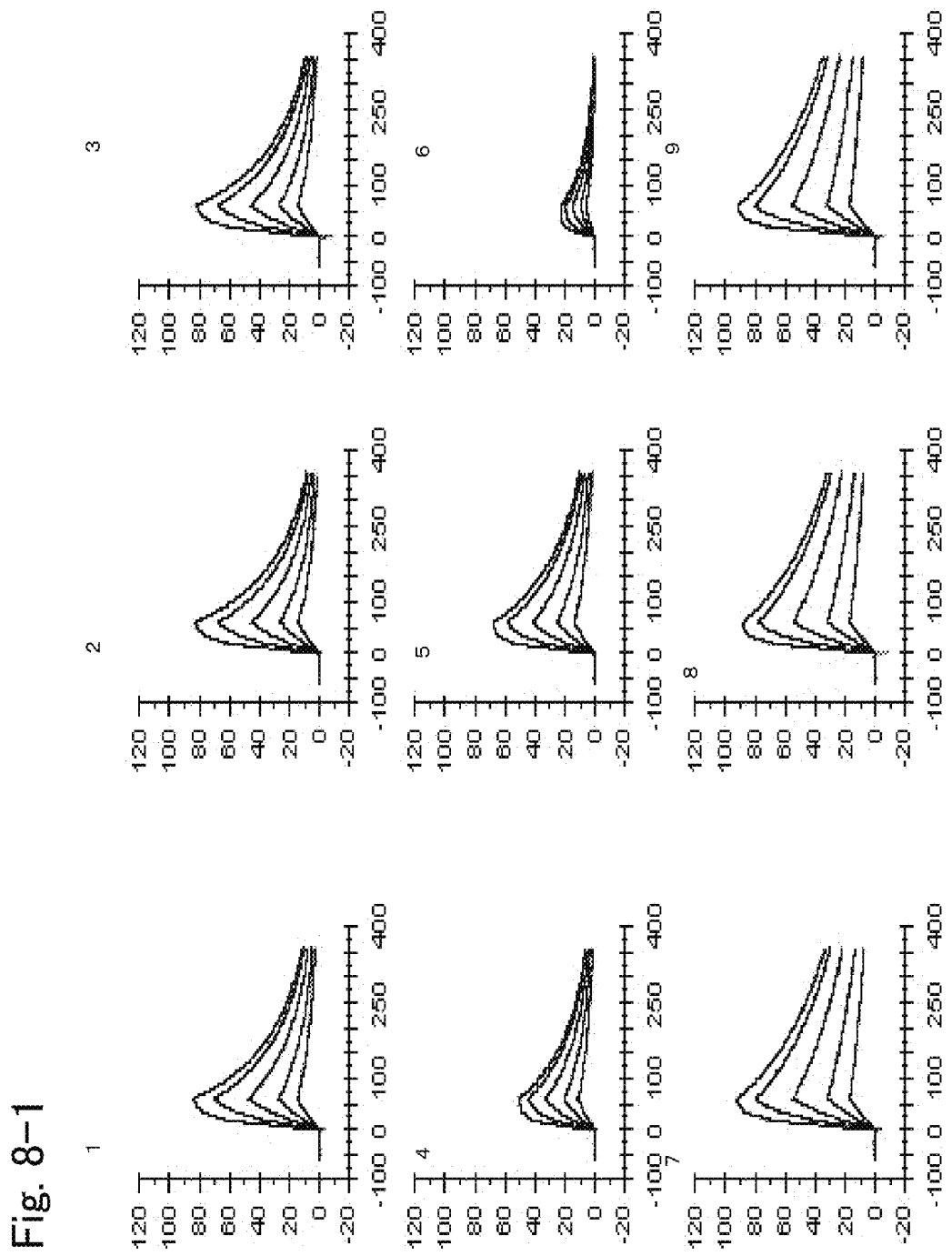

Fig. 8-2

| EntryNo. | Name | Kon (1/Ms) | Koff (1/d) | KD (nM) |
|---|---|---|---|---|
| 1 | hB273_H1/hB273_L1 | 1.804E+06 | 9.837E-03 | 5.45 |
| 2 | hB273_H1/hB273_L2 | 1.441E+06 | 9.409E-03 | 6.53 |
| 3 | hB273_H1/hB273_L3 | 1.527E+06 | 9.218E-03 | 6.04 |
| 4 | hB273_H2/hB273_L1 | 1.853E+06 | 8.087E-03 | 4.36 |
| 5 | hB273_H2/hB273_L2 | 1.711E+06 | 7.694E-03 | 4.47 |
| 6 | hB273_H2/hB273_L3 | 1.889E+06 | 1.020E-02 | 5.40 |
| 7 | hB273_H3/hB273_L1 | 1.809E+06 | 4.340E-03 | 2.40 |
| 8 | hB273_H3/hB273_L2 | 2.117E+06 | 4.645E-03 | 2.19 |
| 9 | hB273_H3/hB273_L3 | 2.027E+06 | 4.363E-03 | 2.15 |

Fig. 10-2

| Entry No | Name | Kon (1/Ms) | Koff (1/d) | KD (nM) |
|---|---|---|---|---|
| 1 | hB273_H1-1/hB273_L1 | 2.074E+06 | 3.787E-03 | 1.83 |
| 2 | hB273_H2-1/hB273_L1 | 2.014E+06 | 4.015E-03 | 1.99 |
| 3 | hB273_H2-2/hB273_L1 | 2.036E+06 | 4.359E-03 | 2.14 |
| 4 | hB273_H2-3/hB273_L1 | 1.770E+06 | 3.755E-03 | 2.12 |
| 5 | hB273_H2-4/hB273_L1 | 2.327E+06 | 3.595E-03 | 1.55 |
| 6 | hB273_H2-5/hB273_L1 | 2.196E+06 | 3.024E-03 | 1.38 |

Fig. 12-2

| Entry No | Name | kon (1/Ms) | koff (1/d) | KD (nM) |
|---|---|---|---|---|
| 1 | hB273_H2-1-NE/hB273_L1-NE | 2.77E+06 | 5.59E-03 | 2.02 |
| 2 | hB273_H2-1-NE/hB273_L1-NF | 2.92E+06 | 5.14E-03 | 1.76 |
| 3 | hB273_H2-1-NE/hB273_L1-NK | 3.34E+06 | 4.63E-03 | 1.39 |
| 4 | hB273_H2-1-NE/hB273_L1-NL | 3.34E+06 | 5.90E-03 | 1.76 |

Fig. 13-3

| Entry No | Name | Tm (°C) |
|---|---|---|
| 1 | hB273_H2-1-NE/hB273_L1-NE | 83.9 |
| 2 | hB273_H2-1-NE/hB273_L1-NF | 84.1 |
| 3 | hB273_H2-1-NE/hB273_L1-NK | 84.5 |
| 4 | hB273_H2-1-NE/hB273_L1-NL | 84.4 |

Fig. 15
A) HCT-15
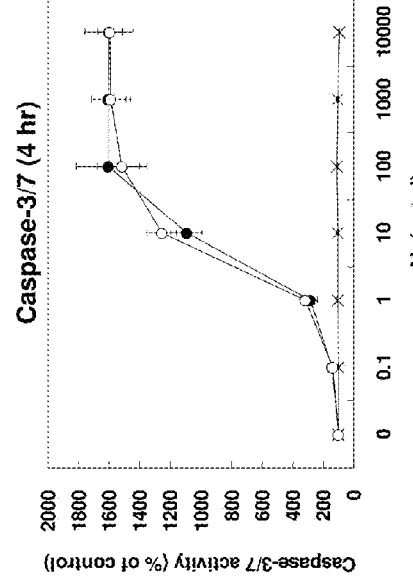
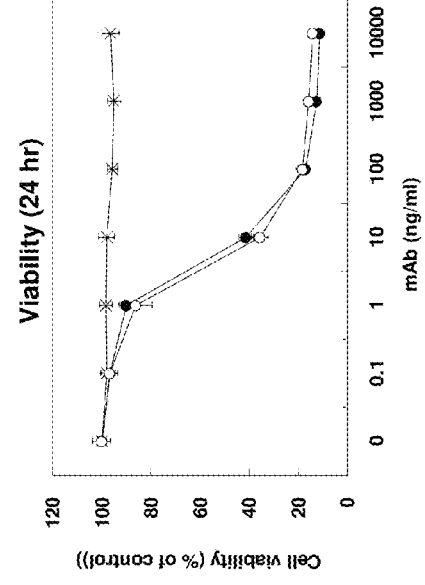
B) U-87MG
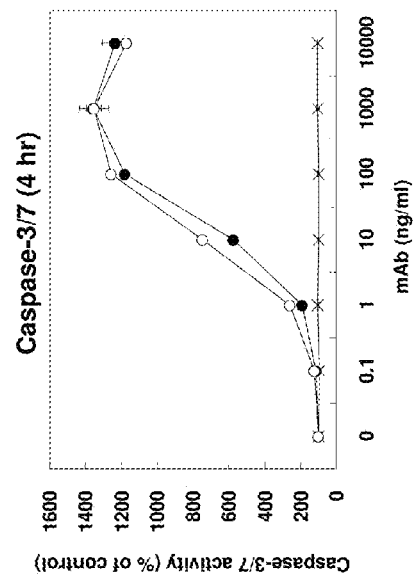
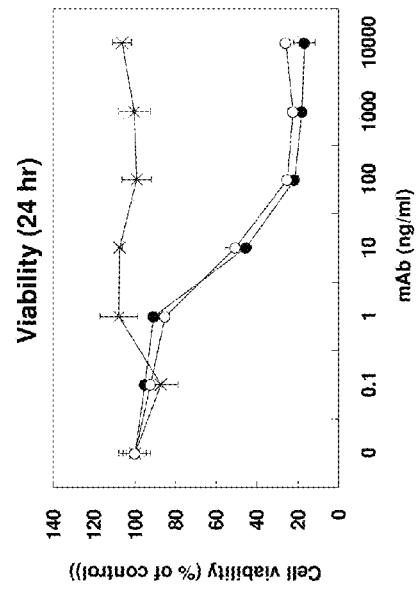

Fig. 28

SEQ ID NO: 7: Nucleotide sequence of cDNA encoding mouse antibody B273 heavy chain
atgggatggagctgtatctttctctttctcctgtcagtaactgtaggtgtgttctctgaggttcagc
tgcagcagtctggacctgagctggtgaagcctggggcttcagtgaagatatcctgcaaggcttctgg
ttactcatttattggctactttatgaactggatgaagcagagccatggaaagagccttgagtggatt
ggacgttttaatccatacaatggtgatactttctacaaccagaagttcaagggcaaggccacattga
ctgtagacaaatcctctaccacagcccacatggagctcctgagcctgacatctgaggactctgcagt
ctattttgtggaagatcggcgtattacttcgatagtggggctactttgactactggggccaaggc
accactctcacagtctcctcagccaaaacgacacccccatctgtctatccactggcccctggatctg
ctgcccaaactaactccatggtgaccctgggatgcctggtcaagggctatttcctgagccagtgac
agtgacctggaactctggatccctgtccagcggtgtgcacaccttcccagctgtcctgcagtctgac
ctctacactctgagcagctcagtgactgtcccctccagcacctggcccagcgagaccgtcacctgca
acgttgcccacccggccagcagcaccaaggtggacaagaaaattgtgcccagggattgtggttgtaa
gccttgcatatgtacagtcccagaagtatcatctgtcttcatcttccccccaaagcccaaggatgtg
ctcaccattactctgactcctaaggtcacgtgtgttgtggtagacatcagcaaggatgatcccgagg
tccagttcagctggtttgtagatgatgtggaggtgcacacagctcagacgcaacccgggaggagca
gttcaacagcactttccgctcagtcagtgaacttcccatcatgcaccaggactggctcaatggcaag
gagttcaaatgcagggtcaacagtgcagctttccctgcccccatcgagaaaaccatctccaaaacca
aaggcagaccgaaggctccacaggtgtacaccattccacctcccaaggagcagatggccaaggataa
agtcagtctgacctgcatgataacagacttcttccctgaagacattactgtggagtggcagtggaat
gggcagccagcggagaactacaagaacactcagcccatcatggacacagatggctcttacttcgtct
acagcaagctcaatgtgcagaagagcaactgggaggcaggaaatactttcacctgctctgtgttaca
tgagggcctgcacaaccaccatactgagaagagcctctcccactctcctggtaaa
Signal sequence (1-57), Variable region (58-423), Constant region (424-1395)

SEQ ID NO: 8: Amino acid sequence of mouse antibody B273 heavy chain
MGWSCIFLFLLSVTVGVFSEVQLQQSGPELVKPGASVKISCKASGYSFIGYFMNWMKQSHGKSLEWI
GRFNPYNGDTFYNQKFKGKATLTVDKSSTTAHMELLSLTSEDSAVYFCGRSAYYFDSGGYFDYWGQG
TTLTVSSAKTTPPSVYPLAPGSAAQTNSMVTLGCLVKGYFPEPVTVTWNSGSLSSGVHTFPAVLQSD
LYTLSSSVTVPSSTWPSETVTCNVAHPASSTKVDKKIVPRDCGCKPCICTVPEVSSVFIFPPKPKDV
LTITLTPKVTCVVVDISKDDPEVQFSWFVDDVEVHTAQTQPREEQFNSTFRSVSELPIMHQDWLNGK
EFKCRVNSAAFPAPIEKTISKTKGRPKAPQVYTIPPPKEQMAKDKVSLTCMITDFFPEDITVEWQWN
GQPAENYKNTQPIMDTDGSYFVYSKLNVQKSNWEAGNTFTCSVLHEGLHNHHTEKSLSHSPGK
Signal sequence (1-19), Variable region (20-141), Constant region (142-465)

Fig. 29

SEQ ID NO: 9: Nucleotide sequence of cDNA encoding mouse antibody B273 light chain
atgaagttgcctgttaggctgttggtgctgatgttctggattcctgcttccagcagtgatgttgtga
tgacccaaactccactctccctgcctgtcagtcttggagatcaagcctccatctcttgcagatctag
tcagagccttgtacacagtaatggaaacacctatctacattggtacctgcagaagccaggccagtct
ccaaagctcctgatctacaaagtttccaaccgattttctggggtcccagacaggttcagtggcagtg
gatcagggacagatttcacactcaagatcagcagagtggaggctgaggatctgggaatttatttctg
ctctcaaagtacacatgttccgtggacgttcggtggaggcaccaagctggaaatcaaacgggctgat
gctgcaccaactgtatccatcttcccaccatccagtgagcagttaacatctggaggtgcctcagtcg
tgtgcttcttgaacaacttctaccccaaagacatcaatgtcaagtggaagattgatggcagtgaacg
acaaaatggcgtcctgaacagttggactgatcaggacagcaaagacagcacctacagcatgagcagc
accctcacgttgaccaaggacgagtatgaacgacataacagctatacctgtgaggccactcacaaga
catcaacttcacccattgtcaagagcttcaacaggaatgagtgt
Signal sequence (1-57), Variable region (58-399), Constant region (400-714)

SEQ ID NO: 10: Amino acid sequence of mouse antibody B273 light chain
MKLPVRLLVLMFWIPASSSDVVMTQTPLSLPVSLGDQASISCRSSQSLVHSNGNTYLHWYLQKPGQS
PKLLIYKVSNRFSGVPDRFSGSGSGTDFTLKISRVEAEDLGIYFCSQSTHVPWTFGGGTKLEIKRAD
AAPTVSIFPPSSEQLTSGGASVVCFLNNFYPKDINVKWKIDGSERQNGVLNSWTDQDSKDSTYSMSS
TLTLTKDEYERHNSYTCEATHKTSTSPIVKSFNRNEC
Signal sequence (1-19), Variable region (20-133), Constant region (134-238)

Fig. 30

SEQ ID NO: 15: Nucleotide sequence of B273 chimera-type light chain
atggtgctgcagacccaggtgttcatctccctgctgctgtggatctccggcgcatatggcgatgttg
tgatgacccaaactccactctccctgcctgtcagtcttggagatcaagcctccatctcttgcagatc
tagtcagagccttgtacacagtaatggaaacacctatctacattggtacctgcagaagccaggccag
tctccaaagctcctgatctacaaagtttccaaccgatttctggggtcccagacaggttcagtggca
gtggatcagggacagatttcacactcaagatcagcagagtggaggctgaggatctgggaatttattt
ctgctctcaaagtacacatgttccgtggacgttcggtggaggcaccaagctggaaatcaaacgtacg
gtggccgccccctccgtgttcatcttccccccctccgacgagcagctgaagtccggcaccgcctccg
tggtgtgcctgctgaataacttctacccagagaggccaaggtgcagtggaaggtggacaacgccct
gcagtccgggaactcccaggagagcgtgaccgagcaggacagcaaggacagcacctacagcctgagc
agcaccctgaccctgagcaaagccgactacgagaagcacaaggtgtacgcctgcgaggtgacccacc
agggcctgagctccccgtcaccaagagcttcaacagggggagtgt
Signal sequence (1-60), Variable region (61-402), Constant region (403-717)

SEQ ID NO: 16: Amino acid sequence of B273 chimera-type light chain
MVLQTQVFISLLLWISGAYGDVVMTQTPLSLPVSLGDQASISCRSSQSLVHSNGNTYLHWYLQKPGQ
SPKLLIYKVSNRFSGVPDRFSGSGSGTDFTLKISRVEAEDLGIYFCSQSTHVPWTFGGGTKLEIKRT
VAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC
Signal sequence (1-20), Variable region (21-134), Constant region (135-239)

Fig. 31

SEQ ID NO: 19: Nucleotide sequence of B273 chimera-type heavy chain
atgaaacacctgtggttcttcctcctgctggtggcagctcccagatgggtgctgagcgaggttcagc
tgcagcagtctggacctgagctggtgaagcctggggcttcagtgaagatatcctgcaaggcttctgg
ttactcatttattggctactttatgaactggatgaagcagagccatggaaagagccttgagtggatt
ggacgttttaatccatacaatggtgatactttctacaaccagaagttcaagggcaaggccacattga
ctgtagacaaatcctctaccacagcccacatggagctcctgagcctgacatctgaggactctgcagt
ctattttgtggaagatcggcgtattacttcgatagtggggctactttgactactggggccaaggc
accactctcacagtcagctcagcctccaccaagggcccaagcgtcttccccctggcaccctcctcca
agagcacctctggcggcacagccgccctgggctgcctggtcaaggactacttccccgaacccgtgac
cgtgagctggaactcaggcgccctgaccagcggcgtgcacaccttcccgctgtcctgcagtccta
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccgcgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatgggcagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region (424-1413)

SEQ ID NO: 20: Amino acid sequence of B273 chimera-type heavy chain
MKHLWFFLLLVAAPRWVLSEVQLQQSGPELVKPGASVKISCKASGYSFIGYFMNWMKQSHGKSLEWI
GRFNPYNGDTFYNQKFKGKATLTVDKSSTTAHMELLSLTSEDSAVYFCGRSAYYFDSGGYFDYWGQG
TTLTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region (142-471)

Fig. 32

SEQ ID NO: 27: Nucleotide sequence of hB273_L1-type light chain
atggtgctgcagacccaggtgttcatctccctgctgctgtggatctccggcgcatatggcgacatcg
taatgacccagtctccgctgagtcttcctgtgactccaggggagcccgcaagcatctcttgtcgcag
cagtcagtcactggtccatagcaatgggaacacttacctgcattggtacctccaaaaaccagggcag
tccccacagctcttgatctacaaggtgtccaatcggttcagtggtgtgcctgaccgcttctccggaa
gtggctccgggacagatttcactcttaagatttcaagagtggaggcagaagacgttggagtctatta
ttgctcacagagcacacatgtcccctggactttcggtcccggcacaaaagtcgagatcaagcgtacg
gtggccgcccctccgtgttcatcttccccccctccgacgagcagctgaagtccggcaccgcctcg
tggtgtgcctgctgaataacttctaccccagagaggccaaggtgcagtggaaggtggacaacgccct
gcagtccgggaactcccaggagagcgtgaccgagcaggacagcaaggacagcacctacagcctgagc
agcaccctgaccctgagcaaagccgactacgagaagcacaaggtgtacgcctgcgaggtgacccacc
agggcctgagctcccccgtcaccaagagcttcaacaggggggagtgt
Signal sequence (1-60), Variable region (61-402), Constant region (403-717)

SEQ ID NO: 28: Amino acid sequence of hB273_L1-type light chain
MVLQTQVFISLLLWISGAYGDIVMTQSPLSLPVTPGEPASISCRSSQSLVHSNGNTYLHWYLQKPGQ
SPQLLIYKVSNRFSGVPDRFSGSGSGTDFTLKISRVEAEDVGVYYCSQSTHVPWTFGPGTKVEIKRT
VAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC
Signal sequence (1-20), Variable region (21-134), Constant region (135-239)

Fig. 33

SEQ ID NO: 29: Nucleotide sequence of hB273_L2-type light chain
atggtgctgcagacccaggtgttcatctccctgctgctgtggatctccggcgcatatggcgacgtcg
tcatgacacagacacctctgagcctgcccgtgtctctgggcgaacccgccagtatttcttgtaggtc
atctcagtctctggtgcacagtaacggaaacacatatctccattggtacctgcagaagccaggtcag
tccccaaagctcctgatctataaggtgagcaacagattctccggagtgcctgatcgattcagcggga
gtggttcagggaccgacttcaccttgaagattagccgggtcgaggccgaggatgttggagtgtattt
ctgtagccagagtacacacgtgccctggaccttcggacctgggactaaagtcgagattaaacgtacg
gtggccgcccctccgtgttcatcttcccccctccgacgagcagctgaagtccggcaccgcctcc
tggtgtgcctgctgaataacttctaccccagagaggccaaggtgcagtggaaggtggacaacgccct
gcagtccgggaactcccaggagagcgtgaccgagcaggacagcaaggacagcacctacagcctgagc
agcaccctgaccctgagcaaagccgactacgagaagcacaaggtgtacgcctgcgaggtgacccacc
agggcctgagctcccccgtcaccaagagcttcaacaggggggagtgt
Signal sequence (1-60), Variable region (61-402), Constant region (403-717)

SEQ ID NO: 30: Amino acid sequence of hB273_L2-type light chain
MVLQTQVFISLLLWISGAYGDVVMTQTPLSLPVSLGEPASISCRSSQSLVHSNGNTYLHWYLQKPGQ
SPKLLIYKVSNRFSGVPDRFSGSGSGTDFTLKISRVEAEDVGVYFCSQSTHVPWTFGPGTKVEIKRT
VAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC
Signal sequence (1-20), Variable region (21-134), Constant region (135-239)

Fig. 34

SEQ ID NO: 31: Nucleotide sequence of hB273_L3-type light chain
atggtgctgcagacccaggtgttcatctccctgctgctgtggatctccggcgcatatggcgacgtgg
tgatgacgcagactccgctgtcactgcccgtatctctgggagagcctgccagcatcagctgcaggag
ctctcaatcactggtgcactctaacggtaatacctacctccactggtatctccagaagccaggacaa
tccccaaagttgctcatatataaagtgtccaaccggttctcaggagtccctgaccggtttagcggta
gtggctctggtacagatttcaccctgaaaatatcaaggggttgaagcggaagacgtaggagtgtattt
ttgcagccagagcacccatgtccctggacatttgggggcggcaccaaggtcgaaatcaagcgtacg
gtggccgcccctccgtgttcatcttccccccctccgacgagcagctgaagtccggcaccgcctccg
tggtgcctgctgaataacttctaccccagagaggccaaggtgcagtggaaggtggacaacgccct
gcagtccgggaactcccaggagagcgtgaccgagcaggacagcaaggacagcacctacagcctgagc
agcaccctgaccctgagcaaagccgactacgagaagcacaaggtgtacgcctgcgaggtgacccacc
agggcctgagctcccccgtcaccaagagcttcaacagggggagtgt
Signal sequence (1-60), Variable region (61-402), Constant region
(403-717)

SEQ ID NO: 32: Amino acid sequence of hB273_L3-type light chain
MVLQTQVFISLLLWISGAYGDVVMTQTPLSLPVSLGEPASISCRSSQSLVHSNGNTYLHWYLQKPGQ
SPKLLIYKVSNRFSGVPDRFSGSGSGTDFTLKISRVEAEDVGVYFCSQSTHVPWTFGGGTKVEIKRT
VAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC
Signal sequence (1-20), Variable region (21-134), Constant region
(135-239)

Fig. 35

SEQ ID NO: 33: Nucleotide sequence of hB273_H1-type heavy chain
ATGAAACACCTGTGGTTCTTCCTCCTGCTGGTGGCAGCTCCCAGATGGGTGCTgagcCAAGTTCAGC
TCGTGCAGTCCGGCGCGGAGGTTAAGAAACCAGGCGCATCCGTTAAAGTGTCATGTAAGGCCAGCGG
GTACTCCTTTATCGGCTACTTTATGAACTGGGTGCGGCAGGCCCCTGGTATGGGCCTGGAGTGGATG
GGACGGTTTAATCCATATAATGGCGATACTTTTTACAACCAGAAATTTAAAGGAAGGGTCACTCTCA
CAGTGGATAAAAGCACTAGTACGGCTTACATGGAACTGTCCTCCCTCAGATCAGAAGATACTGCCGT
CTACTACTGCGCCCGAAGTGCTTACTATTTCGACAGCGGGGGCTACTTTGATTATTGGGGCCAGGGG
ACCCTGGTAACTGTGagcTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAACTCCTGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA
Signal sequence (1-57), Variable region (58-423), Constant region (424-1413)

SEQ ID NO: 34: Amino acid sequence of hB273_H1-type heavy chain
MKHLWFFLLLVAAPRWVLSQVQLVQSGAEVKKPGASVKVSCKASGYSFIGYFMNWVRQAPGMGLEWM
GRFNPYNGDTFYNQKFKGRVTLTVDKSTSTAYMELSSLRSEDTAVYYCARSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region (142-471)

Fig. 36

SEQ ID NO: 35: Nucleotide sequence of hB273_H2-type heavy chain
atgaaacacctgtggttcttcctcctgctggtggcagctcccagatgggtgctgagccaggtccagc
tggtgcagagtggagccgaggtaaaaaaaccaggggctagtgtcaaggtctcctgtaaggcatctgg
ttactcttttataggatacttcatgaactggatgaagcagtctccggtatgtctctggagtggatt
ggcagattcaaccoctacaacggggacactttttataatcagaagttcaaagggaaagccactctga
ccgtggacaagtcaacttccacagcatacatggaattgtcctcactgaggtccgaagataccgcgt
gtacttctgcgctcggagtgcttattatttcgatagcggagggtattttgactattggggcaaggg
accettgtaaccgtgagctcagcctccaccaagggcccaagcgtcttccccctggcaccctcctcca
agagcacctctggcggcacagccgccctgggctgcctggtcaaggactacttccccgaacccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccgcgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatggccagccggagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region
(424-1413)

SEQ ID NO: 36: Amino acid sequence of hB273_H2-type heavy chain
MKHLWFFLLLVAAPRWVLSQVQLVQSGAEVKKPGASVKVSCKASGYSFIGYFMNWMKQSPGMSLEWI
GRFNPYNGDTFYNQKFKGKATLTVDKSTSTAYMELSSLRSEDTAVYFCARSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region
(142-471)

Fig. 37

SEQ ID NO: 37: Nucleotide sequence of hB273_H3-type heavy chain
atgaaacacctgtggttcttcctcctgctggtggcagctcccagatgggtgctgagcgaagtgcagc
tcgtgcaaagcggcgctgaagtgaaaaaaccaggagcctcagtcaaagtgtcctgtaaggcctccgg
gtatagcttcatcggctatttatgaactggatgaagcagagcccgggcaaaagcctcgaatggatc
gggagattcaatccatacaatggtgaccttttacaatcagaaattcaaaggcaaggccacgctga
ctgtagacaaatccaccagcacagcccacatggaattgtcttccctgaggtctgaggataccgcggt
gtacttttgtggccgaagtgcgtattatttcgattcaggcgggtacttcgattactggggtcagggg
acgctcgtcaccgtaagctcagcctccaccaagggcccaagcgtcttccccctggcaccctcctcca
agagcacctctggcggcacagccgccctgggctgcctggtcaaggactacttccccgaacccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccccgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatggccagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region (424-1413)

SEQ ID NO: 38: Amino acid sequence of hB273_H3-type heavy chain
MKHLWFFLLLVAAPRWVLSEVQLVQSGAEVKKPGASVKVSCKASGYSFIGYFMNWMKQSPGKSLEWI
GRFNPYNGDTFYNQKFKGKATLTVDKSTSTAHMELSSLRSEDTAVYFCGRSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region (142-471)

Fig. 38

SEQ ID NO: 39: Nucleotide sequence of hB273_H1-1-type heavy chain
atgaaacacctgtggttcttcctcctgctggtggcagctcccagatgggtgctgagccaggtgcagc
tggtgcagtctggcgccgaagtgaagaaacctggcgcttctgtgaaggtgtcctgcaaggccagcgg
ctacagcttcatcggctacttcatgaactggatgcggcaggcccctggcatgggactggaatggatg
ggccggttcaaccctacaacggcgacaccttctacaaccagaaattcaagggcagagtgaccctga
ccgtggacaagagcaccagcaccgcctacatggaactgagcagcctgcggagcgaggataccgccgt
gtatttctgcggcagaagcgcctactacttcgacagcggcggctacttcgactactggggccaggc
accctggtcacagtgagctcagcctccaccaagggcccaagcgtcttccccctggcaccctcctcca
agagcacctctggcggcacagccgccctgggctgcctggtcaaggactacttccccgaaccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccgcgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatggccagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region
(424-1413)

SEQ ID NO: 40: Amino acid sequence of hB273_H1-1-type heavy chain
MKHLWFFLLLVAAPRWVLSQVQLVQSGAEVKKPGASVKVSCKASGYSFIGYFMNWMRQAPGMGLEWM
GRFNPYNGDTFYNQKFKGRVTLTVDKSTSTAYMELSSLRSEDTAVYFCGRSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region
(142-471)

Fig. 39

SEQ ID NO: 41: Nucleotide sequence of hB273_H2-1-type heavy chain
atgaaacacctgtggttcttcctcctgctggtggcagctcccagatgggtgctgagcgaggtgcagc
tggtgcagtctggcgccgaagtgaagaaacctggagccagcgtgaaggtgtcctgcaaggccagcgg
ctacagcttcatcggctacttcatgaactggatgaagcagagccccggcatgagcctggaatggatc
ggccggttcaaccctacaacggcgacaccttctacaaccagaagttcaagggaaaggccaccctga
cagtggacaagagcaccagcaccgcctacatggaactgagcagcctgcggagcgaggataccgccgt
gtacttctgcgccagaagcgcctactacttcgacagcggcggctacttcgactactggggccaggc
accctggtgacagtgagctcagcctccaccaagggcccaagcgtcttccccctggcaccctcctcca
agagcacctctgggggcacagccgccctgggctgcctggtcaaggactacttccccgaacccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccccgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatggccagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region (424-1413)

SEQ ID NO: 42: Amino acid sequence of hB273_H2-1-type heavy chain
MKHLWFFLLLVAAPRWVLSEVQLVQSGAEVKKPGASVKVSCKASGYSFIGYFMNWMKQSPGMSLEWI
GRFNPYNGDTFYNQKFKGKATLTVDKSTSTAYMELSSLRSEDTAVYFCARSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region (142-471)

Fig. 40

SEQ ID NO: 43: Nucleotide sequence of hB273_H2-2-type heavy chain
atgaaacacctgtggttcttcctcctgctggtggcagctcccagatgggtgctgagccaggtgcagc
tggtgcagtctggcgccgaagtgaagaaacctggagccagcgtgaaggtgtcctgcaaggccagcgg
ctacagcttcatcggctacttcatgaactggatgaagcagagccccggcatgagcctggaatggatc
ggccggttcaaccnctacaacggcgacaccttctacaaccagaagttcaagggaaaggccaccctga
cagtggacaagagcaccagcacnwgcccacatggaactgagcagcctgcggagcgaggataccgccgt
gtacttctgcgccagaagcgcctactacttcgacagcggcggctacttcgactactggggccagggc
accctggtgacagtgagctcagcctccaccaagggcccaagcgtcttccccctggcaccctcctcca
agagcacctctggcggcacagccgccctgggctgcctggtcaaggactacttccccgaacccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccccgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatggccagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region (424-1413)

SEQ ID NO: 44: Amino acid sequence of hB273_H2-2-type heavy chain
MKHLWFFLLLVAAPRWVLSQVQLVQSGAEVKKPGASVKVSCKASGYSFIGYFMNWMKQSPGMSLEWI
GRFNPYNGDTFYNQKFKGKATLTVDKSTSTAHMELSSLRSEDTAVYFCARSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region (142-471)

Fig. 41

SEQ ID NO: 45: Nucleotide sequence of hB273_H2-3-type heavy chain
atgaaacacctgtggttcttcctcctgctggtggcagctcccagatgggtgctgagcgaggtgcagc
tggtgcagtctggcgccgaagtgaagaaacctggagccagcgtgaaggtgtcctgcaaggccagcgg
ctacagcttcatcggctacttcatgaactggatgaagcagagccccggcatgagcctggaatggatc
ggccggttcaaccsctacaacggcgacaccttctacaaccagaagttcaagggaaaggccaccctga
cagtggacaagagcaccagcaccgcccacatggaactgagcagcctgcgggagcgaggataccgccgt
gtacttctgcgccagaagcgcctactacttcgacagcggcggctacttcgactactggggccaggdc
accctggtgacagtgagctcagcctccaccaagggcccaagcgtcttccccctggcaccctcctcca
agagcacctctggcggcacagccgccctgggctgcctggtcaaggactacttccccgaaccgtgac
cgtgagctggaactcaggcgccctgaccagcggcgtgcacaccttcccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccccgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatggccagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region
(424-1413)

SEQ ID NO: 46: Amino acid sequence of hB273_H2-3-type heavy chain
MKHLWFFLLLVAAPRWVLSEVQLVQSGAEVKKPGASVKVSCKASGYSFIGYFMNWMKQSPGMSLEWI
GRFNPYNGDTFYNQKFKGKATLTVDKSTSTAHMELSSLRSEDTAVYFCARSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region
(142-471)

Fig. 42

SEQ ID NO: 47: Nucleotide sequence of hB273_H2-4-type heavy chain
atgaaacacctgtggttcttcctcctgctggtggcagctcccagatgggtgctgagccaggtgcagc
tggtgcagtctggcgccgaagtgaagaaacctggagccagcgtgaaggtgtcctgcaaggccagcgg
ctacagcttcatcggctacttcatgaactggatgaagcagagccccggcatgagcctggaatggatc
ggccggttcaaccctacaacggcgacaccttctacaaccagaagttcaagggaaaggccaccctga
cagtggacaagagcaccagcaccgcctacatggaactgagcagcctgcggagcgaggataccgccgt
gtacttctgcggcagaagcgcctactacttcgacagcggcggctacttcgactactggggccagggc
accctggtgacagtgagctcagcctccaccaagggcccaagcgtcttccccctggcaccctcctca
agagcacctctggcggcacagccgccctgggctgcctggtcaaggactacttccccgaaccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccccgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatggccagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region (424-1413)

SEQ ID NO: 48: Amino acid sequence of hB273_H2-4-type heavy chain
MKHLWFFLLLVAAPRWVLSQVQLVQSGAEVKKPGASVKVSCKASGYSFIGYFMNWMKQSPGMSLEWI
GRFNPYNGDTFYNQKFKGKATLTVDKSTSTAYMELSSLRSEDTAVYFCGRSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region (142-471)

Fig. 43

SEQ ID NO: 49: Nucleotide sequence of hB273_H2-5-type heavy chain
atgaaacacctgtggttcttcctcctgctggtggcagctcccagatgggtgctgagccaggtgcagc
tggtgcagtctggcgccgaagtgaagaaacctggagccagcgtgaaggtgtcctgcaaggccagcgg
ctacagcttcatcggctacttcatgaactggatgaagcagagccccggcaagagcctggaatggatc
ggccggttcaaccoctacaacggcgacaccttctacaaccagaagttcaagggaaaggccaccctga
cagtggacaagagcaccagcaccgcctacatggaactgagcagcctgcggagcgaggataccgccgt
gtacttctgcggcagaagcgcctactacttcgacagcggcggctacttcgactactggggccagggc
accctggtgacagtgagctcagcctccaccaagggcccaagcgtcttccccctggcaccctcctcca
agagcacctctggcggcacagccgccctgggctgcctggtcaaggactacttccccgaacccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccccgggaggagcagtacaacagcacgtaccgggtggtcagcgtcctcaccgtcctgcaccag
gactggctgaatggcaaggagtacaagtgcaaggtctccaacaaagcctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatgggcagccggagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region
(424-1413)

SEQ ID NO: 50: Amino acid sequence of hB273_H2-5-type heavy chain
MKHLWFFLLLVAAPRWVLSQVQLVQSGAEVKKPGASVKVSCKASGYSFIGYFMNWMKQSPGKSLEWI
GRFNPYNGDTFYNQKFKGKATLTVDKSTSTAYMELSSLRSEDTAVYFCGRSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region
(142-471)

Fig. 44

SEQ ID NO: 51: Nucleotide sequence of hB273_L1-NE-type light chain
atggtgctgcagacccaggtgttcatctccctgctgctgtggatctccggcgcatatggcgacatcg
taatgacccagtctccgctgagtcttcctgtgactccaggggagcccgcaagcatctcttgtcgcag
cagtcagtcactggtccatagcaatgagaacacttacctgcattggtacctccaaaaaccagggcag
tccccacagctcttgatctacaaggtgtccaatcggttcagtggtgtgcctgaccgcttctccggaa
gtggctccgggacagatttcactcttaagatttcaagagtggaggcagaagacgttggagtctatta
ttgctcacagagcacacatgtcccctggactttcggtcccggcacaaaagtcgagatcaagcgtacg
gtggccgcccctccgtgttcatcttccccccctccgacgagcagctgaagtccggcaccgcctccg
tggtgtgcctgctgaataacttctacccagagaggccaaggtgcagtggaaggtggacaacgccct
gcagtccgggaactcccaggagagcgtgaccgagcaggacagcaaggacagcacctacagcctgagc
agcaccctgaccctgagcaaagccgactacgagaagcacaaggtgtacgcctgcgaggtgacccacc
agggcctgagctccccgtcaccaagagcttcaacagggggagtgt
Signal sequence (1-60), Variable region (61-402), Constant region
(403-717)

SEQ ID NO: 52: Amino acid sequence of hB273_L1-NE-type light chain
MVLQTQVFISLLLWISGAYGDIVMTQSPLSLPVTPGEPASISCRSSQSLVHSNENTYLHWYLQKPGQ
SPQLLIYKVSNRFSGVPDRFSGSGSGTDFTLKISRVEAEDVGVYYCSQSTHVPWTFGPGTKVEIKRT
VAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC
Signal sequence (1-20), Variable region (21-134), Constant region
(135-239)

Fig. 45

SEQ ID NO: 57: Nucleotide sequence of hB273_L1-NF-type light chain
atggtgctgcagacccaggtgttcatctccctgctgctgtggatctccggcgcatatggcgacatcg
taatgacccagtctccgctgagtcttcctgtgactccaggggagcccgcaagcatctcttgtcgcag
cagtcagtcactggtccatagcaatttcaacacttacctgcattggtacctccaaaaaccagggcag
tccccacagctcttgatctacaaggtgtccaatcggttcagtggtgtgcctgaccgcttctccggaa
gtggctccgggacagatttcactcttaagatttcaagagtggaggcagaagacgttggagtctatta
ttgctcacagagcacacatgtccctggactttcggtcccggcacaaaagtcgagatcaagcgtacg
gtggccgcccctccgtgttcatcttcccccctccgacgagcagctgaagtccggcaccgcctccg
tggtgtgcctgctgaataacttctaccccagagaggccaaggtgcagtggaaggtggacaacgccct
gcagtccgggaactcccaggagagcgtgaccgagcaggacagcaaggacagcacctacagcctgagc
agcaccctgaccctgagcaaagccgactacgagaagcacaaggtgtacgcctgcgaggtgacccacc
agggcctgagctccccgtcaccaagagcttcaacaggggggagtgt
Signal sequence (1-60), Variable region (61-402), Constant region
(403-717)

SEQ ID NO: 58: Amino acid sequence of hB273_L1-NF-type light chain
MVLQTQVFISLLLWISGAYGDIVMTQSPLSLPVTPGEPASISCRSSQSLVHSNFNTYLHWYLQKPGQ
SPQLLIYKVSNRFSGVPDRFSGSGSGTDFTLKISRVEAEDVGVYYCSQSTHVPWTFGPGTKVEIKRT
VAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC
Signal sequence (1-20), Variable region (21-134), Constant region
(135-239)

Fig. 46

SEQ ID NO: 61: Nucleotide sequence of hB273_L1-NK-type light chain
atggtgctgcagacccaggtgttcatctccctgctgctgtggatctccggcgcatatggcgacatcg
taatgacccagtctccgctgagtcttcctgtgactccaggggagcccgcaagcatctcttgtcgcag
cagtcagtcactggtccatagcaataagaacacttacctgcattggtacctccaaaaaccagggcag
tccccacagctcttgatctacaaggtgtccaatcggttcagtggtgtgcctgaccgcttctccggaa
gtggctccgggacagatttcactcttaagatttcaagagtggaggcagaagacgttggagtctatta
ttgctcacagagcacacatgtcccctggactttcggtcccggcacaaaagtcgagatcaagcgtacg
gtggccgcccctccgtgttcatcttccccccctccgacgagcagctgaagtccggcaccgcctccg
tggtgtgcctgctgaataacttctaccccagagaggccaaggtgcagtggaaggtggacaacgccct
gcagtccgggaactcccaggagagcgtgaccgagcaggacagcaaggacagcacctacagcctgagc
agcaccctgaccctgagcaaagccgactacgagaagcacaaggtgtacgcctgcgaggtgacccacc
agggcctgagctcccccgtcaccaagagcttcaacaggggggagtgt
Signal sequence (1-60), Variable region (61-402), Constant region
(403-717)

SEQ ID NO: 62: Amino acid sequence of hB273_L1-NK-type light chain
MVLQTQVFISLLLWISGAYGDIVMTQSPLSLPVTPGEPASISCRSSQSLVHSNKNTYLHWYLQKPGQ
SPQLLIYKVSNRFSGVPDRFSGSGSGTDFTLKISRVEAEDVGVYYCSQSTHVPWTFGPGTKVEIKRT
VAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC
Signal sequence (1-20), Variable region (21-134), Constant region
(135-239)

Fig. 47

SEQ ID NO: 65: Nucleotide sequence of hB273_L1-NL-type light chain
atggtgctgcagacccaggtgttcatctccctgctgctgtggatctccggcgcatatggcgacatcg
taatgacccagtctccgctgagtcttcctgtgactccaggggagcccgcaagcatctcttgtcgcag
cagtcagtcactggtccatagcaatctgaacacttacctgcattggtacctccaaaaaccagggcag
tccccacagctcttgatctacaaggtgtccaatcggttcagtggtgtgcctgaccgcttctccggaa
gtggctccgggacagatttcactcttaagatttcaagagtggaggcagaagacgttggagtctatta
ttgctcacagagcacacatgtcccctggactttcggtcccggcacaaaagtcgagatcaagcgtacg
gtggccgcccctccgtgttcatcttccccccctccgacgagcagctgaagtccggcaccgcctccg
tggtgtgcctgctgaataacttctaccccagagaggccaaggtgcagtggaaggtggacaacgccct
gcagtccgggaactcccaggagagcgtgaccgagcaggacagcaaggacagcacctacagcctgagc
agcaccctgaccctgagcaaagccgactacgagaagcacaaggtgtacgcctgcgaggtgacccacc
agggcctgagctcccccgtcaccaagagcttcaacagggggagtgt
Signal sequence (1-60), Variable region (61-402), Constant region
(403-717)

SEQ ID NO: 66: Amino acid sequence of hB273_L1-NL-type light chain
MVLQTQVFISLLLWISGAYGDIVMTQSPLSLPVTPGEPASISCRSSQSLVHSNLNTYLHWYLQKPGQ
SPQLLIYKVSNRFSGVPDRFSGSGSGTDFTLKISRVEAEDVGVYYCSQSTHVPWTFGPGTKVEIKRT
VAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC
Signal sequence (1-20), Variable region (21-134), Constant region
(135-239)

Fig. 48

SEQ ID NO: 69: Nucleotide sequence of hB273_H2-1-NE-type heavy chain
atgaaacacctgtggttcttcctcctgctggtggcagctcccagatgggtgctgagcgaggtgcagc
tggtgcagtctggcgccgaagtgaagaaacctggagccagcgtgaaggtgtcctgcaaggccagcgg
ctacagcttcatcggctacttcatgaactggatgaagcagagccccggcatgagcctggaatggatc
ggccggttcaaccoctacaacgaggacaccttctacaaccagaagttcaagggaaaggccaccctga
cagtggacaagagcaccagcaccgcctacatggaactgagcagcctgcggagcgaggataccgccgt
gtacttctgcgccagaagcgcctactacttcgacagcggcggctacttcgactactggggccagggc
accctggtgacagtgagctcagctccaccaagggcccaagcgtcttccccctggcaccctcctcca
agagcacctctggcggcacagccgccctgggctgcctggtcaaggactacttccccgaacccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccccgggaggagcagtacaacagcacgtaccgggtggtcagcgtcctcaccgtcctgcaccag
gactggctgaatggcaaggagtacaagtgcaaggtctccaacaaagccctcccagcccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatgggcagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region (424-1413)

SEQ ID NO: 70: Amino acid sequence of hB273_H2-1-NE-type heavy chain
MKHLWFFLLLVAAPRWVLSEVQLVQSGAEVKKPGASVKVSCKASGYSFIGYFMNWMKQSPGMSLEWI
GRFNPYNEDTFYNQKFKGKATLTVDKSTSTAYMELSSLRSEDTAVYFCARSAYYFDSGGYFDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region (142-471)

Fig. 49

SEQ ID NO: 75: Nucleotide sequence of cDNA encoding conatumumab light chain
atggtgctgcagacccaggtgttcatctccctgctgctgtggatctccggcgcatatggcgaaatcg
tgttgacacagagtcccggcactcttagccttagcccgggtgaacgcgccaccctgtcctgccgcgc
ctctcagggaatctctcgctcttacctcgcgtggtaccagcagaaacccggccaggcccccagtttg
ctgatatacggtgcctctagccgagcaactggcatcccagaccggttctcaggatctggctccggga
ctgacttcactctgaccatctccagactggagcccgaggatttcgcggtatattactgccagcagtt
cggcagcagtccttggaccttcggacagggtactaaggtggagattaaacgtacggtggccgccccc
tccgtgttcatcttccccccctccgacgagcagctgaagtccggcaccgcctccgtggtgtgcctgc
tgaataacttctacccagagaggccaaggtgcagtggaaggtggacaacgccctgcagtccgggaa
ctcccaggagagcgtgaccgagcaggacagcaaggacagcacctacagcctgagcagcaccctgacc
ctgagcaaagccgactacgagaagcacaaggtgtacgcctgcgaggtgacccaccagggcctgagct
cccccgtcaccaagagcttcaacaggggggagtgt
Signal sequence (1-60), Variable region (61-390), Constant region (400-705)

SEQ ID NO: 76: Amino acid sequence of conatumumab light chain
MVLQTQVFISLLLWISGAYGEIVLTQSPGTLSLSPGERATLSCRASQGISRSYLAWYQQKPGQAPSL
LIYGASSRATGIPDRFSGSGSGTDFTLTISRLEPEDFAVYYCQQFGSSPWTFGQGTKVEIKRTVAAP
SVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC
Signal sequence (1-20), Variable region (21-130), Constant region (131-235)

Fig. 50

SEQ ID NO: 77: Nucleotide sequence of cDNA encoding conatumumab heavy chain
atgaaacacctgtggttcttcctcctgctggtggcagctcccagatgggtgctgagccaggtgcagc
ttcaggaaagcgggcccggcctcgtgaagccctcccagaccctgtctcttacttgtacagtgagcgg
tggcagcatttcttcaggcgattacttctggagttggattcgccaactgcctggtaaagggctggaa
tggatcgggcatattcacaattcaggaaccacatattataacccttcactgaagagccgggtaacta
tctccgttgacactagcaagaaacagttctccctccggctgtcttctgtcacagccgctgacaccgc
tgtttactactgtgcaagagatcggggtggcgactactattacggcatggatgtttggggacaggga
accacggtaacagtgagctcagcctccaccaagggcccaagcgtcttccccctggcaccctcctcca
agagcacctctggcggcacagccgccctgggctgcctggtcaaggactacttccccgaacccgtgac
cgtgagctggaactcaggcgccctgaccagcggcgtgcacaccttccccgctgtcctgcagtcctca
ggactctactccctcagcagcgtggtgaccgtgccctccagcagcttgggcacccagacctacatct
gcaacgtgaatcacaagcccagcaacaccaaggtggacaagagagttgagcccaaatcttgtgacaa
aactcacacatgcccaccctgcccagcacctgaactcctggggggaccctcagtcttcctcttcccc
ccaaaacccaaggacaccctcatgatctcccggacccctgaggtcacatgcgtggtggtggacgtga
gccacgaagaccctgaggtcaagttcaactggtacgtggacggcgtggaggtgcataatgccaagac
aaagccccgggaggagcagtacaacagcacgtaccgggtggtcagcgtcctcaccgtcctgcaccag
gactggctgaatggcaaggagtacaagtgcaaggtctccaacaaagcctcccagccccccatcgaga
aaaccatctccaaagccaaaggccagccccgggaaccacaggtgtacaccctgcccccatcccggga
ggagatgaccaagaaccaggtcagcctgacctgcctggtcaaaggcttctatcccagcgacatcgcc
gtggagtgggagagcaatggccagcccgagaacaactacaagaccacccctcccgtgctggactccg
acggctccttcttcctctacagcaagctcaccgtggacaagagcaggtggcagcagggcaacgtctt
ctcatgctccgtgatgcatgaggctctgcacaaccactacacccagaagagcctctccctgtctccc
ggcaaa
Signal sequence (1-57), Variable region (58-423), Constant region (424-1413)

SEQ ID NO: 78: Amino acid sequence of conatumumab heavy chain
MKHLWFFLLLVAAPRWVLSQVQLQESGPGLVKPSQTLSLTCTVSGGSISSGDYFWSWIRQLPGKGLE
WIGHIHNSGTTYYNPSLKSRVTISVDTSKKQFSLRLSSVTAADTAVYYCARDRGGDYYYGMDVWGQG
TTVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK
Signal sequence (1-19), Variable region (20-141), Constant region (142-471)

ANTI-DR5 ANTIBODIES, POLYNUCLEOTIDES AND METHODS

CROSS-REFERENCES TO RELATED APPLICATIONS

This application is a continuation of U.S. patent application Ser. No. 13/881,645, filed Apr. 25, 2013, which is the National Stage of International Application No. PCT/JP2011/074866, filed Oct. 27, 2011, which claims priority from Japanese Patent Application No. 2010-243549, filed Oct. 29, 2010. Each application is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 53290_SEQ_Final_2015-09-01.TXT. The text file is 213 KB; was created on Sep. 1, 2015; and is being submitted via EFS-Web with the filing of the specification.

TECHNICAL FIELD

The present invention relates to an antibody which binds to a cell surface receptor involved in apoptosis induction and is useful as a therapeutic and/or preventive agent for tumors, and also relates to a method of treating and/or preventing cancer, an autoimmune disease, or an inflammatory disease using the antibody.

BACKGROUND ART

Apoptosis is a phenomenon essential to the physiological process of removing unnecessary cells or damaged cells and maintaining the number of normal cells in vivo. Owing to progress in elucidation of the fact that the regulatory mechanism of apoptosis is often impaired in cancer or immune diseases and also elucidation of the regulatory pathway of apoptosis, the development of a novel apoptosis inducer which can be used in the treatment of cancer or immune diseases has been advanced. In particular, an antibody which has a binding affinity for a ligand for a cell surface receptor involved in apoptosis induction typified by a death receptor or an antibody which has a binding affinity for said death receptor is expected to have a therapeutic effect on these diseases (see, for example, Non-patent document 1). Death receptor 5 (DR5) which is one of the death receptors is sometimes also called KILLER, TRICK 2A, TRAIL-R2, TRICK B, or CD262, and a plurality of agonistic antibodies which induce apoptosis in cells are known (see, for example, Non-patent document 2 or 3, or Patent documents 1 to 6). Some antibodies are currently being developed in clinical trials as candidate therapeutic agents and are expected to have a therapeutic effect such that the antibodies specifically act in an agonistic manner on cells (cancer cells or immune disease-related cells) which express the receptor in order to kill the cells. In order for such an antibody to have an antitumor effect, it is essential that the cells express DR5, however, it has been revealed that there is no correlation between the effect and the expression level of DR5 in a preclinical trial (Non-patent document 4). It is considered that this is because a cellular response is regulated by many factors such as the expression level of intracellular signaling molecules (such as caspase-8 or Bcl-2) involved in apoptosis pathways (Non-patent document 5).

PRIOR ART DOCUMENTS

Patent Document 1
WO 98/51793
Patent Document 2
WO 2001/83560
Patent Document 3
WO 2002/94880
Patent Document 4
WO 2003/54216
Patent Document 5
WO 2006/83971
Patent Document 6
WO 2007/22157
Non-Patent Document 1
Cell Death and Differentiation, 10:66-75 (2003)
Non-Patent Document 2
Journal of Immunology, 162:2597-2605 (1999)
Non-Patent Document 3
Nature Medicine, 7(8):954-960 (2001)
Non-Patent Document 4
Cell Death and Differentiation, 10:66-75 (2003)
Non-Patent Document 5
Journal of Clinical Oncology, 26:3621-3630 (2008)

SUMMARY OF THE INVENTION

Problems that the Invention is to Solve

An object of the invention is to provide an antibody or a functional fragment of the antibody to be used in a pharmaceutical having a therapeutic effect on cancer, and a polynucleotide encoding the antibody or a functional fragment of the antibody.

Means for Solving the Problems

The present inventors made intensive studies in order to achieve the above object, and as a result, they found an antibody which exhibits a potent apoptosis-inducing activity in cells, and thus completed the invention. This also brings about an effective therapeutic effect in patients in whom a sufficient therapeutic effect of currently available antibodies cannot be obtained.

That is, the invention includes the following inventions.

(1) An antibody characterized in that:
a heavy chain sequence contains a variable region having CDRH1, CDRH2, and CDRH3, and the CDRH1 comprises an amino acid sequence represented by SEQ ID NO: 82, the CDRH2 comprises either one of the amino acid sequences represented by SEQ ID NOS: 83 and 89, and the CDRH3 comprises an amino acid sequence represented by SEQ ID NO: 84; and
a light chain sequence contains a variable region having CDRL1, CDRL2, and CDRL3, and the CDRL1 comprises any one of the amino acid sequences represented by SEQ ID NOS: 79, 85, 86, 87, and 88, the CDRL2 comprises an amino acid sequence represented by SEQ ID NO: 80, and the CDRL3 comprises an amino acid sequence represented by SEQ ID NO: 81, or a functional fragment of the antibody.

(2) The antibody or a functional fragment of the antibody according to (1), characterized by containing a heavy chain variable region sequence comprising amino acid residues 20 to 141 of the amino acid sequence represented by SEQ ID NO: 20 and a light chain variable region sequence comprising amino acid residues 21 to 134 of the amino acid sequence represented by SEQ ID NO: 16.

(3) The antibody or a functional fragment of the antibody according to (1) or (2), characterized in that the antibody is a chimeric antibody.

(4) The antibody or a functional fragment of the antibody according to (3), characterized by containing a heavy chain sequence comprising amino acid residues 20 to 471 of the amino acid sequence represented by SEQ ID NO: 20 and a light chain sequence comprising amino acid residues 21 to 239 of the amino acid sequence represented by SEQ ID NO: 16.

(5) The antibody or a functional fragment of the antibody according to (1), characterized in that the antibody is humanized.

(6) The antibody or a functional fragment of the antibody according to (5), characterized by containing:

(a) a heavy chain variable region sequence selected from the group consisting of the following amino acid sequences:

a1) an amino acid sequence comprising amino acid residues 20 to 141 of the amino acid sequence represented by SEQ ID NO: 42;

a2) an amino acid sequence comprising amino acid residues 20 to 141 of the amino acid sequence represented by SEQ ID NO: 70;

a3) an amino acid sequence having a homology of at least 95% with an amino acid sequence selected from a1) and a2);

a4) an amino acid sequence having a homology of at least 99% with an amino acid sequence selected from a1) and a2); and a5) an amino acid sequence including a substitution, deletion, or addition of one to several amino acid residues in either one of the amino acid sequences selected from a1) and a2); and (b) a light chain variable region sequence selected from the group consisting of the following amino acid sequences:

b1) an amino acid sequence comprising amino acid residues 21 to 134 of the amino acid sequence represented by SEQ ID NO: 28;

b2) an amino acid sequence comprising amino acid residues 21 to 134 of the amino acid sequence represented by SEQ ID NO: 52;

b3) an amino acid sequence comprising amino acid residues 21 to 134 of the amino acid sequence represented by SEQ ID NO: 58;

b4) an amino acid sequence comprising amino acid residues 21 to 134 of the amino acid sequence represented by SEQ ID NO: 62;

b5) an amino acid sequence comprising amino acid residues 21 to 134 of the amino acid sequence represented by SEQ ID NO: 66;

b6) an amino acid sequence having a homology of at least 95% with any one of the amino acid sequences selected from b1) to a5);

b7) an amino acid sequence having a homology of at least 99% with any one of the amino acid sequences selected from b1) to b5); and b8) an amino acid sequence including a substitution, deletion, or addition of one to several amino acid residues in any one of the amino acid sequences selected from b1) to b5).

(7) The antibody or a functional fragment of the antibody according to (6), characterized by containing a heavy chain variable region sequence comprising amino acid residues 20 to 141 of the amino acid sequence represented by SEQ ID NO: 42 and a light chain variable region sequence comprising amino acid residues 21 to 134 of the amino acid sequence represented by SEQ ID NO: 28.

(8) The antibody or a functional fragment of the antibody according to (6), characterized by containing a heavy chain variable region sequence comprising amino acid residues 20 to 141 of the amino acid sequence represented by SEQ ID NO: 70 and a light chain variable region sequence comprising amino acid residues 21 to 134 of the amino acid sequence represented by SEQ ID NO: 52.

(9) The antibody or a functional fragment of the antibody according to (6), characterized by containing a heavy chain variable region sequence comprising amino acid residues 20 to 141 of the amino acid sequence represented by SEQ ID NO: 70 and a light chain variable region sequence comprising amino acid residues 21 to 134 of the amino acid sequence represented by SEQ ID NO: 58.

(10) The antibody or a functional fragment of the antibody according to (6), characterized by containing a heavy chain variable region sequence comprising amino acid residues 20 to 141 of the amino acid sequence represented by SEQ ID NO: 70 and a light chain variable region sequence comprising amino acid residues 21 to 134 of the amino acid sequence represented by SEQ ID NO: 62.

(11) The antibody or a functional fragment of the antibody according to (6), characterized by containing a heavy chain variable region sequence comprising amino acid residues 20 to 141 of the amino acid sequence represented by SEQ ID NO: 70 and a light chain variable region sequence comprising amino acid residues 21 to 134 of the amino acid sequence represented by SEQ ID NO: 66.

(12) The antibody or a functional fragment of the antibody according to (6), characterized by containing a heavy chain sequence comprising amino acid residues 20 to 471 of the amino acid sequence represented by SEQ ID NO: 42 and a light chain sequence comprising amino acid residues 21 to 239 of the amino acid sequence represented by SEQ ID NO: 28.

(13) The antibody or a functional fragment of the antibody according to (6), characterized by containing a heavy chain sequence comprising amino acid residues 20 to 471 of the amino acid sequence represented by SEQ ID NO: 70 and a light chain sequence comprising amino acid residues 21 to 239 of the amino acid sequence represented by SEQ ID NO: 52.

(14) The antibody or a functional fragment of the antibody according to (6), characterized by containing a heavy chain sequence comprising amino acid residues 20 to 471 of the amino acid sequence represented by SEQ ID NO: 70 and a light chain sequence comprising amino acid residues 21 to 239 of the amino acid sequence represented by SEQ ID NO: 58.

(15) The antibody or a functional fragment of the antibody according to (6), characterized by containing a heavy chain sequence comprising amino acid residues 20 to 471 of the amino acid sequence represented by SEQ ID NO: 70 and a light chain sequence comprising amino acid residues 21 to 239 of the amino acid sequence represented by SEQ ID NO: 62.

(16) The antibody or a functional fragment of the antibody according to (6), characterized by containing a heavy chain sequence comprising amino acid residues 20 to 471 of the amino acid sequence represented by SEQ ID NO: 70 and a light chain sequence comprising amino acid residues 21 to 239 of the amino acid sequence represented by SEQ ID NO: 66.

(17) The functional fragment of the antibody according to any one of (1) to (16), which is selected from the group consisting of Fab, F(ab')2, Fab' and Fv.

(18) A pharmaceutical composition characterized by comprising at least one of the antibodies or functional fragments of the antibodies according to (1) to (17).

(19) The pharmaceutical composition according to (18), characterized by being a pharmaceutical composition for treating and/or preventing cancer.

(20) A pharmaceutical composition for treating and/or preventing cancer, characterized by comprising at least one of the antibodies or functional fragments of the antibodies according to (1) to (17) and at least one member selected from the group consisting of paclitaxel, carboplatin, CPT-11, and vinblastine.

(21) The pharmaceutical composition according to (19) or (20), wherein the cancer is selected from the group consisting of lung cancer, prostate cancer, thyroid cancer, stomach cancer, liver cancer, ovarian cancer, colon cancer, breast cancer, pancreatic cancer, renal cancer, uterine cancer, melanoma, fibrosarcoma, glioblastoma, and blood cell cancer.

(22) A method of treating and/or preventing cancer, characterized by administering at least one of the antibodies or functional fragments of the antibodies according to (1) to (17).

(23) A method of treating and/or preventing cancer, characterized by simultaneously or sequentially administering at least one of the antibodies or functional fragments of the antibodies according to (1) to (17) and at least one member selected from the group consisting of paclitaxel, carboplatin, CPT-11, vinblastine, and 5-FU.

(24) The treatment and/or prevention method according to (22) or (23), wherein the cancer is selected from the group consisting of lung cancer, prostate cancer, thyroid cancer, stomach cancer, liver cancer, ovarian cancer, colon cancer, breast cancer, pancreatic cancer, uterine cancer, melanoma, glioblastoma, and blood cell cancer.

(25) A polynucleotide encoding the antibody according to any one of (2), (4), and (6) to (16).

(26) The polynucleotide according to (25), characterized by containing a nucleotide sequence comprising nucleotides 58 to 423 of the nucleotide sequence represented by SEQ ID NO: 19 and a nucleotide sequence comprising nucleotides 61 to 402 of the nucleotide sequence represented by SEQ ID NO: 15.

(27) The polynucleotide according to (25), characterized by containing a nucleotide sequence comprising nucleotides 58 to 1413 of the nucleotide sequence represented by SEQ ID NO: 19 and a nucleotide sequence comprising nucleotides 61 to 717 of the nucleotide sequence represented by SEQ ID NO: 15.

(28) The polynucleotide according to (25), characterized by containing:

(a) a polynucleotide selected from the group consisting of the following nucleotide sequences:

a1) a nucleotide sequence comprising nucleotides 58 to 423 of the nucleotide sequence represented by SEQ ID NO: 41;

a2) a nucleotide sequence comprising nucleotides 58 to 423 of the nucleotide sequence represented by SEQ ID NO: 69;

a3) a nucleotide sequence of a polynucleotide which hybridizes to a polynucleotide comprising a nucleotide sequence complementary to a nucleotide sequence selected from a1) and a2) under stringent conditions; and a4) a nucleotide sequence including a substitution, deletion, or addition of one to several nucleotides in a nucleotide sequence selected from a1) and a2); and (b) a polynucleotide selected from the group consisting of the following nucleotide sequences:

b1) a nucleotide sequence comprising nucleotides 61 to 402 of the nucleotide sequence represented by SEQ ID NO: 27;

b2) a nucleotide sequence comprising nucleotides 61 to 402 of the nucleotide sequence represented by SEQ ID NO: 51;

b3) a nucleotide sequence comprising nucleotides 61 to 402 of the nucleotide sequence represented by SEQ ID NO: 57;

b4) a nucleotide sequence comprising nucleotides 61 to 402 of the nucleotide sequence represented by SEQ ID NO: 61;

b5) a nucleotide sequence comprising nucleotides 61 to 402 of the nucleotide sequence represented by SEQ ID NO: 65;

b6) a nucleotide sequence of a polynucleotide which hybridizes to a polynucleotide comprising a nucleotide sequence complementary to any one of the nucleotide sequences selected from b1) to a5) under stringent conditions; and b7) a nucleotide sequence including a substitution, deletion, or addition of one to several nucleotides in any one of the nucleotide sequences selected from b1) to b5).

(29) The polynucleotide according to (28), characterized by containing a polynucleotide comprising a nucleotide sequence comprising nucleotides 58 to 423 of the nucleotide sequence represented by SEQ ID NO: 41, and a polynucleotide comprising a nucleotide sequence comprising nucleotides 61 to 402 of the nucleotide sequence represented by SEQ ID NO: 27.

(30) The polynucleotide according to (28), characterized by containing a polynucleotide comprising a nucleotide sequence comprising nucleotides 58 to 423 of the nucleotide sequence represented by SEQ ID NO: 69, and a polynucleotide comprising a nucleotide sequence comprising nucleotides 61 to 402 of the nucleotide sequence represented by SEQ ID NO: 51.

(31) The polynucleotide according to (28), characterized by containing a polynucleotide comprising a nucleotide sequence comprising nucleotides 58 to 423 of the nucleotide sequence represented by SEQ ID NO: 69, and a polynucleotide comprising a nucleotide sequence comprising nucleotides 61 to 402 of the nucleotide sequence represented by SEQ ID NO: 57.

(32) The polynucleotide according to (28), characterized by containing a polynucleotide comprising a nucleotide sequence comprising nucleotides 58 to 423 of the nucleotide sequence represented by SEQ ID NO: 69, and a polynucleotide comprising a nucleotide sequence comprising nucleotides 61 to 402 of the nucleotide sequence represented by SEQ ID NO: 61.

(33) The polynucleotide according to (28), characterized by containing a polynucleotide comprising a nucleotide sequence comprising nucleotides 58 to 423 of the nucleotide sequence represented by SEQ ID NO: 69, and a polynucleotide comprising a nucleotide sequence comprising nucleotides 61 to 402 of the nucleotide sequence represented by SEQ ID NO: 65.

(34) The polynucleotide according to (28), characterized by containing a polynucleotide comprising a nucleotide sequence comprising nucleotides 58 to 1413 of the nucleotide sequence represented by SEQ ID NO: 41, and a polynucleotide comprising a nucleotide sequence comprising nucleotides 61 to 717 of the nucleotide sequence represented by SEQ ID NO: 27.

(35) The polynucleotide according to (28), characterized by containing a polynucleotide comprising a nucleotide sequence comprising nucleotides 58 to 1413 of the nucleotide sequence represented by SEQ ID NO: 69, and a polynucleotide comprising a nucleotide sequence comprising nucleotides 61 to 717 of the nucleotide sequence represented by SEQ ID NO: 51.

(36) The polynucleotide according to (28), characterized by containing a polynucleotide comprising a nucleotide sequence comprising nucleotides 58 to 1413 of the nucleotide sequence represented by SEQ ID NO: 69, and a polynucleotide comprising a nucleotide sequence comprising nucleotides 61 to 717 of the nucleotide sequence represented by SEQ ID NO: 57.

(37) The polynucleotide according to (28), characterized by containing a polynucleotide comprising a nucleotide sequence comprising nucleotides 58 to 1413 of the nucleotide sequence represented by SEQ ID NO: 69, and a polynucleotide comprising a nucleotide sequence comprising nucleotides 61 to 717 of the nucleotide sequence represented by SEQ ID NO: 61.

(38) The polynucleotide according to (28), characterized by containing a polynucleotide comprising a nucleotide sequence comprising nucleotides 58 to 1413 of the nucleotide sequence represented by SEQ ID NO: 69, and a polynucleotide comprising a nucleotide sequence comprising nucleotides 61 to 717 of the nucleotide sequence represented by SEQ ID NO: 65.

(39) A vector comprising any one of the polynucleotides according to (25) to (38).

(40) A transformed host cell comprising any one of the polynucleotides according to (25) to (38).

(41) A transformed host cell comprising the vector according to (39).

(42) A method of producing the antibody according to any one of (2), (4), and (6) to (16), comprising the step of culturing the host cell according to (40) or (41) and purifying the antibody from the resulting cultured product.

(43) An antibody or a functional fragment of the antibody, characterized by binding to the same epitope as an antibody containing a heavy chain sequence comprising amino acid residues 20 to 471 of the amino acid sequence represented by SEQ ID NO: 20 and a light chain sequence comprising amino acid residues 21 to 239 of the amino acid sequence represented by SEQ ID NO: 16.

(44) An antibody or a functional fragment of the antibody, characterized by competing with an antibody containing a heavy chain sequence comprising amino acid residues 20 to 471 of the amino acid sequence represented by SEQ ID NO: 20 and a light chain sequence comprising amino acid residues 21 to 239 of the amino acid sequence represented by SEQ ID NO: 16.

(45) The antibody or a functional fragment of the antibody according to (43) or (44), characterized in that a Fab fragment of the antibody prepared by papain digestion, when binding the recombinant protein represented by SEQ ID NO: 23, lies adjacent to the glycine residue at position 26, the isoleucine residue at position 34, the glutamic acid residue at position 36, the aspartic acid residue at position 37, the glycine residue at position 38, the aspartic acid residue at position 56, the leucine residue at position 57, the leucine residue at position 58, the phenylalanine residue at position 59, the leucine residue at position 61, and the arginine residue at position 62 of the recombinant protein represented by SEQ ID NO: 23 at a distance of 4 Å or less.

(46) The antibody or a functional fragment of the antibody according to (45), characterized in that the distance between each amino acid residue constituting the recombinant protein represented by SEQ ID NO: 23 and the Fab fragment is determined by a complex structural analysis using X-ray diffraction data.

Advantage of the Invention

According to the invention, a therapeutic agent for cancer whose mechanism of action is primarily through apoptosis induction in cells can be obtained.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 is a figure showing binding activities of a cB273 antibody and sTRAIL to a DR5 extracellular domain protein.

FIG. 7 is a view showing the interaction between DR5 and the H or L chain of cB273 Fab. A) is a view illustrating amino acid residues of the H chain of cB273 Fab which lie at a distance of 4 Å or less from DR5 and vice versa as a stick model. Ile34, Glu36, Asp37, Gly38, Asp56, Leu57, Leu58, Phe59, Leu61, and Arg62 shown on the left side of the drawing are amino acid residues derived from DR5, and the respective amino acid residue numbers correspond to those in the amino acid sequence represented by SEQ ID NO: 23 in the Sequence Listing. Further, Phe33, Arg50, Asn52, Tyr54, Asn55, Phe59, Tyr101, Tyr102, Phe103, and Asp104 on the right side of the drawing are amino acid residues derived from the heavy chain of cB273, and the respective amino acid residue numbers are given by using a glutamic acid residue at position 20 of SEQ ID NO: 20 in the Sequence Listing as a starting point. B) is a view illustrating amino acid residues of the L chain of cB273 Fab which lie at a distance of 4 Å or less from DR5 and vice versa with some as a stick model and others as a ribbon model. Gly26, Glu36, Asp37, and Gly38 on the left side of the drawing are amino acid residues derived from DR5, and the respective amino acid residue numbers correspond to those in the amino acid sequence represented by SEQ ID NO: 23 in the Sequence Listing. Further, His31, Asn33, Val99, and Trp101 on the right side of the drawing are amino acid residues derived from the light chain of cB273, and the respective amino acid residue numbers are given by using an aspartic acid residue at position 21 of SEQ ID NO: 16 in the Sequence Listing as a starting point. The amino acid residues of DR5 which lie at a distance of 4 Å or less from the Fab fragment of cB273 were a glycine residue at position 26, an isoleucine residue at position 34, a glutamic acid residue at position 36, an aspartic acid residue at position 37, a glycine residue at position 38, an aspartic acid residue at position 56, a leucine residue at position 57, a leucine residue at position 58, a phenylalanine residue at position 59, a leucine residue at position 61, and an arginine residue at position 62 of the amino acid sequence represented by SEQ ID NO: 23 in the Sequence Listing.

FIG. 8-1 is a figure showing the binding activity of hB273 antibodies to human DR5 using Biacore™, and shows measurement charts for the respective antibodies.

FIG. 8-2 is a table showing the binding activity of hB273 antibodies to human DR5 using Biacore™, and shows Kon, Koff, and KD values of the respective antibodies calculated using analysis software. Incidentally, the number given to each chart in FIG. 8-1 corresponds to the Entry No. of the table in FIG. 8-2.

FIG. 10-1 is a figure showing the binding activity of hB273 antibodies to human DR5 using Biacore™, and shows measurement charts for the respective antibodies.

FIG. 10-2 is a table showing the binding activity of hB273 antibodies to human DR5 using Biacore™, and shows Kon, Koff, and KD values of the respective antibodies calculated using analysis software. Incidentally, the number given to each chart in FIG. 10-1 corresponds to the Entry No. in the table in FIG. 10-2.

FIG. 12-1 is a view the showing binding activity of CDR-modified hB273 antibodies to human DR5 using Biacore™, and shows measurement charts for the respective antibodies.

FIG. 12-2 is a table the showing binding activity of CDR-modified hB273 antibodies to human DR5 using Biacore™, and shows Kon, Koff, and KD values of the respective antibodies calculated using analysis software. Incidentally, the number given to each chart in FIG. 12-1 corresponds to the Entry No. in the table in FIG. 12-2.

FIG. 13-1 is a figure showing evaluation of thermal stability of CDR-modified hB273 antibodies using differential scanning calorimetry (DSC), and shows measurement charts for the respective antibodies.

FIG. 13-2 is a figure showing evaluation of thermal stability of CDR-modified hB273 antibodies using differential scanning calorimetry (DSC), and shows measurement charts for the respective antibodies.

FIG. 13-3 shows Tm values of the respective antibodies calculated from the charts shown in FIGS. 13-1 and 13-2. Incidentally, the number given to each chart in FIGS. 13-1 and 13-2 corresponds to the Entry No. in FIG. 13-3.

FIG. 15 is a view showing the caspase-3/7 activation effect and the in vitro cytocidal activity of a hB273_H2-1-NE/L1-NK antibody on human cancer cell lines. A) shows the results for a human colon cancer cell line HCT-15, and B) shows the results for a human glioblastoma cell line U-87MG.

FIG. 28 is a figure showing the nucleotide sequence of a cDNA encoding a mouse antibody B273 heavy chain and the amino acid sequence of the mouse antibody B273 heavy chain.

FIG. 29 is a figure showing the nucleotide sequence of a cDNA encoding a mouse antibody B273 light chain and the amino acid sequence of the mouse antibody B273 light chain.

FIG. 30 is a figure showing a nucleotide sequence encoding a B273 chimera-type light chain and the amino acid sequence of the B273 chimera-type light chain.

FIG. 31 is a figure showing a nucleotide sequence encoding a B273 chimera-type heavy chain and the amino acid sequence of the B273 chimera-type heavy chain.

FIG. 32 is a figure showing a nucleotide sequence encoding a hB273_L1-type light chain and the amino acid sequence of the hB273_L1-type light chain.

FIG. 33 is a figure showing a nucleotide sequence encoding a hB273_L2-type light chain and the amino acid sequence of the hB273_L2-type light chain.

FIG. 34 is a figure showing a nucleotide sequence encoding a hB273_L3-type light chain and the amino acid sequence of the hB273_L3-type light chain.

FIG. 35 is a figure showing a nucleotide sequence encoding a hB273_H1-type heavy chain and the amino acid sequence of the hB273_H1-type heavy chain.

FIG. 36 is a figure showing a nucleotide sequence encoding a hB273_H2-type heavy chain and the amino acid sequence of the hB273_H2-type heavy chain.

FIG. 37 is a figure showing a nucleotide sequence encoding a hB273_H3-type heavy chain and the amino acid sequence of the hB273_H3-type heavy chain.

FIG. 38 is a figure showing a nucleotide sequence encoding a hB273_H1-1-type heavy chain and the amino acid sequence of the hB273_H1-1-type heavy chain.

FIG. 39 is a figure showing a nucleotide sequence encoding a hB273_H2-1-type heavy chain and the amino acid sequence of the hB273_H2-1-type heavy chain.

FIG. 40 is a figure showing a nucleotide sequence encoding a hB273_H2-2-type heavy chain and the amino acid sequence of the hB273_H2-2-type heavy chain.

FIG. 41 is a figure showing a nucleotide sequence encoding a hB273_H2-3-type heavy chain and the amino acid sequence of the hB273_H2-3-type heavy chain.

FIG. 42 is a figure showing a nucleotide sequence encoding a hB273_H2-4-type heavy chain and the amino acid sequence of the hB273_H2-4-type heavy chain.

FIG. 43 is a figure showing a nucleotide sequence encoding a hB273_H2-5-type heavy chain and the amino acid sequence of the hB273_H2-5-type heavy chain.

FIG. 44 is a figure showing a nucleotide sequence encoding a hB273_L1-NE-type light chain and the amino acid sequence of the hB273_L1-NE-type light chain.

FIG. 45 is a figure showing a nucleotide sequence encoding a hB273_L1-NF-type light chain and the amino acid sequence of the hB273_L1-NF-type light chain.

FIG. 46 is a figure showing a nucleotide sequence encoding a hB273_L1-NK-type light chain and the amino acid sequence of the hB273_L1-NK-type light chain.

FIG. 47 is a figure showing a nucleotide sequence encoding a hB273_L1-NL-type light chain and the amino acid sequence of the hB273_L1-NL-type light chain.

FIG. 48 is a figure showing a nucleotide sequence encoding a hB273_H2-1-NE-type heavy chain and the amino acid sequence of the hB273_H2-1-NE-type heavy chain.

FIG. 49 is a figure showing the nucleotide sequence of a cDNA encoding a conatumumab light chain and the amino acid sequence of the conatumumab light chain.

FIG. 50 is a figure showing the nucleotide sequence of a cDNA encoding a conatumumab heavy chain and the amino acid sequence of the conatumumab heavy chain.

MODE FOR CARRYING OUT THE INVENTION

Figure 1:
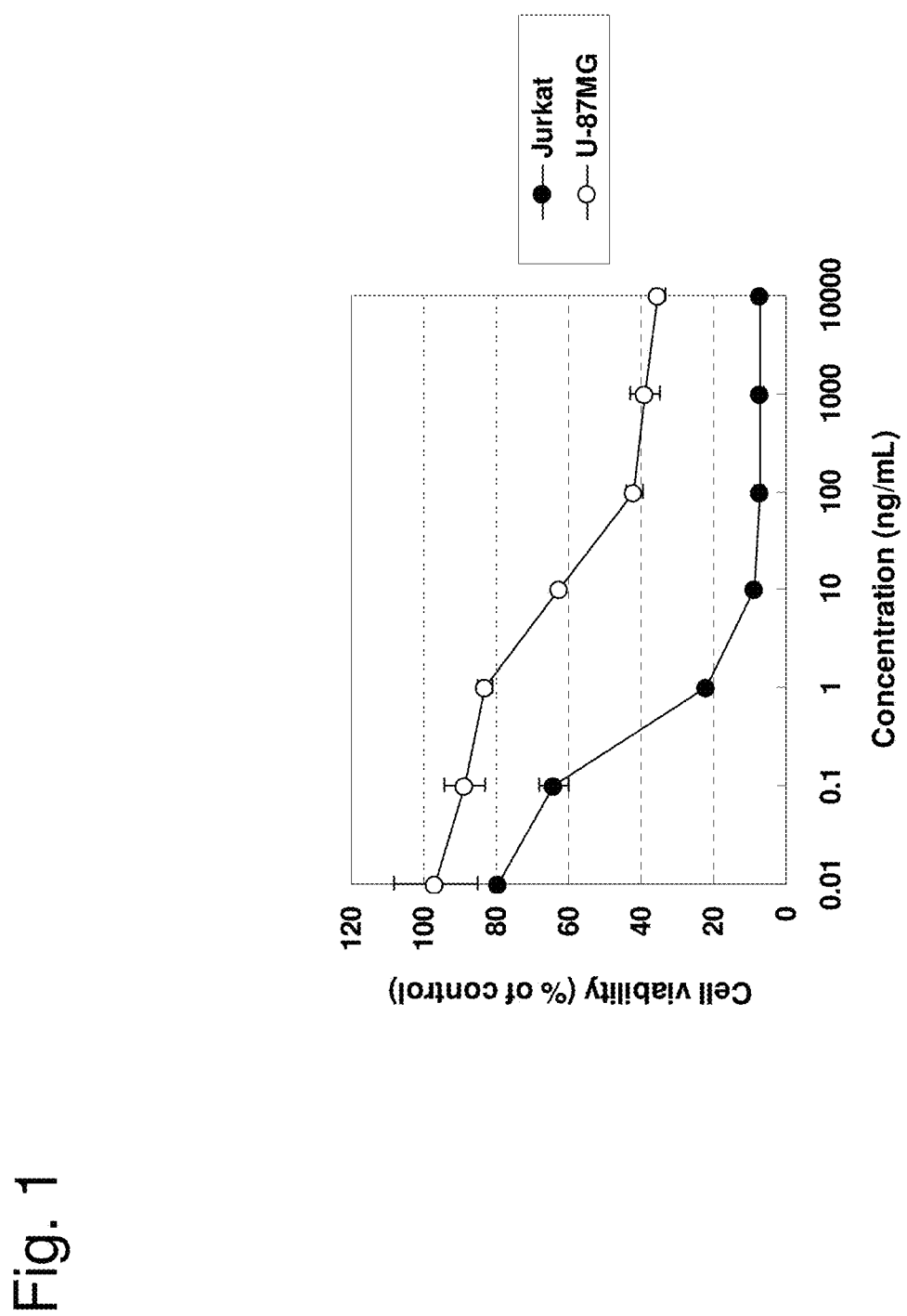
FIG. 1 is a figure showing the cytocidal effect of a mouse B273 antibody.

The terms "cancer" and "tumor" as used herein are used with the same meaning. The term "gene" as used herein includes not only DNA, but also mRNA thereof, cDNA and cRNA thereof.

The term "polynucleotide" as used herein is used with the same meaning as a "nucleic acid" and also includes DNA, RNA, probes, oligonucleotides, and primers.

The terms "polypeptide" and "protein" as used herein are used without distinction.

The term "RNA fraction" as used herein refers to a fraction containing RNA.

The term "cell" as used herein also includes cells in an animal individual and cultured cells.

The term "malignant transformation of cells" as used herein refers to a state in which cells show abnormal proliferation, for example, cells lose their sensitivity to contact inhibition phenomenon, cells show anchorage-independent proliferation, and so on, and cells which show such abnormal proliferation are referred to as "cancer cells".

The term "cell injury" as used herein refers to a state in which a pathological change is caused in cells in a form of some kind, and the cell injury is not limited to direct injury and includes all sorts of damage to the structure and function of cells such as DNA cleavage, base-dimer formation, chromosomal cleavage, damage to cell division machinery, and a decrease in various enzymatic activities.

The term "cytotoxic activity" as used herein refers to an activity of causing the above-described cell injury.

The term "death domain-containing receptor" (which includes Fas, TNFRI, DR3, DR4, DR5, and DR6, though is not limited thereto) as used herein refers to a receptor molecule having an apoptotic signal transduction region called a "death domain" showing homology with a *Drosophila* suicide gene, reaper, in an intracellular domain.

The term "functional fragment of an antibody" as used herein refers to a partial fragment of an antibody having an antigen binding activity and includes Fab, F(ab')$_2$, scFv, and the like. The term also includes Fab' which is a monovalent fragment in a variable region of an antibody obtained by treating F(ab')$_2$ under reducing conditions. However, the term is not limited to these molecules as long as the fragment has a binding affinity for an antigen. Further, these functional fragments include not only a fragment obtained by treating a full-length molecule of an antibody protein with an appropriate enzyme, but also a protein produced in an appropriate host cell using a genetically modified antibody gene.

The term "Fab" as used herein refers to a monovalent fragment in a variable region of an antibody obtained by treating F(ab')$_2$ under reducing conditions as described above. However, Fab' produced using a genetically modified antibody gene is also included within the Fab' of the invention.

The term "single-chain variable fragment antibody" as used herein is used with the same meaning as a single-chain Fv (scFv).

The term "epitope" as used herein refers to a partial peptide or a partial tertiary structure of an antigen to which a specific antibody binds. The epitope which is a partial peptide of an antigen can be determined by methods well known to those skilled in the art such as an immunoassay, and for example, the following method can be employed. First, various partial structures of an antigen are produced. In the production of the partial structures, a known oligopeptide synthesis technique can be used. For example, a series of polypeptides having appropriately reduced lengths obtained by sequentially shortening the antigen from the C terminus or N terminus are produced using a genetic recombination technique known to those skilled in the art. Thereafter, the reactivity of an antibody against these polypeptides is examined and a recognition site is roughly determined. Then, peptides having shorter lengths are synthesized and the reactivity with these peptides is examined, whereby the epitope can be determined. Further, the epitope which is a partial tertiary structure of an antigen binding to a specific antibody can be determined by specifying the amino acid residues of the antigen which lie adjacent to the antibody by X-ray structural analysis.

The term "antibodies which bind to the same epitope" as used herein refers to different antibodies which bind to a common epitope. If a second antibody binds to a partial peptide or a partial tertiary structure to which a first antibody binds, it can be determined that the first antibody and the second antibody bind to the same epitope. Further, by confirming that the second antibody competes with the first antibody for the binding to an antigen (that is, the second antibody inhibits the binding between the first antibody and the antigen), it can be determined that the first antibody and the second antibody bind to the same epitope even if the specific epitope sequence or structure has not been determined. Further, when the first antibody and the second antibody bind to the same epitope and also the first antibody has a special effect such as an apoptosis-inducing activity, it can be expected that the second antibody also has the same activity.

The term "CDR" as used herein refers to a complementarity determining region (CDR), and it is known that each heavy and light chain of an antibody molecule has three complementarity determining regions (CDRs). The CDR is also called the hypervariable domain, and is present in a variable region of each heavy and light chain of an antibody. It is a site which has unusually high variability in its primary structure, and there are three separate CDRs in the primary structure of each heavy and light polypeptide chain. In this specification, as for the CDRs of an antibody, the CDRs of the heavy chain are represented by CDRH1, CDRH2, and CDRH3 from the amino-terminal side of the amino acid sequence of the heavy chain, and the CDRs of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The term "secondary antibody" as used herein refers to an antibody which binds specifically to an antibody molecule, thereby crosslinking the antibody molecules.

The phrase "hybridization is performed under stringent conditions" as used herein refers to a process in which hybridization is performed under conditions under which identification can be achieved by performing hybridization at 68° C. in a commercially available hybridization solution ExpressHyb Hybridization Solution™ (manufactured by Clontech, Inc.) or by performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

The term "several amino acids" in the description of "an amino acid sequence including a substitution, deletion, or addition of one to several amino acids" as used herein refers to an arbitrary number of amino acid residues selected from 2 to 10. More specifically, when 10 or fewer amino acids, 5 to 6 or fewer amino acids, or 2 to 3 or fewer amino acids are substituted, deleted or added, the description of "an amino acid sequence including a substitution, deletion, or addition of several amino acids" is used.

The description of, for example, "a heavy chain variable region having an amino acid sequence comprising amino acid residues 20 to 141 of SEQ ID NO: 34" as used herein is used with the same meaning as the description of "a heavy chain variable region sequence comprising amino acid residues 20 to 141 of SEQ ID NO: 34". Further, the description of, for example, "a heavy chain having an amino acid sequence comprising amino acid residues 20 to 471 of SEQ ID NO: 34" is used with the same meaning as the description of "a heavy chain sequence comprising amino acid residues 20 to 471 of SEQ ID NO: 34".

1. Regarding Apoptosis-Related Gene

An antibody according to the invention is required to bind to a specific antigen and exhibit a cytotoxic activity via the antigen. Further, it is necessary to select the antigen specifically present in tumor cells to prevent normal cells from being killed. One example of such an antigen group can include tumor necrosis factor (hereinafter, referred to as "TNF" in the specification) related apoptosis-inducing ligand (hereinafter, referred to as "TRAIL" in the specification) receptor groups. TRAIL is a member of the TNF family of proteins and includes Fas ligands and TNF-α (Wiley S R, et al., Immunity 1995 December; 3 6):673-82). These proteins are strong apoptosis-inducing factors.

Receptors for these TNF family proteins are characterized by cysteine-rich repeat sequences in the extracellular domain. Among these, Fas which is a receptor for Fas ligands, and TNF receptor I (hereinafter, referred to as "TNFRI" in the specification) which is a receptor for TNFα have, in an intracellular domain, a region essential for apoptotic signal transduction called the "death domain" which is a region showing homology with the *Drosophila* suicide gene, reaper, (Golstein, P., et al., (1995) Cell 81, 185-186; and White, K, et al., (1994) Science 264, 677-683), and are collectively called death domain-containing receptors.

Five receptors for TRAIL have been identified, and among them, two receptors (DR4 (TRAIL-R1) and DR5 (TRAIL-R2)) are capable of transducing an apoptotic signal, and the other three receptors (DcR1 (TRAIL-R3), DcR2 (TRAIL-R4), and osteoprotegerin (OPG)) do not transduce an apoptotic signal. Similarly to Fas and TNFRI, both DR4 and DR5 include a death domain in an intracellular segment and transduce an apoptotic signal via a pathway containing a Fas-associated death domain protein (hereinafter referred to as "FADD" in the specification) and caspase 8 (Chaudhary P M, et al., Immunity 1997 December; 7(6):813-20; and Schneider P, et al. Immunity 1997 December; 7(6):821-30). For the Fas, TNFRI, DR4, or DR5 described above, it is known that an antibody which binds to any of these molecules and functions as an agonist exhibits an apoptosis-inducing activity against cells bearing the molecule on the cell surface (Journal of Cellular Physiology, 209: 1221-1028

(2006); Leukemia, Apl; 21(4):805-812 (2007); Blood, 99:1666-1675 (2002); and Cellular Immunology, January; 153(1):184-193 (1994)). The pharmacological effect of the above-described agonistic antibody is enhanced by cross-linking with a secondary antibody or an effector cell (Journal of Immunology, 149:3166-3173 (1992); and European Journal of Immunology, October; 23(10):2676-2681 (1993)).

The nucleotide sequence of a human DR5 (death receptor 5) gene and the amino acid sequence thereof have been registered as GI:22547118 (Accession No: NM 147187) in GenBank. Incidentally, a nucleotide sequence encoding a protein, which has an amino acid sequence including a substitution, deletion, or addition of one to several amino acids in the amino acid sequence of DR5 and also has a biological activity equivalent to that of DR5 is also included within the meaning of the term "nucleotide sequence of the DR5 gene". Further, a protein which has an amino acid sequence including a substitution, deletion, or addition of one to several amino acids in the amino acid sequence of DR5 and also has a biological activity equivalent to that of DR5 is also included within the meaning of the term "DR5".

2. Production of Anti-DR5 Antibody

The antibody against DR5 of the invention can be obtained by immunizing an animal with DR5 or an arbitrary polypeptide selected from the amino acid sequence of DR5 and collecting and purifying the antibody produced in vivo according to a common procedure. The biological species of the DR5 to be used as an antigen is not limited to human, and an animal can be immunized with DR5 derived from an animal other than humans such as a mouse or a rat. In this case, by examining the cross-reactivity between an antibody which binds to the obtained heterologous DR5 and human DR5, an antibody applicable to a human disease can be selected.

Further, a monoclonal antibody can be obtained by fusing antibody-producing cells which produce an antibody against DR5 with myeloma cells to establish a hybridoma according to a known method (for example, Kohler and Milstein, Nature, (1975) 256, pp. 495-497, Kennet, R. ed., Monoclonal Antibodies, pp. 365-367, Plenum Press, N.Y. (1980)).

Incidentally, DR5 to be used as an antigen can be obtained by genetic engineering to cause a host cell to express a DR5 gene.

Specifically, a vector capable of expressing a DR5 gene is produced, and the resulting vector is transfected into a host cell to express the gene, and then the expressed DR5 is purified. Hereinafter, a method of obtaining an antibody against DR5 will be specifically described.

(1) Preparation of Antigen

Examples of the antigen to be used for producing the anti-DR5 antibody include DR5, a polypeptide comprising a partial amino acid sequence containing at least 6 consecutive amino acids of DR5, and a derivative obtained by adding a given amino acid sequence or carrier thereto.

DR5 can be purified directly from human tumor tissues or tumor cells and used. Further, DR5 can be obtained by synthesizing it in vitro or by causing a host cell to produce it by genetic engineering.

With respect to genetic engineering, specifically, DR5 cDNA is integrated into a vector capable of expressing DR5 cDNA and DR5 is synthesized in a solution containing an enzyme, a substrate, and an energy substance required for transcription and translation, or another prokaryotic or eucaryotic host cell is transformed to express DR5, whereby the antigen can be obtained.

Further, the antigen can also be obtained as a secretory protein by expressing a fusion protein obtained by joining the extracellular domain of DR5, which is a membrane protein, to the constant region of an antibody in an appropriate host-vector system.

DR5 cDNA can be obtained by, for example, the so-called PCR method in which a polymerase chain reaction (hereinafter referred to as "PCR") is performed using a cDNA library containing DR5 cDNA as a template and primers which specifically amplify DR5 cDNA (see Saiki, R. K., et al., Science, (1988) 239, pp. 487-489).

As for the system for in vitro synthesis of the polypeptide, the Rapid Translation System (RTS) manufactured by Roche Diagnostics, Inc. can be exemplified, but it is not limited thereto.

Examples of the prokaryotic host cell include *Escherichia coli* and *Bacillus subtilis*. In order to transform the host cell with a target gene, the host cell is transformed using a plasmid vector containing a replicon, i.e., a replication origin derived from a species compatible with the host, and a regulatory sequence. Further, the vector preferably has a sequence capable of imposing phenotypic selectivity on the transformed cell.

Examples of the eucaryotic host cell include vertebrate cells, insect cells, and yeast cells. As the vertebrate cells, for example, dihydrofolate reductase-deficient strains (Urlaub, G. and Chasin, L. A., Proc. Natl. Acad. Sci. USA (1980) 77, pp. 4126-4220) of simian COS cells (Gluzman, Y., Cell, (1981) 23, pp. 175-182, ATCC CRL-1650), murine fibroblasts NIH3T3 (ATCC No. CRL-1658), and Chinese hamster ovarian cells (CHO cells; ATCC: CCL-61); and the like are often used, however, they are not limited thereto.

The thus obtained transformant can be cultured according to a common procedure, and by the culturing of the transformant, a target polypeptide is produced intracellularly or extracellularly.

A suitable medium to be used for the culturing can be selected from various commonly used culture media depending on the employed host cell. If *Escherichia coli* is employed, for example, LB medium supplemented with an antibiotic such as ampicillin or IPMG, as needed, can be used.

A recombinant protein produced intracellularly or extracellularly by the transformant through such culturing can be separated and purified by any of various known separation methods utilizing a physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues to a recombinant protein to be expressed, the protein can be efficiently purified with a nickel affinity column. Alternatively, by attaching an IgG Fc region to a recombinant protein to be expressed, the protein can be efficiently purified with a protein A column.

By combining the above-described methods, a large amount of a target polypeptide can be easily produced in high yield and high purity.

(2) Production of Anti-DR5 Monoclonal Antibody

Examples of the antibody which specifically binds to DR5 include a monoclonal antibody which specifically binds to DR5, and a method of obtaining the antibody is as described below.

The production of a monoclonal antibody generally requires the following operational steps of:

(a) purifying a biopolymer to be used as an antigen;

(b) preparing antibody-producing cells by immunizing an animal by injection of the antigen, collecting the blood, assaying its antibody titer to determine when the spleen is to be excised;

(c) preparing myeloma cells (hereinafter referred to as "myeloma");

(d) fusing the antibody-producing cells with the myeloma;

(e) screening a group of hybridomas producing a target antibody;

(f) dividing the hybridomas into single cell clones (cloning);

(g) optionally, culturing the hybridoma or rearing an animal implanted with the hybridoma for producing a large amount of a monoclonal antibody;

(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, DR5 prepared by the method as described above or a partial peptide thereof can be used.

Further, a membrane fraction prepared from recombinant cells expressing DR5 or the recombinant cells expressing DR5 themselves, and also a partial peptide of the protein of the invention chemically synthesized by a method known to those skilled in the art can also be used as the antigen.

(b) Preparation of Antibody-Producing Cells

The antigen obtained in step (a) is mixed with an adjuvant such as Freund's complete or incomplete adjuvant, or aluminum potassium sulfate and the resulting mixture is used as an immunogen to immunize an experimental animal. As the experimental animal, any animal used in a known hybridoma production method can be used without any trouble. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of mouse or rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 can be used, and in the case of a rat, for example, Wistar, Low, Lewis, Sprague, Dawley, ACI, BN, Fischer, and the like can be used.

Among these, in consideration of compatibility of fusing with myeloma cells as described below, in the case of a mouse, BALB/c strain, and in the case of a rat, Wistar and Low strains are particularly preferred as the animal to be immunized.

Further, in consideration of antigenic homology between humans and mice, it is also preferred to use a mouse having decreased biological function to remove autoantibodies, that is, a mouse with an autoimmune disease.

The age of the mouse or rat at the time of immunization is preferably 5 to 12 weeks of age, more preferably 6 to 8 weeks of age.

In order to immunize an animal with DR5 or a recombinant protein thereof, for example, a known method described in detail in, for example, Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Springfield, Ill. (1964), or the like can be used.

Spleen cells or lymphocytes including antibody-producing cells are aseptically removed from the immunized animal. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495).

(c) Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8 (X63), NS1-ANS/1 (NS1), P3X63-Ag8.U1 (P3U1), X63-Ag8.653 (X63.653), SP2/0-Ag14 (SP2/0), MPC11-45.6TG1.7 (45.6TG), F0, S149/5XXO, and BU.1 derived from mice; 210.RSY3.Ag.1.2.3 (Y3) derived from rats; and U266AR (SKO-007), GM1500•GTG-A12 (GM1500), UC729-6, LICR-LOW-HMy2 (HMy2) and 8226AR/NIP4-1 (NP41) derived from humans.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987), Kabat, E. A. and Mayer, M. M., Experimental Immunochemistry, Charles C Thomas Publisher, Springfield, Ill. (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used.

(e) Selection of a Group of Hybridomas

The method of selecting hybridomas obtained by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT-deficient strain which cannot survive in the presence of aminopterin.

That is, by culturing unfused cells and hybridomas in HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell™-HY Selection Medium D (manufactured by StemCell Technologies, Inc., #03804) and cultured. Then, the formed hybridoma colonies are collected, whereby monoclonal hybridomas can be obtained. The collected respective hybridoma colonies are cultured, and a hybridoma which has been confirmed to have a stable antibody titer in an obtained hybridoma culture supernatant is selected as a DR5 monoclonal antibody-producing hybridoma strain.

Examples of the thus established hybridoma strain include DR5 hybridoma B273. Incidentally, in this specification, an antibody produced by the hybridoma B273 is referred to as "B273 antibody" or simply "B273". The heavy chain of the B273 antibody has an amino acid sequence represented by SEQ ID NO: 8 in the Sequence Listing. Further, the light chain of the B273 antibody has an amino acid sequence represented by SEQ ID NO: 10 in the Sequence Listing. Incidentally, in the heavy chain amino acid sequence represented by SEQ ID NO: 8 in the Sequence Listing, an amino acid sequence comprising amino acid residues 1 to 19 is a signal sequence, an amino acid sequence comprising amino acid residues 20 to 141 is a variable region, and an amino acid sequence comprising amino acid residues 142 to 465 is a constant region. Further, in the light chain amino acid sequence represented by SEQ ID NO: 10 in the Sequence Listing, an amino acid sequence comprising amino acid residues 1 to 19 is a signal sequence, an amino acid sequence comprising amino acid residues 20 to 133 is a variable region, and an amino acid sequence comprising amino acid residues 134 to 238 is a constant region.

The heavy chain amino acid sequence represented by SEQ ID NO: 8 in the Sequence Listing is encoded by a nucleotide sequence represented by SEQ ID NO: 7 in the Sequence Listing. In the nucleotide sequence represented by SEQ ID NO: 7 in the Sequence Listing, a nucleotide sequence comprising nucleotides 1 to 57 encodes the heavy chain signal sequence of the antibody, a nucleotide sequence comprising nucleotides 58 to 423 encodes the heavy chain variable region of the antibody, and a nucleotide sequence comprising nucleotides 424 to 1395 encodes the heavy chain constant region of the antibody.

The light chain amino acid sequence represented by SEQ ID NO: 10 in the Sequence Listing is encoded by a nucleotide sequence represented by SEQ ID NO: 9 in the Sequence Listing. In the nucleotide sequence represented by SEQ ID NO: 9 in the Sequence Listing, a nucleotide sequence comprising nucleotides 1 to 57 encodes the light chain signal sequence of the antibody, a nucleotide sequence comprising nucleotides 58 to 399 encodes the light chain variable region of the antibody, and a nucleotide sequence comprising nucleotides 400 to 714 encodes the light chain constant region of the antibody.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma obtained by the method described above can be stored in a frozen state in liquid nitrogen or in a freezer at −80° C. or below.

After completion of cloning, the medium is changed from HT medium to a normal medium, and the hybridoma is cultured.

Large-scale culture is performed by rotation culture using a large culture bottle or by spinner culture. From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be obtained.

In the case where the hybridoma is administered in the abdominal cavity, if a mineral oil such as 2,6,10,14-tetramethyl pentadecane (pristane) is administered prior to (3 to 7 days before) administration of the hybridoma, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is injected into the abdominal cavity of the mouse. In general, when the abdomen is expanded and filled with the ascites, the ascites is collected from the mouse. By this method, the monoclonal antibody can be obtained at a concentration which is about 100 times or more higher than that in the culture solution.

The monoclonal antibody obtained by the above-described method can be purified by a method described in, for example, Weir, D. M.: Handbook of Experimental Immunology Vol. I, II, III, Blackwell Scientific Publications, Oxford (1978).

The thus obtained monoclonal antibody has high antigen specificity for DR5.

(h) Assay of Monoclonal Antibody

The isotype and subclass of the thus obtained monoclonal antibody can be determined as follows.

First, examples of the identification method include an Ouchterlony method, an ELISA method and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer® Kit manufactured by Bio-Rad Laboratories, Inc.) or the like can also be used.

Further, the quantitative determination of a protein can be performed by the Folin Lowry method and a method of calculation based on the absorbance at 280 nm [1.4 (OD 280)=Immunoglobulin 1 mg/ml].

Further, even when the monoclonal antibody is separately and independently obtained by performing again the steps of (a) to (h) in the above (2), it is possible to obtain an antibody having a cytotoxic activity equivalent to that of B273. As one example of such an antibody, an antibody which binds to the same epitope as the B273 antibody can be exemplified. If a newly produced monoclonal antibody binds to a partial peptide or a partial tertiary structure to which the B273 antibody binds, it can be determined that the monoclonal antibody binds to the same epitope as the B273 antibody. Further, by confirming that the monoclonal antibody competes with the B273 antibody for binding to DR5 (that is, the monoclonal antibody inhibits the binding between the B273 antibody and DR5), it can be determined that the monoclonal antibody binds to the same epitope as the B273 antibody even if the specific epitope sequence or structure has not been determined. In the case where the monoclonal antibody binds to the same epitope as the B273 antibody, the monoclonal antibody is strongly expected to have a cytotoxic activity equivalent to that of B273.

Further, as shown in Example 4, it is possible to specify an amino acid residue on the side of DR5 which lies adjacent to a Fab fragment of an antibody from the data of X-ray diffraction of a complex between the Fab fragment and DR5. Specifically, in the case where a Fab fragment derived from an arbitrary antibody lies adjacent to a glycine residue at position 26, an isoleucine residue at position 34, a glutamic acid residue at position 36, an aspartic acid residue at position 37, a glycine residue at position 38, an aspartic acid residue at position 56, a leucine residue at position 57, a leucine residue at position 58, a phenylalanine residue at position 59, a leucine residue at position 61, and an arginine residue at position 62 of an amino acid sequence represented by SEQ ID NO: 23 in the Sequence Listing, at a distance of 4 Å or less, it can be determined that the antibody has specificity for the same epitope as B273.

(3) Other Antibodies

The antibody of the invention includes not only the above-described monoclonal antibody against DR5 but also a recombinant antibody obtained by artificial modification for the purpose of decreasing heterologous antigenicity in humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is joined to a human-derived constant region can be exemplified (see Proc. Natl. Acad. Sci. USA, 81, 6851-6855, (1984)). A chimeric antibody derived from a mouse anti-human DR5 antibody B273 is an antibody comprising a heavy chain containing a heavy chain variable region having an amino acid sequence comprising amino acid residues 20 to 141 of SEQ ID NO: 20 and a light chain containing a light chain variable region having an amino acid sequence comprising amino acid residues 21 to 134 of SEQ ID NO: 16, and may have an arbitrary constant region. As one example of such a chimeric antibody, an antibody comprising a heavy chain having an amino acid sequence comprising amino acid residues 20 to 471 of SEQ ID NO: 20 in the Sequence Listing and a light chain having an amino acid sequence comprising amino acid residues 21 to 239 of SEQ ID NO: 16 can be exemplified. Incidentally, in the heavy chain sequence represented by SEQ ID NO: 20 in the Sequence Listing, an amino acid sequence comprising amino acid residues 1 to 19 is a signal sequence, an amino acid sequence comprising amino acid residues 20 to 141 is a variable region, and an amino acid sequence comprising amino acid residues 142 to 471 is a constant region. Further, in the light chain amino acid sequence represented by SEQ ID NO: 16 in the Sequence Listing, an amino acid sequence comprising amino acid residues 1 to 20 is a signal sequence, an amino acid sequence comprising amino acid residues 21 to 134 is a variable region, and an amino acid sequence comprising amino acid residues 135 to 239 is a constant region.

The heavy chain amino acid sequence represented by SEQ ID NO: 20 in the Sequence Listing is encoded by a nucleotide sequence represented by SEQ ID NO: 19 in the Sequence Listing. In the nucleotide sequence represented by SEQ ID NO: 19 in the Sequence Listing, a nucleotide sequence comprising nucleotides 1 to 57 encodes the heavy chain signal sequence of the antibody, a nucleotide sequence comprising nucleotides 58 to 423 encodes the heavy chain variable region of the antibody, and a nucleotide sequence comprising nucleotides 424 to 1413 encodes the heavy chain constant region of the antibody.

The light chain amino acid sequence represented by SEQ ID NO: 16 in the Sequence Listing is encoded by a nucleotide sequence represented by SEQ ID NO: 15 in the Sequence Listing. In the nucleotide sequence represented by SEQ ID NO: 15 in the Sequence Listing, a nucleotide sequence comprising nucleotides 1 to 60 encodes the light chain signal sequence of the antibody, a nucleotide sequence comprising nucleotides 61 to 402 encodes the light chain variable region of the antibody, and a nucleotide sequence comprising nucleotides 403 to 717 encodes the light chain constant region of the antibody.

As the humanized antibody, an antibody obtained by integrating only the complementarity determining regions (CDRs) into a human-derived antibody (see Nature (1986) 321, pp. 522-525), and an antibody obtained by grafting a part of the amino acid residues of the framework as well as the CDR sequences to a human antibody by a CDR-grafting method (WO 90/07861) can be exemplified.

However, the humanized antibody derived from the B273 antibody is not limited to a specific humanized antibody as long as the humanized antibody has all 6 types of CDR sequences of B273 and has the activity of inducing apoptosis in cells. Incidentally, the heavy chain variable region of the B273 antibody has CDRH1 (GYFMN) consisting of an amino acid sequence represented by SEQ ID NO: 82 in the Sequence Listing, CDRH2 (RFNPYNGDTFYNQKFKG) consisting of an amino acid sequence represented by SEQ ID NO: 83, and CDRH3 (SAYYFDSGGYFDY) consisting of an amino acid sequence represented by SEQ ID NO: 84. Further, the light chain variable region of the B273 antibody has CDRL1 (RSSQSLVHSNGNTYLH) consisting of an amino acid sequence represented by SEQ ID NO: 79 in the Sequence Listing, CDRL2 (KVSNRFS) consisting of an amino acid sequence represented by SEQ ID NO: 80, and CDRL3 (SQSTHVPWT) consisting of an amino acid sequence represented by SEQ ID NO: 81.

Further, a sequence including the substitution, deletion, or addition of one to several amino acid residues in one of the above-described CDRs can be used as a CDR sequence which a CDR-modified antibody derived from the B273 antibody has. Examples of the sequence including a substitution of one amino acid residue in CDRL1 include a sequence (RSSQSLVHSNENTYLH) consisting of an amino acid sequence represented by SEQ ID NO: 85 in the Sequence Listing, a sequence (RSSQSLVHSNFNTYLH)

consisting of an amino acid sequence represented by SEQ ID NO: 86, a sequence (RSSQSLVHSNKNTYLH) consisting of an amino acid sequence represented by SEQ ID NO: 87, and a sequence (RSSQSLVHSNLNTYLH) consisting of an amino acid sequence represented by SEQ ID NO: 88. Further, examples of the sequence including a substitution of one amino acid residue in CDRH2 include a sequence (RFNPYNEDTFYNQKFKG) consisting of an amino acid sequence represented by SEQ ID NO: 89.

In general, the deamidation of asparagine in a protein proceeds through the formation of a transition state of cyclic succinimide between the asparagine and an adjacent amino acid on the C-terminal side (Geiger, T. and Clarke, S. (1987) Deamidation, Isomerization, and racemization at asparaginyl and aspartyl residues in peptides. Succinimide-linked reactions that contribute to protein degradation. J. Biol. Chem. 262, 785-794). A rate-limiting factor for the formation of a transition state of cyclic succinimide is the size of a side chain of the adjacent amino acid, and therefore, glycine which has the smallest side chain can achieve the fastest deamidation rate. On the other hand, by substituting the adjacent group on the C-terminal side with an amino acid having a large side chain, the deamidation rate can be suppressed. The B273 antibody has a -N-G- (asparagine-glycine) sequence which is susceptible to deamidation in CDRL1 and CDRH2. Therefore, the present inventors produced point mutants in which the adjacent group was changed from glycine to lysine, phenylalanine, leucine, or glutamic acid, each of which has a larger side chain than glycine. That is, in CDRH2, the -N-G- (asparagine-glycine) sequence is mutated to a -N-E- (asparagine-glutamic acid) sequence, and in CDRL1, the -N-G- (asparagine-glycine) sequence is mutated to a -N-L-(asparagine-leucine) sequence, a -N-F- (asparagine-phenylalanine) sequence, a -N-K-(asparagine-lysine) sequence, or a -N-E- (asparagine-glutamic acid) sequence, whereby the deamidation of the antibody is suppressed.

As an example of an antibody having the above-described CDRs, an antibody containing a heavy chain variable region having CDRH1 consisting of an amino acid sequence represented by SEQ ID NO: 82 in the Sequence Listing, CDRH2 consisting of an amino acid sequence represented by SEQ ID NO: 83, and CDRH3 consisting of an amino acid sequence represented by SEQ ID NO: 84, and a light chain variable region having CDRL1 consisting of an amino acid sequence represented by SEQ ID NO: 79 in the Sequence Listing, CDRL2 consisting of an amino acid sequence represented by SEQ ID NO: 80, and CDRL3 consisting of an amino acid sequence represented by SEQ ID NO: 81; an antibody containing a heavy chain variable region having CDRH1 consisting of an amino acid sequence represented by SEQ ID NO: 82 in the Sequence Listing, CDRH2 consisting of an amino acid sequence represented by SEQ ID NO: 89, and CDRH3 consisting of an amino acid sequence represented by SEQ ID NO: 84, and a light chain variable region having CDRL1 consisting of an amino acid sequence represented by SEQ ID NO: 85 in the Sequence Listing, CDRL2 consisting of an amino acid sequence represented by SEQ ID NO: 80, and CDRL3 consisting of an amino acid sequence represented by SEQ ID NO: 81; an antibody containing a heavy chain variable region having CDRH1 consisting of an amino acid sequence represented by SEQ ID NO: 82 in the Sequence Listing, CDRH2 consisting of an amino acid sequence represented by SEQ ID NO: 89, and CDRH3 consisting of an amino acid sequence represented by SEQ ID NO: 84, and a light chain variable region having CDRL1 consisting of an amino acid sequence represented by SEQ ID NO: 86 in the Sequence Listing, CDRL2 consisting of an amino acid sequence represented by SEQ ID NO: 80, and CDRL3 consisting of an amino acid sequence represented by SEQ ID NO: 81; an antibody containing a heavy chain variable region having CDRH1 consisting of an amino acid sequence represented by SEQ ID NO: 82 in the Sequence Listing, CDRH2 consisting of an amino acid sequence represented by SEQ ID NO: 89, and CDRH3 consisting of an amino acid sequence represented by SEQ ID NO: 84, and a light chain variable region having CDRL1 consisting of an amino acid sequence represented by SEQ ID NO: 87 in the Sequence Listing, CDRL2 consisting of an amino acid sequence represented by SEQ ID NO: 80, and CDRL3 consisting of an amino acid sequence represented by SEQ ID NO: 81; and an antibody containing a heavy chain variable region having CDRH1 consisting of an amino acid sequence represented by SEQ ID NO: 82 in the Sequence Listing, CDRH2 consisting of an amino acid sequence represented by SEQ ID NO: 89, and CDRH3 consisting of an amino acid sequence represented by SEQ ID NO: 84, and a light chain variable region having CDRL1 consisting of an amino acid sequence represented by SEQ ID NO: 88 in the Sequence Listing, CDRL2 consisting of an amino acid sequence represented by SEQ ID NO: 80, and CDRL3 consisting of an amino acid sequence represented by SEQ ID NO: 81 can be exemplified.

As an example of the humanized antibody of the mouse antibody B273 (including a CDR-modified antibody), an arbitrary combination of a heavy chain containing a heavy chain variable region comprising an amino acid sequence comprising amino acid residues 20 to 141 of any one of SEQ ID NOS: 34, 36, 38, 40, 42, 44, 46, 48, 50, and 70 in the Sequence Listing with a light chain containing a light chain variable region comprising an amino acid sequence comprising amino acid residues 21 to 134 of any one of SEQ ID NOS: 28, 30, 32, 52, 58, 62, and 66 can be exemplified.

As a preferred combination, an antibody characterized by containing a heavy chain variable region comprising an amino acid sequence comprising amino acid residues 20 to 141 of SEQ ID NO: 34 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 34 and a light chain variable region comprising an amino acid sequence comprising amino acid residues 21 to 134 of SEQ ID NO: 30; an antibody characterized by containing a heavy chain variable region comprising an amino acid sequence comprising amino acid residues 20 to 141 of SEQ ID NO: 34 and a light chain variable region comprising an amino acid sequence comprising amino acid residues 21 to 134 of SEQ ID NO: 32; an antibody characterized by containing a heavy chain variable region comprising an amino acid sequence comprising amino acid residues 20 to 141 of SEQ ID NO: 36 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 36 and a light chain variable region comprising an amino acid sequence comprising amino acid residues 21 to 134 of SEQ ID NO: 30; an antibody characterized by containing a heavy chain variable region comprising an amino acid sequence comprising amino acid residues 20 to 141 of SEQ ID NO: 36 and a light chain variable region comprising an amino acid sequence comprising amino acid residues 21 to 134 of SEQ ID NO: 32; an antibody characterized by containing a heavy chain variable region comprising an amino acid sequence comprising amino acid residues 20 to 141 of SEQ ID NO: 38 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 38 and a light chain variable region comprising an amino acid sequence comprising amino acid residues 21 to 134 of SEQ ID NO: 30; an antibody characterized by containing a heavy chain variable region comprising an amino acid sequence comprising amino acid residues 20 to 141 of SEQ ID NO: 38 and a light chain variable region comprising an amino acid sequence comprising amino acid residues 21 to 134 of SEQ ID NO: 32; an antibody characterized by containing a heavy chain variable region comprising an amino acid sequence comprising amino acid residues 20 to 141 of SEQ ID NO: 40 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 42 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 44 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 46 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 48 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 50 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 70 and a light chain variable region comprising an amino acid sequence comprising amino acid residues 21 to 134 of SEQ ID NO: 52; an antibody characterized by containing a heavy chain variable region comprising an amino acid sequence comprising amino acid residues 20 to 141 of SEQ ID NO: 70 and a light chain variable region comprising an amino acid sequence comprising amino acid residues 21 to 134 of SEQ ID NO: 58; an antibody characterized by containing a heavy chain variable region comprising an amino acid sequence comprising amino acid residues 20 to 141 of SEQ ID NO: 70 and a light chain variable region comprising an amino acid sequence comprising amino acid residues 21 to 134 of SEQ ID NO: 62; and an antibody characterized by containing a heavy chain variable region comprising an amino acid sequence comprising amino acid residues 20 to 141 of SEQ ID NO: 70 and a light chain variable region comprising an amino acid sequence comprising amino acid residues 21 to 134 of SEQ ID NO: 66 can be exemplified.

As a more preferred combination, an antibody comprising a heavy chain having an amino acid sequence comprising amino acid residues 20 to 471 of SEQ ID NO: 34 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 34 and a light chain having an amino acid sequence comprising amino acid residues 21 to 239 of SEQ ID NO: 30; an antibody comprising a heavy chain having an amino acid sequence comprising amino acid residues 20 to 471 of SEQ ID NO: 34 and a light chain having an amino acid sequence comprising amino acid residues 21 to 239 of SEQ ID NO: 32; an antibody comprising a heavy chain having an amino acid sequence comprising amino acid residues 20 to 471 of SEQ ID NO: 36 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 36 and a light chain having an amino acid sequence comprising amino acid residues 21 to 239 of SEQ ID NO: 30; an antibody comprising a heavy chain having an amino acid sequence comprising amino acid residues 20 to 471 of SEQ ID NO: 36 and a light chain having an amino acid sequence comprising amino acid residues 21 to 239 of SEQ ID NO: 32; an antibody comprising a heavy chain having an amino acid sequence comprising amino acid residues 20 to 471 of SEQ ID NO: 38 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 38 and a light chain having an amino acid sequence comprising amino acid residues 21 to 239 of SEQ ID NO: 30; an antibody comprising a heavy chain having an amino acid sequence comprising amino acid residues 20 to 471 of SEQ ID NO: 38 and a light chain having an amino acid sequence comprising amino acid residues 21 to 239 of SEQ ID NO: 32; an antibody comprising a heavy chain having an amino acid sequence comprising amino acid residues 20 to 471 of SEQ ID NO: 40 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 42 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 44 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 46 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 48 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 50 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 70 and a light chain having an amino acid sequence comprising amino acid residues 21 to 239 of SEQ ID NO: 52; an antibody comprising a heavy chain having an amino acid sequence comprising amino acid residues 20 to 471 of SEQ ID NO: 70 and a light chain having an amino acid sequence comprising amino acid residues 21 to 239 of SEQ ID NO: 58; an antibody comprising a heavy chain having an amino acid sequence comprising amino acid residues 20 to 471 of SEQ ID NO: 70 and a light chain having an amino acid sequence comprising amino acid residues 21 to 239 of SEQ ID NO: 62; and an antibody comprising a heavy chain having an amino acid sequence comprising amino acid residues 20 to 471 of SEQ ID NO: 70 and a light chain having an amino acid sequence comprising amino acid residues 21 to 239 of SEQ ID NO: 66 can be exemplified.

As a further more preferred combination, an antibody characterized by containing a heavy chain variable region comprising an amino acid sequence comprising amino acid residues 20 to 141 of SEQ ID NO: 42 and a light chain variable region comprising an amino acid sequence comprising amino acid residues 21 to 134 of SEQ ID NO: 28; an antibody characterized by containing a heavy chain variable region comprising an amino acid sequence comprising amino acid residues 20 to 141 of SEQ ID NO: 70 and a light chain variable region comprising an amino acid sequence comprising amino acid residues 21 to 134 of SEQ ID NO: 52; an antibody characterized by containing a heavy chain variable region comprising an amino acid sequence comprising amino acid residues 20 to 141 of SEQ ID NO: 70 and a light chain variable region comprising an amino acid sequence comprising amino acid residues 21 to 134 of SEQ ID NO: 58; an antibody characterized by containing a heavy chain variable region comprising an amino acid sequence comprising amino acid residues 20 to 141 of SEQ ID NO: 70 and a light chain variable region comprising an amino acid sequence comprising amino acid residues 21 to 134 of SEQ ID NO: 62; and an antibody characterized by containing a heavy chain variable region comprising an amino acid sequence comprising amino acid residues 20 to 141 of SEQ ID NO: 70 and a light chain variable region comprising an amino acid sequence comprising amino acid residues 21 to 134 of SEQ ID NO: 66 can be exemplified.

As a most preferred combination, an antibody comprising a heavy chain having an amino acid sequence comprising amino acid residues 20 to 471 of SEQ ID NO: 42 and a light chain having an amino acid sequence comprising amino acid residues 21 to 239 of SEQ ID NO: 28; an antibody comprising a heavy chain having an amino acid sequence comprising amino acid residues 20 to 471 of SEQ ID NO: 70 and a light chain having an amino acid sequence comprising amino acid residues 21 to 239 of SEQ ID NO: 52; an antibody comprising a heavy chain having an amino acid sequence comprising amino acid residues 20 to 471 of SEQ ID NO: 70 and a light chain having an amino acid sequence comprising amino acid residues 21 to 239 of SEQ ID NO: 58; an antibody comprising a heavy chain having an amino acid sequence comprising amino acid residues 20 to 471 of SEQ ID NO: 70 and a light chain having an amino acid sequence comprising amino acid residues 21 to 239 of SEQ ID NO: 62; and an antibody comprising a heavy chain having an amino acid sequence comprising amino acid residues 20 to 471 of SEQ ID NO: 70 and a light chain having an amino acid sequence comprising amino acid residues 21 to 239 of SEQ ID NO: 66 can be exemplified.

By combining a sequence having a high homology with the above-described heavy chain amino acid sequence with a sequence having a high homology with the above-described light chain amino acid sequence, it is possible to select an antibody having a cytotoxic activity equivalent to that of each of the above-described antibodies. The homology is generally a homology of 80% or more, preferably a homology of 90% or more, more preferably a homology of 95% or more, most preferably a homology of 99% or more. Further, by combining an amino acid sequence including a substitution, deletion, or addition of one to several amino acid residues in the heavy chain or light chain amino acid sequence, it is also possible to select an antibody having a cytotoxic activity equivalent to that of each of the above-described antibodies. The number of amino acid residues to be substituted, deleted, or added is generally 10 or fewer, preferably 5 to 6 or fewer, more preferably 2 to 3 or fewer, most preferably 1.

The homology between two amino acid sequences can be determined using the Blast algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402) with default parameters. The Blast algorithm can also be used through the Internet by accessing the site www.ncbi.nlm.nih.gov/blast. Incidentally, two types of percentage values of identity (or identities) and positivity (or positivities) are calculated by the Blast algorithm. The former is a value when amino acid residues match each other in two amino acid sequences for which a degree of homology is to be determined, and the latter is a value obtained by also considering amino acid residues having a similar chemical structure. In this specification, the value of the identity when amino acid residues match each other is used as the homology value.

Incidentally, in the heavy chain amino acid sequence represented by SEQ ID NO: 34, 36, 38, 40, 42, 44, 46, 48, 50, or 70 in the Sequence Listing, an amino acid sequence consisting of amino acid residues 1 to 19 is a signal sequence, an amino acid sequence consisting of amino acid residues 20 to 141 is a variable region, and an amino acid sequence consisting of amino acid residues 142 to 471 is a constant region. Further, in the light chain amino acid sequence represented by SEQ ID NO: 28, 30, 32, 52, 58, 62, or 66 in the Sequence Listing, an amino acid sequence consisting of amino acid residues 1 to 20 is a signal sequence, an amino acid sequence consisting of amino acid residues 21 to 134 is a variable region, and an amino acid sequence consisting of amino acid residues 135 to 239 is a constant region.

The heavy chain amino acid sequence represented by SEQ ID NO: 34, 36, 38, 40, 42, 44, 46, 48, 50, or 70 in the Sequence Listing is encoded by a nucleotide sequence represented by SEQ ID NO: 33, 35, 37, 39, 41, 43, 45, 47, 49, or 69 in the Sequence Listing. In each of the above nucleotide sequences, a nucleotide sequence consisting of nucleotides 1 to 57 encodes the heavy chain signal sequence of the antibody, a nucleotide sequence consisting of nucleotides 58 to 423 encodes the heavy chain variable region of the antibody, and a nucleotide sequence consisting of nucleotides 424 to 1413 encodes the heavy chain constant region of the antibody.

The light chain amino acid sequence represented by SEQ ID NO: 28, 30, 32, 52, 58, 62, or 66 in the Sequence Listing is encoded by a nucleotide sequence represented by SEQ ID NO: 27, 29, 31, 51, 57, 61, or 65 in the Sequence Listing. In each of the above nucleotide sequences, a nucleotide sequence consisting of nucleotides 1 to 60 encodes the light chain signal sequence of the antibody, a nucleotide sequence consisting of nucleotides 61 to 402 encodes the light chain variable region of the antibody, and a nucleotide sequence consisting of nucleotides 403 to 717 encodes the light chain constant region of the antibody.

The homology between any of these nucleotide sequences and a nucleotide sequence of another antibody can also be determined using the Blast algorithm.

Further, the antibody of the invention includes a human antibody which binds to the same epitope as the B273 antibody. A human anti-DR5 antibody refers to a human antibody only having a gene sequence of an antibody derived from a human chromosome. A human anti-DR5 antibody can be obtained by a method using a human antibody-producing mouse having a human chromosome fragment containing heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matsuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a genetic engineering technique, by using cDNAs encoding such a heavy chain and a light chain of a human antibody, respectively, and preferably a vector containing the cDNAs, eukaryotic cells are transformed, and a transformant which produces a recombinant human monoclonal antibody is cultured, whereby the antibody can also be obtained from the culture supernatant.

Here, as the host, for example, eukaryotic cells, preferably mammalian cells such as CHO cells, lymphocytes or myeloma cells can be used.

Further, a method of obtaining a phage display-derived human antibody screened from a human antibody library (see Wormstone, I. M. et al., Investigative Ophthalmology & Visual Science (2002) 43(7), pp. 2301-2308; Carmen, S. et al., Briefings in Functional Genomics and Proteomics (2002), 1(2), pp. 189-203; Siriwardena, D. et al., Ophthalmology (2002) 109(3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23(9), pp. 1105-1116) can be used.

By analyzing the gene of the phage selected based on the binding to an antigen, a DNA sequence encoding the variable region of a human antibody which binds to an antigen can be determined.

If the DNA sequence of a scFv which binds to an antigen is determined, a human antibody can be obtained by preparing an expression vector having the sequence and introducing the vector into an appropriate host to express it (WO 92/01047, WO 92/20791, WO 93/06213, WO 93/11236, WO 93/19172, WO 95/01438, WO 95/15388, Annu. Rev. Immunol. (1994) 12, pp. 433-455, Nature Biotechnology (2005) 23(9), pp. 1105-1116).

If a newly produced human antibody binds to a partial peptide or a partial tertiary structure to which the B273 antibody binds, it can be determined that the human antibody and the B273 antibody bind to the same epitope. Further, by confirming that the human antibody competes with the B273 antibody for the binding to DR5 (that is, the human antibody inhibits the binding between the B273 antibody and DR5), it can be determined that the human antibody and the B273 antibody bind to the same epitope even if the specific epitope sequence or structure has not been determined. When it is confirmed that the human antibody and the B273 antibody bind to the same epitope, the human antibody is strongly expected to have a cytotoxic activity equivalent to that of B273.

Further, as shown in Example 4, it is possible to specify an amino acid residue on the side of DR5 which lies adjacent to a Fab fragment of an antibody from the data of X ray diffraction of a complex between the Fab fragment and DR5. Specifically, in the case where a Fab fragment derived from an arbitrary antibody lies adjacent to a glycine residue at position 26, an isoleucine residue at position 34, a glutamic acid residue at position 36, an aspartic acid residue at position 37, a glycine residue at position 38, an aspartic acid residue at position 56, a leucine residue at position 57, a leucine residue at position 58, a phenylalanine residue at position 59, a leucine residue at position 61, and an arginine residue at position 62 of an amino acid sequence represented by SEQ ID NO: 23 in the Sequence Listing, at a distance of 4 Å or less, it can be determined that the antibody binds to the same epitope as B273.

The chimeric antibodies, humanized antibodies, or human antibodies obtained by the above-described method are evaluated for the property of binding to an antigen by a method shown in Example 3 or the like, and a preferred antibody can be selected. As one example of another index for use in the comparison of the properties of antibodies, the stability of antibodies can be exemplified. The differential scanning calorimetry (DSC) shown in Example 10 is a device capable of quickly and accurately measuring a thermal denaturation midpoint temperature (Tm) to be used as a favorable index of the relative conformational stability of proteins. By measuring the Tm values using DSC and comparing the values, the difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following factors: the yield in an appropriate host cell is high and the aggregability in an aqueous solution is low. For example, an antibody which shows the highest yield does not always show the highest thermal stability, and therefore, it is necessary to select an antibody most suitable for the administration to humans by making a comprehensive evaluation based on the above-described indices.

Further, a method in which the full-length heavy and light chain sequences of an antibody are connected using an appropriate linker, whereby a single-chain immunoglobulin is obtained is also known (Lee, H-S, et. al., Molecular Immunology (1999) 36, pp. 61-71; Shirrmann, T. et. al., mAbs (2010), 2(1) pp. 1-4). By dimerizing such a single-chain immunoglobulin, the resulting dimer can have a structure and an activity similar to those of an antibody which is a tetramer itself. Further, the antibody of the invention may be an antibody which has a single heavy chain variable region and does not have a light chain sequence. Such an antibody is called a single domain antibody (sdAb) or a nanobody, and in fact, such an antibody is observed in camels and llamas and has been reported to have an antigen-binding affinity (Muyldemans S. et. al., Protein Eng. (1994) 7(9), 1129-35, Hamers-Casterman C. et. al., Nature (1993) 363(6428), 446-8). The above-described antibodies are included in the antibody according to the invention.

Further, by controlling glycosylation in which a glycan is bound to the antibody of the invention, it is possible to enhance antibody-dependent cytotoxic activity. As the technique for controlling the glycosylation of antibodies, WO 99/54342, WO 00/61739, WO 02/31140, etc. are known. However, it is not limited thereto.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately. In cases where eukaryotic cells are used as the host, animal cells, plant cells, and eukaryotic microorganisms can be used. As the animal cells, (1) mammalian cells, for example, dihydrofolate reductase-deficient strains (Urlaub, G. and Chasin, L. A., Proc. Natl. Acad. Sci. USA (1980) 77, pp. 4126-4220) of simian COS cells (Gluzman, Y., Cell, (1981) 23, pp. 175-182, ATCC CRL-1650), murine fibroblasts NIH3T3 (ATCC No. CRL-1658), and Chinese hamster ovarian cells (CHO cells; ATCC: CCL-61) can be exemplified. Further, in the case where prokaryotic cells are used, for example, *Escherichia coli* and *Bacillus subtilis* can be exemplified. By introducing a target antibody gene into these cells through transformation, and culturing the thus transformed cells in vitro, the antibody can be obtained. In the above-described culture method, the yield may sometimes vary depending on the sequence of the antibody, and therefore, it is possible to select an antibody which is easily produced as a pharmaceutical by using the yield as an index among the antibodies having comparable binding activity.

There is no limitation on isotype of the antibody of the invention, and examples thereof include IgG (IgG1, IgG2, IgG3, IgG4), IgM, IgA (IgA1, IgA2), IgD, and IgE, and preferred examples thereof include IgG and IgM, and furthermore preferred examples thereof include IgG1 and IgG2.

Further, the antibody of the invention may be a functional fragment of the antibody having an antigen-binding site of the antibody or a modified fragment thereof. The fragment of the antibody can be obtained by treating the antibody with a protease such as papain or pepsin, or modifying the antibody gene according to a genetic engineering technique and expressing the modified gene in suitable cultured cells. Among these antibody fragments, a fragment having all or part of the functions of the full-length molecule of the antibody can be called a functional fragment of the antibody. As the functions of the antibody, generally an antigen-binding activity, an activity of neutralizing the activity of an antigen, an activity of enhancing the activity of an antigen, an antibody-dependent cytotoxic activity, a complement-dependent cytotoxic activity, and a complement-dependent cellular cytotoxic activity can be exemplified. The function of the functional fragment of the antibody according to the invention is the activity of binding to DR5, preferably the activity of inducing apoptosis in cells, more preferably the cytotoxic activity through the induction of apoptosis in cancer cells. However, the antibody of the invention may have antibody-dependent cytotoxic activity, complement-dependent cytotoxic activity, and/or complement-dependent cellular cytotoxic activity as well as the activity of inducing apoptosis in cells.

Examples of the fragment of the antibody include Fab, F(ab')2, Fv, single-chain Fv (scFv) in which Fv molecules of the heavy chain and the light chain are connected via an appropriate linker, a diabody (diabodies), a linear antibody, and a polyspecific antibody composed of the antibody fragment. Further, Fab' which is a monovalent fragment in a variable region of an antibody obtained by treating F(ab')2 under reducing conditions is also included in the fragment of the antibody.

Further, the antibody of the invention may be a polyspecific antibody with specificity for at least two different antigens. In general, such a molecule binds to two antigens (that is, bispecific antibody), however, the term "polyspecific antibody" as used herein includes an antibody having specificity for two or more (for example, three) antigens.

The polyspecific antibody of the invention may be a full-length antibody or a fragment of such an antibody (for example, a F(ab')2 bispecific antibody). The bispecific antibody can be produced by connecting the heavy and light chains (HL pairs) of two types of antibodies, or can also be produced by fusing hybridomas which produce different monoclonal antibodies to prepare bispecific antibody-producing fused cells (Millstein et al., Nature (1983) 305, pp. 537-539).

The antibody of the invention may be a single-chain antibody (also referred to as scFv). The single-chain antibody can be obtained by connecting the heavy chain variable region and the light chain variable region of the antibody via a polypeptide linker (Pluckthun, The Pharmacology of Monoclonal Antibodies, 113 (edited by Rosenburg and Moore), Springer Verlag, New York, pp. 269-315 (1994), Nature Biotechnology (2005), 23, pp. 1126-1136). Further, a BiscFv fragment produced by connecting two scFv molecules via a polypeptide linker can also be used as the bispecific antibody.

A method of producing a single-chain antibody is known in this technical field (see, for example, U.S. Pat. Nos. 4,946,778, 5,260,203, 5,091,513, 5,455,030, etc.). In this scFv, the heavy chain variable region and the light chain variable region are connected via a linker which does not form a conjugate, preferably via a polypeptide linker (Huston, J. S. et al., Proc. Natl. Acad. Sci. USA (1988), 85, pp. 5879-5883). In the scFv, the heavy chain variable region and the light chain variable region may be derived from the same antibody or different antibodies.

As the polypeptide linker to be used for connecting the variable regions, a given single-chain peptide composed of 12 to 19 residues is used, for example.

DNA encoding scFv can be obtained by performing amplification using a DNA encoding the entire amino acid sequence or a desired partial amino acid sequence of a DNA selected from a DNA encoding the heavy chain or the heavy chain variable region of the above-described antibody and a DNA encoding the light chain or the light chain variable region thereof as a template by a PCR method using a primer pair that defines both ends thereof, and further performing amplification by combining a DNA encoding a polypeptide linker portion and a primer pair that defines both ends thereof so as to connect the both ends to the heavy chain and the light chain, respectively.

Further, once DNA encoding a scFv is produced, an expression vector containing the same and a host transformed by the expression vector can be obtained according to a common procedure. Further, by using the resulting host, scFv can be obtained according to a common procedure. An antibody fragment thereof can be produced in a host by obtaining a gene and expressing the gene in the same manner as described above.

The antibody of the invention may be multimerized to increase its affinity for an antigen. The antibody to be multimerized may be one type of antibody or a plurality of antibodies which recognize a plurality of epitopes of the same antigen. As a method of multimerization of the antibody, binding of the IgG CH3 domain to two scFv molecules, binding to streptavidin, introduction of a helix-turn-helix motif, and the like can be exemplified.

The antibody of the invention may be a polyclonal antibody which is a mixture of plural types of anti-DR5 antibodies having different amino acid sequences. As one example of the polyclonal antibody, a mixture of plural types of antibodies having different CDR can be exemplified. As such a polyclonal antibody, antibodies obtained by culturing a mixture of cells which produce different antibodies and then purifying the antibodies from the resulting culture can be used (see WO 2004/061104).

As a modified antibody, an antibody bound to any of various types of molecules such as polyethylene glycol (PEG) can also be used.

Further, the antibody of the invention may be in the form of a conjugate formed between any of these antibodies and another medicinal agent (immunoconjugate). Examples of such an antibody include one in which the antibody is conjugated to a radioactive material or a compound having a pharmacological action (Nature Biotechnology (2005) 23, pp. 1137-1146).

The obtained antibody can be purified to homogeneity. The separation and purification of the antibody can be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified.

For example, as a column using a Protein A column, Hyper D™, POROS®, Sepharose® FF (Pharmacia) and the like can be exemplified. Further, by using a carrier having an antigen immobilized thereon, the antibody can also be purified utilizing the binding property of the antibody to the antigen.

(4) Specific Examples of Other Anti-DR5 Antibodies

Anti-DR5 antibodies which induce apoptosis in DR5-expressing cells are described in, for example, WO 98/51793, WO 2001/83560, WO 2002/94880, WO 2003/54216, WO 2006/83971, and WO 2007/22157. Further, anti-DR5 antibodies called tigatuzumab (CS-1008), lexatumumab (HGS-ETR2), HGS-TR2J, drozitumab (APOMAB), conatumumab (AMG-655), and LBY135 are still in clinical trials or were in clinical trials in the past. The anti-DR5 antibodies which were still in clinical trials on the date when this application was filed are tigatuzumab, lexatumumab, and conatumumab. The novel anti-DR5 antibodies described in this specification have a superior in vitro and/or in vivo antitumor activity as compared with the above-described tigatuzumab, lexatumumab, conatumumab, and drozitumab.

3. Pharmaceutical Containing Anti-DR5 Antibody

The antibodies obtained by the method described in the above item "2. Production of anti-DR5 antibody" can be used as a pharmaceutical, particularly a therapeutic and/or preventive agent for cancer since the antibodies each function as an agonist for an apoptosis-related receptor, DR5, in vivo and induce apoptosis in cancer cells via the receptor to exhibit a cytotoxic activity.

The cytocidal activity exhibited by an antibody in vitro can be determined by measuring their activity in inhibiting the proliferation of cells which overexpress an apoptosis-related receptor.

For example, a cancer cell line which overexpresses DR5 is cultured, an antibody is added to the culture system at different concentrations, and inhibitory activity against focus formation, colony formation, and spheroid proliferation can be measured.

The in vivo therapeutic effect of an antibody on cancer using experimental animals can be determined by, for example, measuring a change in cancer cells by administering the antibody to nude mice implanted with a tumor cell line which overexpresses DR5.

Examples of the type of cancer include lung cancer, prostate cancer, thyroid cancer, stomach cancer, liver cancer, ovarian cancer, colon cancer, breast cancer, pancreatic cancer, kidney cancer, uterine cancer including endometrial cancer, melanocarcinoma including melanoma, fibrosarcoma, glioblastoma, and blood cell cancer (such as leukemia and lymphoma), however, the type of cancer is not limited thereto as long as the cancer cell to be treated expresses DR5.

Further, it is known that an antibody against DR5 induces apoptosis in inflammatory cells (J. Clin. Invest. 1996, 98(2), 271-278; Int. Immunol. 1996, 8(10), 1595-1602). Therefore, the antibody of the invention can be also used as a therapeutic agent for an autoimmune disease or an inflammatory disease. Examples of the autoimmune disease or inflammatory disease include systemic lupus erythematosus, Hashimoto's disease, rheumatoid arthritis, a graft-versus-host disease, Sjogren's syndrome, pernicious anemia, Addison's disease, scleroderma, Goodpasture's syndrome, Crohn's disease, autoimmune hemolytic anemia, sterility, myasthenia gravis, multiple sclerosis, Basedow's disease, thrombopenia purpura, insulin-dependent diabetes mellitus, allergy, asthma, an atopic disease, arteriosclerosis, myocarditis, cardiomyopathy, glomerulonephritis, aplastic anemia, and rejection after organ transplantation.

A substance to be used in a preparation acceptable in the pharmaceutical composition according to the invention is preferably non-toxic to a person to whom the pharmaceutical composition is to be administered in terms of the dose and concentration.

The pharmaceutical composition of the invention can contain a substance for pharmaceutical use which is capable of changing or maintaining the pH, osmotic pressure, viscosity, transparency, color, isotonicity, aseptic condition, stability, solubility, release rate, absorption rate, and permeability thereof. Examples of such a substance for pharmaceutical use include, but are not limited to, amino acids such as glycine, alanine, glutamine, asparagine, arginine, and lysine; antimicrobial agents; antioxidants such as ascorbic acid, sodium sulfate, and sodium hydrogen sulfite; buffers such as phosphate, citrate, borate buffers, sodium hydrogen carbonate, and Tris-HCl solutions; fillers such as mannitol and glycine; chelating agents such as ethylenediamine tetraacetate (EDTA); complexing agents such as caffeine, polyvinylpyrrolidine, β-cyclodextrin, and hydroxypropyl-β-cyclodextrin; expanders such as glucose, mannose, and dextrin; other carbohydrates such as monosaccharides and disaccharides; coloring agents; flavors; diluents; emulsifying agents; hydrophilic polymers such as polyvinylpyrrolidine; preservatives such as low molecular weight polypeptides, salt forming counter ions, benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as sorbitan ester, polysorbates including polysorbate 20 and polysorbate 80, Triton®, tromethamine, lecithin, and cholesterol; stability enhancing agents such as sucrose and sorbitol; elasticity enhancing agents such as sodium chloride, potassium chloride, and mannitol and sorbitol; transport agents; excipients; and/or pharmaceutical adjuvants. The amount of these substances for pharmaceutical use is preferably from 0.01 to 100 times, particularly preferably from 0.1 to 10 times the weight of the anti-DR5 antibody. Those skilled in the art can appropriately determine a preferred formulation of the pharmaceutical composition in a preparation depending on the disease to which the composition is applied, the route of administration to be applied, or the like.

The excipient or carrier in the pharmaceutical composition may be in the form of a liquid or a solid. An appropriate excipient or carrier may be injectable water, physiological saline, an artificial cerebral spinal fluid, or other substance commonly used for parenteral administration. Further, neutral physiological saline or physiological saline containing serum albumin can also be used as a carrier. The pharmaceutical composition may contain a Tris buffer of pH 7.0 to 8.5, an acetate buffer of pH 4.0 to 5.5, or a citrate buffer of pH 3.0 to 6.2. Further, such a buffer may be supplemented with sorbitol or another compound.

Examples of the pharmaceutical composition of the invention include a pharmaceutical composition containing the anti-DR5 antibody and a pharmaceutical composition containing the anti-DR5 antibody and at least one therapeutic agent for cancer. The pharmaceutical composition of the invention is prepared in the form of a lyophilized product or a liquid as a medicinal agent having a selected composition and a required purity. The pharmaceutical composition containing the anti-DR5 antibody and the pharmaceutical composition containing the anti-DR5 antibody and at least one therapeutic agent for cancer can also be formed into a lyophilized product using an appropriate excipient such as sucrose.

In the above-described pharmaceutical composition, the therapeutic agent for cancer to be incorporated along with the anti-DR5 antibody may be administered simultaneously with, separately from, or sequentially with the anti-DR5 antibody, or the therapeutic agent and the anti-DR5 antibody may be administered at different dosage intervals. Examples of such a therapeutic agent for cancer include abraxane, carboplatin, cisplatin, gemcitabine, irinotecan (CPT-11), paclitaxel, pemetrexed, sorafenib, vinblastin, 5-FU, and medicinal agents described in WO 2003/038043, however, the agent is not limited thereto as long as the agent is a medicinal agent having an antitumor activity.

The pharmaceutical composition of the invention can be prepared for parenteral administration or for gastrointestinal absorption through oral administration. The composition and concentration of a preparation can be determined depending on the administration method. The higher the affinity of the anti-DR5 antibody contained in the pharmaceutical composition of the invention is for DR5, that is, the lower the dissociation constant (Kd value) thereof is for DR5, the more the anti-DR5 antibody can exhibit its drug efficacy even when decreasing the dose for humans. Hence, the dose of the pharmaceutical composition of the invention for humans can also be determined based on this fact. As for the dose, in the case where a human anti-DR5 antibody is administered to humans, the antibody may be administered at a dose of from about 0.1 to 100 mg/kg once per one to 180 days.

Examples of the dosage form of the pharmaceutical composition of the invention include injections including infusions, suppositories, transnasal agents, sublingual agents, and percutaneous absorbents.

Hereinafter, the invention will be more specifically described with reference to the Examples, however, the invention is not limited thereto. Note that the respective operations regarding gene manipulation in the following Examples were performed according to the methods described in "Molecular Cloning" (written by Sambrook, J., Fritsch, E. F. and Maniatis, T., published by Cold Spring Harbor Laboratory Press in 1989), or in the case of using commercially available reagents or kits, they are used according to the protocols attached thereto unless otherwise stated.

Example 1 Production of Mouse Antibody B273

1)-1 Production of Human DR5 Protein (Human DR5 Extracellular Domain/Human Fc Fusion Protein)

1)-1-1 Production of Human DR5 Extracellular Domain Expression Vector

A vector expressing human DR5 protein (isoform 2: NP_671716) was constructed by inserting a gene, in which a human DR5 extracellular domain was fused to a human IgG1/Fc region, downstream of the CMV promoter.

1)-1-2 Production of Human DR5 Protein

The introduction of the expression vector into 293 FreeStyle™ cells and the collection of the culture supernatant were performed by Invitrogen Corporation (currently Life Technologies Japan Ltd.).

1)-1-3 Purification of Human DR5 Protein

The culture supernatant obtained in the above b) was purified using Protein A affinity column chromatography. 5 L of the culture supernatant was applied to "HiTrap™ Protein A_FF" (GE Healthcare Bio-Sciences Co., Ltd., Cat. No. 17-5079-01) equilibrated with PBS, followed by washing with PBS. Subsequently, a 2 M arginine solution (pH 4.0) was added to the column, and a fraction containing the human DR5 protein was collected. The fraction was added to a centrifugal filter device (Amicon Ultra-4, fractional molecular weight: 10 K, Millipore Co., Ltd.), and liquid replacement with PBS and condensation were performed. The final volume was made up to 6 ml, which was used as a purified sample (rDR5-hFc). The quantitative determination of the purified product of protein was performed using "Micro BCA™ Protein Assay Kit" (PIERCE #23235). As a reference standard, the "Albumin Standard" contained in the kit was used.

1)-2 Immunization

BALB/cAJcl mice (CLEA Japan, Inc.) at 5 to 6 weeks of age were used. On day 0, a mixture of 50 µg of rDR5-hFc prepared in 1)-1-3 and Freund's complete adjuvant (manufactured by Wako Pure Chemical Industries, Ltd.) (at a volume ratio of 1:1) was subcutaneously administered in the vicinity of the neck of each mouse. On days 14 and 28, a mixture of 50 µg of rDR5-hFc and Freund's incomplete adjuvant (manufactured by Wako Pure Chemical Industries, Ltd.) (at a volume ratio of 1:1) was subcutaneously administered in the dorsal region of each mouse. On day 42, 50 µg of rDR5-hFc was administered into the abdominal cavity of each mouse, and on day 45, the spleen was excised from each mouse and used for the production of hybridomas.

1)-3 Production of Hybridomas

Spleen cells and mouse myeloma P3X63Ag8U.1 cells were subjected to cell fusion using PEG 4000 (manufactured by Immuno-biological Laboratories Co., Ltd.), and the resulting fused cells were diluted with ClonaCell™-HY Selection Medium D (manufactured by StemCell Technologies, Inc., #03804) and cultured. Then, the hybridoma colonies formed were collected, whereby monoclonal hybridomas were produced. The collected hybridoma colonies were separately cultured, and by using the obtained culture supernatant of each hybridoma, an anti-DR5 antibody-producing hybridoma was screened.

1)-4 Screening of Antibody by Cell-ELISA Method

1)-4-1 Construction of Human DR5 Mutant Expression Vector (pcDNA3.1-DR5M)

A cDNA encoding the human DR5 protein (isoform 2: NP_671716) was cloned into a pcDNA3.1(+) vector, and a death domain-modified expression vector pcDNA3.1-DR5M which was designed so as to express a protein in which the amino acid L at position 334 in the death domain is substituted with D was constructed.

1)-4-2 Preparation of Antigen Gene-Expressing Cells

HEK 293 cells were prepared at $7.5 \times 10^5$ cells/ml in DMEM medium containing 10% FBS. Then, the HEK 293 cells were transfected with the death domain-modified DR5 expression vector pcDNA3.1-DR5M or pcDNA3.1-mock serving as a control using Lipofectamine® 2000 (manufactured by Life Technologies Japan Ltd.), and each cell suspension was dispensed at 50 µl/well in a 96-well half area microplate (manufactured by Corning Incorporated). The cells were cultured overnight in DMEM medium containing 10% FBS under the conditions of 37° C. and 5% $CO_2$. The thus obtained transfected cells in an adherent state were used as such in a cell-ELISA.

1)-4-3 Cell-ELISA

After the supernatant was removed from the culture of the HEK 293 cells transfected with the expression vector prepared in 1)-4-2, the hybridoma culture supernatant was added to each of the HEK 293 cells transfected with pcDNA3.1-DR5M and the HEK 293 cells transfected with pcDNA3.1-mock, and the plate was left to stand at 4° C. for 1 hour. After the cells in each well were washed once with PBS containing 5% FBS, goat anti-mouse IgG, peroxidase conjugated (manufactured by Chemicon Co., Ltd., #AP181P) diluted to 500-fold with PBS containing 5% FBS was added to each well, and the plate was left to stand at 4° C. for 1 hour. After the cells in each well were washed 5 times with PBS containing 5% FBS, an OPD color developing solution (o-phenylenediamine dihydrochloride (manufactured by Wako Pure Chemical Industries, Ltd.) and $H_2O_2$ were dissolved at 0.4 mg/ml and 0.6% (v/v), respectively, in a solution for dissolving OPD (0.05 M trisodium citrate and 0.1 M disodium hydrogen phosphate dodecahydrate, pH 4.5)) was added at 25 µl/well. A color development reaction was allowed to proceed while sometimes stirring the reaction mixture, and the color development reaction was stopped by adding 1 M HCl at 25 µl/well. Thereafter, an absorbance at 490 nm was measured using a plate reader (ARVO, manufactured by Perkin Elmer, Inc.). In order to select a hybridoma which produces an antibody that specifically binds to DR5 expressed on the cell membrane, a hybridoma which produces a culture supernatant showing a higher absorbance in the HEK 293 cells transfected with the pcDNA3.1-DR5M expression vector as compared with the HEK 293 cells transfected with the pcDNA3.1-mock (control) was selected to be positive for the production of an anti-DR5 antibody.

1)-5 Screening of Antibody by Flow Cytometric Method

1)-5-1 Preparation of Antigen Gene-Expressing Cells 293T cells were seeded at $5 \times 10^4$ cells/cm$^2$ in a 225-cm$^2$ flask (manufactured by Sumitomo Bakelite Co., Ltd.), and cultured overnight in DMEM medium containing 10% FBS under the conditions of 37° C. and 5% $CO_2$. On the next day, the 293T cells were transfected with pcDNA3.1-DR5M or pcDNA3.1-mock serving as a control using Lipofectamine® 2000, and further cultured overnight under the conditions of 37° C. and 5% $CO_2$. On the next day, the 293T cells transfected with the expression vector were treated with TrypLE™ Express (manufactured by Life Technologies Japan Ltd.). Then, the cells were washed with DMEM containing 10% FBS, and thereafter suspended in PBS containing 5% FBS. The thus obtained cell suspension was used in a flow cytometric analysis.

1)-5-2 Flow Cytometric Analysis

The 293T cell suspension prepared in 1)-5-1 was centrifuged and the supernatant was removed. Then, the hybridoma culture supernatant was added to each of the 293T cells transfected with pcDNA3.1-DR5M and the 293T cells transfected with pcDNA3.1-mock to suspend the cells, and the cells were left to stand at 4° C. for 1 hour. After the cells were washed twice with PBS containing 5% FBS, fluorescein-conjugated goat IgG fraction to mouse IgG (whole molecule) (manufactured by Cappel Co., Ltd., #55493) diluted 1000-fold with PBS containing 5% FBS was added thereto to suspend the cells, and the cells were left to stand at 4° C. for 1 hour. After the cells were washed 3 times with PBS containing 5% FBS, the cells were resuspended in PBS containing 5% FBS supplemented with 2 µg/ml 7-aminoactinomycin D (manufactured by Invitrogen (Molecular Probes) Corporation), and the detection was performed using a flow cytometer (FC500, Beckman Coulter, Inc.). The data was analyzed using Flowjo® (Tree Star, Inc.). 7-Aminoactinomycin D-positive dead cells were excluded using a gate. Then, the FITC fluorescence intensity histograms of viable cells were created. A hybridoma which produced a sample that gave a higher fluorescence intensity in the fluorescence intensity histogram of the 293T cells transfected with pcDNA3.1-DR5M than in the fluorescence intensity histogram of the 293T cells transfected with pcDNA3.1-mock serving as the control was selected to be positive for the production of an anti-DR5 antibody.

1)-6 Screening in Terms of Cytocidal Effect

By using the culture supernatants of the hybridomas selected to be positive for the production of an anti-DR5 antibody in 1)-4 and 1)-5, a cell death-inducing effect on a human T-lymphoma cell line Jurkat was confirmed. AffiniPure goat anti-mouse IgG Fc specific (manufactured by Jackson ImmunoResearch Laboratories, Inc., #115-005-071) prepared at 50 µg/ml with 5 mM Tris-HCl (pH 8.5) was dispensed at 25 µL/well in a 96-well half area microplate (manufactured by Corning Incorporated), and the plate was left to stand overnight at 4° C. After each well was washed twice with PBS, a hybridoma culture supernatant was added to each well and the plate was left to stand overnight at 4° C. After each well was washed twice with PBS, Jurkat cells prepared at $4.0 \times 10^4$ cells/ml in RPMI 1640 medium containing 10% FBS were added at 25 µl/well and cultured under the conditions of 37° C. and 5% $CO_2$ for 20 hours. The cytocidal effect of the anti-DR5 monoclonal antibody present in the hybridoma culture supernatant was evaluated by quantitatively determining the amount of ATP derived from viable cells using a CellTiter-Glo® luminescent cell viability assay kit (manufactured by Promega Corporation, #G7571). As a result, hybridomas which produce 5 types of monoclonal antibodies (B086, B139, B192, B273, and B467), each of which exhibited a decrease in the amount of ATP by 80% or more as compared with the case of adding the medium for culturing the hybridoma, were established.

1)-7 Isotype Determination of Monoclonal Antibody

The isotypes of the monoclonal antibodies were determined using Mouse monoclonal isotyping kit (manufactured by AbD Serotec, Inc.). As a result, the isotype of B086, B139, B192, B273, and B467 was confirmed to be IgG1, κ chain.

1)-8 Preparation of Monoclonal Antibody

The monoclonal antibody was purified from the ascites of a mouse implanted with a hybridoma (hereinafter, referred to as a "starting material for antibody purification").

The mouse ascites was prepared as follows. First, BALB/cAJcl-nu/nu (Japan SLC, Inc.) mice of 7 to 8 weeks of age were treated with pristane (manufactured by Sigma Co., Ltd.), and after about 3 weeks, a hybridoma washed with physiological saline was implanted into the abdominal cavity at $1 \times 10^7$ cells per mouse. After 1 to 2 weeks, the ascites accumulated in the abdominal cavity was collected and sterilized through a 0.22-µm mesh filter, and the resulting material was used as a starting material for antibody purification.

The antibody was purified by Hitrap® MabSelect™ SuRe™ (manufactured by GE Healthcare Bio-Sciences Co., Ltd.). That is, the starting material for antibody purification was added to a column, and the column was washed with PBS, and thereafter, elution was performed with 2 M Arginine-HCl pH 4.0. After the eluted antibody solution was neutralized, the buffer was replaced with PBS. The concentration of the antibody was obtained by eluting the antibody bound to POROS® G 20 µm Column PEEK, 4.6 mm×50 mm, 0.83 ml (Applied Biosystems, Inc.) and measuring the absorbance (O.D. 280 nm) of the eluate. Specifically, an antibody sample diluted with PBS was added to POROS® G 20 µm equilibrated with an equilibrating buffer (30.6 mM sodium dihydrogen phosphate dodecahydrate, 19.5 mM monopotassium phosphate, 0.15 M NaCl, pH 7.0). Then, the column was washed with the equilibrating buffer, and the antibody bound to the column was then eluted with an eluent (0.1% (v/v) HCl, 0.15 M NaCl). The peak area of the absorbance (O.D. 280 nm) of the eluate was measured, and the concentration was calculated according to the following equation: Concentration of antibody sample (mg/ml)=(Peak area of antibody sample)/(Peak area of reference standard (human IgG1))×Concentration of reference standard (mg/ml)×Dilution factor of sample. Moreover, the concentration of endotoxin contained in the obtained antibody was measured using Limulus ES-II Single Test Wako (Wako Pure Chemical Industries, Ltd., 295-51030 containing control standard endotoxin) and a toxinometer (Wako Pure Chemical Industries, Ltd., ET-301 or ET-5000) and was confirmed to be 1 EU/mg or less. The resulting antibody was used in the subsequent experiment.

1)-9 In Vitro Cytocidal Activity of Mouse Antibody B273 Against Human Cancer Cell Lines Each of a human T-lymphoma cell line Jurkat and a human glioblastoma cell line U-87MG was prepared at $4.4 \times 10^4$ cells/ml in RPMI 1640 medium containing 10% FBS or MEM (Minimum Essential Medium) medium containing 10% FBS and added to a white clear bottom 96-well microplate (manufactured by Corning Incorporated) at 45 Owen, and cultured overnight under the conditions of 37° C. and 5% $CO_2$. The mouse B273 antibody or the mouse IgG1 antibody (manufactured by R&D Systems, Inc.) was mixed with the same concentration of AffiniPure goat anti-mouse IgG Fc specific (manufactured by Jackson ImmunoResearch Laboratories, Inc., #115-005-071), and the resulting mixture was added at 5 µl/well such that the final concentration of the mouse B273 antibody or the mouse IgG1 antibody was 10,000 to 0.01 ng/ml, and the cells were cultured under the conditions of 37° C. and 5% $CO_2$ for 24 hours. The amount of ATP derived from viable cells in each well was measured by a luminometer (manufactured by Perkin Elmer, Inc.) using a CellTiter-Glo® luminescent cell viability assay kit (manufactured by Promega Corporation, #G7571) according to the attached protocol. The cytocidal activity was evaluated by taking the value obtained from the well to which the medium was added in place of the antibody solution as 100% (FIG. 1). In each graph, the cell viability is expressed as a mean±standard deviation (n=3). As a result, it was found that the mouse B273 antibody exhibits a cytocidal effect on both cell lines in an antibody concentration-dependent manner.

Example 2 Cloning of Mouse Antibody B273 Gene and Production of Human Chimeric Antibody Gene 2)-1 Cloning of Mouse Antibody B273 cDNA and Determination of Sequence 2)-1-1 Determination of N-Terminal Amino Acid Sequences of Heavy and Light Chains of Mouse Antibody B273

In order to determine the N-terminal amino acid sequences of the heavy and light chains of the mouse antibody B273, the mouse antibody B273 purified in Example 1-8 was separated by SDS-PAGE. The protein in the gel was transferred from the gel, after separation, to a PVDF membrane (pore size: 0.45 µm, manufactured by Invitrogen Corporation). The membrane was washed with a washing buffer (25 mM NaCl, 10 mM sodium borate buffer pH 8.0), and thereafter stained by being immersed in a dye solution (50% methanol, 20% acetic acid, 0.05% Coomassie brilliant blue) for 5 minutes, followed by destaining with 90% methanol. The portions of the band corresponding to the heavy chain (the band with smaller mobility) and the band corresponding to the light chain (the band with larger mobility) visualized on the PVDF membrane were excised, and an attempt was made to identify their respective N-terminal amino acid sequences by an automatic Edman method (see Edman et al. (1967) Eur. J. Biochem. 1, 80) using Procise (registered trademark) cLC Protein Sequencer Model 492cLC (Applied Biosystems, Inc.). As a result, the N-terminal amino acid sequence of the band corresponding to the heavy chain of the mouse antibody B273 was EVQLQQSGPELVKPG (SEQ ID NO: 1 in the Sequence Listing), and the N-terminal amino acid sequence of the band corresponding to the light chain of the mouse antibody B273 was DVVMTQTPLSLPVSLGDQAS (SEQ ID NO: 2 in the Sequence Listing).

2)-1-2 Preparation of mRNA from Mouse Antibody B273-Producing Hybridoma

In order to clone cDNAs encoding the heavy chain and the light chain of the mouse antibody B273, respectively, mRNA was prepared from the mouse antibody B273-producing hybridoma using Quick-Prep™ mRNA Purification Kit (GE Healthcare Bio-Sciences Co., Ltd.).

2)-1-3 Cloning of Mouse Antibody B273 cDNA and Determination of Sequence

With reference to the findings that the isotypes of the heavy and light chains of the mouse antibody B273 are γ1 and κ found in Example 1-7, and the N-terminal amino acid sequences of the heavy and light chains determined in the above 2)-1-1, and the database of the amino acid sequences of antibodies prepared by Kabat et al. (see Kabat, E. A. et al., (1991) in Sequences of Proteins of Immunological Interest Vol. I and II, U.S. Department of Health and Human Services), several oligonucleotide primers hybridizing to the 5'-terminal region of an antibody gene coding region and the 3'-terminal region thereof containing a stop codon, respectively, were synthesized, and a cDNA encoding the heavy chain and a cDNA encoding the light chain were amplified using the mRNA prepared in 2)-1-2 and TaKaRa One Step RNA PCR Kit (AMV) (TaKaRa Bio, Inc.). As a result, the cDNA encoding the heavy chain of the antibody and the cDNA encoding the light chain of the antibody could be amplified by the following primer sets.

A primer set for the heavy chain

5'-aagaattcatgggatggagctgtatc-3' (MH258E1F1: SEQ ID NO: 3 in the Sequence Listing)

5'-aagatatcttatttaccaggagagtgggagag-3' (G1EVR1: SEQ ID NO: 4 in the Sequence Listing)

A primer set for the light chain

5'-aagaattcatgaagttgcctgttagg-3' (MK19EIF1: SEQ ID NO: 5 in the Sequence Listing)

5'-aagatatcttaacactcattcctgttgaagct-3' (KEVR1: SEQ ID NO: 6 in the Sequence Listing)

Each of the cDNA encoding the heavy chain and the cDNA encoding the light chain amplified by PCR was cloned using pEF6/V5-His TOPO® TA Expression Kit (Invitrogen Corporation), and each of the nucleotide sequences of the heavy chain and the light chain cloned was determined using a gene sequence analyzer ("ABI PRISM 3700 DNA Analyzer; Applied Biosystems" or "Applied Biosystems 3730xl Analyzer; Applied Biosystems"). In the sequencing reaction, GeneAmp™ 9700 (Applied Biosystems, Inc.) was used.

The determined nucleotide sequence of the cDNA encoding the heavy chain of the mouse antibody B273 is represented by SEQ ID NO: 7 in the Sequence Listing, and the amino acid sequence thereof is represented by SEQ ID NO: 8. The nucleotide sequence of the cDNA encoding the light chain of the mouse antibody B273 is represented by SEQ ID NO: 9 in the Sequence Listing, and the amino acid sequence thereof is represented by SEQ ID NO: 10 in the Sequence Listing. The sequences of SEQ ID NOS: 7 and 8 are shown in FIG. 28, and the sequences of SEQ ID NOS: 9 and 10 are shown in FIG. 29.

Further, the amino acid sequences of the heavy chain and the light chain were analyzed by comparison using Kabat-Man (see PROTEINS: Structure, Function and Genetics, 25 (1996), 130-133), which is the database of the amino acid sequences of antibodies. As a result, it was found that in the heavy chain of the mouse antibody B273, the amino acid sequence represented by amino acid numbers 20 to 141 of SEQ ID NO: 8 in the Sequence Listing is a variable region. It was also found that in the light chain of the mouse antibody B273, the amino acid sequence represented by amino acid numbers 20 to 133 of SEQ ID NO: 10 in the Sequence Listing is a variable region.

2)-2 Production of Chimeric Antibody B273 Expression Vector

2)-2-1 Production of Universal Expression Vectors pEF6KCL and pEF1FCCU

2)-2-1-1 Construction of Chimeric and Humanized Light Chain Expression Vector pEF6KCL By performing PCR using the plasmid pEF6/V5-HisB (Invitrogen Corporation) as a template and also using the following primers, a DNA fragment from immediately downstream of BGHpA (Sequence Position: 2174) to SmaI (Sequence Position: 2958) (a DNA fragment containing f1 origin of replication and SV40 promoter and origin, hereinafter referred to as "fragment A") was obtained.

5'-ccacgcgccctgtagcggcgcattaagc-3' (primer EFF1: SEQ ID NO: 11 in the Sequence Listing)

5'-aaacccgggagcttttgcaaaagcctagg-3' (primer EFsmaR: SEQ ID NO: 12 in the Sequence Listing)

The obtained fragment A and a DNA fragment (SEQ ID NO: 13, hereinafter referred to as "fragment B") containing a DNA sequence encoding a human κ chain secretory signal, a human κ chain constant region, and a human poly-A additional signal were ligated to each other by overlap extension PCR. The thus obtained DNA fragment in which the fragment A and the fragment B were ligated to each other was digested with the restriction enzymes KpnI and SmaI, which was ligated to the plasmid pEF6/V5-HisB (Invitrogen Corporation) which was digested with the restriction enzymes KpnI and SmaI, whereby a chimeric and humanized light chain expression vector pEF6KCL having a signal sequence, a cloning site, a human κ chain constant region, and a human poly-A additional signal sequence downstream of the EF1 promoter was constructed.

2)-2-1-2 Construction of pEF1/KCL

A DNA fragment obtained by cleaving the pEF6KCL obtained by the above-described method with the restriction enzymes KpnI and SmaI was ligated to pEF1/myc-HisB (Invitrogen Corporation) which was digested with KpnI and SmaI, whereby a plasmid pEF1KCL was constructed.

2)-2-1-3 Construction of Chimeric and Humanized Heavy Chain Expression Vector pEF1FCCU A DNA fragment (SEQ ID NO: 14) containing a DNA sequence encoding amino acids of a signal sequence and a constant region of human IgG1 was digested with the restriction enzymes NheI and PmeI and was ligated to the plasmid pEF1KCL which was digested with NheI and PmeI, whereby a chimeric and humanized heavy chain expression vector pEF1FCCU having a signal sequence, a cloning site, a human heavy chain constant region, and a human poly-A additional signal sequence downstream of the EF1 promoter was constructed.

2)-2-2 Construction of B273 Chimera-Type Light Chain Expression Vector

By using the cDNA encoding the light chain of the mouse antibody B273 as a template and also using KOD-Plus- (TOYOBO, Co., Ltd.) and the following primer set, a region containing the cDNA encoding the light chain variable region was amplified. A DNA fragment obtained by cleaving the amplified product with the restriction enzymes NdeI and BsiWI was inserted into the universal chimeric and humanized antibody light chain expression vector (pEF6KCL) at the site cleaved with the restriction enzymes NdeI and BsiWI, whereby a B273 chimera-type light chain expression vector was constructed. The thus obtained expression vector was named "pEF6KCL/B273L". The nucleotide sequence of the B273 chimera-type light chain is represented by SEQ ID NO: 15 in the Sequence Listing, and the amino acid sequence thereof is represented by SEQ ID NO: 16. The sequences of SEQ ID NOS: 15 and 16 are shown in FIG. 30. Incidentally, the amino acid residue at position 134 in the amino acid sequence of the chimera-type light chain represented by SEQ ID NO: 16 in the Sequence Listing is located in the carboxyl terminus of the light chain variable region and corresponds to the alanine residue at position 133 in the amino acid sequence of the mouse antibody B273 light chain represented by SEQ ID NO: 10 in the Sequence Listing, however, in the amino acid sequence represented by SEQ ID NO: 16, the residue has already been substituted with a threonine residue derived from a human antibody light chain.

The primer set for the light chain:
5'-aaacatatggcgatgttgtgatgacccaaactccactctcc-3'
(B273LF: SEQ ID NO: 17 in the Sequence Listing)
5'-aaacgtacgtttgatttccagcttggtgcctccaccgaacg-3'
(B273LR: SEQ ID NO: 18 in the Sequence Listing)

2)-2-3 Construction of B273 Chimera-Type Heavy Chain Expression Vector

By using the cDNA encoding the heavy chain of the mouse antibody B273 as a template and also using KOD-Plus- (TOYOBO, Co., Ltd.) and the following primer set, a region containing the cDNA encoding the heavy chain variable region was amplified. A DNA fragment obtained by cleaving the amplified product with the restriction enzyme BlpI was inserted into the universal chimeric and humanized antibody heavy chain expression vector (pEF1FCCU) at the site cleaved with the restriction enzyme BlpI, whereby a B273 chimera-type heavy chain expression vector was constructed. The thus obtained expression vector was named "pEF1FCCU/B273H". The nucleotide sequence of the B273 chimera-type heavy chain is represented by SEQ ID NO: 19 in the Sequence Listing, and the amino acid sequence thereof is represented by SEQ ID NO: 20. The sequences of SEQ ID NOS: 19 and 20 are shown in FIG. 31.

The primer set for the heavy chain:
5'-aaagctgagcgaggttcagctgcagcagtctggacctgagc-3'
(B273HF: SEQ ID NO: 21 in the Sequence Listing)
5'-aaagctgagctgactgtgagagtggtgccttggccccagtag-3'
(B273HR: SEQ ID NO: 22 in the Sequence Listing)

2)-3 Preparation of Chimeric Antibody B273

2)-3-1 Production of Chimeric Antibody B273

$1.2 \times 10^9$ cells of FreeStyle™ 293F cells (Invitrogen Corporation) in the logarithmic growth phase were seeded into 1.2 L of fresh FreeStyle™ 293 Expression Medium (Invitrogen Corporation) and cultured for 1 hour by shaking at 90 rpm at 37° C. in an 8% $CO_2$ incubator. 3.6 mg of polyethyleneimine (Polyscience #24765) was dissolved in 20 ml of Opti-Pro™ SFM medium (Invitrogen Corporation). Subsequently, pEF1FCCU/B273H (0.4 mg) and pEF6KCL/B273L (0.8 mg) prepared with PureLink™ HiPure Plasmid Kit (Invitrogen Corporation) were suspended in 20 ml of Opti-Pro™ SFM medium. Then, 20 ml of the obtained expression vectors/Opti-Pro™ SFM mixed liquid was added to 20 ml of the obtained polyethyleneimine/Opti-Pro™ SFM mixed liquid, and the resulting mixture was gently stirred and then left for 5 minutes. Thereafter, the mixture was added to the FreeStyle™ 293F cells, and culture shaking at 90 rpm was performed for 7 days at 37° C. in an 8% $CO_2$ incubator. The resulting culture supernatant was filtered through a disposable capsule filter (Advantec #CCS-045-E1H).

A chimeric antibody B273 obtained by a combination of pEF1FCCU/B273H and pEF6KCL/B273L was named "cB273".

2)-3-2 Purification of cB273

The culture supernatant obtained in the above 2)-3-1 was purified by a two-step process including rProtein A affinity chromatography (at 4 to 6° C.) and ceramic hydroxyapatite (at room temperature). A buffer replacement step after the purification by rProtein A affinity chromatography and after the purification by ceramic hydroxyapatite was performed at room temperature. First, 1100 to 1200 ml of the culture supernatant was applied to MabSelect SuRe™ (manufactured by GE Healthcare Bio-Sciences Co., Ltd., two HiTrap™ columns (volume: 1 ml) connected in series) equilibrated with PBS. After all culture solution was poured into the column, the column was washed with 15 to 30 ml of PBS. Subsequently, elution was performed with a 2 M arginine hydrochloride solution (pH 4.0), and a fraction containing the antibody was collected. The fraction was applied to a desalting column (manufactured by GE Healthcare Bio-Sciences Co., Ltd., two HiTrap™ desalting columns (volume: 5 ml) connected in series), whereby the buffer was replaced with a buffer containing 5 mM sodium phosphate, 50 mM MES, and 20 mM NaCl at pH 6.5. Further, the antibody solution subjected to buffer replacement was applied to a ceramic hydroxyapatite column (Japan Bio-Rad Laboratories, Inc., Bio-Scale CHT2-1 hydroxyapatite column (volume: 2 ml)) equilibrated with a buffer containing 5 mM NaPi, 50 mM MES, and 20 mM NaCl at pH 6.5. Then, linear concentration gradient elution with sodium chloride was performed, and a fraction containing the antibody was collected. The fraction was applied to a desalting column (manufactured by GE Healthcare Bio-Sciences Co., Ltd., two HiTrap™ desalting columns (volume: 5 ml) connected in series), whereby the liquid was replaced with CBS (10 mM citrate buffer containing 140 mM sodium chloride, pH 6.0). Finally, the resulting solution was concentrated using Centrifugal UF Filter Device VIVASPIN® 20 (fractional molecular weight: 30 K, Sartorius Co., Ltd., at 4° C.), and the concentration of IgG was adjusted to 1.0 mg/ml or more, and the thus obtained solution was used as a purified sample.

Example 3 Measurement of Activity of Human Chimeric B273 (cB273) Antibody (In Vitro)

Figures 1, 13:
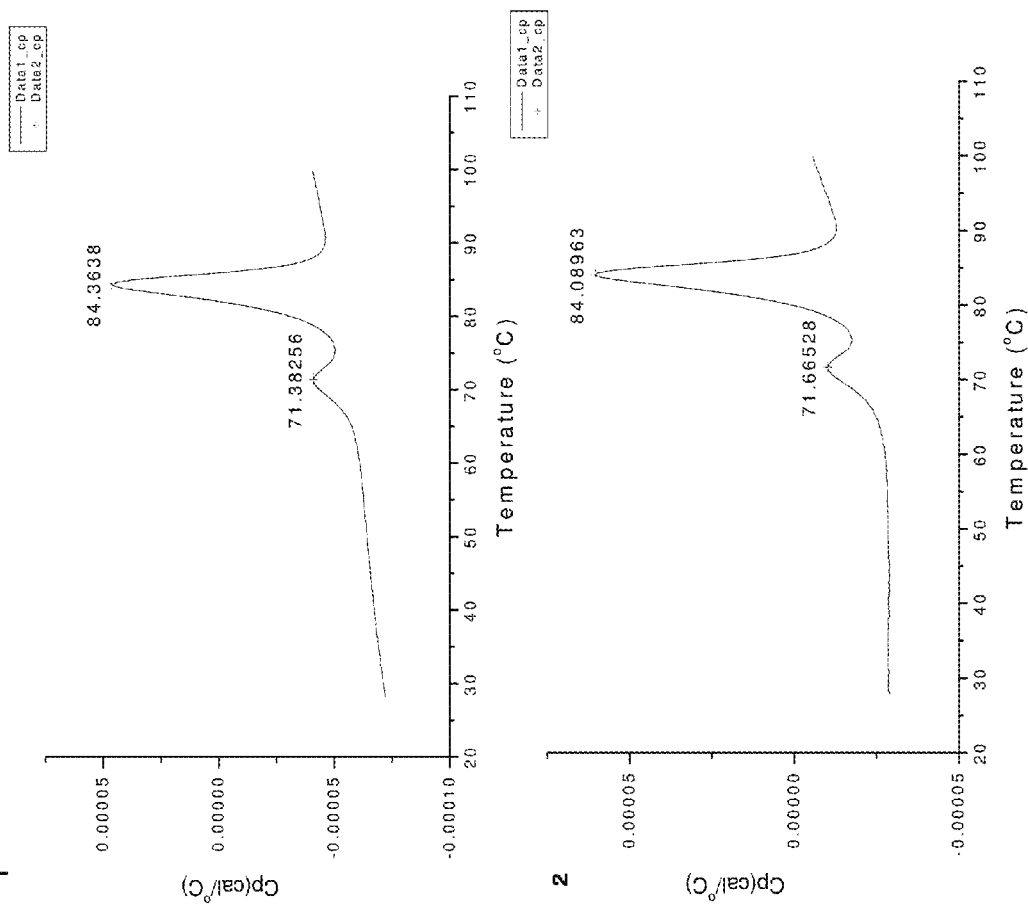
Figures 2, 13:
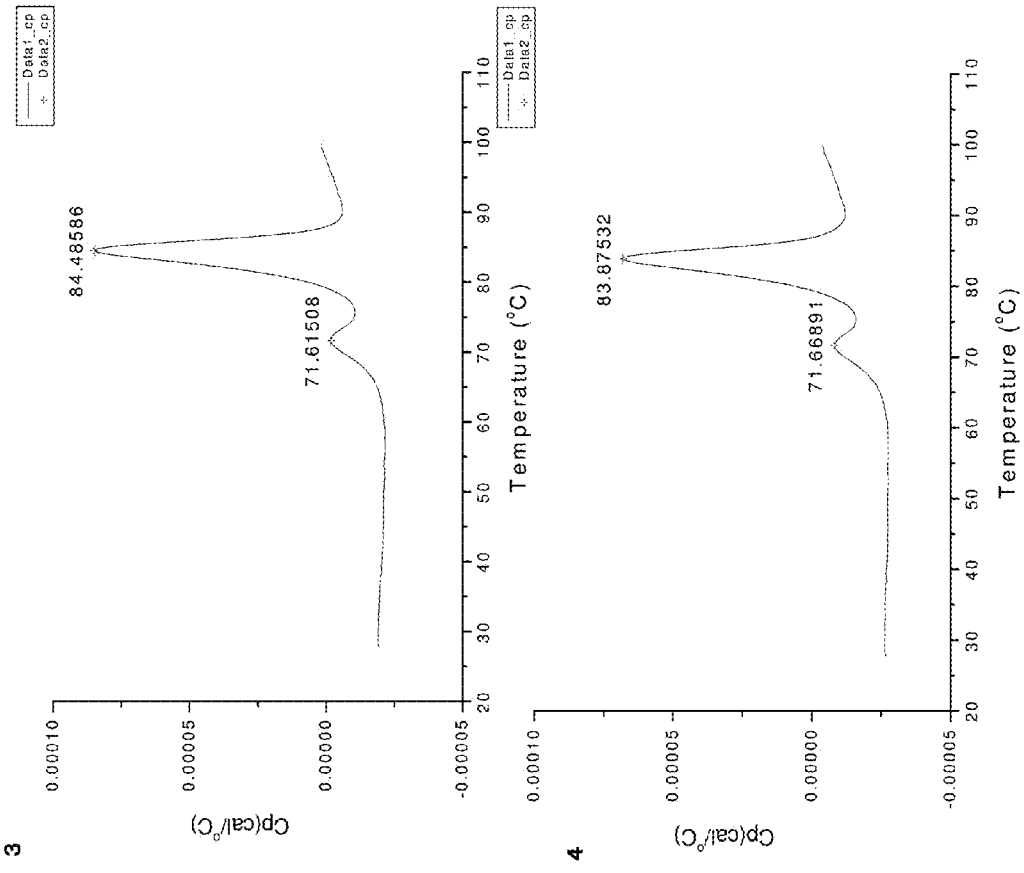

3)-1 Study of Selective Binding Property of cB273 Antibody to Human DR5 Extracellular Domain The binding property of cB273 to extracellular domain proteins of human TRAIL R1 to R4 and mouse TRAIL R2 (manufactured by R&D Systems, Inc.) was studied by a direct ELISA method described below. First, each of the extracellular domain proteins of TRAIL Rs was diluted to 1 μg/ml with PBS, and the diluted solution was dispensed at 50 μl/well into an immunoplate (manufactured by Nunc, Inc., #442404), and the plate was left to stand overnight at 4° C., whereby the protein was adsorbed to the plate. On the next day, the liquid in each well was removed and each well was washed once with PBS. Thereafter, in order to suppress the non-specific adsorption of proteins, PBS containing 3% fetal bovine serum was dispensed at 200 μl/well, and the plate was left to stand at room temperature for 1.5 hours. The liquid in each well was removed and cB273 or soluble human TRAIL (manufactured by ALEXIS Corporation, #ALX-522-003) diluted with PBS containing 3% fetal bovine serum was added thereto at 50 µl/well. After the plate was left to stand at room temperature for 1.5 hours, PBS was added to each well, and then, the liquid in the well was removed and the well was washed twice with PBS. Then, to the well to which the cB273 antibody was added, goat anti-Human IgG F(ab')₂ fragment specific, peroxidase conjugated (manufactured by Jackson ImmunoResearch Laboratories, Inc., #109-035-097) diluted 2500-fold with PBS containing 3% fetal bovine serum was added at 50 µl/well, and to the well to which the soluble TRAIL was added, anti-FLAG M2 monoclonal antibody-peroxidase conjugate diluted 2000-fold was added at 50 µl/well, and the plate was left to stand at room temperature for 1 hour. After PBS was added to each well, the liquid in the well was removed, and the well was washed twice with PBS. Thereafter, an OPD color developing liquid was added at 100 µl/well, whereby a color was developed. Then, 1 M HCl was added at 100 µl/well, whereby the color developing reaction was stopped. Thereafter, the absorbance at 492 nm was measured using a plate reader. FIG. 2A shows the results for cB273, and FIG. 2B shows the results for the soluble TRAIL. The data in the graphs are expressed by a mean±standard deviation (n=3). As a result, it was shown that cB273 selectively binds to the extracellular domain of human TRAIL R2.

3)-2 Evaluation of Binding Activity of cB273 Antibody Using Biacore™

3)-2-1 Preparation of Human DR5 Extracellular Domain Protein

3)-2-1-1 Production of DR5 Extracellular Domain Protein Expression Vector

In order to construct a vector which expresses a region (hereinafter referred to as "sDR5") composed of an amino acid sequence shown by amino acid numbers 1 to 130 of human DR5 represented by SEQ ID NO: 23 in the Sequence Listing, a PCR reaction was performed using a primer set for amplifying sDR5:

DR5 Ndefw: 5'-gtggcatatggctctgatcacccaacaa-3' (SEQ ID NO: 24 in the Sequence Listing) and DR5 Xhorv: 5'-cgcctcgagtgattctttgtggacaca-3' (SEQ ID NO: 25 in the Sequence Listing) and also using a cDNA encoding a human DR5 extracellular domain as a template. The resulting PCR product was cleaved with NdeI and XhoI and cloned into the NdeI/XhoI site of pET21b(+) (manufactured by Novagen, Inc.) (hereinafter abbreviated as "pET21b(+)-sDR5"). Further, a recombinant protein expressed by "pET21b(+)-sDR5" is referred to as "rsDR5" (SEQ ID NO: 26 in the Sequence Listing) hereinafter and in the drawings.

3)-2-1-2 Production of DR5 Extracellular Domain Protein (rsDR5)

*Escherichia coli* Origami™ B (DE3) (manufactured by Novagen, Inc.) was transformed with the expression plasmid pET21b(+)-sDR5 and cultured in 2-YT medium supplemented with 100 µg/ml ampicillin (manufactured by Sigma Co., Ltd.) and 15 µg/ml kanamycin (manufactured by Wako Pure Chemical Industries, Ltd.), and the expression of a partial protein of DR5 was induced by the addition of 0.5 mM IPTG. The cells were collected by centrifugation at 6000 rpm for 20 minutes and suspended in a binding buffer (50 mM Tris-HCl pH 7.5, 300 mM NaCl), followed by ultrasonic homogenization on ice. The resulting homogenate was centrifuged at 25000 rpm for 20 minutes. The supernatant was recovered and applied to Ni-NTA (manufactured by Invitrogen Corporation). After washing was performed with the binding buffer, elution was performed with an elution buffer (50 mM Tris-HCl pH 7.5, 300 mM NaCl and 300 mM imidazole). The eluted sample was dialyzed with a dialysis buffer (50 mM Tris-HCl pH 8.0, 20 mM NaCl) and applied to MONO Q, and gradient elution was performed with an elution buffer (50 mM Tris-HCl pH 8.0, 1 M NaCl). The eluted sample was further purified by gel filtration column chromatography (Superdex® 75 16/60, manufactured by GE Healthcare Bio-Sciences Co., Ltd.) using PBS as a solvent. The concentration of the thus obtained recombinant protein was measured at UV 280 nm (molar absorbance constant: 14855).

3)-2-2 Measurement of Binding Activity Using Biacore™

Figure 3:
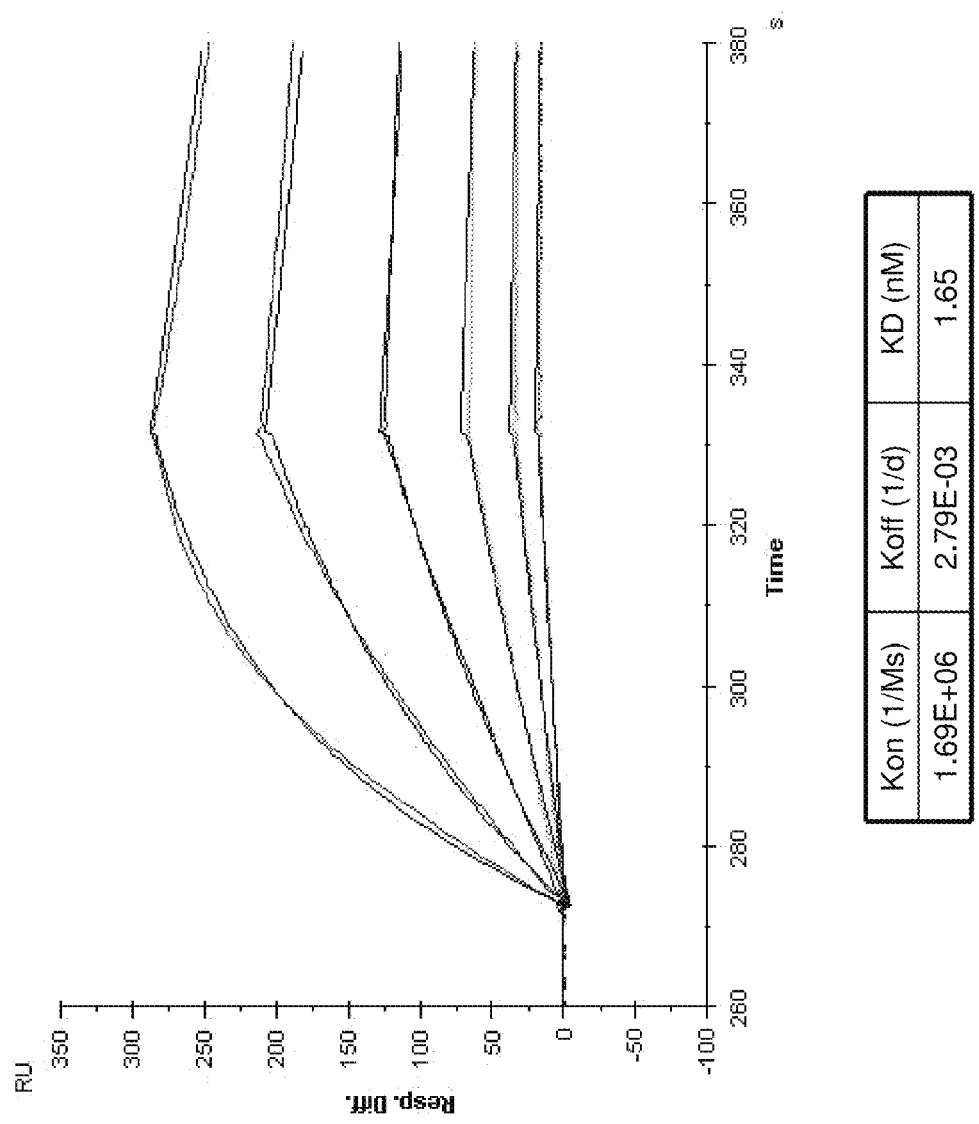
FIG. 3 is a figure showing the binding activity of a cB273 antibody to human DR5 using Biacore™. On the upper side of the figure, a measurement chart is shown, in which the ordinate represents resonance units (RU), and the abscissa represents time (sec). On the lower side of the figure, Kon, Koff, and KD values of the cB273 antibody calculated using analysis software are shown.

The dissociation constant of each of the cB273 antibody and rsDR5 was measured using Biacore™ 3000 (GE Healthcare Bio-Sciences Co., Ltd.) by a capture method in which an antibody is captured by an immobilized anti-human IgG (Fc) antibody and the measurement is performed using an antigen as an analyte. The anti-human IgG (Fc) antibody (Human Antibody Capture Kit, GE Healthcare Bio-Sciences Co., Ltd.) was covalently immobilized onto a sensor chip CM5 (BIAcore, Inc.) at about 8000 RU by an amine coupling method. Immobilization was performed also onto a reference cell in the same manner. As a running buffer, HBS-EP (10 mM HEPES pH 7.4, 0.15 M NaCl, 3 mM EDTA, and 0.05% surfactant P20) was used. Onto the chip having the anti-human IgG (Fc) antibody immobilized thereon, a 50 nM cB273 antibody solution was added at a flow rate of 10 µl/min for 60 seconds, and then, a dilution series of rsDR5 (0.63-20 nM) was added at a flow rate of 30 µl/min for 60 seconds, and subsequently, the dissociation phase was monitored for 300 seconds. As a regeneration solution, 3 M magnesium chloride was added at a flow rate of 10 µl/min for 30 seconds. In the data analysis, analysis software (BIAevaluation software, version 3.1) was used with a one-to-one binding model, and an association rate constant (kon), a dissociation rate constant (koff), and a dissociation constant (KD; KD=koff/kon) were calculated. The results obtained by the measurement using Biacore™ for the cB273 antibody are shown in FIG. 3.

3)-3 In Vitro Cytocidal Effect of cB273 Antibody on Human Cancer Cell Lines

The cytocidal effect of the cB273 antibody on various cancer cell lines was studied by the following method. A2780, SK-OV-3, SK-CO-1, Caov-3, and NIH:OVCAR-5 (all of which are human ovarian cancer cell lines), HCT-15, COLO 205, HT29, SW480, SW620, DLD-1, COLO 201, and WiDr (all of which are human colon cancer cell lines), NCI-H1975, NCI-H292, NCI-H460, and NCI-H358 (all of which are human lung cancer cell lines), MDA-MB-231 and ZR-75-1 (both of which are human breast cancer cell lines) were purchased from American Type Culture Collection (ATCC). Each of these cell lines was prepared at $1\times10^5$ cells/ml with a medium containing 10% fetal bovine serum (manufactured by HyClone Laboratories, Inc.) (hereinafter referred to as "the medium") and seeded at 50 µl/well in a white clear bottom 96-well microplate (manufactured by Corning Incorporated). The cB273 antibody was prepared at 20000 ng/ml with a 1 µg/ml solution of a secondary antibody (goat anti-human IgG Fc, manufactured by MP Biomedicals, LLC.), and then prepared at 2000, 200, 20, and 2 ng/ml with the medium, and each of the resulting solutions was added to the plate at 50 µl/well (the final concentration of the antibody: 10000, 1000, 100, 10, and 1 ng/ml). After the plate was incubated under the conditions of 37° C. and 5% $CO_2$ for 72 hours, the amount of ATP derived from viable cells in each well was measured using a CellTiter-Glo® Luminescent Cell Viability Assay kit (manufactured by Promega Corporation, #G7571) by a luminometer (manufactured by Berthold Technologies) according to the attached protocol.

Figure 4:
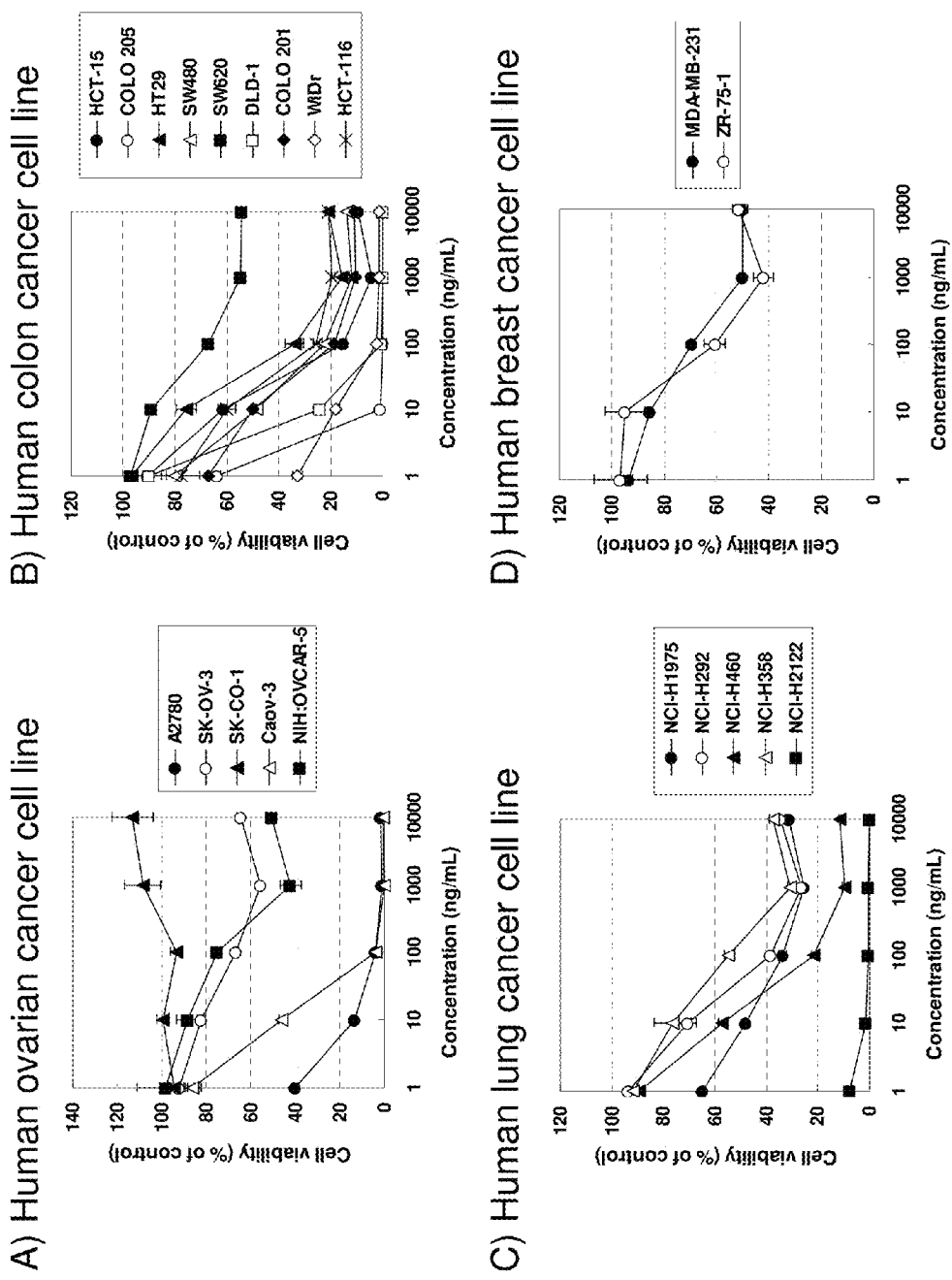
FIG. 4 is a figure showing the in vitro cytocidal effect of a cB273 antibody on human cancer cell lines. A) shows the results for a human ovarian cancer cell line, B) shows the results for a human colon cancer cell line, C) shows the results for a human lung cancer cell line, and D) shows the results for a human breast cancer cell line.

A well to which the medium and the cell suspension were added was prepared as a negative control well and a well to which only the medium was added was prepared as a background well, and cell viability in each test well was calculated. In FIG. 4, a mean±standard error (n=3) of the cell viability for each cancer cell line treated with the cB273 antibody is shown. The cB273 antibody exhibited a cytocidal activity against the cell lines except for SK-CO-1.

Figure 5:
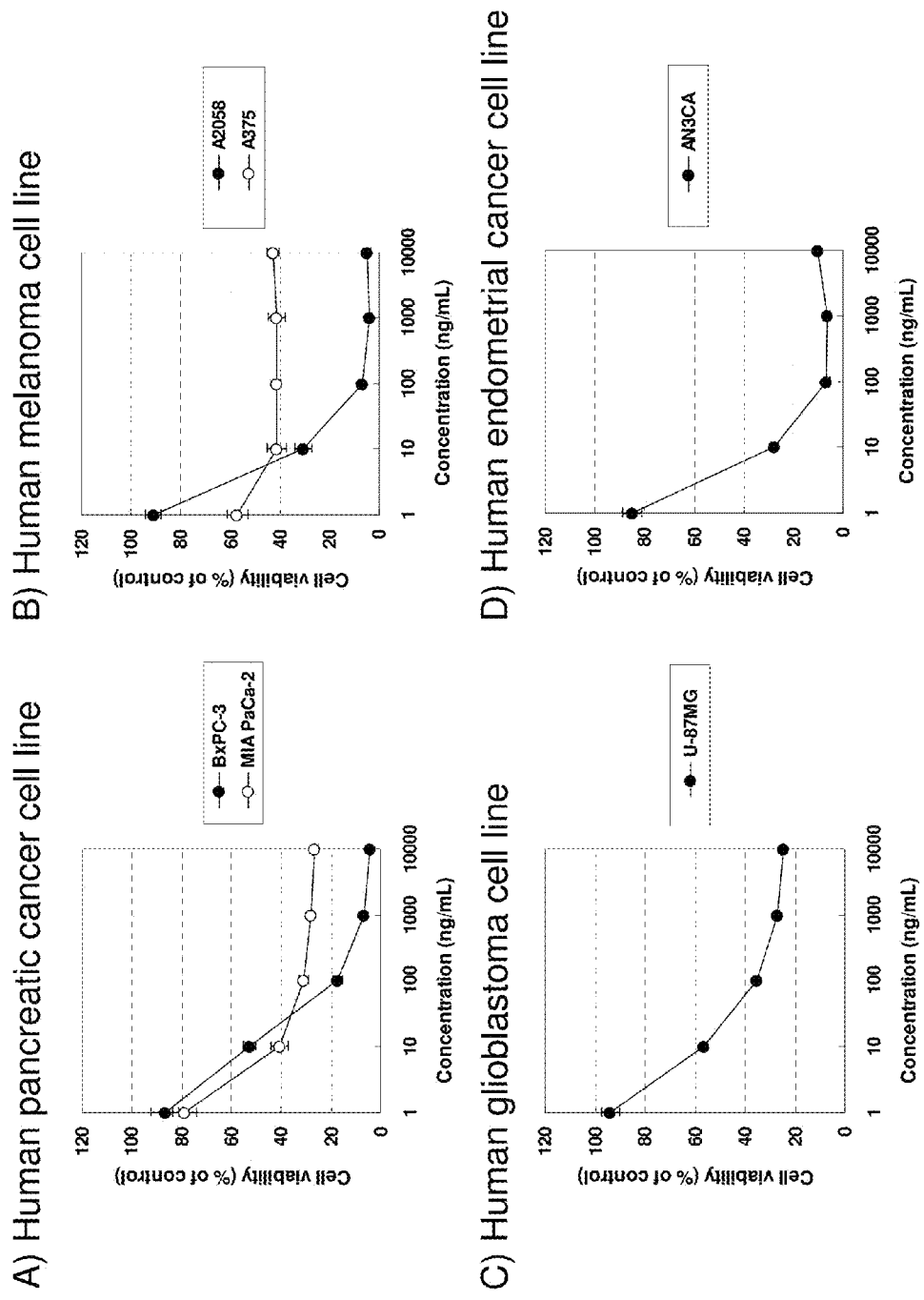
FIG. 5 is a figure showing the in vitro cytocidal effect of a cB273 antibody on human cancer cell lines. A) shows the results for a human pancreatic cancer cell line, B) shows the results for a human melanoma cell line, C) shows the results for a human glioblastoma cell line, and D) shows the results for a human endometrial cancer cell line.

An in vitro cytocidal effect on various cancer cell lines was studied using BxPC-3 and MIA PaCa-2 (both of which are human pancreatic cancer cell lines), A2058 and A375 (both of which are human melanoma cell lines), U-87MG (a human glioblastoma cell line), AN3CA (a human endometrial cancer cell line) as test subjects. Each of these cell lines was prepared at $4.4 \times 10^4$ cells/ml with a medium containing 10% FBS and added at 45 µl/well in a white clear bottom 96-well microplate (manufactured by Corning Incorporated), and the plate was incubated overnight under the conditions of 37° C. and 5% $CO_2$. The cB273 antibody was mixed with the same concentration of goat anti-human IgG Fc (manufactured by MP Biomedicals, LLC.), and then the resulting mixture was added to the plate at 5 µl/well such that the final concentration of the cB273 antibody was from 10,000 to 1 ng/ml, and the plate was incubated under the conditions of 37° C. and 5% $CO_2$ for 24 hours. The amount of ATP derived from viable cells in each well was measured using a CellTiter-Glo® Luminescent Cell Viability Assay kit (manufactured by Promega Corporation, #G7571) by a luminometer (manufactured by Perkin Elmer Inc.) according to the attached protocol. Each graph shows the cell viability expressed by a mean±standard deviation (n=3). As a result, the cB273 antibody exhibited a cytocidal effect on all of the cancer cell lines studied (FIG. 5).

Example 4 Identification of Epitope of cB273 Antibody

4)-1 Production of cB273 Fab Fragment

The cB273 was dialyzed with PBS, and then diluted to 2 mg/ml with PBS and prepared to a final volume of 17 ml. Cysteine (manufactured by Sigma Co., Ltd.) prepared at 0.1 mM with PBS in an amount of 1.7 ml and papain (manufactured by Sigma Co., Ltd.) diluted to 0.1 mg/ml with PBS in an amount of 2.04 ml were added thereto, and the reaction was allowed to proceed at 37° C. for 5 hours. After 5 hours, N ethylmaleimide (manufactured by Tokyo Chemical Industry Co., Ltd.) dissolved at 120 mM in PBS in an amount of 6.33 ml was added thereto to stop the reaction. The reaction solution was added to Superdex® 200 26/60 (manufactured by GE Healthcare, Co., Ltd.) equilibrated with 50 mM Tris-HCl containing 20 mM NaCl, and 14 ml of a fraction corresponding to the Fab fragment was collected.

4)-2 Preparation of cB273 Fab Fragment-rsDR5 Complex Sample

The cB273 Fab fragment was concentrated to 9.46 mg/ml using Amicon® Ultra-15 (MWCO: 10 K) (manufactured by Millipore Co., Ltd.), and 2 ml of the thus concentrated cB273 Fab fragment was mixed with 2 ml of rsDR5 concentrated to 5.6 mg/ml using Amicon® Ultra-15 (MWCO: 3 K), and the resulting mixture was added to Superdex® 200 16/60 equilibrated with 20 mM Tris-HCl containing 50 mM NaCl. 8 ml of a fraction corresponding to the complex was collected.

4)-3 Crystallization and Structural Analysis of cB273 Fab Fragment-rsDR5 Complex The thus obtained rsDR5-cB273 Fab complex was concentrated to 25 mg/ml, which was used for crystallization. For crystallization, a vapor diffusion method was used. A solution obtained by adding an equal amount of a precipitant solution (6 to 8% (w/v) polyethylene glycol 4000, 20% (v/v) isopropanol, 0.1 M lithium chloride, 0.1 M citrate buffer (pH 5.6)) to 0.45 to 1.0 µl of a protein solution was placed in an airtight container, in which 0.45 ml of the precipitant solution had already been placed, such that both solutions did not come into contact with each other, and the container was left to stand at 22° C. After 3 days, a plate-shaped crystal (0.4 mm×0.3 mm×0.03 mm) was obtained.

The thus obtained crystal was immersed in the precipitant solution supplemented with 30% (v/v) glycerol, and then frozen in a nitrogen stream at −180° C. X-ray diffraction data were collected in a nitrogen stream at 95 K on BL17A at the Photon Factory of the Institute of Materials Structure Science in the High Energy Accelerator Research Organization. From the obtained diffraction image, a diffraction intensity was quantified using HKL-2000 software (produced by HKL Research, Inc.), and crystal structure factors were calculated. The obtained crystal belonged to the monoclinic system, the space group was C2, and the crystal had unit-cell parameters: a=152.0 Å, b=75.5 Å, c=116.3 Å, and β=110.2.

A molecular replacement method was carried out using the thus obtained structure factors and the three-dimensional structure coordinates of DR5 (PDB code: 2H9G) and Herceptin® Fab (PDB code: 1N8Z), and phases were determined. In the calculation, a software phaser (CCP4: Collaborative Computational Project No. 4) was used. The crystal contained two complexes in the asymmetric unit.

The structure was refined using CNX software (Accerlys Inc.), and the model was corrected using the Coot software. This procedure was repeated, and a final R value of 25.0% and a free R value of 28.7% were obtained at a resolution of 2.1 Å. The final model was composed of two complexes, and contains the amino acid residues 1 to 218 of the cB273 Fab L chain (both molecules), the amino acid residues 1 to 222 of the H chain (both molecules), the amino acid residues 18 to 92 and 98 to 127 of one molecule of the DR5 among the two molecules, the amino acid residues 21 to 92 and 98 to 127 of the other molecule of the DR5, and 324 water molecules. No clear electron density was observed for the amino acid residues 93 to 97 of the DR5, 17 or 20 residues in the N terminus of the DR5, 6 residues and a His tag in the C terminus of the DR5, one residue in the C terminus of the cB273 Fab L chain and 5 residues in the C terminus of the cB273 Fab H chain, and therefore, a model was not constructed. The model was validated by a Ramachandran plot, and it was found that only Val 56 of the L chain was located outside the allowed region, and this amino acid Val 56 has a structure characteristic of CDR L2.

Figure 6:
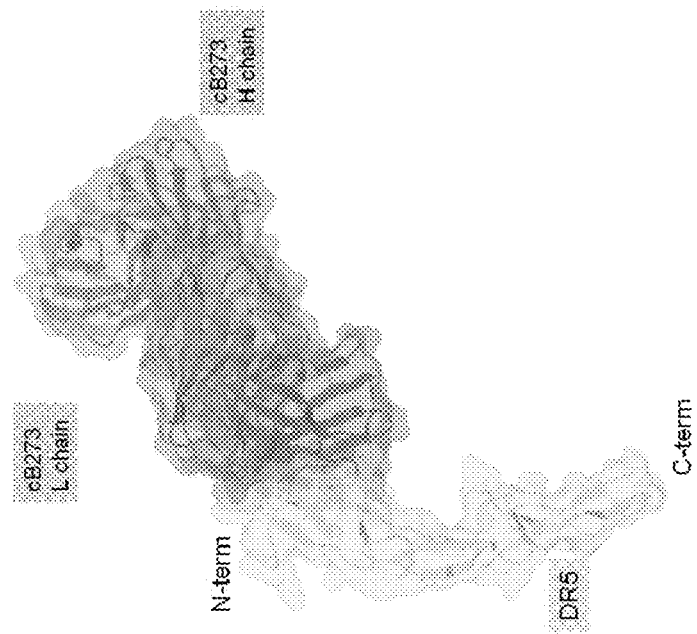
FIG. 6 is a view showing a DR5-cB273 Fab complex structure.

The interactions determined between the DR5 and cB273 Fab were substantially equal in the two molecules in the asymmetric unit. The amino acid residues (the position of each amino acid residue corresponds to that of SEQ ID NO: 23) of the DR5 which lay at a distance of 4 Å or less from the cB273 Fab were as follows: Gly26, Ile34, Glu36, Asp37, Gly38, Asp56, Leu57, Leu58, Phe59, Leu61, and Arg62. FIG. 6 shows a ribbon model of the entire complex and the surface thereof, and FIG. 7 shows the interaction between the DR5 and the H or L chain of the cB273 Fab.

Example 5 Humanization of cB273 Antibody (1)

5)-1 Designing of Humanized B273 (hB273)

5)-1-1 Molecular Modeling of B273 Variable Regions

The molecular modeling of the B273 variable regions was performed according to a method generally known as homology modeling (Methods in Enzymology, 203, 121-153, (1991)). The primary sequences (three-dimensional structures derived from the X-ray crystal structures are available) of the variable regions of human immunoglobulin registered in Protein Data Bank (Nuc. Acid Res., 28, 235-242 (2000)) were compared with the B273 variable regions determined above. As a result, 1T66 was selected as a sequence having the highest sequence homology with the B273 light chain variable region. Further, 1XIW was selected as a sequence having the highest sequence homology with the B273 heavy chain variable region. The three-dimensional structure of a framework region was prepared based on a "framework model" by combining the coordinates of 1T66 and 1XIW corresponding to the B273 light chain and heavy chain. For the B273 CDRs, CDRL1, CDRL2, CDRL3, CDRH1, and CDRH2 were assigned to clusters 16A, 7A, 9A, 10A, and 10A, respectively, according to the classification of Thornton et al. (J. Mol. Biol., 263, 800-815, (1996)). The CDRH3 was classified in k(11)—according to the H3 rules (FEBS letters, 399, 1-8 (1996)). Subsequently, the representative conformation of each CDR was incorporated in the framework model.

Finally, in order to obtain a possible molecular model of the B273 variable region in terms of energy, an energy calculation was performed for excluding disadvantageous interatomic contact. The above procedure was carried out using the commercially available protein tertiary structure prediction program Prime and coordinate search program MacroModel (Schrödinger, LLC).

5)-1-2 Designing of Amino Acid Sequence of Humanized B273

A humanized B273 antibody was constructed according to a method generally known as CDR grafting (Proc. Natl. Acad. Sci. USA, 86, 10029-10033 (1989)). An acceptor antibody was selected based on the amino acid homology within the framework region.

The sequence of the framework region of B273 was compared with all human framework sequences in the Kabat Database (Nuc. Acid Res., 29, 205-206 (2001)) of antibody amino acid sequences. As a result, a HuMc3 antibody was selected as an acceptor based on a sequence homology of 76% in the framework region. The amino acid residues in the framework region of HuMc3 were aligned with the amino acid residues of B273, and the positions where different amino acids were used were identified. The positions of these residues were analyzed using the three-dimensional model of B273 constructed above. Then, donor residues to be grafted onto the acceptor were selected according to the criteria provided by Queen et al. (Proc. Natl. Acad. Sci. USA, 86, 10029-10033 (1989)).

By transferring some selected donor residues to the acceptor antibody, humanized B273 sequences were constructed as described in the following Example.

5)-1-2 Humanization of B273 Light Chain

5)-1-2-1 hB273_L1-Type Light Chain:

A humanized B273 light chain designed by substituting amino acid numbers 22 (valine), 27 (threonine), 34 (serine), 35 (leucine), 37 (aspartic acid), 38 (glutamine), 70 (lysine), 108 (leucine), 110 (isoleucine), 112 (phenylalanine), 125 (glycine), and 129 (leucine) of the cB273 light chain represented by SEQ ID NO: 16 in the Sequence Listing with isoleucine, serine, threonine, proline, glutamic acid, proline, glutamine, valine, valine, tyrosine, proline, and valine, respectively, was named "hB273_L1-type light chain".

A nucleotide sequence encoding the hB273_L1-type light chain is represented by SEQ ID NO: 27 in the Sequence Listing. Further, the amino acid sequence of the hB273_L1-type light chain is represented by SEQ ID NO: 28 in the Sequence Listing. The sequences of SEQ ID NOS: 27 and 28 are also shown in FIG. 32.

5)-1-2-2 hB273_L2-Type Light Chain:

A humanized B273 light chain designed by substituting amino acid numbers 37 (aspartic acid), 38 (glutamine), 108 (leucine), 110 (isoleucine), 125 (glycine), and 129 (leucine) of the cB273 light chain represented by SEQ ID NO: 16 in the Sequence Listing with glutamic acid, proline, valine, valine, proline, and valine, respectively, was named "hB273_L2-type light chain".

A nucleotide sequence encoding the hB273_L2-type light chain is represented by SEQ ID NO: 29 in the Sequence Listing. Further, the amino acid sequence of the hB273_L2-type light chain is represented by SEQ ID NO: 30 in the Sequence Listing. The sequences of SEQ ID NOS: 29 and 30 are also shown in FIG. 33.

5)-1-2-3 hB273_L3-Type Light Chain:

A humanized B273 light chain designed by substituting amino acid numbers 37 (aspartic acid), 38 (glutamine), 108 (leucine), 110 (isoleucine), and 129 (leucine) of the cB273 light chain represented by SEQ ID NO: 16 in the Sequence Listing with glutamic acid, proline, valine, valine, and valine, respectively, was named "hB273_L3-type light chain".

A nucleotide sequence encoding the hB273_L3-type light chain is represented by SEQ ID NO: 31 in the Sequence Listing. Further, the amino acid sequence of the hB273_L3-type light chain is represented by SEQ ID NO: 32 in the Sequence Listing. The sequences of SEQ ID NOS: 31 and 32 are also shown in FIG. 34.

5)-1-3 Humanization of B273 Heavy Chain

5)-1-3-1 hB273_H1-Type Heavy Chain:

A humanized B273 heavy chain designed by substituting amino acid numbers 20 (glutamic acid), 24 (glutamine), 28 (proline), 30 (leucine), 31 (valine), 39 (isoleucine), 56 (methionine), 57 (lysine), 59 (serine), 60 (histidine), 62 (lysine), 63 (serine), 67 (isoleucine), 86 (lysine), 87 (alanine), 95 (serine), 96 (threonine), 99 (histidine), 103 (leucine), 106 (threonine), 110 (serine), 114 (phenylalanine), 116 (glycine), 136 (threonine), and 137 (leucine) of the cB273 heavy chain represented by SEQ ID NO: 20 in the Sequence Listing with glutamine, valine, alanine, valine, lysine, valine, valine, arginine, alanine, proline, methionine, glycine, methionine, arginine, valine, threonine, serine, tyrosine, serine, arginine, threonine, tyrosine, alanine, leucine, and valine, respectively, was named "hB273_H1-type heavy chain".

A nucleotide sequence encoding the hB273_H1-type heavy chain is represented by SEQ ID NO: 33 in the Sequence Listing. Further, the amino acid sequence of the hB273_H1-type heavy chain is represented by SEQ ID NO: 34 in the Sequence Listing. The sequences of SEQ ID NOS: 33 and 34 are also shown in FIG. 35.

5)-1-3-2 hB273_H2-Type Heavy Chain:

A humanized B273 heavy chain designed by substituting amino acid numbers 20 (glutamic acid), 24 (glutamine), 28 (proline), 30 (leucine), 31 (valine), 39 (isoleucine), 60 (histidine), 62 (lysine), 95 (serine), 96 (threonine), 99 (histidine), 103 (leucine), 106 (threonine), 110 (serine), 116 (glycine), 136 (threonine), and 137 (leucine) of the cB273 heavy chain represented by SEQ ID NO: 20 in the Sequence Listing with glutamine, valine, alanine, valine, lysine, valine, proline, methionine, threonine, serine, tyrosine, serine, arginine, threonine, alanine, leucine, and valine, respectively, was named "hB273_H2-type heavy chain".

A nucleotide sequence encoding the hB273_H2-type heavy chain is represented by SEQ ID NO: 35 in the Sequence Listing. Further, the amino acid sequence of the hB273_H2-type heavy chain is represented by SEQ ID NO:

36 in the Sequence Listing. The sequences of SEQ ID NOS: 35 and 36 are also shown in FIG. 36.

5)-1-3-3 hB273_H3-Type Heavy Chain:

A humanized B273 heavy chain designed by substituting amino acid numbers 24 (glutamine), 28 (proline), 30 (leucine), 31 (valine), 39 (isoleucine), 60 (histidine), 95 (serine), 96 (threonine), 103 (leucine), 106 (threonine), 110 (serine), 136 (threonine), and 137 (leucine) of the cB273 heavy chain represented by SEQ ID NO: 20 in the Sequence Listing with valine, alanine, valine, lysine, valine, proline, threonine, serine, serine, arginine, threonine, leucine, and valine, respectively, was named "hB273_H3-type heavy chain".

A nucleotide sequence encoding the hB273_H3-type heavy chain is represented by SEQ ID NO: 37 in the Sequence Listing. Further, the amino acid sequence of the hB273_H3-type heavy chain is represented by SEQ ID NO: 38 in the Sequence Listing. The sequences of SEQ ID NOS: 37 and 38 are also shown in FIG. 37.

5)-2 Construction of hB273_L1, hB273_L2, and hB273_L3-Type Light Chain Expression Vectors DNAs containing a gene encoding a hB273_L1, hB273_L2, or hB273_L3-type light chain variable region represented by amino acid numbers 21 to 134 of SEQ ID NO: 28, amino acid numbers 21 to 134 of SEQ ID NO: 30, or amino acid numbers 21 to 134 of SEQ ID NO: 32 were synthesized (GENEART, Inc. Artificial Gene Synthesis Service). Then, each of the DNA fragments obtained by cleaving the synthesized DNAs with the restriction enzymes NdeI and BsiWI was inserted into the universal humanized antibody light chain expression vector (pEF6KCL) at the site cleaved with the restriction enzymes NdeI and BsiWI, whereby hB273_L1, hB273_L2, and hB273_L3-type light chain expression vectors were constructed. The thus obtained expression vectors were named "pEF6KCL/hB273_L1", "pEF6KCL/hB273_L2", and "pEF6KCL/hB273_L3", respectively.

5)-3 Construction of hB273_H1, hB273_H2, and hB273_H3-Type Heavy Chain Expression Vectors DNAs containing a gene encoding a hB273_H1, hB273_H2, or hB273_H3-type heavy chain variable region represented by amino acid numbers 20 to 141 of SEQ ID NO: 34 in the Sequence Listing, amino acid numbers 20 to 141 of SEQ ID NO: 36, or amino acid numbers 20 to 141 of SEQ ID NO: 38 were synthesized (GENEART, Inc. Artificial Gene Synthesis Service). Then, each of the DNA fragments obtained by cleaving the synthesized DNAs with the restriction enzyme BlpI was inserted into the universal humanized antibody heavy chain expression vector (pEF1FCCU) at the site cleaved with the restriction enzyme BlpI, whereby hB273_H1, hB273_H2, and hB273_H3-type heavy chain expression vectors were constructed. The thus obtained expression vectors were named "pEF1FCCU/hB273_H1", "pEF1FCCU/hB273_H2", and "pEF1FCCU/hB273_H3", respectively.

5)-4 Preparation of Humanized Antibody

5)-4-1 Production of Humanized Antibody $1.2 \times 10^9$ cells of FreeStyle™ 293F cells (Invitrogen Corporation) in the logarithmic growth phase were seeded into 1.2 L of fresh FreeStyle™ 293 Expression Medium (Invitrogen Corporation) and cultured for 1 hour by shaking at 90 rpm at 37° C. in an 8% $CO_2$ incubator. 3.6 mg of polyethyleneimine (Polyscience #24765) was dissolved in 20 ml of Opti-Pro™ SFM medium (Invitrogen Corporation). Subsequently, a heavy chain expression vector (0.4 mg) and a light chain expression vector (0.8 mg) prepared with PureLink™ HiPure Plasmid Kit (Invitrogen Corporation) were suspended in 20 ml of Opti-Pro™ SFM medium. Then, 20 ml of the obtained expression vectors/Opti-Pro™ SFM mixed liquid was added to 20 ml of the obtained polyethyleneimine/Opti-Pro™ SFM mixed liquid, and the resulting mixture was gently stirred and then left for 5 minutes. Thereafter, the mixture was added to the FreeStyle™ 293F cells. After 3 hours, Z-VAD-FMK (PEPTIDE INSTITUTE, Inc.) was added thereto at a final concentration of 10 μM, and culture shaking at 90 rpm was performed for 7 days at 37° C. in an 8% $CO_2$ incubator. The resulting culture supernatant was filtered through a disposable capsule filter (Advantec #CCS-045-E1H).

A humanized antibody of cB273 obtained by a combination of pEF1FCCU/hB273_H1 and pEF6KCL/hB273_L1 was named "hB273_H1/hB273_L1", a humanized antibody of cB273 obtained by a combination of pEF1FCCU/hB273_H1 and pEF6KCL/hB273_L2 was named "hB273_H1/hB273_L2", a humanized antibody of cB273 obtained by a combination of pEF1FCCU/hB273_H1 and pEF6KCL/hB273_L3 was named "hB273_H1/hB273_L3", a humanized antibody of cB273 obtained by a combination of pEF1FCCU/hB273_H2 and pEF6KCL/hB273_L1 was named "hB273_H2/hB273_L1", a humanized antibody of cB273 obtained by a combination of pEF1FCCU/hB273_H2 and pEF6KCL/hB273_L2 was named "hB273_H2/hB273_L2", a humanized antibody of cB273 obtained by a combination of pEF1FCCU/hB273_H2 and pEF6KCL/hB273_L3 was named "hB273_H2/hB273_L3", a humanized antibody of cB273 obtained by a combination of pEF1FCCU/hB273_H3 and pEF6KCL/hB273_L1 was named "hB273_H3/hB273_L1", a humanized antibody of cB273 obtained by a combination of pEF1FCCU/hB273_H3 and pEF6KCL/hB273_L2 was named "hB273_H3/hB273_L2", and a humanized antibody of cB273 obtained by a combination of pEF1FCCU/hB273_H3 and pEF6KCL/hB273_L3 was named "hB273_H3/hB273_L3".

5)-4-2 Purification of Humanized Antibody

The culture supernatant obtained in the above 5)-4-1 was purified by a two-step process including rProtein A affinity chromatography (at 4 to 6° C.) and ceramic hydroxyapatite (at room temperature). A buffer replacement step after the purification by rProtein A affinity chromatography and after the purification by ceramic hydroxyapatite was performed at room temperature. First, 1100 to 1200 ml of the culture supernatant was applied to MabSelect SuRe™ (manufactured by GE Healthcare Bio-Sciences Co., Ltd., two HiTrap™ columns (volume: 1 ml) connected in series) equilibrated with PBS. After all culture solution was poured into the column, the column was washed with 15 to 30 ml of PBS. Subsequently, elution was performed with a 2 M arginine hydrochloride solution (pH 4.0), and a fraction containing the antibody was collected. The fraction was applied to a desalting column (manufactured by GE Healthcare Bio-Sciences Co., Ltd., two HiTrap™ desalting columns (volume: 5 ml) connected in series), whereby the buffer was replaced with a buffer containing 5 mM sodium phosphate, 50 mM MES, and 20 mM NaCl at pH 6.5. Further, the antibody solution subjected to buffer replacement was applied to a ceramic hydroxyapatite column (Japan Bio-Rad Laboratories, Inc., Bio-Scale™ CHT™ 2-1 hydroxyapatite column (volume: 2 ml)) equilibrated with a buffer containing 5 mM NaPi, 50 mM MES, and 20 mM NaCl at pH 6.5. Then, linear concentration gradient elution with sodium chloride was performed, and a fraction containing the antibody was collected. The fraction was applied to a desalting column (manufactured by GE Healthcare Bio-Sciences Co., Ltd., two HiTrap™ desalting columns (volume: 5 ml) connected in series), whereby the liquid was replaced with CBS (10 mM citrate buffer containing 140 mM sodium chloride, pH 6.0). Finally, the resulting solution was concentrated using Centrifugal UF Filter Device VIVASPIN® 20 (fractional molecular weight: 30 K, Sartorius Co., Ltd., at 4° C.), and the concentration of IgG was adjusted to 1.0 mg/ml or more, and the thus obtained solution was used as a purified sample.

Example 6 Measurement of Activity of Humanized B273 (hB273) Antibody (1)

6)-1 Evaluation of Binding Activity of hB273 Antibody Using Biacore™

The dissociation constant of each of the humanized anti-DR5 antibodies and rsDR5 was measured using Biacore™ T100 (GE Healthcare Bio-Sciences Co., Ltd.) by a capture method in which an antibody is captured by an immobilized anti-human IgG (Fc) antibody and the measurement is performed using an antigen as an analyte. The anti-human IgG (Fc) antibody (Human Antibody Capture Kit, GE Healthcare Bio-Sciences Co., Ltd.) was covalently immobilized onto a sensor chip CM5 (BIAcore, Inc.) at about 10,000 RU by an amine coupling method. Immobilization was also performed onto a reference cell in the same manner. As a running buffer, HBS-EP (10 mM HEPES pH 7.4, 0.15 M NaCl, 3 mM EDTA, and 0.05% surfactant P20) was used. Onto the chip having the anti-human IgG (Fc) antibody immobilized thereon, an antibody solution at about 20 nM was added at a flow rate of 10 µl/min for 60 seconds, and then, a dilution series of rsDR5 (3.13-50 nM) was added at a flow rate of 30 µl/min for 120 seconds, and subsequently, the dissociation phase was monitored for 180 seconds. As a regeneration solution, 3 M magnesium chloride was added at a flow rate of 10 µl/min for 30 seconds. In the data analysis, analysis software (Biacore™ T100 Evaluation software, version 2.0.1) was used with a one-to-one binding model, and an association rate constant (kon), a dissociation rate constant (koff), and a dissociation constant (KD; KD=koff/kon) were calculated. The results obtained by the measurement using Biacore™ for the 9 types of humanized DR5 antibodies are shown in FIG. 8.

Figure 9:
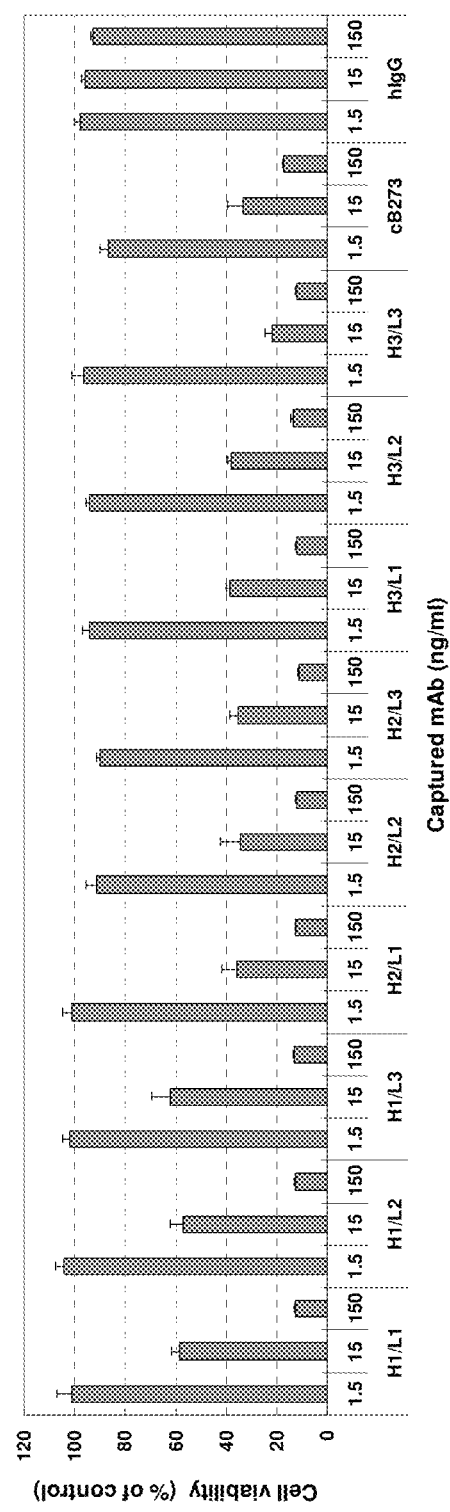
FIG. 9 is a figure showing the in vitro cytocidal activity of hB273 antibodies against Jurkat cells which are a human T lymphoma-derived cell line.

6)-2 In Vitro Cytocidal Activity of hB273 Antibody Against Human Cancer Cell Line AffiniPure F(ab')$_2$ fragment goat anti-human IgG Fc fragment specific (manufactured by Jackson ImmunoResearch Laboratories, Inc., #109-006-098) prepared at 50 µg/ml with 50 mM Tris-HCl (pH 8.5) was dispensed at 45 µL/well in a 96-well microplate (manufactured by Corning Incorporated), and the plate was left to stand overnight at 4° C. After each well was washed twice with PBS, the culture supernatant of 293F which was allowed to produce the antibody in 5)-4-1, the purified cB273 antibody (Example 2-3-2), or commercially available human IgG (manufactured by Jackson ImmunoResearch Laboratories, Inc., #009-000-003) was added at 50 µL/well such that the final concentration of the antibody was from 150 to 1.5 ng/ml, and the plate was left to stand overnight at 4° C. After each well was washed twice with PBS, Jurkat cells prepared at 4.0×10$^4$ cells/ml in RPMI 1640 medium containing 10% FBS were added at 50 µl/well and cultured under the conditions of 37° C. and 5% $CO_2$ for 23 hours. The amount of ATP derived from viable cells was quantitatively determined using a CellTiter-Glo® luminescent cell viability assay kit (manufactured by Promega Corporation, #G7571), and the cytocidal effect of each of the hB273 antibodies was evaluated by taking the value obtained from a well to which the medium was added in place of the antibody solution as 100%. As a result, as shown in FIG. 9, with respect to the humanization of the B273 heavy chain, a tendency was observed that the antibodies comprising the H1-type heavy chain exhibited a slightly lower cytocidal effect than the antibodies comprising the H2 or H3-type heavy chain. On the other hand, with respect to the humanization of the B273 light chain, it was found that the antibodies comprising any of the designed L1, L2, and L3-type light chains can exhibit substantially the same cytocidal effect.

Example 7 Humanization of the cB273 Antibody (2)

7)-1 Designing of Humanized B273 (hB273)

7)-1-1 Designing of Amino Acid Sequence of Humanized B273

Based on the results of the designing of the humanized antibodies (1) shown in Examples 5 and 6, by transferring some donor residues to the acceptor antibody, humanized B273 sequences were constructed as described in the following Example.

7)-1-2 Designing of Amino Acid Sequence of Humanized B273

7)-1-2-1 hB273_H1-1-Type Heavy Chain:

A humanized B273 heavy chain designed by substituting amino acid numbers 20 (glutamic acid), 24 (glutamine), 28 (proline), 30 (leucine), 31 (valine), 39 (isoleucine), 57 (lysine), 59 (serine), 60 (histidine), 62 (lysine), 63 (serine), 67 (isoleucine), 86 (lysine), 87 (alanine), 95 (serine), 96 (threonine), 99 (histidine), 103 (leucine), 106 (threonine), 110 (serine), 136 (threonine), and 137 (leucine) of the cB273 heavy chain represented by SEQ ID NO: 20 in the Sequence Listing with glutamine, valine, alanine, valine, lysine, valine, arginine, alanine, proline, methionine, glycine, methionine, arginine, valine, threonine, serine, tyrosine, serine, arginine, threonine, leucine, and valine, respectively, was named "hB273_H1-1-type heavy chain".

A nucleotide sequence encoding the hB273_H1-1-type heavy chain is represented by SEQ ID NO: 39 in the Sequence Listing. Further, the amino acid sequence of the hB273_H1-1-type heavy chain is represented by SEQ ID NO: 40 in the Sequence Listing. The sequences of SEQ ID NOS: 39 and 40 are also shown in FIG. 38.

7)-1-2-2 hB273_H2-1-Type Heavy Chain:

A humanized B273 heavy chain designed by substituting amino acid numbers 24 (glutamine), 28 (proline), 30 (leucine), 31 (valine), 39 (isoleucine), 60 (histidine), 62 (lysine), 95 (serine), 96 (threonine), 99 (histidine), 103 (leucine), 106 (threonine), 110 (serine), 116 (glycine), 136 (threonine), and 137 (leucine) of the cB273 heavy chain represented by SEQ ID NO: 20 in the Sequence Listing with valine, alanine, valine, lysine, valine, proline, methionine, threonine, serine, tyrosine, serine, arginine, threonine, alanine, leucine, and valine, respectively, was named "hB273_H2-1-type heavy chain".

A nucleotide sequence encoding the hB273_H2-1-type heavy chain is represented by SEQ ID NO: 41 in the Sequence Listing. Further, the amino acid sequence of the hB273_H2-1-type heavy chain is represented by SEQ ID NO: 42 in the Sequence Listing. The sequences of SEQ ID NOS: 41 and 42 are also shown in FIG. 39.

7)-1-2-3 hB273_H2-2-Type Heavy Chain:

A humanized B273 heavy chain designed by substituting amino acid numbers 20 (glutamic acid), 24 (glutamine), 28 (proline), 30 (leucine), 31 (valine), 39 (isoleucine), 60 (histidine), 62 (lysine), 95 (serine), 96 (threonine), 103 (leucine), 106 (threonine), 110 (serine), 116 (glycine), 136

(threonine), and 137 (leucine) of the cB273 heavy chain represented by SEQ ID NO: 20 in the Sequence Listing with glutamine, valine, alanine, valine, lysine, valine, proline, methionine, threonine, serine, serine, arginine, threonine, alanine, leucine, and valine, respectively, was named "hB273_H2-2-type heavy chain".

A nucleotide sequence encoding the hB273_H2-2-type heavy chain is represented by SEQ ID NO: 43 in the Sequence Listing. Further, the amino acid sequence of the hB273_H2-2-type heavy chain is represented by SEQ ID NO: 44 in the Sequence Listing. The sequences of SEQ ID NOS: 43 and 44 are also shown in FIG. 40.

7)-1-2-4 hB273_H2-3-Type Heavy Chain:

A humanized B273 heavy chain designed by substituting amino acid numbers 24 (glutamine), 28 (proline), 30 (leucine), 31 (valine), 39 (isoleucine), 60 (histidine), 62 (lysine), 95 (serine), 96 (threonine), 103 (leucine), 106 (threonine), 110 (serine), 116 (glycine), 136 (threonine), and 137 (leucine) of the cB273 heavy chain represented by SEQ ID NO: 20 in the Sequence Listing with valine, alanine, valine, lysine, valine, proline, methionine, threonine, serine, serine, arginine, threonine, alanine, leucine, and valine, respectively, was named "hB273_H2-3-type heavy chain".

A nucleotide sequence encoding the hB273_H2-3-type heavy chain is represented by SEQ ID NO: 45 in the Sequence Listing. Further, the amino acid sequence of the hB273_H2-3-type heavy chain is represented by SEQ ID NO: 46 in the Sequence Listing. The sequences of SEQ ID NOS: 45 and 46 are also shown in FIG. 41.

7)-1-2-5 hB273_H2-4-Type Heavy Chain:

A humanized B273 heavy chain designed by substituting amino acid numbers 20 (glutamic acid), 24 (glutamine), 28 (proline), 30 (leucine), 31 (valine), 39 (isoleucine), 60 (histidine), 62 (lysine), 95 (serine), 96 (threonine), 99 (histidine), 103 (leucine), 106 (threonine), 110 (serine), 136 (threonine), and 137 (leucine) of the cB273 heavy chain represented by SEQ ID NO: 20 in the Sequence Listing with glutamine, valine, alanine, valine, lysine, valine, proline, methionine, threonine, serine, tyrosine, serine, arginine, threonine, leucine, and valine, respectively, was named "hB273_H2-4-type heavy chain".

A nucleotide sequence encoding the hB273_H2-4-type heavy chain is represented by SEQ ID NO: 47 in the Sequence Listing. Further, the amino acid sequence of the hB273_H2-4-type heavy chain is represented by SEQ ID NO: 48 in the Sequence Listing. The sequences of SEQ ID NOS: 47 and 48 are also shown in FIG. 42.

7)-1-2-6 hB273_H2-5-Type Heavy Chain:

A humanized B273 heavy chain designed by substituting amino acid numbers 20 (glutamic acid), 24 (glutamine), 28 (proline), 30 (leucine), 31 (valine), 39 (isoleucine), 60 (histidine), 95 (serine), 96 (threonine), 99 (histidine), 103 (leucine), 106 (threonine), 110 (serine), 136 (threonine), and 137 (leucine) of the cB273 heavy chain represented by SEQ ID NO: 20 in the Sequence Listing with glutamine, valine, alanine, valine, lysine, valine, proline, threonine, serine, tyrosine, serine, arginine, threonine, leucine, and valine, respectively, was named "hB273_H2-5-type heavy chain".

A nucleotide sequence encoding the hB273_H2-5-type heavy chain is represented by SEQ ID NO: 49 in the Sequence Listing. Further, the amino acid sequence of the hB273_H2-5-type heavy chain is represented by SEQ ID NO: 50 in the Sequence Listing. The sequences of SEQ ID NOS: 49 and 50 are also shown in FIG. 43.

7)-2 Construction of hB273_H1-1, hB273_H2-1, hB273_H2-2, hB273_H2-3, hB273_H2-4, and hB273_H2-5-type heavy chain expression vectors DNAs containing a gene encoding a hB273_H1-1, hB273_H2-1, hB273_H2-2, hB273_H2-3, hB273_H2-4, or hB273_H2-5-type heavy chain variable region represented by amino acid numbers 20 to 141 of SEQ ID NO: 40 in the Sequence Listing, amino acid numbers 20 to 141 of SEQ ID NO: 42, amino acid numbers 20 to 141 of SEQ ID NO: 44, amino acid numbers 20 to 141 of SEQ ID NO: 46, amino acid numbers 20 to 141 of SEQ ID NO: 48, or amino acid numbers 20 to 141 of SEQ ID NO: 50 were synthesized (GENEART, Inc. Artificial Gene Synthesis Service). Then, each of the DNA fragments obtained by cleaving the synthesized DNAs with the restriction enzyme BlpI was inserted into the universal humanized antibody heavy chain expression vector (pEF1FCCU) at the site cleaved with the restriction enzyme BlpI, whereby hB273_H1-1, hB273_H2-1, hB273_H2-2, hB273_H2-3, hB273_H2-4, and hB273_H2-5-type heavy chain expression vectors were constructed. The thus obtained expression vectors were named "pEF1FCCU/hB273_H1-1", "pEF1FCCU/hB273_H2-1", "pEF1FCCU/hB273_H2-2", "pEF1FCCU/hB273_H2-3", "pEF1FCCU/hB273_H2-4", and "pEF1FCCU/hB273_H2-5", respectively.

7)-3 Preparation of Humanized Antibody

7)-3-1 Production of Humanized Antibody $1.2 \times 10^9$ cells of FreeStyle™ 293F cells (Invitrogen Corporation) in the logarithmic growth phase were seeded into 1.2 L of fresh FreeStyle™ 293 Expression Medium (Invitrogen Corporation) and cultured for 1 hour by shaking at 90 rpm at 37° C. in an 8% $CO_2$ incubator. 3.6 mg of polyethyleneimine (Polyscience #24765) was dissolved in 20 ml of Opti-Pro™ SFM medium (Invitrogen Corporation). Subsequently, a heavy chain expression vector (0.4 mg) and a light chain expression vector (0.8 mg) prepared with PureLink™ HiPure Plasmid Kit (Invitrogen Corporation) were suspended in 20 ml of Opti-Pro™ SFM medium. Then, 20 ml of the obtained expression vectors/Opti-Pro™ SFM mixed liquid was added to 20 ml of the obtained polyethyleneimine/Opti-Pro™ SFM mixed liquid, and the resulting mixture was gently stirred and then left for 5 minutes. Thereafter, the mixture was added to the FreeStyle™ 293F cells. After 3 hours, Z-VAD-FMK (PEPTIDE INSTITUTE, Inc.) was added thereto at a final concentration of 10 μM, and culture shaking at 90 rpm was performed for 7 days at 37° C. in an 8% $CO_2$ incubator. The resulting culture supernatant was filtered through a disposable capsule filter (Advantec #CCS-045-E1H).

A humanized antibody of cB273 obtained by a combination of pEF1FCCU/hB273_H1-1 and pEF6KCL/hB273_L1 was named "hB273_H1-1/hB273_L1", a humanized antibody of cB273 obtained by a combination of pEF1FCCU/hB273_H2-1 and pEF6KCL/hB273_L1 was named "hB273_H2-1/hB273_L1", a humanized antibody of cB273 obtained by a combination of pEF1FCCU/hB273_H2-2 and pEF6KCL/hB273_L1 was named "hB273_H2-2/hB273_L1", a humanized antibody of cB273 obtained by a combination of pEF1FCCU/hB273_H2-3 and pEF6KCL/hB273_L1 was named "hB273_H2-3/hB273_L1", a humanized antibody of cB273 obtained by a combination of pEF1FCCU/hB273_H2-4 and pEF6KCL/hB273_L1 was named "hB273_H2-4/hB273_L1", and a humanized antibody of cB273 obtained by a combination of pEF1FCCU/hB273_H2-5 and pEF6KCL/hB273_L1 was named "hB273_H2-5/hB273_L1".

7)-3-2 Purification of Humanized Antibody

The culture supernatant obtained in the above 7)-3-1 was purified by a two-step process including rProtein A affinity chromatography (at 4 to 6° C.) and ceramic hydroxyapatite (at room temperature). A buffer replacement step after the purification by rProtein A affinity chromatography and after the purification by ceramic hydroxyapatite was performed at room temperature. First, 1100 to 1200 ml of the culture supernatant was applied to MabSelect SuRe™ (manufactured by GE Healthcare Bio-Sciences Co., Ltd., two HiTrap™ columns (volume: 1 ml) connected in series) equilibrated with PBS. After all the culture solution was poured into the column, the column was washed with 15 to 30 ml of PBS. Subsequently, elution was performed with a 2 M arginine hydrochloride solution (pH 4.0), and a fraction containing the antibody was collected. The fraction was applied to a desalting column (manufactured by GE Healthcare Bio-Sciences Co., Ltd., two HiTrap™ desalting columns (volume: 5 ml) connected in series), whereby the buffer was replaced with a buffer containing 5 mM sodium phosphate, 50 mM MES, and 20 mM NaCl at pH 6.5. Further, the antibody solution subjected to buffer replacement was applied to a ceramic hydroxyapatite column (Japan Bio-Rad Laboratories, Inc., Bio-Scale™ $\overline{CHT}$™ 2-1 hydroxyapatite column (volume: 2 ml)) equilibrated with a buffer containing 5 mM NaPi, 50 mM MES, and 20 mM NaCl at pH 6.5. Then, linear concentration gradient elution with sodium chloride was performed, and a fraction containing the antibody was collected. The fraction was applied to a desalting column (manufactured by GE Healthcare Bio-Sciences Co., Ltd., two HiTrap™ desalting columns (volume: 5 ml) connected in series), whereby the liquid was replaced with CBS (10 mM citrate buffer containing 140 mM sodium chloride, pH 6.0). Finally, the resulting solution was concentrated using Centrifugal UF Filter Device VIVASPIN® 20 (fractional molecular weight: 30 K, Sartorius Co., Ltd., at 4° C.), and the concentration of IgG was adjusted to 1.0 mg/ml or more, and the thus obtained solution was used as a purified sample.

Example 8 Measurement of Activity of Humanized B273 (hB273) Antibody (2)

8)-1 Evaluation of Binding Activity of hB273 Antibody Using Biacore™

Figures 1, 10:
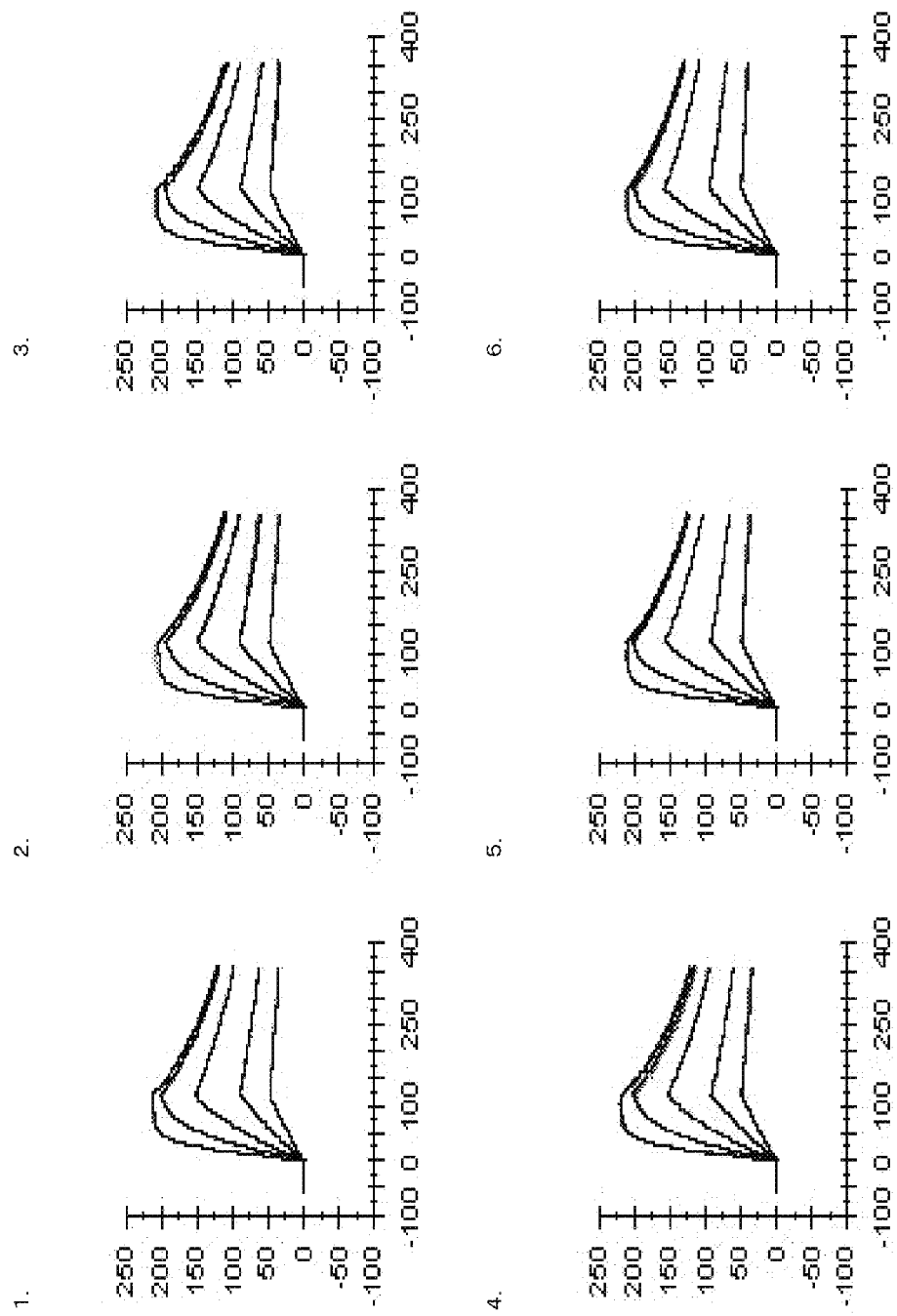

The dissociation constant of each of the humanized anti-DR5 antibodies and rsDR5 was measured using Biacore™ T100 (GE Healthcare Bio-Sciences Co., Ltd.) by a capture method in which an antibody is captured by an immobilized anti-human IgG (Fc) antibody and the measurement is performed using an antigen as an analyte. The anti-human IgG (Fc) antibody (Human Antibody Capture Kit, GE Healthcare Bio-Sciences Co., Ltd.) was covalently immobilized onto a sensor chip CM5 (BIAcore, Inc.) at about 10,000 RU by an amine coupling method. Immobilization was also performed onto a reference cell in the same manner. As a running buffer, HBS-EP (10 mM HEPES pH 7.4, 0.15 M NaCl, 3 mM EDTA, and 0.05% surfactant P20) was used. Onto the chip having the anti-human IgG (Fc) antibody immobilized thereon, an antibody solution at about 20 nM was added at a flow rate of 10 μl/min for 60 seconds, and then, a dilution series of rsDR5 (3.13-50 nM) was added at a flow rate of 30 μl/min for 120 seconds, and subsequently, the dissociation phase was monitored for 180 seconds. As a regeneration solution, 3 M magnesium chloride was added at a flow rate of 10 μl/min for 30 seconds. In the data analysis, analysis software (Biacore™ T100 Evaluation software, version 2.0.1) was used with a one-to-one binding model, and an association rate constant (kon), a dissociation rate constant (koff), and a dissociation constant (KD; KD=koff/kon) were calculated. The results obtained by the measurement using Biacore™ for the 6 types of humanized DR5 antibodies are shown in FIG. 10.

Figure 11:
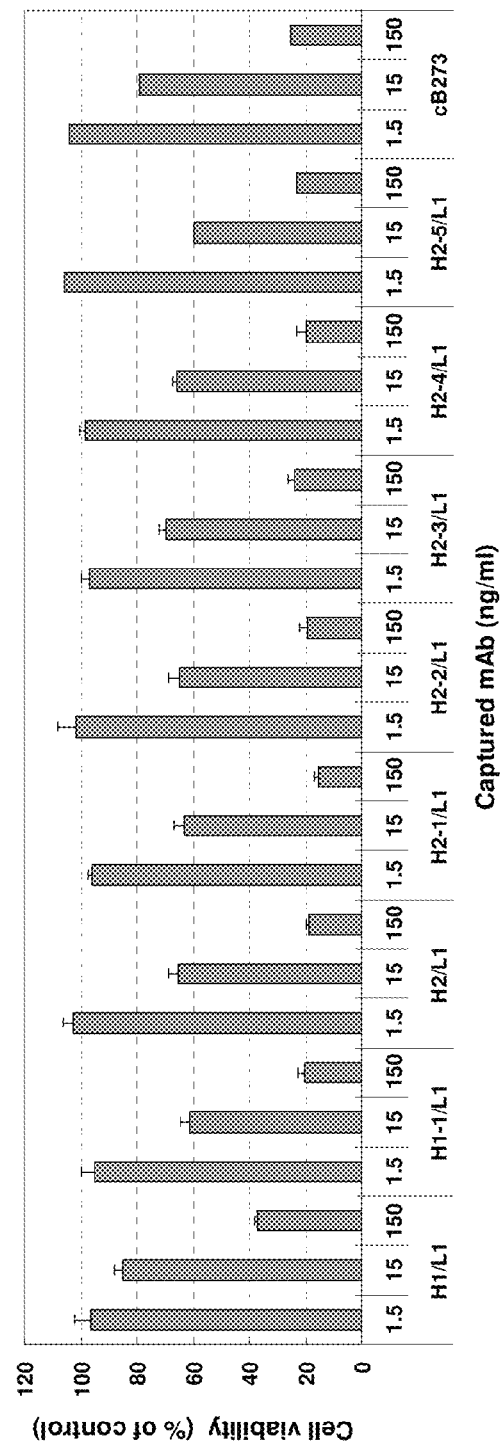
FIG. 11 is a figure showing the in vitro cytocidal activity of hB273 antibodies against Jurkat cells which are a human T lymphoma-derived cell line.

8)-2 In Vitro Cytocidal Activity of hB273 Antibody Against Human Cancer Cell Line AffiniPure F(ab')$_2$ fragment goat anti-human IgG Fc fragment specific (manufactured by Jackson ImmunoResearch Laboratories, Inc., #109-006-098) prepared at 50 μg/ml with 50 mM Tris-HCl (pH 8.5) was dispensed at 45 μL/well in a 96-well microplate (manufactured by Corning Incorporated), and the plate was left to stand overnight at 4° C. After each well was washed twice with PBS, the culture supernatant of 293F which was allowed to produce the antibody in 7)-3-1 was added at 50 μL/well such that the final concentration of the antibody was from 150 to 1.5 ng/ml, and the plate was left to stand overnight at 4° C. After each well was washed twice with PBS, Jurkat cells prepared at 4.0×10$^4$ cells/ml in RPMI 1640 medium containing 10% FBS were added at 50 μl/well and cultured under the conditions of 37° C. and 5% CO$_2$ for 23 hours. The amount of ATP derived from viable cells was quantitatively determined using a CellTiter-Glo® luminescent cell viability assay kit (manufactured by Promega Corporation, #G7571), and the cytocidal effect of each of the hB273 antibodies was evaluated by taking the value obtained from a well to which the medium was added in place of the antibody solution as 100%. As a result, as shown in FIG. 11, a tendency was observed for the hB273_H1-1/L1 antibody to exhibit a higher cytocidal activity than the hB273_H1/L1 antibody, on the basis of which antibody the hB273_H1-1/L1 antibody had been designed. On the other hand, the hB273_H2-1/L1 to hB273_H2-5/L1 antibodies exhibited substantially the same cytocidal effect as the hB273_H2/L1 antibody, on the basis of which antibody the hB273_H2-1/L1 to hB273_H2-5/L1 antibodies had been designed.

Example 9 Removal of Deamidation Site from cB273 Antibody CDR

9)-1 Designing of Mutant and Construction of Expression Vector

9)-1-1 Designing of Mutant

In general, the deamidation of asparagine in a protein proceeds through the formation of a transition state of cyclic succinimide between the asparagine and an adjacent amino acid on the C-terminal side (Geiger, T. and Clarke, S. (1987) Deamidation, Isomerization, and racemization at asparaginyl and aspartyl residues in peptides. Succinimide-linked reactions that contribute to protein degradation. J. Biol. Chem. 262, 785-794). A rate-limiting factor for the formation of a transition state of cyclic succinimide is the size of the side chain of the adjacent amino acid, and therefore, glycine which has the smallest side chain can achieve the fastest deamidation rate. On the other hand, by substituting the adjacent group on the C-terminal side with an amino acid having a large side chain, the deamidation rate can be suppressed. The B273 antibody has a -N-G- (asparagine-glycine) sequence which is susceptible to deamidation in both the L chain and the H chain. Therefore, the present inventors produced point mutants in which the adjacent group was changed from glycine to lysine, phenylalanine, leucine, or glutamic acid, each of which has a larger side chain than glycine. That is, designing of mutants was performed such that in the H chain, the -N-G- (asparagine-glycine) sequence was mutated to a -N-E- (asparagine-glutamic acid) sequence, and in the L chain, the -N-G- (asparagine-glycine) sequence was mutated to a -N-L-(asparagine-leucine) sequence, a -N-F- (asparagine-phenylalanine) sequence, a -N-K-(asparagine-lysine) sequence, or a -N-E- (asparagine-glutamic acid) sequence.

9)-1-2 Construction of hB273_L1-NE-Type Light Chain Expression Vector

By using pEF6KCL/hB273_L1 which is the hB273_L1-type light chain expression vector produced in Example 5 as a template, a DNA fragment obtained by performing PCR using a primer set A and a DNA fragment obtained by performing PCR using a primer set B were ligated to each other by overlap extension PCR using a primer set C. A DNA fragment obtained by cleaving the thus obtained DNA fragment with the restriction enzymes NheI and PmeI was inserted into the universal humanized antibody light chain expression vector (pEF6KCL) at the site cleaved with the restriction enzymes NheI and PmeI, whereby a hB273_L1-NE-type light chain expression vector in which glycine at amino acid number 54 of SEQ ID NO: 28 was substituted with glutamic acid was constructed. The thus obtained expression vector was named "pEF6KCL/hB273 L1-NE".

A nucleotide sequence encoding the hB273_L1-NE-type light chain is represented by SEQ ID NO: 51 in the Sequence Listing. Further, the amino acid sequence of the hB273_L1-NE-type light chain is represented by SEQ ID NO: 52 in the Sequence Listing. The sequences of SEQ ID NOS: 51 and 52 are also shown in FIG. 44.

Primer Set A
5'-aggtaagcttgctagcgccaccatggtgctgc-3' (L-F1: SEQ ID NO: 53 in the Sequence Listing)
5'-ccaatgcaggtaagtgttctcattgctatggaccagtgactg-3' (L-NE-R2: SEQ ID NO: 54 in the Sequence Listing)

Primer Set B
5'-cagtcactggtccatagcaatgagaacacttacctgcattgg-3' (L-NE-F2: SEQ ID NO: 55 in the Sequence Listing)
5'-ggatgccacccgtttaaacgggcccctaacac-3' (L-R1: SEQ ID NO: 56 in the Sequence Listing)

Primer Set C
5'-aggtaagcttgctagcgccaccatggtgctgc-3' (L-F1: SEQ ID NO: 53 in the Sequence Listing)
5'-ggatgccacccgtttaaacgggcccctaacac-3' (L-R1: SEQ ID NO: 56 in the Sequence Listing)

9)-1-3 Construction of hB273_L1-NF-Type Light Chain Expression Vector

By using pEF6KCL/hB273_L1 which is the hB273_L1-type light chain expression vector produced in Example 5 as a template, a DNA fragment obtained by performing PCR using a primer set A and a DNA fragment obtained by performing PCR using a primer set B were ligated to each other by overlap extension PCR using a primer set C. A DNA fragment obtained by cleaving the thus obtained DNA fragment with the restriction enzymes NheI and PmeI was inserted into the universal humanized antibody light chain expression vector (pEF6KCL) at the site cleaved with the restriction enzymes NheI and PmeI, whereby a hB273_L1-NF-type light chain expression vector in which glycine at amino acid number 54 of SEQ ID NO: 28 was substituted with phenylalanine was constructed. The thus obtained expression vector was named "pEF6KCL/hB273_L1-NF".

A nucleotide sequence encoding the hB273_L1-NF-type light chain is represented by SEQ ID NO: 57 in the Sequence Listing. Further, the amino acid sequence of the hB273_L1-NF-type light chain is represented by SEQ ID NO: 58 in the Sequence Listing. The sequences of SEQ ID NOS: 57 and 58 are also shown in FIG. 45.

Primer Set A
5'-aggtaagcttgctagcgccaccatggtgctgc-3' (L-F1: SEQ ID NO: 53 in the Sequence Listing)
5'-ccaatgcaggtaagtgttgaaattgctatggaccagtgactg-3' (L-NF-R2: SEQ ID NO: 59 in the Sequence Listing)

Primer Set B
5'-cagtcactggtccatagcaatttcaacacttacctgcattgg-3' (L-NF-F2: SEQ ID NO: 60 in the Sequence Listing)
5'-ggatgccacccgtttaaacgggcccctaacac-3' (L-R1: SEQ ID NO: 56 in the Sequence Listing)

Primer Set C
5'-aggtaagcttgctagcgccaccatggtgctgc-3' (L-F1: SEQ ID NO: 53 in the Sequence Listing)
5'-ggatgccacccgtttaaacgggcccctaacac-3' (L-R1: SEQ ID NO: 56 in the Sequence Listing)

9)-1-4 Construction of hB273_L1-NK-Type Light Chain Expression Vector

By using pEF6KCL/hB273_L1 which is the hB273_L1-type light chain expression vector produced in Example 5 as a template, a DNA fragment obtained by performing PCR using a primer set A and a DNA fragment obtained by performing PCR using a primer set B were ligated to each other by overlap extension PCR using a primer set C. A DNA fragment obtained by cleaving the thus obtained DNA fragment with the restriction enzymes NheI and PmeI was inserted into the universal humanized antibody light chain expression vector (pEF6KCL) at the site cleaved with the restriction enzymes NheI and PmeI, whereby a hB273_L1-NK-type light chain expression vector in which glycine at amino acid number 54 of SEQ ID NO: 28 was substituted with lysine was constructed. The thus obtained expression vector was named "pEF6KCL/hB273_L1-NK".

A nucleotide sequence encoding the hB273_L1-NK-type light chain is represented by SEQ ID NO: 61 in the Sequence Listing. Further, the amino acid sequence of the hB273_L1-NK-type light chain is represented by SEQ ID NO: 62 in the Sequence Listing. The sequences of SEQ ID NOS: 61 and 62 are also shown in FIG. 46.

Primer Set A
5'-aggtaagcttgctagcgccaccatggtgctgc-3' (L-F1: SEQ ID NO: 53 in the Sequence Listing)
5'-ccaatgcaggtaagtgttcttattgctatggaccagtgactg-3' (L-NK-R2: SEQ ID NO: 63 in the Sequence Listing)

Primer Set B
5'-cagtcactggtccatagcaataagaacacttacctgcattgg-3' (L-NK-F2: SEQ ID NO: 64 in the Sequence Listing)
5'-ggatgccacccgtttaaacgggcccctaacac-3' (L-R1: SEQ ID NO: 56 in the Sequence Listing)

Primer Set C
5'-aggtaagcttgctagcgccaccatggtgctgc-3' (L-F1: SEQ ID NO: 53 in the Sequence Listing)
5'-ggatgccacccgtttaaacgggcccctaacac-3' (L-R1: SEQ ID NO: 56 in the Sequence Listing)

9)-1-5 Construction of hB273_L1-NL-Type Light Chain Expression Vector

By using pEF6KCL/hB273_L1 which is the hB273_L1-type light chain expression vector produced in Example 5 as a template, a DNA fragment obtained by performing PCR using a primer set A and a DNA fragment obtained by performing PCR using a primer set B were ligated to each other by overlap extension PCR using a primer set C. A DNA fragment obtained by cleaving the thus obtained DNA fragment with the restriction enzymes NheI and PmeI was inserted into the universal humanized antibody light chain expression vector (pEF6KCL) at the site cleaved with the restriction enzymes NheI and PmeI, whereby a hB273_L1-NL-type light chain expression vector in which glycine at amino acid number 54 of SEQ ID NO: 28 was substituted with leucine was constructed. The thus obtained expression vector was named "pEF6KCL/hB273_L1-NL".

A nucleotide sequence encoding the hB273_L1-NL-type light chain is represented by SEQ ID NO: 65 in the Sequence Listing. Further, the amino acid sequence of the hB273_L1-NL-type light chain is represented by SEQ ID NO: 66 in the Sequence Listing. The sequences of SEQ ID NOS: 65 and 66 are also shown in FIG. 47.

Primer Set A

5'-aggtaagcttgctagcgccaccatggtgctgc-3' (L-F1: SEQ ID NO: 53 in the Sequence Listing)

5'-ccaatgcaggtaagtgttcagattgctatggaccagtgactg-3' (L-NL-R2: SEQ ID NO: 67 in the Sequence Listing)

Primer Set B

5'-cagtcactggtccatagcaatctgaacacttacctgcattgg-3' (L-NL-F2: SEQ ID NO: 68 in the Sequence Listing)

5'-ggatgccacccgtttaaacgggcccctaacac-3' (L-R1: SEQ ID NO: 56 in the Sequence Listing)

Primer Set C

5'-aggtaagcttgctagcgccaccatggtgctgc-3' (L-F1: SEQ ID NO: 53 in the Sequence Listing)

5'-ggatgccacccgtttaaacgggcccctaacac-3' (L-R1: SEQ ID NO: 56 in the Sequence Listing)

9)-1-6 Construction of hB273_H2-1-NE-Type Heavy Chain Expression Vector

By using pEF1FCCU/hB273_H2-1 which is the hB273_H2-1-type heavy chain expression vector produced in Example 7 as a template, a DNA fragment obtained by performing PCR using a primer set A and a DNA fragment obtained by performing PCR using a primer set B were ligated to each other by overlap extension PCR using a primer set C. A DNA fragment obtained by cleaving the thus obtained DNA fragment with the restriction enzymes NheI and PmeI was inserted into the universal humanized antibody heavy chain expression vector (pEF1FCCU) at the site cleaved with the restriction enzymes NheI and PmeI, whereby a hB273_H2-1-NE-type heavy chain expression vector in which glycine at amino acid number 75 of SEQ ID NO: 42 was substituted with glutamic acid was constructed. The thus obtained expression vector was named "pEF1FCCU/hB273_H2-1-NE".

A nucleotide sequence encoding the hB273_H2-1-NE-type heavy chain is represented by SEQ ID NO: 69 in the Sequence Listing. Further, the amino acid sequence of the hB273_H2-1-NE-type heavy chain is represented by SEQ ID NO: 70 in the Sequence Listing. The sequences of SEQ ID NOS: 69 and 70 are also shown in FIG. 48.

Primer Set A

5'-aggtaagcttgctagcgccaccatgaaacacc-3' (H-F1: SEQ ID NO: 71 in the Sequence Listing)

5'-ctggttgtagaaggtgtcctcgttgtaggggttgaaccggcc-3' (H-NE-R2: SEQ ID NO: 72 in the Sequence Listing)

Primer Set B

5'-ggccggttcaaccccctacaacgaggacaccttctacaaccag-3' (H-NE-F2: SEQ ID NO: 73 in the Sequence Listing)

5'-ggatgccacccgtttaaacgggcccgatatctc-3' (H-R1: SEQ ID NO: 74 in the Sequence Listing)

Primer Set C

5'-aggtaagcttgctagcgccaccatgaaacacc-3' (H-F1: SEQ ID NO: 71 in the Sequence Listing)

5'-ggatgccacccgtttaaacgggcccgatatctc-3' (H-R1: SEQ ID NO: 74 in the Sequence Listing)

9)-2 Preparation of CDR-Modified hB273 Antibody

9)-2-1 Production of CDR-Modified hB273 Antibody $1.2 \times 10^9$ cells of FreeStyle™ 293F cells (Invitrogen Corporation) in the logarithmic growth phase were seeded into 1.2 L of fresh FreeStyle™ 293 Expression Medium (Invitrogen Corporation) and cultured for 1 hour by shaking at 90 rpm at 37° C. in an 8% $CO_2$ incubator. 3.6 mg of polyethyleneimine (Polyscience #24765) was dissolved in 20 ml of Opti-Pro™ SFM medium (Invitrogen Corporation). Subsequently, a heavy chain expression vector (0.4 mg) and a light chain expression vector (0.8 mg) prepared with PureLink™ HiPure Plasmid Kit (Invitrogen Corporation) were suspended in 20 ml of Opti-Pro™ SFM medium. Then, 20 ml of the obtained expression vectors/Opti-Pro™ SFM mixed liquid was added to 20 ml of the obtained polyethyleneimine/Opti-Pro™ SFM mixed liquid, and the resulting mixture was gently stirred and then left for 5 minutes. Thereafter, the mixture was added to the FreeStyle™ 293F cells. After 3 hours, Z-VAD-FMK (PEPTIDE INSTITUTE, Inc.) was added thereto at a final concentration of 10 μM, and culture shaking at 90 rpm was performed for 7 days at 37° C. in an 8% $CO_2$ incubator. The resulting culture supernatant was filtered through a disposable capsule filter (Advantec #CCS-045-E1H).

A humanized antibody of cB273 obtained by a combination of pEF1FCCU/hB273_H2-1-NE and pEF6KCL/hB273_L1-NE was named "hB273_H2-1-NE/hB273_L1-NE", a humanized antibody of cB273 obtained by a combination of pEF1FCCU/hB273_H2-1-NE and pEF6KCL/hB273_L1-NF was named "hB273_H2-1-NE/hB273_L1-NF", a humanized antibody of cB273 obtained by a combination of pEF1FCCU/hB273_H2-1-NE and pEF6KCL/hB273_L1-NK was named "hB273_H2-1-NE/hB273_L1-NK", and a humanized antibody of cB273 obtained by a combination of pEF1FCCU/hB273_H2-1-NE and ppEF6KCL/hB273_L1-NL was named "hB273_H2-1-NE/hB273_L1-NL".

9)-2-2 Purification of CDR-Modified hB273 Antibody

The culture supernatant obtained in the above 9)-2-1 was purified by a two-step process including rProtein A affinity chromatography (at 4 to 6° C.) and ceramic hydroxyapatite (at room temperature). A buffer replacement step after the purification by rProtein A affinity chromatography and after the purification by ceramic hydroxyapatite was performed at room temperature. First, 1100 to 1200 ml of the culture supernatant was applied to MabSelect SuRe™ (manufactured by GE Healthcare Bio-Sciences Co., Ltd., two HiTrap™ columns (volume: 1 ml) connected in series) equilibrated with PBS. After all the culture solution was poured into the column, the column was washed with 15 to 30 ml of PBS. Subsequently, elution was performed with a 2 M arginine hydrochloride solution (pH 4.0), and a fraction containing the antibody was collected. The fraction was applied to a desalting column (manufactured by GE Healthcare Bio-Sciences Co., Ltd., two HiTrap™ desalting columns (volume: 5 ml) connected in series), whereby the buffer was replaced with a buffer containing 5 mM sodium phosphate, 50 mM MES, and 20 mM NaCl at pH 6.5. Further, the antibody solution subjected to buffer replacement was applied to a ceramic hydroxyapatite column (Japan Bio-Rad Laboratories, Inc., Bio-Scale™ $\overline{CHT}$™ $\overline{2}$-1 hydroxyapatite column (volume: 2 ml)) equilibrated with a buffer containing 5 mM NaPi, 50 mM MES, and 20 mM NaCl at pH 6.5. Then, linear concentration gradient elution with sodium chloride was performed, and a fraction containing the antibody was collected. The fraction was applied to a desalting column (manufactured by GE Healthcare Bio-Sciences Co., Ltd., two HiTrap™ desalting columns (volume: 5 ml) connected in series), whereby the liquid was replaced with CBS (10 mM citrate buffer containing 140 mM sodium chloride, pH 6.0). Finally, the resulting solution was concentrated using Centrifugal UF Filter Device VIVASPIN® 20 (fractional molecular weight: 30 K, Sartorius Co., Ltd., at 4° C.), and the concentration of IgG was adjusted to 1.0 mg/ml or more, and the thus obtained solution was used as a purified sample.

Example 10 Measurement of Activity of CDR-Modified hB273 Antibody

10)-1 Evaluation of Binding Activity of CDR-Modified hB273 Antibody Using Biacore™

Figures 1, 12:
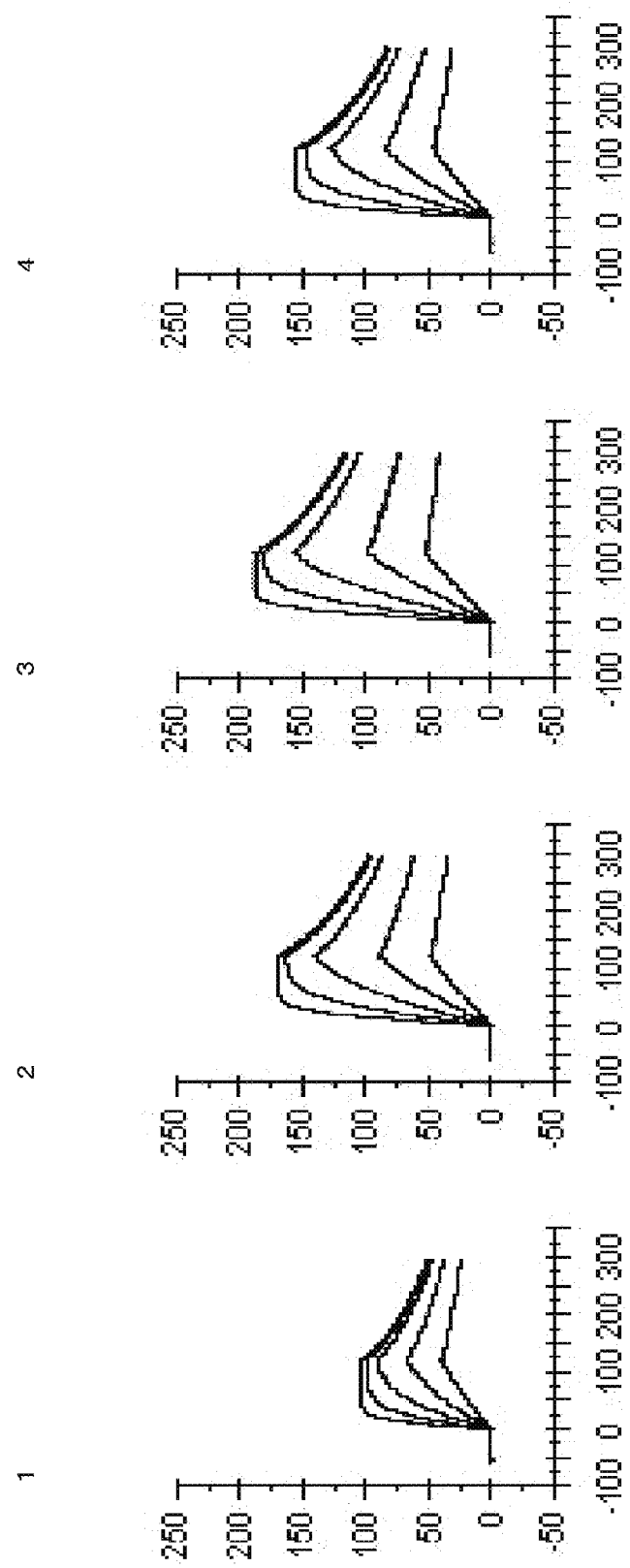

The dissociation constant of each of the humanized anti-DR5 antibodies and rsDR5 was measured using Biacore™ T100 (GE Healthcare Bio-Sciences Co., Ltd.) by a capture method in which an antibody is captured by an immobilized anti-human IgG (Fc) antibody and the measurement is performed using an antigen as an analyte. The anti-human IgG (Fc) antibody (Human Antibody Capture Kit, GE Healthcare Bio-Sciences Co., Ltd.) was covalently immobilized onto a sensor chip CM5 (BIAcore, Inc.) at about 10,000 RU by an amine coupling method. Immobilization was performed also onto a reference cell in the same manner. As a running buffer, HBS-EP (10 mM HEPES pH 7.4, 0.15 M NaCl, 3 mM EDTA, and 0.05% surfactant P20) was used. Onto the chip having the anti-human IgG (Fc) antibody immobilized thereon, an antibody solution at about 20 nM was added at a flow rate of 10 µl/min for 60 seconds, and then, a dilution series of rsDR5 (3.13-50 nM) was added at a flow rate of 30 µl/min for 120 seconds, and subsequently, the dissociation phase was monitored for 180 seconds. As a regeneration solution, 3 M magnesium chloride was added at a flow rate of 10 µl/min for 30 seconds. In the data analysis, analysis software (Biacore™ T100 Evaluation software, version 2.0.1) was used with a one-to-one binding model, and an association rate constant (kon), a dissociation rate constant (koff), and a dissociation constant (KD; KD=koff/kon) were calculated. The results obtained by the measurement using Biacore for the 4 types of humanized DR5 antibodies are shown in FIG. 12.

10)-2 Measurement of Thermal Stability of Humanized Anti-DR5 Antibody and Mutant Thereof Using Differential Scanning Calorimetry (DSC)

The measurement of thermal stability was performed using differential scanning calorimetry (DSC). A sample was dissolved in a CBS buffer (containing 10 mM citric acid and 140 mM NaCl and prepared at pH 6.0) at 0.5 mg/ml, and 400 µl aliquots thereof were used as sample solutions for DSC measurement. The DSC measurement conditions were set as follows: initial temperature: 20° C.; final temperature: 100° C.; temperature increasing rate: 200° C./hour; filtering period: 2 seconds; and feedback mode: low. As a reference solution, CBS was used. As a DSC measurement device, VP-Capillary DSC Platform manufactured by MicroCal, Inc. (US) (currently GE Healthcare Bio-Sciences Co., Ltd.) was used for all measurements. Baseline correction was carried out by subtracting the baseline (a scanning curve obtained by also filling a sample cell with the reference solution) from a scanning curve obtained from the sample solution. The value of the peak top temperature in the whole thermogram was defined as the thermal denaturation midpoint Tm of the Fab region. The results of DSC measurement of 4 types of humanized DR5 antibodies are shown in FIG. 13.

Figure 14:
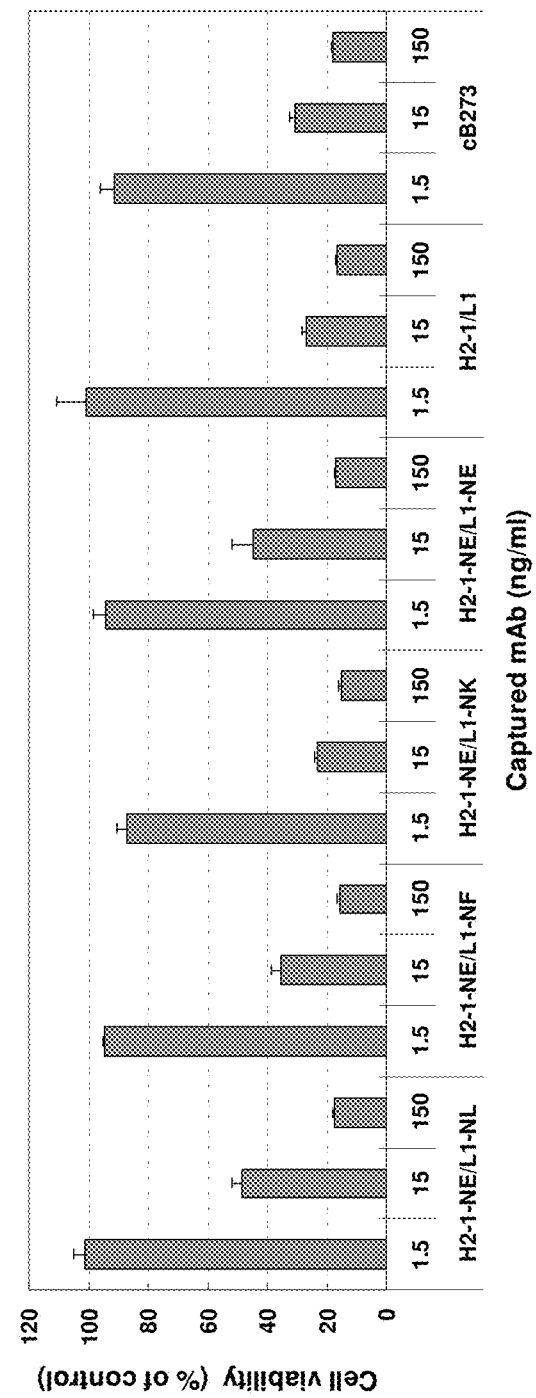
FIG. 14 is a figure showing the in vitro cytocidal activities of CDR-modified hB273 antibodies against Jurkat cells which are a human T lymphoma-derived cell line.

10)-3 In Vitro Cytocidal Activity of CDR-Modified hB273 Antibody Against Human Cancer Cell Line AffiniPure F(ab')$_2$ fragment goat anti-human IgG Fc fragment specific (manufactured by Jackson ImmunoResearch Laboratories, Inc., #109-006-098) prepared at 50 µg/ml with 50 mM Tris-HCl (pH 8.5) was dispensed at 45 µL/well in a 96-well microplate (manufactured by Corning Incorporated), and the plate was left to stand overnight at 4° C. After each well was washed twice with PBS, the culture supernatant of 293F which was allowed to produce the antibody in 9)-2-1 was added at 50 µL/well such that the final concentration of the antibody was from 150 to 1.5 ng/ml, and the plate was left to stand overnight at 4° C. After each well was washed twice with PBS, Jurkat cells prepared at 4.0×10$^4$ cells/ml in RPMI 1640 medium containing 10% FBS were added at 50 µl/well and cultured under the conditions of 37° C. and 5% $CO_2$ for 23 hours. The amount of ATP derived from viable cells was quantitatively determined using a CellTiter-Glo® luminescent cell viability assay kit (manufactured by Promega Corporation, #G7571), and the cytocidal effect of each of the hB273 antibodies was evaluated by taking the value obtained from a well to which the medium was added in place of the antibody solution as 100%. The cytocidal activity of each of the 4 types of CDR-modified antibodies is shown in FIG. 14.

10)-4 Caspase-3/7 Activation Effect and In Vitro Cytocidal Activity of hB273_H2-1-NE/L1-NK Antibody on Human Cancer Cell Lines Each of a human colon cancer cell line HCT-15 and a human glioblastoma cell line U-87MG was prepared at 1.1×10$^5$ cells/ml in RPMI 1640 medium containing 10% FBS or MEM (Minimum Essential Medium) medium containing 10% FBS and added to a white clear bottom 96-well microplate (manufactured by Corning Incorporated) at 45 µl/well, and cultured overnight under the conditions of 37° C. and 5% $CO_2$. The hB273_H2-1-NE/L1-NK antibody, the cB273 antibody, or human IgG (manufactured by Jackson ImmunoResearch Laboratories, Inc.) was mixed with the same concentration of AffiniPure goat anti-human IgG Fcγ fragment specific (manufactured by Jackson ImmunoResearch Laboratories, Inc., #109-005-098), and the resulting mixture was added at 5 µl/well such that the final concentration of the hB273_H2-1-NE/L1-NK antibody, the cB273 antibody, or human IgG was 10,000 to 0.1 ng/ml, and the cells were cultured under the conditions of 37° C. and 5% $CO_2$ for 4 hours. The caspase-3/7 activity in each well was measured by a luminometer (manufactured by Perkin Elmer, Inc.) using a Caspase-Glo® 3/7 Assay kit (manufactured by Promega Corporation, #G8093). The measurement was performed after incubation at room temperature for 30 minutes according to the protocol attached to the kit. Then, the caspase-3/7 activity was evaluated by taking the value obtained from a well to which the medium was added in place of the antibody solution as 100%. Further, the in vitro cytocidal activity was evaluated by measuring the amount of ATP at 24 hours after treatment with the antibody according to the method shown in Example 3-3. As a result, it was found that the hB273_H2-1-NE/L1-NK antibody has a caspase-3/7 activation effect and a cytocidal effect comparable to those of the cB273 antibody (FIG. 15).

Example 11 In Vivo Antitumor Effect of cB273 Antibody

11)-1 Antitumor Activity of cB273 Antibody

11)-1-1 Antitumor Activity in Nude Mice Implanted with Human Colon Cancer Cell Line COLO 205

2×10$^6$ cells of a human colon cancer cell line COLO 205 (purchased from ATCC) were implanted subcutaneously in the axillary region of nude mice (CAnN.Cg-Foxn1$^{nu}$/Crl-Crlj, purchased from Charles River Laboratories Japan, Inc.). On days 7, 14, and 21 after the implantation, the cB273 antibody was administered to tumor-bearing mice through the tail vein at a dose of 1, 3, or 10 mg/kg (n=10). The major axis and the minor axis of the implanted tumor were measured twice a week using an electronic digital caliper (manufactured by Mitutoyo Corporation), and the tumor volume was calculated according to the following calculation formula.

$$\text{Tumor volume (mm}^3\text{)} = 1/2 \times (\text{Minor axis})^2 \text{ (mm)} \times (\text{Major axis})^2 \text{ (mm)}$$

Figure 16:
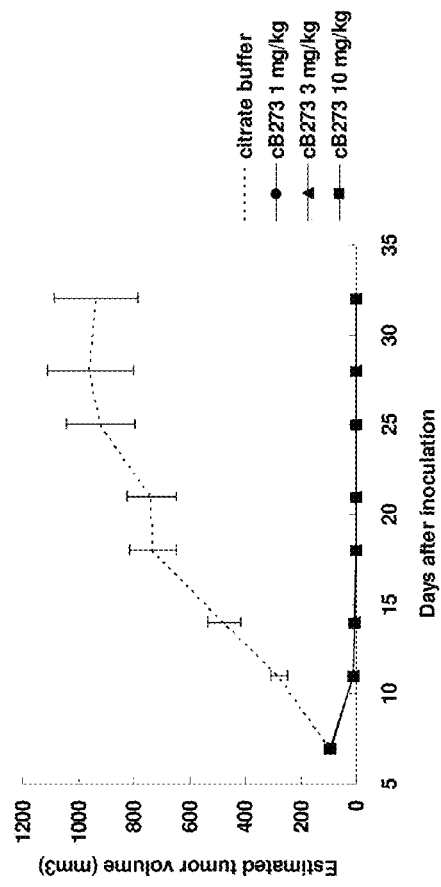
FIG. 16 is a figure showing the in vivo antitumor activity of a cB273 antibody in nude mice implanted with a human colon cancer cell line COLO 205.

The results are shown in FIG. 16. The complete degeneration of the tumor was observed in all mice in the cB273 antibody administration group.

11)-1-2 Antitumor Activity in Nude Mice Implanted with Human Pancreatic Cancer Cell Line MIAPaCa-2

$3 \times 10^6$ cells of a human pancreatic cancer cell line MIAPaCa-2 (purchased from ATCC) were implanted subcutaneously in the axillary region of nude mice. On days 11, 19, 26, and 33 after the implantation, the cB273 antibody was administered to tumor-bearing mice through the tail vein at a dose of 3 or 10 mg/kg (n=10). In the same manner as described above, the major axis and the minor axis of the implanted tumor were measured, and the tumor volume was calculated.

Figure 17:
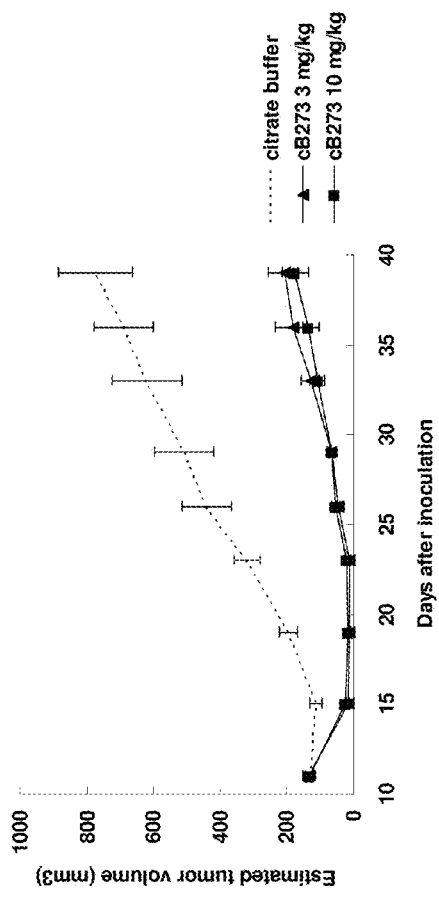
FIG. 17 is a figure showing the in vivo antitumor activity of a cB273 antibody in nude mice implanted with a human pancreatic cancer cell line MIAPaCa-2.

The results are shown in FIG. 17. The tumor growth inhibitory rate on day 39 after the implantation, which was the final day of the measurement, was 73.5% in the 3 mg/kg administration group and 77.4% in the 10 mg/kg administration group.

11)-1-3 Antitumor Activity in Nude Mice Implanted with Human Glioblastoma Cell Line U-87MG $5 \times 10^6$ cells of a human glioblastoma cell line U-87MG (purchased from ATCC) were implanted subcutaneously in the axillary region of nude mice. On days 4, 11, 18, and 25 after the implantation, the cB273 antibody was administered to tumor-bearing mice through the tail vein at a dose of 1, 3, or 10 mg/kg (n=10). In the same manner as described above, the major axis and the minor axis of the implanted tumor were measured, and the tumor volume was calculated.

Figure 18:
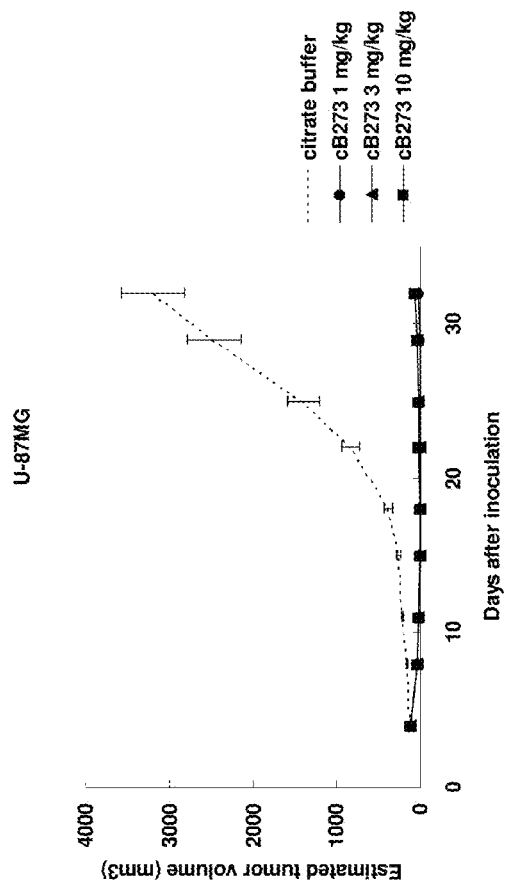
FIG. 18 is a figure showing the in vivo antitumor activity of a cB273 antibody in nude mice implanted with a human glioblastoma cell line U-87MG.

The results are shown in FIG. 18. The tumor growth inhibitory rate on day 32 after the implantation, which was the final day of the measurement, was 99.7% in the 1 mg/kg administration group, 97.8% in the 3 mg/kg administration group, and 98.0% in the 10 mg/kg administration group. Further, the complete degeneration of the tumor was observed in 2 out of 10 mice in the 1 mg/kg administration group, 5 out of 10 mice in the 3 mg/kg administration group, and 3 out of 10 mice in the 10 mg/kg administration group.

11)-1-4 Antitumor Activity in Nude Mice Implanted with Human Lung Cancer Cell Line NCI-H2122 (in Combination with Paclitaxel and Carboplatin)

$5 \times 10^6$ cells of a human lung cancer cell line NCI-H2122 (purchased from ATCC) were implanted subcutaneously in the axillary region of nude mice. On days 13 and 20 after the implantation, the cB273 antibody was administered to tumor-bearing mice through the tail vein at a dose of 10 mg/kg. Paclitaxel was subcutaneously administered at a dose of 6.25 mg/kg on days 13, 14, 15, 16, and 17 after the implantation. Carboplatin was intraperitoneally administered at a dose of 100 mg/kg on day 13 after the implantation (n=10). In the same manner as described above, the major axis and the minor axis of the implanted tumor were measured, and the tumor volume was calculated.

Figure 19:
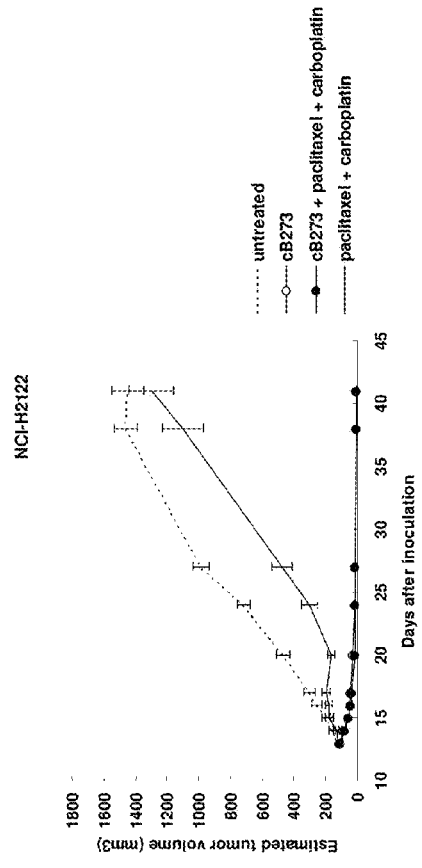
FIG. 19 is a figure showing the in vivo antitumor activity of a cB273 antibody in nude mice implanted with a human lung cancer cell line NCI-H2122 (in combination with paclitaxel and carboplatin).

The results are shown in FIG. 19. The tumor growth inhibitory rate on day 41 after the implantation, which was the final day of the measurement, was 99.6% in the cB273 antibody administration group, 10.2% in the group of combined administration of paclitaxel and carboplatin, and 99.7% in the group of combined administration of the cB273 antibody, paclitaxel, and carboplatin.

11)-1-5 Antitumor Activity in Nude Mice Implanted with Human Lung Cancer Cell Line NCI-H460 (in Combination with Paclitaxel and Carboplatin)

$5 \times 10^6$ cells of a human lung cancer cell line NCI-H460 (purchased from ATCC) were implanted subcutaneously in the axillary region of nude mice. On day 6 after the implantation, the cB273 antibody was intraperitoneally administered to tumor-bearing mice at a dose of 10 mg/kg. Paclitaxel was subcutaneously administered at a dose of 6.25 mg/kg on days 6, 7, 8, 9, and 10 after the implantation. Carboplatin was intraperitoneally administered at a dose of 100 mg/kg on day 6 after the implantation (n=10). In the same manner as described above, the major axis and the minor axis of the implanted tumor were measured, and the tumor volume was calculated.

Figure 20:
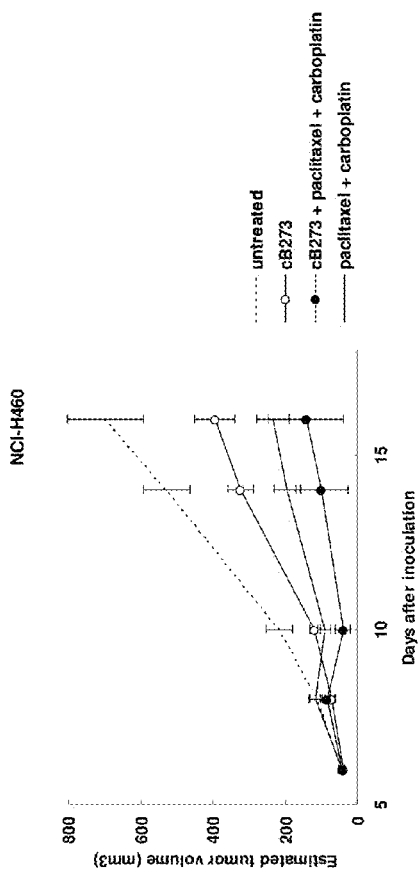
FIG. 20 is a figure showing the in vivo antitumor activity of a cB273 antibody in nude mice implanted with a human lung cancer cell line NCI-H460 (in combination with paclitaxel and carboplatin).

The results are shown in FIG. 20. The tumor growth inhibitory rate on day 16 after the implantation, which was the final day of the measurement, was 43.3% in the cB273 antibody administration group, 66.4% in the group of combined administration of paclitaxel and carboplatin, and 79.6% in the group of combined administration of the cB273 antibody, paclitaxel, and carboplatin.

11)-1-6 Antitumor Activity in Nude Mice Implanted with Human Colon Cancer Cell Line DLD-1 (in Combination with CPT-11)

$5 \times 10^6$ cells of a human colon cancer cell line DLD-1 (purchased from ATCC) were implanted subcutaneously in the axillary region of nude mice. On day 35 after the implantation, the cB273 antibody was intraperitoneally administered to tumor-bearing mice at a dose of 10 mg/kg. CPT-11 was intraperitoneally administered at a dose of 80 mg/kg on days 35, 40, and 43 after the implantation (n=10). In the same manner as described above, the major axis and the minor axis of the implanted tumor were measured, and the tumor volume was calculated.

Figure 21:
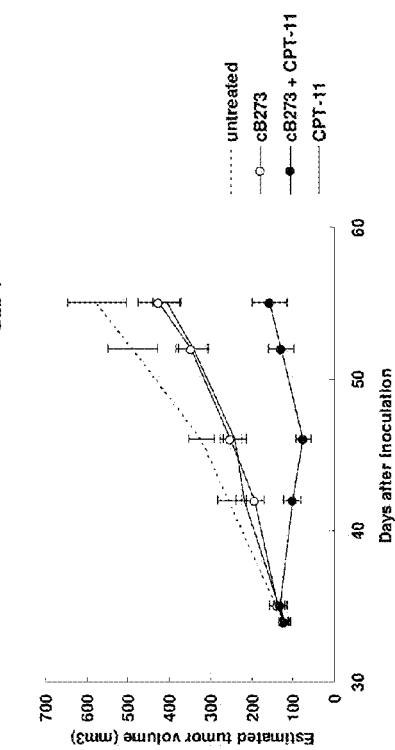
FIG. 21 is a figure showing the in vivo antitumor activity of a cB273 antibody in nude mice implanted with a human colon cancer cell line DLD-1 (in combination with CPT-11).

The results are shown in FIG. 21. The tumor growth inhibitory rate on day 55 after the implantation, which was the final day of the measurement, was 25.9% in the cB273 antibody administration group, 29.5% in the CPT-11 administration group, and 72.7% in the group of combined administration of the cB273 antibody and CPT-11.

11)-1-7 Antitumor Activity in Nude Mice Implanted with Human Colon Cancer Cell Line HCT-15 (in Combination with CPT-11)

$5 \times 10^6$ cells of a human colon cancer cell line HCT-15 (purchased from ATCC) were implanted subcutaneously in the axillary region of nude mice. On day 7 after the implantation, the cB273 antibody was administered to tumor-bearing mice through the tail vein at a dose of 10 mg/kg. CPT-11 was intraperitoneally administered at a dose of 80 mg/kg on days 7, 10, and 14 after the implantation (n=10). In the same manner as described above, the major axis and the minor axis of the implanted tumor were measured, and the tumor volume was calculated.

Figure 22:
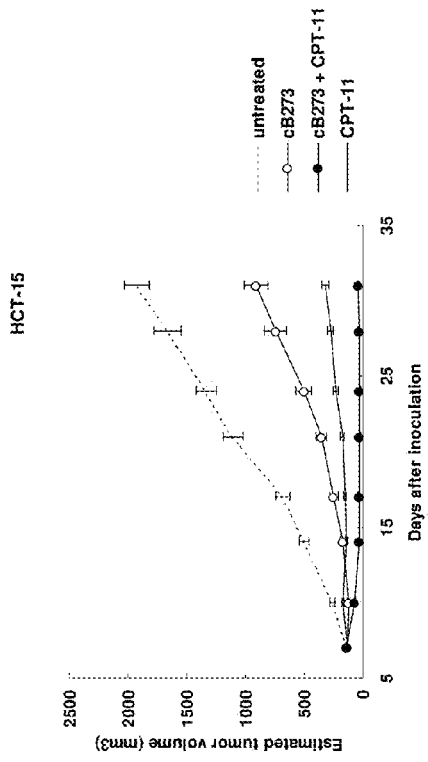
FIG. 22 is a figure showing the in vivo antitumor activity of a cB273 antibody in nude mice implanted with a human colon cancer cell line HCT-15 (in combination with CPT-11).

The results are shown in FIG. 22. The tumor growth inhibitory rate on day 31 after the implantation, which was the final day of the measurement, was 52.8% in the cB273 antibody administration group, 83.5% in the CPT-11 administration group, and 97.8% in the group of combined administration of the cB273 antibody and CPT-11.

11)-1-8 Antitumor Activity in Nude Mice Implanted with Human Colon Cancer Cell Line HCT-116 (in Combination with CPT-11)

$1 \times 10^7$ cells of a human colon cancer cell line HCT-116 (purchased from ATCC) were implanted subcutaneously in the axillary region of nude mice. On day 7 after the implantation, the cB273 antibody was administered to tumor-bearing mice through the tail vein at a dose of 10 mg/kg. CPT-11 was intraperitoneally administered at a dose of 65 mg/kg on days 7, 10, and 14 after the implantation (n=10). In the same manner as described above, the major axis and the minor axis of the implanted tumor were measured, and the tumor volume was calculated.

Figure 23:
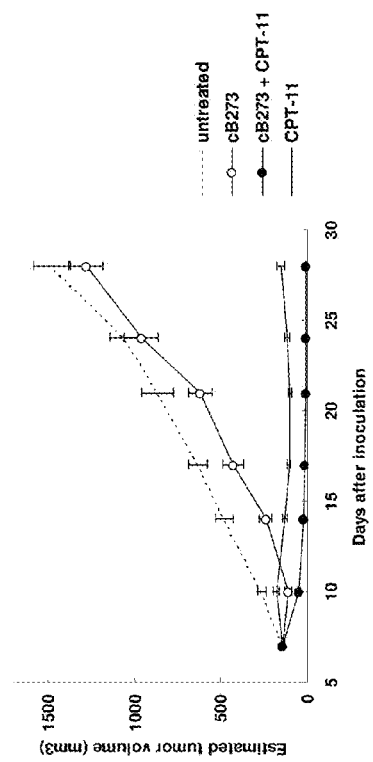
FIG. 23 is a figure showing the in vivo antitumor activity of a cB273 antibody in nude mice implanted with a human colon cancer cell line HCT-116 (in combination with CPT-11).

The results are shown in FIG. 23. The tumor growth inhibitory rate on day 28 after the implantation, which was the final day of the measurement, was 13.9% in the cB273 antibody administration group, 89.8% in the CPT-11 administration group, and 99.7% in the group of combined administration of the cB273 antibody and CPT-11.

11)-1-9 Antitumor Activity in Nude Mice Implanted with Human Melanoma Cell Line A375 (in Combination with Vinblastine)

$2 \times 10^6$ cells of a human melanoma cell line A375 (purchased from ATCC) were implanted subcutaneously in the axillary region of nude mice. On days 10, 17, and 24 after the implantation, the cB273 antibody was administered to tumor-bearing mice through the tail vein at a dose of 10 mg/kg. Vinblastine was administered through the tail vein at a dose of 10 mg/kg on 10 days after the implantation (n=10). In the same manner as described above, the major axis and the minor axis of the implanted tumor were measured, and the tumor volume was calculated.

Figure 24:
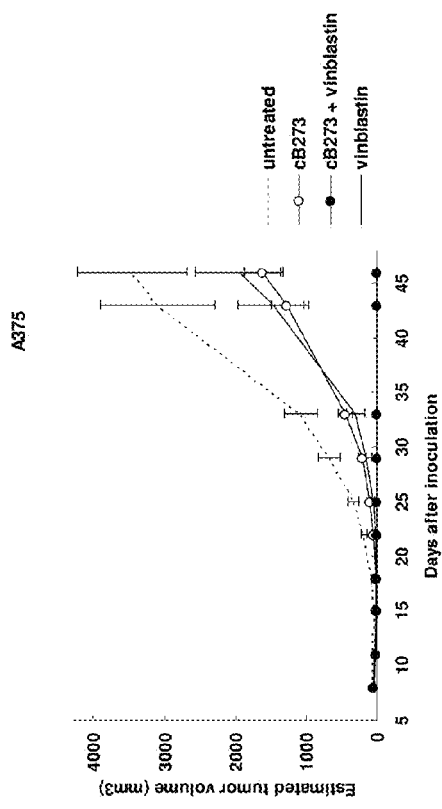
FIG. 24 is a figure showing the in vivo antitumor activity of a cB273 antibody in nude mice implanted with a human melanoma cell line A375 (in combination with vinblastine).

The results are shown in FIG. 24. The tumor growth inhibitory rate on day 46 after the implantation, which was the final day of the measurement, was 53.1% in the cB273 antibody administration group, 43.6% in the vinblastine administration group, and 100% in the group of combined administration of the cB273 antibody and vinblastine, and the complete degeneration of the tumor was observed in all mice in the group of combined administration of the cB273 antibody and vinblastine.

11)-2 Comparison of Antitumor Activity Between the cB273 Antibody and Conatumumab 11)-2-1 Preparation of Conatumumab Conatumumab was prepared based on the amino acid sequences of the light and heavy chains described in WHO Drug Information, Vol. 22, No. 2, 2008, pp. 129-130.

11)-2-1-1 Construction of Conatumumab Light Chain Expression Vector

A DNA containing a gene encoding a conatumumab light chain variable region represented by amino acid numbers 21 to 130 of SEQ ID NO: 76 was synthesized (GENEART, Inc. Artificial Gene Synthesis Service). Then, a DNA fragment obtained by cleaving the synthesized DNA with the restriction enzymes NdeI and BsiWI was inserted into the universal humanized antibody light chain expression vector (pEF6KCL) at the site cleaved with the restriction enzymes NdeI and BsiWI, whereby a conatumumab light chain expression vector was constructed. The thus obtained expression vector was named "pEF6KCL/Conatumumab_L".

11)-2-1-2 Construction of Conatumumab Heavy Chain Expression Vector

A DNA containing a gene encoding a conatumumab heavy chain variable region represented by amino acid numbers 20 to 141 of SEQ ID NO: 78 in the Sequence Listing was synthesized (GENEART, Inc. Artificial Gene Synthesis Service). Then, a DNA fragment obtained by cleaving the synthesized DNA with the restriction enzyme BlpI was inserted into the universal humanized antibody heavy chain expression vector (pEF1FCCU) at the site cleaved with the restriction enzyme BlpI, whereby a conatumumab heavy chain expression vector was constructed. The thus obtained expression vector was named "pEF1FCCU/Conatumumab_H".

11)-2-1-3 Production of Conatumumab $1.2 \times 10^9$ cells of FreeStyle™ 293F cells (Invitrogen Corporation) in the logarithmic growth phase were seeded into 1.2 L of fresh FreeStyle™ 293 Expression Medium (Invitrogen Corporation) and cultured for 1 hour by shaking at 90 rpm at 37° C. in an 8% $CO_2$ incubator. 3.6 mg of polyethyleneimine (Polyscience #24765) was dissolved in 20 ml of Opti-Pro™ SFM medium (Invitrogen Corporation). Subsequently, the heavy chain expression vector pEF1FCCU/Conatumumab_H (0.4 mg) and the light chain expression vector pEF6KCL/Conatumumab_L (0.8 mg) prepared with PureLink™ HiPure Plasmid Kit (Invitrogen Corporation) were suspended in 20 ml of Opti-Pro™ SFM medium. Then, 20 ml of the obtained expression vectors/Opti-Pro™ SFM mixed liquid was added to 20 ml of the obtained polyethyleneimine/Opti-Pro™ SFM mixed liquid, and the resulting mixture was gently stirred and then left for 5 minutes. Thereafter, the mixture was added to the FreeStyle™ 293F cells, and culture shaking at 90 rpm was performed for 7 days at 37° C. in an 8% $CO_2$ incubator. The resulting culture supernatant was filtered through a disposable capsule filter (Advantec #CCS-045-E1H).

11)-2-1-4 Purification of Conatumumab

The culture supernatant obtained in the above 11)-2-1-3 was purified by a two-step process including rProtein A affinity chromatography (at 4 to 6° C.) and ceramic hydroxyapatite (at room temperature). A buffer replacement step after the purification by rProtein A affinity chromatography and after the purification by ceramic hydroxyapatite was performed at room temperature. First, 1100 to 1200 ml of the culture supernatant was applied to MabSelect SuRe™ (manufactured by GE Healthcare Bio-Sciences Co., Ltd., two HiTrap™ columns (volume: 1 ml) connected in series) equilibrated with PBS. After all the culture solution was poured into the column, the column was washed with 15 to 30 ml of PBS. Subsequently, elution was performed with a 2 M arginine hydrochloride solution (pH 4.0), and a fraction containing the antibody was collected. The fraction was applied to a desalting column (manufactured by GE Healthcare Bio-Sciences Co., Ltd., two HiTrap™ desalting columns (volume: 5 ml) connected in series), whereby the buffer was replaced with a buffer containing 5 mM sodium phosphate, 50 mM MES, and 20 mM NaCl at pH 6.5. Further, the antibody solution subjected to buffer replacement was applied to a ceramic hydroxyapatite column (Japan Bio-Rad Laboratories, Inc., Bio-Scale CHT2-1 hydroxyapatite column (volume: 2 ml)) equilibrated with a buffer containing 5 mM NaPi, 50 mM MES, and 20 mM NaCl at pH 6.5. Then, linear concentration gradient elution with sodium chloride was performed, and a fraction containing the antibody was collected. The fraction was applied to a desalting column (manufactured by GE Healthcare Bio-Sciences Co., Ltd., two HiTrap™ desalting columns (volume: 5 ml) connected in series), whereby the liquid was replaced with CBS (10 mM citrate buffer containing 140 mM sodium chloride, pH 6.0). Finally, the resulting solution was concentrated using Centrifugal UF Filter Device VIVASPIN® 20 (fractional molecular weight: 30 K, Sartorius Co., Ltd., at 4° C.), and the concentration of IgG was adjusted to 1.0 mg/ml or more, and the thus obtained solution was used as a purified sample.

11)-2-2 Comparison of Antitumor Activity in Nude Mice Implanted with Human Colon Cancer Cell Line HCT-15 Between the cB273 Antibody and Conatumumab $1 \times 10^7$ cells of a human colon cancer cell line HCT-15 (purchased from ATCC) were implanted subcutaneously in the axillary region of nude mice. On days 6, 13, and 20 after the implantation, the cB273 antibody or conatumumab was administered to tumor-bearing mice through the tail vein at a dose of 3, 10, or 30 mg/kg (n=10). In the same manner as described above, the major axis and the minor axis of the implanted tumor were measured, and the tumor volume was calculated.

Figure 25:
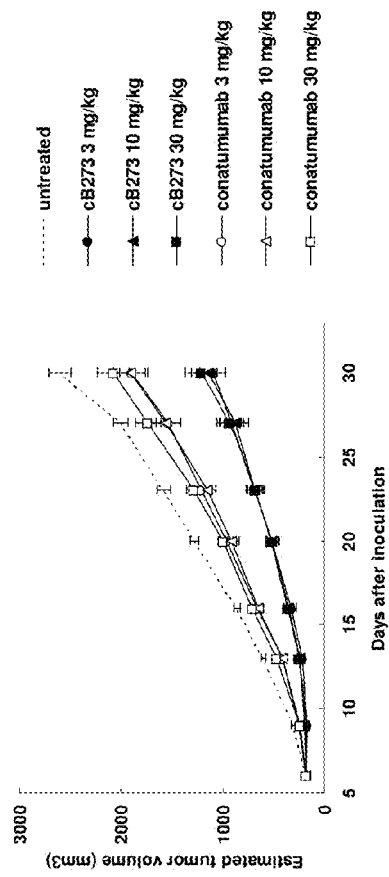
FIG. 25 is a figure showing a comparison of the in vivo antitumor activity in nude mice implanted with a human colon cancer cell line HCT-15 between a cB273 antibody and conatumumab.

The results are shown in FIG. 25. The tumor growth inhibitory rate on day 30 after the implantation, which was the final day of the measurement, was 57.9% in the group administered the cB273 antibody at 3 mg/kg, 56.0% in the group administered the cB273 antibody at 10 mg/kg, 53.6% in the group administered the cB273 antibody at 30 mg/kg, 27.4% in the group administered conatumumab at 3 mg/kg, 26.9% in the group administered conatumumab at 10 mg/kg, and 20.3% in the group administered conatumumab at 30 mg/kg.

11)-2-3 Comparison of Antitumor Activity in Nude Mice Implanted with Human Lung Cancer Cell Line NCI-H1975 Between the cB273 Antibody and Conatumumab $3\times10^6$ cells of a human lung cancer cell line NCI-H1975 (purchased from ATCC) were implanted subcutaneously in the axillary region of nude mice. On days 12, 19, and 26 after the implantation, the cB273 antibody or conatumumab was administered to tumor-bearing mice through the tail vein at a dose of 3 or 10 mg/kg (n=10). In the same manner as described above, the major axis and the minor axis of the implanted tumor were measured, and the tumor volume was calculated.

Figure 26:
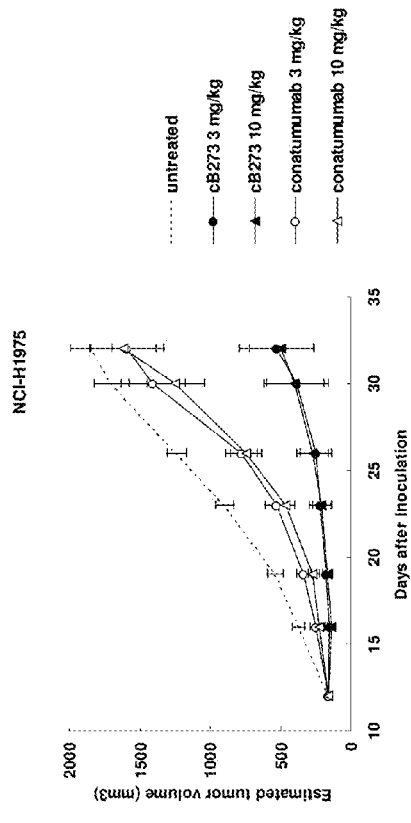
FIG. 26 is a figure showing a comparison of the in vivo antitumor activity in nude mice implanted with a human lung cancer cell line NCI-H1975 between a cB273 antibody and conatumumab.

The results are shown in FIG. 26. The tumor growth inhibitory rate on day 32 after the implantation, which was the final day of the measurement, was 71.5% in the group administered the cB273 antibody at 3 mg/kg, 73.3% in the group administered the cB273 antibody at 10 mg/kg, 13.5% in the group administered conatumumab at 3 mg/kg, and 12.6% in the group administered conatumumab at 10 mg/kg.

Example 12 In Vivo Antitumor Effect of hB273_H2-1-NE/hB273_L1-NK Antibody

12)-1 Antitumor Activity of hB273_H2-1-NE/hB273_L1-NK Antibody in Nude Mice Implanted with Human Colon Cancer Cell Line COLO 205

$2\times10^6$ cells of a human colon cancer cell line COLO 205 (purchased from ATCC) were implanted subcutaneously in the axillary region of nude mice. On days 8, 15, and 22 after the implantation, the hB273_H2-1-NE/hB273_L1-NK antibody or the cB273 antibody was administered to tumor-bearing mice through the tail vein at a dose of 0.3 or 3 mg/kg (n=10). In the same manner as described above, the major axis and the minor axis of the implanted tumor were measured, and the tumor volume was calculated.

Figure 27:
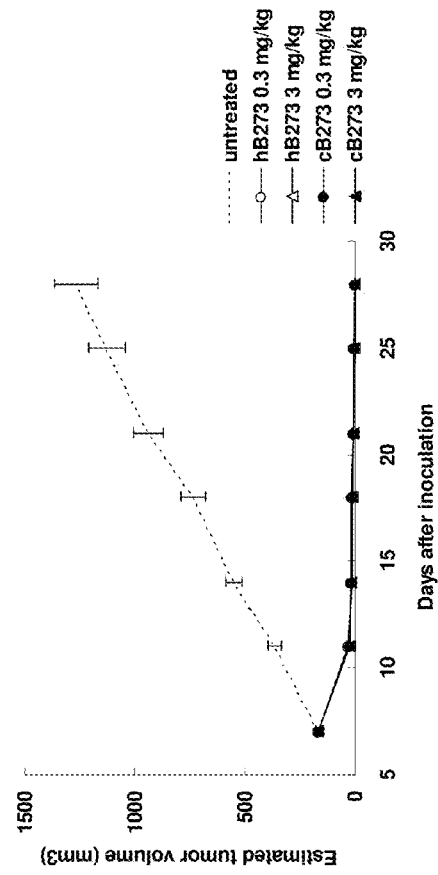
FIG. 27 is a figure showing the in vivo antitumor activity of a hB273_H2-1-NE/L1-NK antibody (denoted as "hB273" in the drawing) in nude mice implanted with a human colon cancer cell COLO 205.

The results are shown in FIG. 27. The complete degeneration of the tumor was observed in all mice in the group administered the hB273_H2-1-NE/hB273_L1-NK antibody at 3 mg/kg and the group administered the cB273 antibody at 0.3 mg/kg. Further, the complete degeneration of the tumor was observed in 9 out of 10 mice in the group administered the hB273_H2-1-NE/hB273_L1-NK antibody at 0.3 mg/kg, and 8 out of 10 mice in the group administered the cB273 antibody at 3 mg/kg.

Example 13 In Vitro Cytocidal Activity of hB273_H2-1-NE/hB273_L1-NK Antibody Against Human Cancer Cell Lines NCI-N87, KATO-III, and SNU-16 (each of which is a human stomach cancer cell line), Caki-1, ACHN, and 786-0 (each of which is a human renal cancer cell line), Hep3B, SK-HEP-1, and HepG2 (C3A) (each of which is a human liver cancer cell line), and HT-1080 (which is a human fibrosarcoma cell line) were purchased from American Type Culture Collection (ATCC). GCIY (which is a human stomach cancer cell line) was purchased from RIKEN. HuH-7 (which is a human liver cancer cell line) was purchased from National Institute of Biomedical Innovation.

The in vitro cytocidal activities against various types of cell lines were measured by the following method. As for the stomach cancer cell line, the renal cancer cell line, and the fibrosarcoma cell line, appropriately subcultured cells were counted by a trypan blue staining method, and thereafter prepared at $1\times10^5$ cells/ml in a medium containing 10% fetal bovine serum (manufactured by HyClone Laboratories, Inc.) (hereinafter referred to as "the medium"). In the medium, the hB273_H2-1-NE/hB273_L1-NK antibody at 20 μg/ml and a secondary antibody (goat anti-human IgG antibody, manufactured by MP Biomedicals, LLC.) at 40 μg/ml were mixed. Then, the resulting mixture was diluted with the medium, whereby solutions were prepared such that the concentration of the hB273_H2-1-NE/hB273_L1-NK antibody was 2000, 200, 20, or 2 ng/ml. Each of the resulting solutions having the respective concentrations was added to a transparent 96-well microplate (manufactured by Corning Incorporated) at 50 μl/well (3 wells per group), and the cell suspension was seeded at 50 μl/well ($5\times10^3$ cells) (the final concentration of the hB273_H2-1-NE/hB273_L1-NK antibody: 10000, 1000, 100, 10, or 1 ng/ml).

As for the liver cancer cell line, appropriately subcultured cells were counted by a trypan blue staining method, and thereafter prepared at $4\times10^4$ cells/ml in the medium. In the medium, the hB273_H2-1-NE/hB273_L1-NK antibody at 2 μg/ml and the secondary antibody at 4 μg/ml were mixed. Then, the resulting mixture was diluted with the medium, whereby solutions were prepared such that the concentration of the hB273_H2-1-NE/hB273_L1-NK antibody was 200, 20, 2, 0.2, or 0.02 ng/ml. Each of the resulting solutions having the respective concentrations was added to a black clear bottom 96-well microplate (manufactured by Corning Incorporated) at 50 μl/well (2 wells per group), and the cell suspension was seeded at 50 μl/well ($2\times10^3$ cells) (the final concentration of the antibody: 1000, 100, 10, 1, 0.1, or 0.01 ng/ml).

The cells were cultured at 37° C. in the presence of 5% $CO_2$ for 72 hours, and the amount of ATP in each well was measured. The measurement of the amount of ATP was performed using a luciferase luminescent reagent (CellTiter-Glo™, manufactured by Promega Corporation) according to the attached protocol. That is, a test solution composed of a cell lysate component and a luminescent substrate component was added to the plate at 100 μl per well, followed by stirring. Thereafter, the luminescence from each well was measured using a luminometer (manufactured by Berthold Technologies). As for the stomach cancer cell line, the renal cancer cell line, and the fibrosarcoma cell line, a test solution in an amount of 100 μl per well was transferred from the transparent 96-well microplate to a white 96-well microplate (manufactured by Corning Incorporated), and then, the luminescence was measured.

A well to which the medium and the cell suspension were added was prepared as a negative control well, a well to which only the medium was added was prepared as a background well, and the cell viability in each test well was calculated according to the following formula.

Cell viability (%)=(Luminescence intensity of test well−Average luminescence intensity of background well)/(Average luminescence intensity of negative control well−Average luminescence intensity of background well)×100

Figure 51:
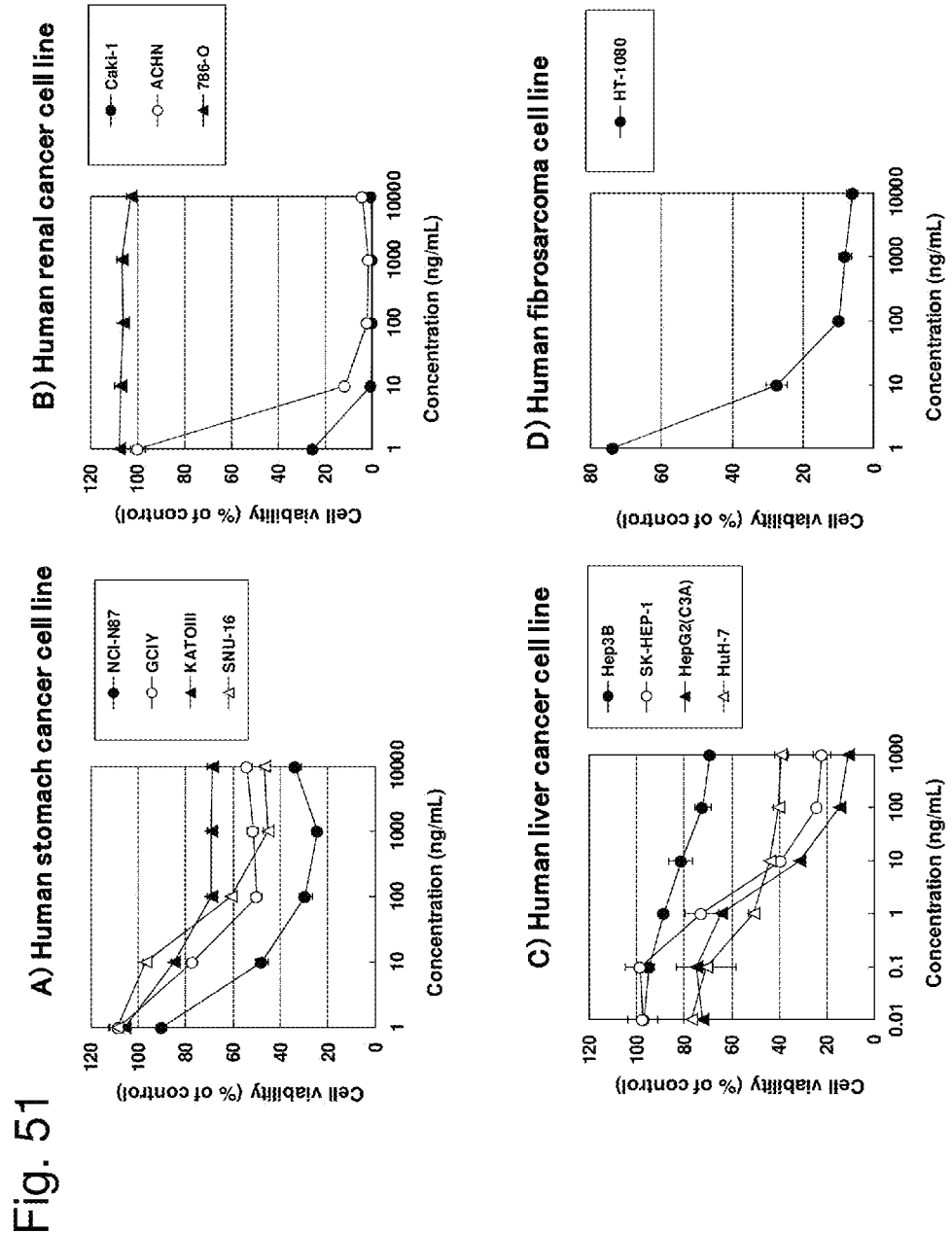
FIG. 51 is a figure showing the in vitro cytocidal activity of a hB273_H2-1-NE/hB273_L1-NK antibody against human cancer cell lines. A) shows the results for a human stomach cancer cell line, B) shows the results for a human renal cancer cell line, C) shows the results for a human liver cancer cell line, and D) shows the results for a human fibrosarcoma cell line.

In FIG. 51, an average of the cell viability of each cell line for the respective concentrations of the antibody used in the treatment is shown. As for the stomach cancer cell line, the renal cancer cell line, and the fibrosarcoma cell line, a standard error is represented by an error bar. The hB273_H2-1-NE/hB273_L1-NK antibody exhibited a cytotoxic activity against all of the cell lines tested except for 786-0.

Example 14 Measurement of In Vivo Activity of hB273_H2-1-NE/hB273_L1-NK Antibody in Combination with a Chemotherapeutic Agent 14)-1 Antitumor Activity of hB273_H2-1-NE/hB273_L1-NK Antibody in Combination with 5-FU in Nude Mice Implanted with Human Colon Cancer Cell Line HCT-15 and Comparison of Activity with Conatumumab $1\times10^7$ cells of a human colon cancer cell line HCT-15 (purchased from ATCC) were implanted subcutaneously in the axillary region of nude mice (CAnN.Cg-Foxn1$^{nu}$/Crl-Crlj, purchased from Charles River Laboratories Japan, Inc.). On days 7, 14, and 21 after the implantation, the hB273_H2-1-NE/hB273_L1-NK antibody or conatumumab was administered to tumor-bearing mice through the tail vein at a dose of 3 mg/kg. 5-FU was administered through the tail vein on day 7 after the implantation at a dose of 160 mg/kg. The experiment was carried out at n=6. The major axis and the minor axis of the implanted tumor were measured twice a week using an electronic digital caliper (manufactured by Mitutoyo Corporation), and the tumor volume was calculated according to the following calculation formula.

Tumor volume (mm$^3$)=1/2×(Minor axis)$^2$ (mm)× (Major axis)$^2$ (mm)

Figure 52:
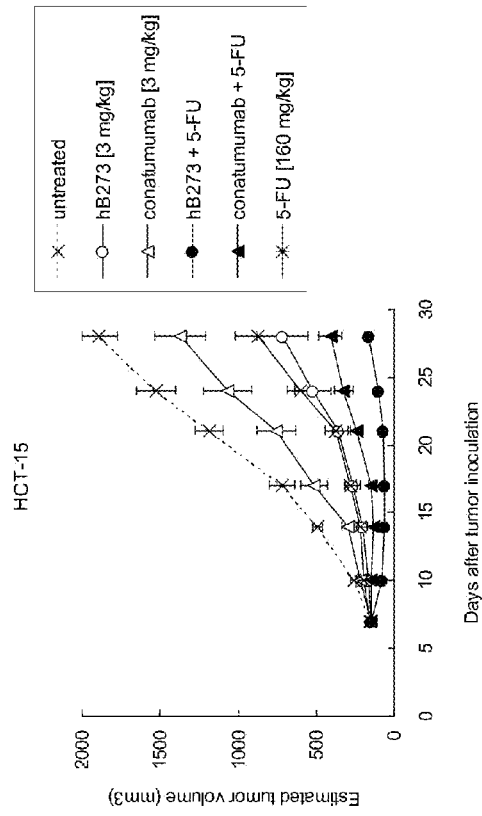
FIG. 52 is a figure showing the in vivo antitumor activity of a hB273_H2-1-NE/hB273_L1-NK antibody (denoted as "hB273" in the drawing) in combination with 5-FU in nude mice implanted with a human colon cancer cell line HCT-15 and a comparison of the activity with conatumumab.

The results are shown in FIG. 52. The tumor growth inhibitory rate on day 28 after the implantation, which was the final day of the measurement, was 62% in the hB273_H2-1-NE/hB273_L1-NK antibody administration group, 27% in the conatumumab administration group, 54% in the 5-FU administration group, 91% in the group of combined administration of the hB273_H2-1-NE/hB273_L1-NK antibody and 5-FU, and 78% in the group of combined administration of conatumumab and 5-FU. That is, a combined effect of the hB273_H2-1-NE/hB273_L1-NK antibody and 5-FU was observed, and further, a higher antitumor activity was observed in the group of combined administration of the hB273_H2-1-NE/hB273_L1-NK antibody and 5-FU than in the group of combined administration of conatumumab and 5-FU.

14)-2 Antitumor activity of hB273_H2-1-NE/hB273_L1-NK antibody in combination with paclitaxel in nude mice implanted with human non-small cell lung cancer cell line NCI-H1975 and comparison of activity with conatumumab $3\times10^6$ cells of a human non-small cell lung cancer cell line NCI-H1975 (purchased from ATCC) were implanted subcutaneously in the axillary region of nude mice. On day 11, 18, and 25 after the implantation, the hB273_H2-1-NE/hB273_L1-NK antibody or conatumumab was administered to tumor-bearing mice through the tail vein at a dose of 3 mg/kg. Paclitaxel was administered to tumor-bearing mice through the tail vein on days 11, 12, 13, and 14 after the implantation at a dose of 6.25 mg/kg. The experiment was carried out at n=6. In the same manner as described above, the major axis and the minor axis of the implanted tumor were measured, and the tumor volume was calculated.

Figure 53:
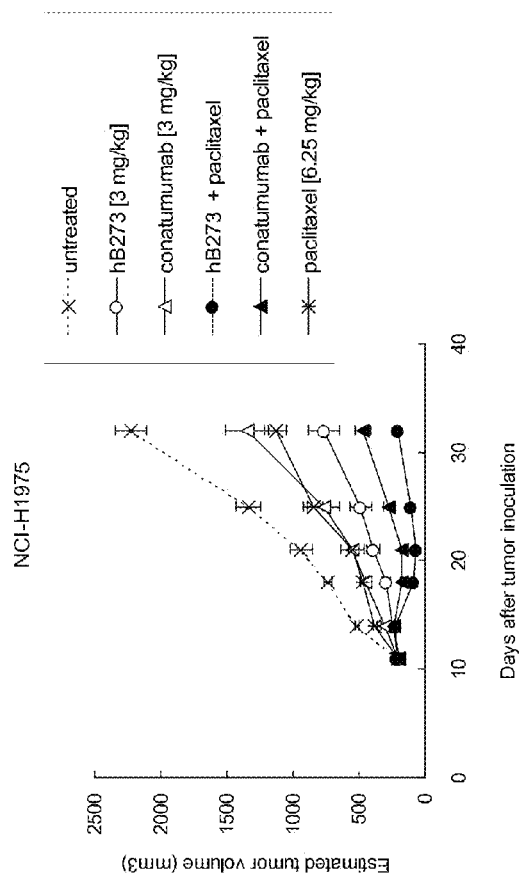
FIG. 53 is a figure showing the in vivo antitumor activity of a hB273_H2-1-NE/hB273_L1-NK antibody (denoted as "hB273" in the drawing) in combination with paclitaxel in nude mice implanted with a human non-small cell lung cancer cell line NCI-H1975 and a comparison of the activity with conatumumab.

The results are shown in FIG. 53. The tumor growth inhibitory rate on day 32 after the implantation, which was the final day of the measurement, was 66% in the hB273_H2-1-NE/hB273_L1-NK antibody administration group, 40% in the conatumumab administration group, 49% in the paclitaxel administration group, 91% in the group of combined administration of the hB273_H2-1-NE/hB273_L1-NK antibody and paclitaxel, and 79% in the group of combined administration of conatumumab and paclitaxel. That is, a combined effect of the hB273_H2-1-NE/hB273_L1-NK antibody and paclitaxel was observed, and further, a higher antitumor activity was observed in the group of combined administration of the hB273_H2-1-NE/hB273_L1-NK antibody and paclitaxel than in the group of combined administration of conatumumab and paclitaxel.

The embodiments of the invention in which an exclusive property or privilege is claimed are defined as follows:

1. An antibody which specifically binds Death Receptor 5 (DR5), wherein the antibody comprises:
    a heavy chain sequence containing a variable region having CDRH1, CDRH2, and CDRH3; the CDRH1 comprising an amino acid sequence represented by SEQ ID NO:82, the CDRH2 comprising an amino acid sequence represented by SEQ ID NO:89, and the CDRH3 comprising an amino acid sequence represented by SEQ ID NO:84; and
    a light chain sequence containing a variable region having CDRL1, CDRL2, and CDRL3; the CDRL1 comprising an amino acid sequence represented by SEQ ID NO:87, the CDRL2 comprising an amino acid sequence represented by SEQ ID NO:80, and the CDRL3 comprising an amino acid sequence represented by SEQ ID NO:81, or a functional fragment of the antibody having DR5 binding activity.

2. The antibody or a functional fragment of the antibody having antigen binding activity according to claim 1, wherein the antibody or functional fragment of the antibody having DR5 binding activity contains a heavy chain variable region sequence comprising amino acid residues 20 to 141 of the amino acid sequence represented by SEQ ID NO:70 and a light chain variable region sequence comprising amino acid residues 21 to 134 of the amino acid sequence represented by SEQ ID NO:62.

3. The antibody or a functional fragment of the antibody having DR5 antigen binding activity according to claim 1, wherein the antibody is a chimeric antibody.

4. The antibody or a functional fragment of the antibody having DR5 antigen binding activity according to claim 1, wherein the antibody is humanized.

5. The antibody or a functional fragment of the antibody having DR5 antigen binding activity according to claim 4, wherein the antibody or functional fragment thereof contains:
    (a) a heavy chain variable region sequence comprising:
        (a1) an amino acid sequence comprising amino acid residues 20 to 141 of the amino acid sequence represented by SEQ ID NO:70;
        (a2) an amino acid sequence having a homology of at least 95% with an amino acid sequence from (a1);
        (a3) an amino acid sequence having a homology of at least 99% with an amino acid sequence from (a1); or
        (a4) an amino acid sequence including a substitution, deletion, or addition of one to several amino acid residues in either one of the amino acid sequences from (a1), (a2) or (a3); and
    (b) a light chain variable region sequence comprising:
        (b1) an amino acid sequence comprising amino acid residues 21 to 134 of the amino acid sequence represented by SEQ ID NO:62;
        (b2) an amino acid sequence having a homology of at least 95% with an amino acid sequence from (b1);
        (b3) an amino acid sequence having a homology of at least 99% with an amino acid sequence from (b1); or
        (b4) an amino acid sequence including a substitution, deletion, or addition of one to several amino acid residues in either one of the amino acid sequences from (b1), (b2) or (b3).

6. The antibody or a functional fragment of the antibody according to claim 5, wherein the heavy claim variable region sequence comprises amino acid residues 20 to 141 of the amino acid sequence represented by SEQ ID NO:70 and a light chain variable region sequence comprising amino acid residues 21 to 134 of the amino acid sequence represented by SEQ ID NO:62.

7. The antibody or a functional fragment of the antibody according to claim 5, wherein the heavy chain sequence comprises amino acid residues 20 to 471 of the amino acid sequence represented by SEQ ID NO:70 and a light chain sequence comprising amino acid residues 21 to 239 of the amino acid sequence represented by SEQ ID NO:62.

8. The functional fragment of the antibody according to any one of claims 1 to 7, wherein the functional fragment of the antibody is a Fab, a F(ab')2, a Fab' or a Fv.

9. A pharmaceutical composition comprising the antibody or functional fragment of the antibody according to any one of claims 1 through 7 and a pharmaceutically acceptable carrier.

10. A pharmaceutical composition comprising the antibody or functional fragment of the antibody according to claim 8 and a pharmaceutically acceptable carrier.

11. The pharmaceutical composition according to claim 9, comprising the pharmaceutical composition formulated for treating cancer.

12. The pharmaceutical composition according to claim 10, comprising the pharmaceutical composition formulated for treating cancer.

13. The pharmaceutical composition according to claim 11, further comprising paclitaxel, carboplatin, CPT-11, or vinblastine.

14. The pharmaceutical composition according to claim 11, wherein the cancer is lung cancer, prostate cancer, thyroid cancer, stomach cancer, liver cancer, ovarian cancer, colon cancer, breast cancer, pancreatic cancer, uterine cancer, melanoma, glioblastoma, or a blood cell cancer.

15. The pharmaceutical composition according to claim 12, further comprising paclitaxel, carboplatin, CPT-11, or vinblastine.

16. The pharmaceutical composition according to claim 12, wherein the cancer is lung cancer, prostate cancer, thyroid cancer, stomach cancer, liver cancer, ovarian cancer, colon cancer, breast cancer, pancreatic cancer, uterine cancer, melanoma, glioblastoma, or a blood cell cancer.

17. A method of treating cancer comprising administering at least one antibody or a functional fragment of the antibody having DR5 binding activity according to claim 1.

18. A method of treating cancer, comprising simultaneously or sequentially administering at least one antibody or a functional fragment of the antibody having DR5 binding activity according to claim 1 and at least one of paclitaxel, carboplatin, CPT-11, vinblastine, or 5-FU.

19. The method according to claim 17, wherein the cancer is lung cancer, prostate cancer, thyroid cancer, stomach cancer, liver cancer, ovarian cancer, colon cancer, breast cancer, pancreatic cancer, uterine cancer, melanoma, glioblastoma, or a blood cell cancer.

20. A polynucleotide encoding the antibody or functional fragment of the antibody having DR5 binding activity according to claim 5.

21. The polynucleotide according to claim 20, wherein the polynucleotide contains a nucleotide comprising nucleotides 58 to 423 of the nucleotide sequence represented by SEQ ID NO:69 and a nucleotide sequence comprising nucleotides 61 to 402 of the nucleotide sequence represented by SEQ ID NO:61.

22. The polynucleotide according to claim 20, wherein the polynucleotide contains a nucleotide sequence comprising nucleotides 58 to 1413 of the nucleotide sequence represented by SEQ ID NO:69 and a nucleotide sequence comprising nucleotides 61 to 717 of the nucleotide sequence represented by SEQ ID NO:61.

23. The polynucleotide according to claim 20, wherein the polynucleotide contains:
 (a1) a polynucleotide comprising nucleotides 58 to 423 of the nucleotide represented by SEQ ID NO:69;
 (a2) a nucleotide sequence of a polynucleotide which hybridizes to a polynucleotide comprising a nucleotide sequence complementary to the nucleotide sequence (a1) under stringent conditions; or
 (a3) a nucleotide sequence including a substitution, deletion, or addition of one to several nucleotides in the nucleotide sequence (a1); and
 (b1) a nucleotide sequence comprising nucleotides 61 to 402 of the nucleotide sequence represented by SEQ ID NO:61;
 (b2) a nucleotide sequence of a polynucleotide which hybridizes to a polynucleotide comprising a nucleotide sequence complementary to the nucleotide sequence (b1) under stringent conditions; or
 (b3) a nucleotide sequence including a substitution, deletion, or addition of one to several nucleotides in the nucleotide sequence (b1).

24. The polynucleotide according to claim 23, wherein the polynucleotide contains a polynucleotide comprising a nucleotide sequence comprising nucleotides 58 to 423 of the nucleotide sequence represented by SEQ ID NO:69, and a polynucleotide comprising a nucleotide sequence comprising nucleotides 61 to 402 of the nucleotide sequence represented by SEQ ID NO:61.

25. The polynucleotide according to claim 23, wherein the polynucleotide contains a polynucleotide comprising a nucleotide sequence comprising nucleotides 58 to 1413 of the nucleotide sequence represented by SEQ ID NO:69, and a polynucleotide comprising a nucleotide sequence comprising nucleotides 61 to 717 of the nucleotide sequence represented by SEQ ID NO:61.

26. A vector comprising any one of the polynucleotides according to claim 23.

27. A transformed host cell comprising a polynucleotide according to claim 23.

28. A transformed host cell comprising the vector according to claim 26.

29. A method for producing an antibody or functional fragment of the antibody having DR5 binding activity, wherein the heavy chain variable region sequence comprises amino acid residues 20 to 141 of the amino acid sequence represented by SEQ ID NO:70 and a light chain variable region sequence comprising amino acid residues 21 to 134 of the amino acid sequence represented by SEQ ID NO:62, comprising the step of culturing the host cell according to any one of claim 27 or 28 and purifying the antibody or functional fragment of the antibody from the resulting cultured product.

* * * * *

SEQUENCE LISTING

```
<160> NUMBER OF SEQ ID NOS: 89

<210> SEQ ID NO 1
<211> LENGTH: 15
<212> TYPE: PRT
<213> ORGANISM: Mus musculus

<400> SEQUENCE: 1

Glu Val Gln Leu Gln Gln Ser Gly Pro Glu Leu Val Lys Pro Gly
1               5                   10                  15

<210> SEQ ID NO 2
<211> LENGTH: 20
<212> TYPE: PRT
<213> ORGANISM: Mus musculus

<400> SEQUENCE: 2

Asp Val Val Met Thr Gln Thr Pro Leu Ser Leu Pro Val Ser Leu Gly
1               5                   10                  15

Asp Gln Ala Ser
            20

<210> SEQ ID NO 3
<211> LENGTH: 26
<212> TYPE: DNA
<213> ORGANISM: Artificial Sequence
```

-continued

```
<220> FEATURE:
<223> OTHER INFORMATION: Primer MH258E1F1

<400> SEQUENCE: 3
aagaattcat gggatggagc tgtatc                                              26

<210> SEQ ID NO 4
<211> LENGTH: 32
<212> TYPE: DNA
<213> ORGANISM: Artificial Sequence
<220> FEATURE:
<223> OTHER INFORMATION: Primer G1EVR1

<400> SEQUENCE: 4
aagatatctt atttaccagg agagtgggag ag                                       32

<210> SEQ ID NO 5
<211> LENGTH: 26
<212> TYPE: DNA
<213> ORGANISM: Artificial Sequence
<220> FEATURE:
<223> OTHER INFORMATION: Primer MK19EIF1

<400> SEQUENCE: 5
aagaattcat gaagttgcct gttagg                                              26

<210> SEQ ID NO 6
<211> LENGTH: 32
<212> TYPE: DNA
<213> ORGANISM: Artificial Sequence
<220> FEATURE:
<223> OTHER INFORMATION: Primer KEVR1

<400> SEQUENCE: 6
aagatatctt aacactcatt cctgttgaag ct                                       32

<210> SEQ ID NO 7
<211> LENGTH: 1395
<212> TYPE: DNA
<213> ORGANISM: Mus musculus
<220> FEATURE:
<221> NAME/KEY: CDS
<222> LOCATION: (1)..(1395)

<400> SEQUENCE: 7 atg gga tgg agc tgt atc ttt ctc ttt ctc ctg tca gta act gta ggt          48
Met Gly Trp Ser Cys Ile Phe Leu Phe Leu Leu Ser Val Thr Val Gly
1               5                   10                  15 gtg ttc tct gag gtt cag ctg cag cag tct gga cct gag ctg gtg aag          96
Val Phe Ser Glu Val Gln Leu Gln Gln Ser Gly Pro Glu Leu Val Lys
            20                  25                  30 cct ggg gct tca gtg aag ata tcc tgc aag gct tct ggt tac tca ttt         144
Pro Gly Ala Ser Val Lys Ile Ser Cys Lys Ala Ser Gly Tyr Ser Phe
        35                  40                  45 att ggc tac ttt atg aac tgg atg aag cag agc cat gga aag agc ctt         192
Ile Gly Tyr Phe Met Asn Trp Met Lys Gln Ser His Gly Lys Ser Leu
    50                  55                  60 gag tgg att gga cgt ttt aat cca tac aat ggt gat act ttc tac aac         240
Glu Trp Ile Gly Arg Phe Asn Pro Tyr Asn Gly Asp Thr Phe Tyr Asn
65                  70                  75                  80 cag aag ttc aag ggc aag gcc aca ttg act gta gac aaa tcc tct acc         288
Gln Lys Phe Lys Gly Lys Ala Thr Leu Thr Val Asp Lys Ser Ser Thr
                85                  90                  95
```

```
aca gcc cac atg gag ctc ctg agc ctg aca tct gag gac tct gca gtc      336
Thr Ala His Met Glu Leu Leu Ser Leu Thr Ser Glu Asp Ser Ala Val
            100                 105                 110 tat ttt tgt gga aga tcg gcg tat tac ttc gat agt ggg ggc tac ttt      384
Tyr Phe Cys Gly Arg Ser Ala Tyr Tyr Phe Asp Ser Gly Gly Tyr Phe
                115                 120                 125 gac tac tgg ggc caa ggc acc act ctc aca gtc tcc tca gcc aaa acg      432
Asp Tyr Trp Gly Gln Gly Thr Thr Leu Thr Val Ser Ser Ala Lys Thr
        130                 135                 140 aca ccc cca tct gtc tat cca ctg gcc cct gga tct gct gcc caa act      480
Thr Pro Pro Ser Val Tyr Pro Leu Ala Pro Gly Ser Ala Ala Gln Thr
145                 150                 155                 160 aac tcc atg gtg acc ctg gga tgc ctg gtc aag ggc tat ttc cct gag      528
Asn Ser Met Val Thr Leu Gly Cys Leu Val Lys Gly Tyr Phe Pro Glu
                165                 170                 175 cca gtg aca gtg acc tgg aac tct gga tcc ctg tcc agc ggt gtg cac      576
Pro Val Thr Val Thr Trp Asn Ser Gly Ser Leu Ser Ser Gly Val His
            180                 185                 190 acc ttc cca gct gtc ctg cag tct gac ctc tac act ctg agc agc tca      624
Thr Phe Pro Ala Val Leu Gln Ser Asp Leu Tyr Thr Leu Ser Ser Ser
        195                 200                 205 gtg act gtc ccc tcc agc acc tgg ccc agc gag acc gtc acc tgc aac      672
Val Thr Val Pro Ser Ser Thr Trp Pro Ser Glu Thr Val Thr Cys Asn
210                 215                 220 gtt gcc cac ccg gcc agc agc acc aag gtg gac aag aaa att gtg ccc      720
Val Ala His Pro Ala Ser Ser Thr Lys Val Asp Lys Lys Ile Val Pro
225                 230                 235                 240 agg gat tgt ggt tgt aag cct tgc ata tgt aca gtc cca gaa gta tca      768
Arg Asp Cys Gly Cys Lys Pro Cys Ile Cys Thr Val Pro Glu Val Ser
                245                 250                 255 tct gtc ttc atc ttc ccc cca aag ccc aag gat gtg ctc acc att act      816
Ser Val Phe Ile Phe Pro Pro Lys Pro Lys Asp Val Leu Thr Ile Thr
            260                 265                 270 ctg act cct aag gtc acg tgt gtt gtg gta gac atc agc aag gat gat      864
Leu Thr Pro Lys Val Thr Cys Val Val Val Asp Ile Ser Lys Asp Asp
        275                 280                 285 ccc gag gtc cag ttc agc tgg ttt gta gat gat gtg gag gtg cac aca      912
Pro Glu Val Gln Phe Ser Trp Phe Val Asp Asp Val Glu Val His Thr
290                 295                 300 gct cag acg caa ccc cgg gag gag cag ttc aac agc act ttc cgc tca      960
Ala Gln Thr Gln Pro Arg Glu Glu Gln Phe Asn Ser Thr Phe Arg Ser
305                 310                 315                 320 gtc agt gaa ctt ccc atc atg cac cag gac tgg ctc aat ggc aag gag     1008
Val Ser Glu Leu Pro Ile Met His Gln Asp Trp Leu Asn Gly Lys Glu
                325                 330                 335 ttc aaa tgc agg gtc aac agt gca gct ttc cct gcc ccc atc gag aaa     1056
Phe Lys Cys Arg Val Asn Ser Ala Ala Phe Pro Ala Pro Ile Glu Lys
            340                 345                 350 acc atc tcc aaa acc aaa ggc aga ccg aag gct cca cag gtg tac acc     1104
Thr Ile Ser Lys Thr Lys Gly Arg Pro Lys Ala Pro Gln Val Tyr Thr
        355                 360                 365 att cca cct ccc aag gag cag atg gcc aag gat aaa gtc agt ctg acc     1152
Ile Pro Pro Pro Lys Glu Gln Met Ala Lys Asp Lys Val Ser Leu Thr
370                 375                 380 tgc atg ata aca gac ttc ttc cct gaa gac att act gtg gag tgg cag     1200
Cys Met Ile Thr Asp Phe Phe Pro Glu Asp Ile Thr Val Glu Trp Gln
385                 390                 395                 400 tgg aat ggg cag cca gcg gag aac tac aag aac act cag ccc atc atg     1248
Trp Asn Gly Gln Pro Ala Glu Asn Tyr Lys Asn Thr Gln Pro Ile Met
                405                 410                 415
```

```
gac aca gat ggc tct tac ttc gtc tac agc aag ctc aat gtg cag aag      1296
Asp Thr Asp Gly Ser Tyr Phe Val Tyr Ser Lys Leu Asn Val Gln Lys
            420                 425                 430 agc aac tgg gag gca gga aat act ttc acc tgc tct gtg tta cat gag      1344
Ser Asn Trp Glu Ala Gly Asn Thr Phe Thr Cys Ser Val Leu His Glu
        435                 440                 445 ggc ctg cac aac cac cat act gag aag agc ctc tcc cac tct cct ggt      1392
Gly Leu His Asn His His Thr Glu Lys Ser Leu Ser His Ser Pro Gly
    450                 455                 460 aaa                                                                    1395
Lys
465

<210> SEQ ID NO 8
<211> LENGTH: 465
<212> TYPE: PRT
<213> ORGANISM: Mus musculus

<400> SEQUENCE: 8

Met Gly Trp Ser Cys Ile Phe Leu Phe Leu Leu Ser Val Thr Val Gly
1               5                   10                  15

Val Phe Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Ile Gly Tyr Phe Met Asn Trp Met Lys Gln Ser His Gly Lys Ser Leu
    50                  55                  60

Glu Trp Ile Gly Arg Phe Asn Pro Tyr Asn Gly Asp Thr Phe Tyr Asn
65                  70                  75                  80

Gln Lys Phe Lys Gly Lys Ala Thr Leu Thr Val Asp Lys Ser Ser Thr
                85                  90                  95

Thr Ala His Met Glu Leu Leu Ser Leu Thr Ser Glu Asp Ser Ala Val
            100                 105                 110

Tyr Phe Cys Gly Arg Ser Ala Tyr Tyr Phe Asp Ser Gly Gly Tyr Phe
        115                 120                 125

Asp Tyr Trp Gly Gln Gly Thr Thr Leu Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Glu Thr Val Thr Cys Asn
    210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Lys Asp Asp
        275                 280                 285
```

```
Pro Glu Val Gln Phe Ser Trp Phe Val Asp Asp Val His Thr
    290                 295                 300
Ala Gln Thr Gln Pro Arg Glu Glu Gln Phe Asn Ser Thr Phe Arg Ser
305                 310                 315                 320
Val Ser Glu Leu Pro Ile Met His Gln Asp Trp Leu Asn Gly Lys Glu
                325                 330                 335
Phe Lys Cys Arg Val Asn Ser Ala Ala Phe Pro Ala Pro Ile Glu Lys
            340                 345                 350
Thr Ile Ser Lys Thr Lys Gly Arg Pro Lys Ala Pro Gln Val Tyr Thr
        355                 360                 365
Ile Pro Pro Pro Lys Glu Gln Met Ala Lys Asp Lys Val Ser Leu Thr
    370                 375                 380
Cys Met Ile Thr Asp Phe Phe Pro Glu Asp Ile Thr Val Glu Trp Gln
385                 390                 395                 400
Trp Asn Gly Gln Pro Ala Glu Asn Tyr Lys Asn Thr Gln Pro Ile Met
                405                 410                 415
Asp Thr Asp Gly Ser Tyr Phe Val Tyr Ser Lys Leu Asn Val Gln Lys
            420                 425                 430
Ser Asn Trp Glu Ala Gly Asn Thr Phe Thr Cys Ser Val Leu His Glu
        435                 440                 445
Gly Leu His Asn His His Thr Glu Lys Ser Leu Ser His Ser Pro Gly
    450                 455                 460
Lys
465

<210> SEQ ID NO 9
<211> LENGTH: 714
<212> TYPE: DNA
<213> ORGANISM: Mus musculus
<220> FEATURE:
<221> NAME/KEY: CDS
<222> LOCATION: (1)..(714)

<400> SEQUENCE: 9 atg aag ttg cct gtt agg ctg ttg gtg ctg atg ttc tgg att cct gct      48
Met Lys Leu Pro Val Arg Leu Leu Val Leu Met Phe Trp Ile Pro Ala
1               5                   10                  15 tcc agc agt gat gtt gtg atg acc caa act cca ctc tcc ctg cct gtc      96
Ser Ser Ser Asp Val Val Met Thr Gln Thr Pro Leu Ser Leu Pro Val
            20                  25                  30 agt ctt gga gat caa gcc tcc atc tct tgc aga tct agt cag agc ctt     144
Ser Leu Gly Asp Gln Ala Ser Ile Ser Cys Arg Ser Ser Gln Ser Leu
        35                  40                  45 gta cac agt aat gga aac acc tat cta cat tgg tac ctg cag aag cca     192
Val His Ser Asn Gly Asn Thr Tyr Leu His Trp Tyr Leu Gln Lys Pro
    50                  55                  60 ggc cag tct cca aag ctc ctg atc tac aaa gtt tcc aac cga ttt tct     240
Gly Gln Ser Pro Lys Leu Leu Ile Tyr Lys Val Ser Asn Arg Phe Ser
65                  70                  75                  80 ggg gtc cca gac agg ttc agt ggc agt gga tca ggg aca gat ttc aca     288
Gly Val Pro Asp Arg Phe Ser Gly Ser Gly Ser Gly Thr Asp Phe Thr
                85                  90                  95 ctc aag atc agc aga gtg gag gct gag gat ctg gga att tat ttc tgc     336
Leu Lys Ile Ser Arg Val Glu Ala Glu Asp Leu Gly Ile Tyr Phe Cys
            100                 105                 110 tct caa agt aca cat gtt ccg tgg acg ttc ggt gga ggc acc aag ctg     384
Ser Gln Ser Thr His Val Pro Trp Thr Phe Gly Gly Gly Thr Lys Leu
        115                 120                 125
```

-continued

| | | | | | | | | | | | | | | | | |
|---|---|---|---|---|---|---|---|---|---|---|---|---|---|---|---|---|
| gaa | atc | aaa | cgg | gct | gat | gct | gca | cca | act | gta | tcc | atc | ttc | cca | cca | 432 |
| Glu | Ile | Lys | Arg | Ala | Asp | Ala | Ala | Pro | Thr | Val | Ser | Ile | Phe | Pro | Pro | |
| 130 | | | | | 135 | | | | | 140 | | | | | | |

| tcc | agt | gag | cag | tta | aca | tct | gga | ggt | gcc | tca | gtc | gtg | tgc | ttc | ttg | 480 |
| Ser | Ser | Glu | Gln | Leu | Thr | Ser | Gly | Gly | Ala | Ser | Val | Val | Cys | Phe | Leu | |
| 145 | | | | | 150 | | | | | 155 | | | | | 160 | |

| aac | aac | ttc | tac | ccc | aaa | gac | atc | aat | gtc | aag | tgg | aag | att | gat | ggc | 528 |
| Asn | Asn | Phe | Tyr | Pro | Lys | Asp | Ile | Asn | Val | Lys | Trp | Lys | Ile | Asp | Gly | |
| | | | | 165 | | | | | 170 | | | | | 175 | | |

| agt | gaa | cga | caa | aat | ggc | gtc | ctg | aac | agt | tgg | act | gat | cag | gac | agc | 576 |
| Ser | Glu | Arg | Gln | Asn | Gly | Val | Leu | Asn | Ser | Trp | Thr | Asp | Gln | Asp | Ser | |
| | | | | 180 | | | | | 185 | | | | | 190 | | |

| aaa | gac | agc | acc | tac | agc | atg | agc | agc | acc | ctc | acg | ttg | acc | aag | gac | 624 |
| Lys | Asp | Ser | Thr | Tyr | Ser | Met | Ser | Ser | Thr | Leu | Thr | Leu | Thr | Lys | Asp | |
| | | | 195 | | | | | 200 | | | | | 205 | | | |

| gag | tat | gaa | cga | cat | aac | agc | tat | acc | tgt | gag | gcc | act | cac | aag | aca | 672 |
| Glu | Tyr | Glu | Arg | His | Asn | Ser | Tyr | Thr | Cys | Glu | Ala | Thr | His | Lys | Thr | |
| 210 | | | | | 215 | | | | | 220 | | | | | | |

| tca | act | tca | ccc | att | gtc | aag | agc | ttc | aac | agg | aat | gag | tgt | | | 714 |
| Ser | Thr | Ser | Pro | Ile | Val | Lys | Ser | Phe | Asn | Arg | Asn | Glu | Cys | | | |
| 225 | | | | | 230 | | | | | 235 | | | | | | |

<210> SEQ ID NO 10
<211> LENGTH: 238
<212> TYPE: PRT
<213> ORGANISM: Mus musculus

<400> SEQUENCE: 10

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Ile Tyr Phe Cys
            100                 105                 110

Ser Gln Ser Thr His Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys

<210> SEQ ID NO 11
<211> LENGTH: 28
<212> TYPE: DNA
<213> ORGANISM: Artificial Sequence
<220> FEATURE:
<223> OTHER INFORMATION: Primer EFF1

<400> SEQUENCE: 11
ccacgcgccc tgtagcggcg cattaagc                                28

<210> SEQ ID NO 12
<211> LENGTH: 30
<212> TYPE: DNA
<213> ORGANISM: Artificial Sequence
<220> FEATURE:
<223> OTHER INFORMATION: Primer EFsmaR

<400> SEQUENCE: 12
aaacccggga gcttttttgca aaagcctagg                              30

<210> SEQ ID NO 13
<211> LENGTH: 1704
<212> TYPE: DNA
<213> ORGANISM: Artificial Sequence
<220> FEATURE:
<223> OTHER INFORMATION: Nucleotide sequence of signal peptide, Fc
      region and poly A addition signal of human kappa chain

<400> SEQUENCE: 13
ggtaccaccc aagctggcta ggtaagcttg ctagcgccac catggtgctg cagacccagg    60
tgttcatctc cctgctgctg tggatctccg gcgcatatgg cgatatcgtg atgattaaac    120
gtacggtggc cgcccctcc gtgttcatct tcccccctc cgacgagcag ctgaagtccg     180
gcaccgcctc cgtggtgtgc ctgctgaata acttctaccc cagagaggcc aaggtgcagt    240
ggaaggtgga caacgccctg cagtccggga actcccagga gagcgtgacc gagcaggaca    300
gcaaggacag cacctacagc ctgagcagca ccctgaccct gagcaaagcc gactacgaga    360
agcacaaggt gtacgcctgc gaggtgaccc accagggcct gagctccccc gtcaccaaga    420
gcttcaacag ggggagtgt taggggcccg tttaaacggg tggcatccct gtgacccctc     480
cccagtgcct ctcctggccc tggaagttgc cactccagtg cccaccagcc ttgtcctaat    540
aaaattaagt tgcatcattt tgtctgacta ggtgtccttc tataatatta tggggtggag    600
gggggtggta tggagcaagg gcaagttgg gaagacaacc tgtagggcct gcggggtcta     660
ttgggaacca agctggagtg cagtggcaca atcttggctc actgcaatct ccgcctcctg    720
ggttcaagcg attctcctgc ctcagcctcc gagttgttg ggattccagg catgcatgac    780
caggctcacc taattttgt tttttttggta gagacggggt ttcaccatat ggccaggct    840 ggtctccaac tcctaatctc aggtgatcta cccaccttgg cctcccaaat tgctgggatt    900
acaggcgtga accactgctc cacgcgccct gtagcggcgc attaagcgcg gcgggtgtgg    960
tggttacgcg cagcgtgacc gctacacttg ccagcgccct agcgcccgct cctttcgctt    1020
tcttcccttc ctttctcgcc acgttcgccg gctttcccg tcaagctcta aatcgggggc    1080
tccctttagg gttccgattt agtgctttac ggcacctcga ccccaaaaaa cttgattagg    1140
gtgatggttc acgtagtggg ccatcgccct gatagacggt ttttcgccct ttgacgttgg    1200
agtccacgtt ctttaatagt ggactcttgt tccaaactgg aacaacactc aaccctatct    1260

-continued

```
cggtctattc tttttgattta aagggatttt tgccgatttc ggcctattgg ttaaaaaatg    1320
agctgattta acaaaaattt aacgcgaatt aattctgtgg aatgtgtgtc agttagggtg    1380
tggaaagtcc ccaggctccc cagcaggcag aagtatgcaa agcatgcatc tcaattagtc    1440
agcaaccagg tgtggaaagt ccccaggctc cccagcaggc agaagtatgc aaagcatgca    1500
tctcaattag tcagcaacca tagtcccgcc cctaactccg cccatcccgc cctaactcc     1560 gcccagttcc gcccattctc cgccccatgg ctgactaatt tttttatttt atgcagaggc    1620
cgaggccgcc tctgcctctg agctattcca gaagtagtga ggaggctttt ttggaggcct    1680
aggcttttgc aaaaagctcc cggg                                          1704
```

<210> SEQ ID NO 14
<211> LENGTH: 1120
<212> TYPE: DNA
<213> ORGANISM: Artificial Sequence
<220> FEATURE:
<223> OTHER INFORMATION: Nucleotide sequence of signal peptide and Fc region of human IgG1 chain

<400> SEQUENCE: 14

```
tgctagcgcc accatgaaac acctgtggtt cttcctcctg ctggtggcag ctcccagatg     60
ggtgctgagc caggtgcaat gtgcaggcg gttagctcag cctccaccaa gggcccaagc    120
gtcttccccc tggcaccctc ctccaagagc acctctggcg cacagccgc cctgggctgc    180 ctggtcaagg actacttccc cgaacccgtg accgtgagct ggaactcagg cgccctgacc    240
agcggcgtgc acaccttccc cgctgtcctg cagtcctcag gactctactc cctcagcagc    300
gtggtgaccg tgccctccag cagcttgggc acccagacct acatctgcaa cgtgaatcac    360
aagcccagca caccaaggt ggacaagaga gttgagccca atcttgtga caaaactcac    420 acatgcccac cctgcccagc acctgaactc ctggggggac cctcagtctt cctcttcccc    480
ccaaaaccca aggacaccct catgatctcc cggacccctg aggtcacatg cgtggtggtg    540
gacgtgagcc acgaagaccc tgaggtcaag ttcaactggt acgtggacgg cgtggaggtg    600
cataatgcca agacaaagcc ccgggaggag cagtacaaca gcacgtaccg ggtggtcagc    660
gtcctcaccg tcctgcacca ggactggctg aatggcaagg agtacaagtg caaggtctcc    720
aacaaagccc tcccagcccc catcgagaaa accatctcca agccaaaagg ccagccccgg    780
gaaccacagg tgtacaccct gccccccatcc cgggaggaga tgaccaagaa ccaggtcagc    840
ctgacctgcc tggtcaaagg cttctatccc agcgacatcg ccgtggagtg ggagagcaat    900
ggccagcccg agaacaacta caagaccacc cctcccgtgc tggactccga cggctccttc    960
ttcctctaca gcaagctcac cgtggacaag agcaggtggc agcagggcaa cgtcttctca    1020
tgctccgtga tgcatgaggc tctgcacaac cactacaccc agaagagcct ctccctgtct    1080
cccggcaaat gagatatcgg gcccgtttaa acgggtggca                         1120
```

<210> SEQ ID NO 15
<211> LENGTH: 717
<212> TYPE: DNA
<213> ORGANISM: Artificial Sequence
<220> FEATURE:
<223> OTHER INFORMATION: Nucleotide sequence coding the light chain of chimera B273
<220> FEATURE:
<221> NAME/KEY: CDS
<222> LOCATION: (1)..(717)

<400> SEQUENCE: 15

| | | |
|---|---|---|
| atg gtg ctg cag acc cag gtg ttc atc tcc ctg ctg ctg tgg atc tcc | 48 | |
| Met Val Leu Gln Thr Gln Val Phe Ile Ser Leu Leu Leu Trp Ile Ser | | |
| 1               5                   10                  15 | | |
| ggc gca tat ggc gat gtt gtg atg acc caa act cca ctc tcc ctg cct | 96 | |
| Gly Ala Tyr Gly Asp Val Val Met Thr Gln Thr Pro Leu Ser Leu Pro | | |
|             20                  25                  30 | | |
| gtc agt ctt gga gat caa gcc tcc atc tct tgc aga tct agt cag agc | 144 | |
| Val Ser Leu Gly Asp Gln Ala Ser Ile Ser Cys Arg Ser Ser Gln Ser | | |
|         35                  40                  45 | | |
| ctt gta cac agt aat gga aac acc tat cta cat tgg tac ctg cag aag | 192 | |
| Leu Val His Ser Asn Gly Asn Thr Tyr Leu His Trp Tyr Leu Gln Lys | | |
|     50                  55                  60 | | |
| cca ggc cag tct cca aag ctc ctg atc tac aaa gtt tcc aac cga ttt | 240 | |
| Pro Gly Gln Ser Pro Lys Leu Leu Ile Tyr Lys Val Ser Asn Arg Phe | | |
| 65                  70                  75                  80 | | |
| tct ggg gtc cca gac agg ttc agt ggc agt gga tca ggg aca gat ttc | 288 | |
| Ser Gly Val Pro Asp Arg Phe Ser Gly Ser Gly Ser Gly Thr Asp Phe | | |
|                 85                  90                  95 | | |
| aca ctc aag atc agc aga gtg gag gct gag gat ctg gga att tat ttc | 336 | |
| Thr Leu Lys Ile Ser Arg Val Glu Ala Glu Asp Leu Gly Ile Tyr Phe | | |
|             100                 105                 110 | | |
| tgc tct caa agt aca cat gtt ccg tgg acg ttc ggt gga ggc acc aag | 384 | |
| Cys Ser Gln Ser Thr His Val Pro Trp Thr Phe Gly Gly Gly Thr Lys | | |
|         115                 120                 125 | | |
| ctg gaa atc aaa cgt acg gtg gcc gcc ccc tcc gtg ttc atc ttc ccc | 432 | |
| Leu Glu Ile Lys Arg Thr Val Ala Ala Pro Ser Val Phe Ile Phe Pro | | |
|     130                 135                 140 | | |
| ccc tcc gac gag cag ctg aag tcc ggc acc gcc tcc gtg gtg tgc ctg | 480 | |
| Pro Ser Asp Glu Gln Leu Lys Ser Gly Thr Ala Ser Val Val Cys Leu | | |
| 145                 150                 155                 160 | | |
| ctg aat aac ttc tac ccc aga gag gcc aag gtg cag tgg aag gtg gac | 528 | |
| Leu Asn Asn Phe Tyr Pro Arg Glu Ala Lys Val Gln Trp Lys Val Asp | | |
|                 165                 170                 175 | | |
| aac gcc ctg cag tcc ggg aac tcc cag gag agc gtg acc gag cag gac | 576 | |
| Asn Ala Leu Gln Ser Gly Asn Ser Gln Glu Ser Val Thr Glu Gln Asp | | |
|             180                 185                 190 | | |
| agc aag gac agc acc tac agc ctg agc agc acc ctg acc ctg agc aaa | 624 | |
| Ser Lys Asp Ser Thr Tyr Ser Leu Ser Ser Thr Leu Thr Leu Ser Lys | | |
|         195                 200                 205 | | |
| gcc gac tac gag aag cac aag gtg tac gcc tgc gag gtg acc cac cag | 672 | |
| Ala Asp Tyr Glu Lys His Lys Val Tyr Ala Cys Glu Val Thr His Gln | | |
|     210                 215                 220 | | |
| ggc ctg agc tcc ccc gtc acc aag agc ttc aac agg ggg gag tgt | 717 | |
| Gly Leu Ser Ser Pro Val Thr Lys Ser Phe Asn Arg Gly Glu Cys | | |
| 225                 230                 235 | | |

<210> SEQ ID NO 16
<211> LENGTH: 239
<212> TYPE: PRT
<213> ORGANISM: Artificial Sequence
<220> FEATURE:
<223> OTHER INFORMATION: Synthetic Construct

<400> SEQUENCE: 16

Met Val Leu Gln Thr Gln Val Phe Ile Ser Leu Leu Leu Trp Ile Ser
1               5                   10                  15

Gly Ala Tyr Gly Asp Val Val Met Thr Gln Thr Pro Leu Ser Leu Pro
            20                  25                  30

Val Ser Leu Gly Asp Gln Ala Ser Ile Ser Cys Arg Ser Ser Gln Ser
        35                  40                  45

```
Leu Val His Ser Asn Gly Asn Thr Tyr Leu His Trp Tyr Leu Gln Lys
 50                  55                  60

Pro Gly Gln Ser Pro Lys Leu Leu Ile Tyr Lys Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Leu Gly Ile Tyr Phe
            100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 17
<211> LENGTH: 41
<212> TYPE: DNA
<213> ORGANISM: Artificial Sequence
<220> FEATURE:
<223> OTHER INFORMATION: Primer B273LF

<400> SEQUENCE: 17
aaacatatgg cgatgttgtg atgacccaaa ctccactctc c        41

<210> SEQ ID NO 18
<211> LENGTH: 41
<212> TYPE: DNA
<213> ORGANISM: Artificial Sequence
<220> FEATURE:
<223> OTHER INFORMATION: Primer B273LR

<400> SEQUENCE: 18
aaacgtacgt ttgatttcca gcttggtgcc tccaccgaac g        41

<210> SEQ ID NO 19
<211> LENGTH: 1413
<212> TYPE: DNA
<213> ORGANISM: Artificial Sequence
<220> FEATURE:
<223> OTHER INFORMATION: Nucleotide sequence coding the heavy chain of
      chimera B273
<220> FEATURE:
<221> NAME/KEY: CDS
<222> LOCATION: (1)..(1413)

<400> SEQUENCE: 19 atg aaa cac ctg tgg ttc ttc ctc ctg ctg gtg gca gct ccc aga tgg   48
Met Lys His Leu Trp Phe Phe Leu Leu Leu Val Ala Ala Pro Arg Trp
 1               5                  10                  15 gtg ctg agc gag gtt cag ctg cag cag tct gga cct gag ctg gtg aag   96
```

```
                  Val Leu Ser Glu Val Gln Leu Gln Gln Ser Gly Pro Glu Leu Val Lys
                               20                  25                  30 cct ggg gct tca gtg aag ata tcc tgc aag gct tct ggt tac tca ttt         144
Pro Gly Ala Ser Val Lys Ile Ser Cys Lys Ala Ser Gly Tyr Ser Phe
            35                  40                  45 att ggc tac ttt atg aac tgg atg aag cag agc cat gga aag agc ctt         192
Ile Gly Tyr Phe Met Asn Trp Met Lys Gln Ser His Gly Lys Ser Leu
 50                  55                  60 gag tgg att gga cgt ttt aat cca tac aat ggt gat act ttc tac aac         240
Glu Trp Ile Gly Arg Phe Asn Pro Tyr Asn Gly Asp Thr Phe Tyr Asn
 65                  70                  75                  80 cag aag ttc aag ggc aag gcc aca ttg act gta gac aaa tcc tct acc         288
Gln Lys Phe Lys Gly Lys Ala Thr Leu Thr Val Asp Lys Ser Ser Thr
                 85                  90                  95 aca gcc cac atg gag ctc ctg agc ctg aca tct gag gac tct gca gtc         336
Thr Ala His Met Glu Leu Leu Ser Leu Thr Ser Glu Asp Ser Ala Val
            100                 105                 110 tat ttt tgt gga aga tcg gcg tat tac ttc gat agt ggg ggc tac ttt         384
Tyr Phe Cys Gly Arg Ser Ala Tyr Tyr Phe Asp Ser Gly Gly Tyr Phe
            115                 120                 125 gac tac tgg ggc caa ggc acc act ctc aca gtc agc tca gcc tcc acc         432
Asp Tyr Trp Gly Gln Gly Thr Thr Leu Thr Val Ser Ser Ala Ser Thr
130                 135                 140 aag ggc cca agc gtc ttc ccc ctg gca ccc tcc tcc aag agc acc tct         480
Lys Gly Pro Ser Val Phe Pro Leu Ala Pro Ser Ser Lys Ser Thr Ser
145                 150                 155                 160 ggc ggc aca gcc gcc ctg ggc tgc ctg gtc aag gac tac ttc ccc gaa         528
Gly Gly Thr Ala Ala Leu Gly Cys Leu Val Lys Asp Tyr Phe Pro Glu
                165                 170                 175 ccc gtg acc gtg agc tgg aac tca ggc gcc ctg acc agc ggc gtg cac         576
Pro Val Thr Val Ser Trp Asn Ser Gly Ala Leu Thr Ser Gly Val His
            180                 185                 190 acc ttc ccc gct gtc ctg cag tcc tca gga ctc tac tcc ctc agc agc         624
Thr Phe Pro Ala Val Leu Gln Ser Ser Gly Leu Tyr Ser Leu Ser Ser
            195                 200                 205 gtg gtg acc gtg ccc tcc agc agc ttg ggc acc cag acc tac atc tgc         672
Val Val Thr Val Pro Ser Ser Ser Leu Gly Thr Gln Thr Tyr Ile Cys
            210                 215                 220 aac gtg aat cac aag ccc agc aac acc aag gtg gac aag aga gtt gag         720
Asn Val Asn His Lys Pro Ser Asn Thr Lys Val Asp Lys Arg Val Glu
225                 230                 235                 240 ccc aaa tct tgt gac aaa act cac aca tgc cca ccc tgc cca gca cct         768
Pro Lys Ser Cys Asp Lys Thr His Thr Cys Pro Pro Cys Pro Ala Pro
                245                 250                 255 gaa ctc ctg ggg gga ccc tca gtc ttc ctc ttc ccc cca aaa ccc aag         816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg         864
Asp Thr Leu Met Ile Ser Arg Thr Pro Glu Val Thr Cys Val Val Val
            275                 280                 285 gac gtg agc cac gaa gac cct gag gtc aag ttc aac tgg tac gtg gac         912
Asp Val Ser His Glu Asp Pro Glu Val Lys Phe Asn Trp Tyr Val Asp
            290                 295                 300 ggc gtg gag gtg cat aat gcc aag aca aag ccc cgg gag gag cag tac         960
Gly Val Glu Val His Asn Ala Lys Thr Lys Pro Arg Glu Glu Gln Tyr
305                 310                 315                 320 aac agc acg tac cgg gtg gtc agc gtc ctc acc gtc ctg cac cag gac        1008
Asn Ser Thr Tyr Arg Val Val Ser Val Leu Thr Val Leu His Gln Asp
                325                 330                 335
```

```
tgg ctg aat ggc aag gag tac aag tgc aag gtc tcc aac aaa gcc ctc    1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg    1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag    1152
Glu Pro Gln Val Tyr Thr Leu Pro Pro Ser Arg Glu Glu Met Thr Lys
370                 375                 380 aac cag gtc agc ctg acc tgc ctg gtc aaa ggc ttc tat ccc agc gac    1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag    1248
Ile Ala Val Glu Trp Glu Ser Asn Gly Gln Pro Glu Asn Asn Tyr Lys
            405                 410                 415 acc acc cct ccc gtg ctg gac tcc gac ggc tcc ttc ttc ctc tac agc    1296
Thr Thr Pro Pro Val Leu Asp Ser Asp Gly Ser Phe Phe Leu Tyr Ser
        420                 425                 430 aag ctc acc gtg gac aag agc agg tgg cag cag ggc aac gtc ttc tca    1344
Lys Leu Thr Val Asp Lys Ser Arg Trp Gln Gln Gly Asn Val Phe Ser
    435                 440                 445 tgc tcc gtg atg cat gag gct ctg cac aac cac tac acc cag aag agc    1392
Cys Ser Val Met His Glu Ala Leu His Asn His Tyr Thr Gln Lys Ser
450                 455                 460 ctc tcc ctg tct ccc ggc aaa                                        1413
Leu Ser Leu Ser Pro Gly Lys
465                 470

<210> SEQ ID NO 20
<211> LENGTH: 471
<212> TYPE: PRT
<213> ORGANISM: Artificial Sequence
<220> FEATURE:
<223> OTHER INFORMATION: Synthetic Construct

<400> SEQUENCE: 20

Met Lys His Leu Trp Phe Phe Leu Leu Leu Val Ala Ala Pro Arg Trp
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Ile Gly Tyr Phe Met Asn Trp Met Lys Gln Ser His Gly Lys Ser Leu
    50                  55                  60

Glu Trp Ile Gly Arg Phe Asn Pro Tyr Asn Gly Asp Thr Phe Tyr Asn
65                  70                  75                  80

Gln Lys Phe Lys Gly Lys Ala Thr Leu Thr Val Asp Lys Ser Ser Thr
                85                  90                  95

Thr Ala His Met Glu Leu Leu Ser Leu Thr Ser Glu Asp Ser Ala Val
            100                 105                 110

Tyr Phe Cys Gly Arg Ser Ala Tyr Phe Asp Ser Gly Gly Tyr Phe
        115                 120                 125

Asp Tyr Trp Gly Gln Gly Thr Thr Leu Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175
```

```
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 21
<211> LENGTH: 41
<212> TYPE: DNA
<213> ORGANISM: Artificial Sequence
<220> FEATURE:
<223> OTHER INFORMATION: Primer B273HF

<400> SEQUENCE: 21
aaagctgagc gaggttcagc tgcagcagtc tggacctgag c                 41

<210> SEQ ID NO 22
<211> LENGTH: 42
<212> TYPE: DNA
<213> ORGANISM: Artificial Sequence
<220> FEATURE:
<223> OTHER INFORMATION: Primer B273HR

<400> SEQUENCE: 22
```

-continued aaagctgagc tgactgtgag agtggtgcct tggccccagt ag 42

<210> SEQ ID NO 23
<211> LENGTH: 130
<212> TYPE: PRT
<213> ORGANISM: Homo sapiens

<400> SEQUENCE: 23

```
Ala Leu Ile Thr Gln Gln Asp Leu Ala Pro Gln Gln Arg Ala Ala Pro
1               5                   10                  15

Gln Gln Lys Arg Ser Ser Pro Ser Glu Gly Leu Cys Pro Pro Gly His
            20                  25                  30

His Ile Ser Glu Asp Gly Arg Asp Cys Ile Ser Cys Lys Tyr Gly Gln
        35                  40                  45

Asp Tyr Ser Thr His Trp Asn Asp Leu Leu Phe Cys Leu Arg Cys Thr
    50                  55                  60

Arg Cys Asp Ser Gly Glu Val Glu Leu Ser Pro Cys Thr Thr Thr Arg
65                  70                  75                  80

Asn Thr Val Cys Gln Cys Glu Glu Gly Thr Phe Arg Glu Glu Asp Ser
                85                  90                  95

Pro Glu Met Cys Arg Lys Cys Arg Thr Gly Cys Pro Arg Gly Met Val
            100                 105                 110

Lys Val Gly Asp Cys Thr Pro Trp Ser Asp Ile Glu Cys Val His Lys
        115                 120                 125

Glu Ser
    130
```

<210> SEQ ID NO 24
<211> LENGTH: 28
<212> TYPE: DNA
<213> ORGANISM: Artificial Sequence
<220> FEATURE:
<223> OTHER INFORMATION: Primer DR5 Ndefw

<400> SEQUENCE: 24
gtggcatatg gctctgatca cccaacaa 28

<210> SEQ ID NO 25
<211> LENGTH: 27
<212> TYPE: DNA
<213> ORGANISM: Artificial Sequence
<220> FEATURE:
<223> OTHER INFORMATION: Primer DR5 Xhorv

<400> SEQUENCE: 25
cgcctcgagt gattctttgt ggacaca 27

<210> SEQ ID NO 26
<211> LENGTH: 139
<212> TYPE: PRT
<213> ORGANISM: Artificial Sequence
<220> FEATURE:
<223> OTHER INFORMATION: rsDR5

<400> SEQUENCE: 26

```
Met Ala Leu Ile Thr Gln Gln Asp Leu Ala Pro Gln Gln Arg Ala Ala
1               5                   10                  15

Pro Gln Gln Lys Arg Ser Ser Pro Ser Glu Gly Leu Cys Pro Pro Gly
            20                  25                  30

His His Ile Ser Glu Asp Gly Arg Asp Cys Ile Ser Cys Lys Tyr Gly
        35                  40                  45
```

```
Gln Asp Tyr Ser Thr His Trp Asn Asp Leu Leu Phe Cys Leu Arg Cys
     50                  55                  60

Thr Arg Cys Asp Ser Gly Glu Val Glu Leu Ser Pro Cys Thr Thr Thr
 65                  70                  75                  80

Arg Asn Thr Val Cys Gln Cys Glu Glu Gly Thr Phe Arg Glu Glu Asp
                 85                  90                  95

Ser Pro Glu Met Cys Arg Lys Cys Arg Thr Gly Cys Pro Arg Gly Met
             100                 105                 110

Val Lys Val Gly Asp Cys Thr Pro Trp Ser Asp Ile Glu Cys Val His
         115                 120                 125

Lys Glu Ser Leu Glu His His His His His His
         130                 135

<210> SEQ ID NO 27
<211> LENGTH: 717
<212> TYPE: DNA
<213> ORGANISM: Artificial Sequence
<220> FEATURE:
<223> OTHER INFORMATION: Nucleotide sequence coding hB273_L1
<220> FEATURE:
<221> NAME/KEY: CDS
<222> LOCATION: (1)..(717)

<400> SEQUENCE: 27 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
 1               5                  10                  15 ggc gca tat ggc gac atc gta atg acc cag tct ccg ctg agt ctt cct      96
Gly Ala Tyr Gly Asp Ile Val Met Thr Gln Ser Pro Leu Ser Leu Pro
             20                  25                  30 gtg act cca ggg gag ccc gca agc atc tct tgt cgc agc agt cag tca     144
Val Thr Pro Gly Glu Pro Ala Ser Ile Ser Cys Arg Ser Ser Gln Ser
         35                  40                  45 ctg gtc cat agc aat ggg aac act tac ctg cat tgg tac ctc caa aaa     192
Leu Val His Ser Asn Gly Asn Thr Tyr Leu His Trp Tyr Leu Gln Lys
     50                  55                  60 cca ggg cag tcc cca cag ctc ttg atc tac aag gtg tcc aat cgg ttc     240
Pro Gly Gln Ser Pro Gln Leu Leu Ile Tyr Lys Val Ser Asn Arg Phe
 65                  70                  75                  80 agt ggt gtg cct gac cgc ttc tcc gga agt ggc tcc ggg aca gat ttc     288
Ser Gly Val Pro Asp Arg Phe Ser Gly Ser Gly Ser Gly Thr Asp Phe
                 85                  90                  95 act ctt aag att tca aga gtg gag gca gaa gac gtt gga gtc tat tat     336
Thr Leu Lys Ile Ser Arg Val Glu Ala Glu Asp Val Gly Val Tyr Tyr
             100                 105                 110 tgc tca cag agc aca cat gtc ccc tgg act ttc ggt ccc ggc aca aaa     384
Cys Ser Gln Ser Thr His Val Pro Trp Thr Phe Gly Pro Gly Thr Lys
         115                 120                 125 gtc gag atc aag cgt acg gtg gcc gcc ccc tcc gtg ttc atc ttc ccc     432
Val Glu Ile Lys Arg Thr Val Ala Ala Pro Ser Val Phe Ile Phe Pro
     130                 135                 140 ccc tcc gac gag cag ctg aag tcc ggc acc gcc tcc gtg gtg tgc ctg     480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac     528
Leu Asn Asn Phe Tyr Pro Arg Glu Ala Lys Val Gln Trp Lys Val Asp
                 165                 170                 175 aac gcc ctg cag tcc ggg aac tcc cag gag agc gtg acc gag cag gac     576
Asn Ala Leu Gln Ser Gly Asn Ser Gln Glu Ser Val Thr Glu Gln Asp
             180                 185                 190
```

```
agc aag gac agc acc tac agc ctg agc agc acc ctg acc ctg agc aaa      624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag      672
Ala Asp Tyr Glu Lys His Lys Val Tyr Ala Cys Glu Val Thr His Gln
    210                 215                 220 ggc ctg agc tcc ccc gtc acc aag agc ttc aac agg ggg gag tgt          717
Gly Leu Ser Ser Pro Val Thr Lys Ser Phe Asn Arg Gly Glu Cys
225                 230                 235
```

<210> SEQ ID NO 28
<211> LENGTH: 239
<212> TYPE: PRT
<213> ORGANISM: Artificial Sequence
<220> FEATURE:
<223> OTHER INFORMATION: Synthetic Construct

<400> SEQUENCE: 28

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Leu Val His Ser Asn Gly Asn Thr Tyr Leu His Trp Tyr Leu Gln Lys
    50                  55                  60

Pro Gly Gln Ser Pro Gln Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Pro Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 29
<211> LENGTH: 717
<212> TYPE: DNA
<213> ORGANISM: Artificial Sequence
<220> FEATURE:
<223> OTHER INFORMATION: Nucleotide sequence coding hB273_L2
<220> FEATURE:
<221> NAME/KEY: CDS
<222> LOCATION: (1)..(717)

```
<400> SEQUENCE: 29 atg gtg ctg cag acc cag gtg ttc atc tcc ctg ctg tgg atc tcc      48
Met Val Leu Gln Thr Gln Val Phe Ile Ser Leu Leu Trp Ile Ser
1               5                   10                  15 ggc gca tat ggc gac gtc gtc atg aca cag aca cct ctg agc ctg ccc  96
Gly Ala Tyr Gly Asp Val Val Met Thr Gln Thr Pro Leu Ser Leu Pro
            20                  25                  30 gtg tct ctg ggc gaa ccc gcc agt att tct tgt agg tca tct cag tct  144
Val Ser Leu Gly Glu Pro Ala Ser Ile Ser Cys Arg Ser Ser Gln Ser
        35                  40                  45 ctg gtg cac agt aac gga aac aca tat ctc cat tgg tac ctg cag aag  192
Leu Val His Ser Asn Gly Asn Thr Tyr Leu His Trp Tyr Leu Gln Lys
    50                  55                  60 cca ggt cag tcc cca aag ctc ctg atc tat aag gtg agc aac aga ttc  240
Pro Gly Gln Ser Pro Lys Leu Leu Ile Tyr Lys Val Ser Asn Arg Phe
65                  70                  75                  80 tcc gga gtg cct gat cga ttc agc ggg agt ggt tca ggg acc gac ttc  288
Ser Gly Val Pro Asp Arg Phe Ser Gly Ser Gly Ser Gly Thr Asp Phe
                85                  90                  95 acc ttg aag att agc cgg gtc gag gcc gag gat gtt gga gtg tat ttc  336
Thr Leu Lys Ile Ser Arg Val Glu Ala Glu Asp Val Gly Val Tyr Phe
            100                 105                 110 tgt agc cag agt aca cac gtg ccc tgg acc ttc gga cct ggg act aaa  384
Cys Ser Gln Ser Thr His Val Pro Trp Thr Phe Gly Pro Gly Thr Lys
        115                 120                 125 gtc gag att aaa cgt acg gtg gcc gcc ccc tcc gtg ttc atc ttc ccc  432
Val Glu Ile Lys Arg Thr Val Ala Ala Pro Ser Val Phe Ile Phe Pro
    130                 135                 140 ccc tcc gac gag cag ctg aag tcc ggc acc gcc tcc gtg gtg tgc ctg  480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac  528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac  576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa  624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag  672
Ala Asp Tyr Glu Lys His Lys Val Tyr Ala Cys Glu Val Thr His Gln
    210                 215                 220 ggc ctg agc tcc ccc gtc acc aag agc ttc aac agg ggg gag tgt      717
Gly Leu Ser Ser Pro Val Thr Lys Ser Phe Asn Arg Gly Glu Cys
225                 230                 235

<210> SEQ ID NO 30
<211> LENGTH: 239
<212> TYPE: PRT
<213> ORGANISM: Artificial Sequence
<220> FEATURE:
<223> OTHER INFORMATION: Synthetic Construct

<400> SEQUENCE: 30

Met Val Leu Gln Thr Gln Val Phe Ile Ser Leu Leu Trp Ile Ser
1               5                   10                  15

Gly Ala Tyr Gly Asp Val Val Met Thr Gln Thr Pro Leu Ser Leu Pro
            20                  25                  30

Val Ser Leu Gly Glu Pro Ala Ser Ile Ser Cys Arg Ser Ser Gln Ser
```

```
                35                  40                  45
Leu Val His Ser Asn Gly Asn Thr Tyr Leu His Trp Tyr Leu Gln Lys
     50                  55                  60

Pro Gly Gln Ser Pro Lys Leu Leu Ile Tyr Lys Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Phe
                100                 105                 110

Cys Ser Gln Ser Thr His Val Pro Trp Thr Phe Gly Pro Gly Thr Lys
                115                 120                 125

Val Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 31
<211> LENGTH: 717
<212> TYPE: DNA
<213> ORGANISM: Artificial Sequence
<220> FEATURE:
<223> OTHER INFORMATION: Nucleotide sequence coding hB273_L3
<220> FEATURE:
<221> NAME/KEY: CDS
<222> LOCATION: (1)..(717)

<400> SEQUENCE: 31 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
 1               5                  10                  15 ggc gca tat ggc gac gtg gtg atg acg cag act ccg ctg tca ctg ccc      96
Gly Ala Tyr Gly Asp Val Val Met Thr Gln Thr Pro Leu Ser Leu Pro
                20                  25                  30 gta tct ctg gga gag cct gcc agc atc agc tgc agg agc tct caa tca     144
Val Ser Leu Gly Glu Pro Ala Ser Ile Ser Cys Arg Ser Ser Gln Ser
            35                  40                  45 ctg gtg cac tct aac ggt aat acc tac ctc cac tgg tat ctc cag aag     192
Leu Val His Ser Asn Gly Asn Thr Tyr Leu His Trp Tyr Leu Gln Lys
        50                  55                  60 cca gga caa tcc cca aag ttg ctc ata tat aaa gtg tcc aac cgg ttc     240
Pro Gly Gln Ser Pro Lys Leu Leu Ile Tyr Lys Val Ser Asn Arg Phe
 65                  70                  75                  80 tca gga gtc cct gac cgg ttt agc ggt agt ggc tct ggt aca gat ttc     288
Ser Gly Val Pro Asp Arg Phe Ser Gly Ser Gly Ser Gly Thr Asp Phe
                 85                  90                  95 acc ctg aaa ata tca agg gtt gaa gcg gaa gac gta gga gta tat ttt     336
Thr Leu Lys Ile Ser Arg Val Glu Ala Glu Asp Val Gly Val Tyr Phe
                100                 105                 110
```

```
tgc agc cag agc acc cat gtc ccc tgg aca ttt ggg ggc ggc acc aag    384
Cys Ser Gln Ser Thr His Val Pro Trp Thr Phe Gly Gly Gly Thr Lys
        115                 120                 125 gtc gaa atc aag cgt acg gtg gcc gcc ccc tcc gtg ttc atc ttc ccc    432
Val Glu Ile Lys Arg Thr Val Ala Ala Pro Ser Val Phe Ile Phe Pro
130                 135                 140 ccc tcc gac gag cag ctg aag tcc ggc acc gcc tcc gtg gtg tgc ctg    480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac    528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac    576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa    624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag    672
Ala Asp Tyr Glu Lys His Lys Val Tyr Ala Cys Glu Val Thr His Gln
210                 215                 220 ggc ctg agc tcc ccc gtc acc aag agc ttc aac agg ggg gag tgt        717
Gly Leu Ser Ser Pro Val Thr Lys Ser Phe Asn Arg Gly Glu Cys
225                 230                 235

<210> SEQ ID NO 32
<211> LENGTH: 239
<212> TYPE: PRT
<213> ORGANISM: Artificial Sequence
<220> FEATURE:
<223> OTHER INFORMATION: Synthetic Construct

<400> SEQUENCE: 32

Met Val Leu Gln Thr Gln Val Phe Ile Ser Leu Leu Leu Trp Ile Ser
1               5                   10                  15

Gly Ala Tyr Gly Asp Val Val Met Thr Gln Thr Pro Leu Ser Leu Pro
            20                  25                  30

Val Ser Leu Gly Glu Pro Ala Ser Ile Ser Cys Arg Ser Ser Gln Ser
        35                  40                  45

Leu Val His Ser Asn Gly Asn Thr Tyr Leu His Trp Tyr Leu Gln Lys
    50                  55                  60

Pro Gly Gln Ser Pro Lys Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Ser Gln Ser Thr His Val Pro Trp Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
```

|     |     |     |     |     |     |     |     |     |     |     |     |     |
| --- | --- | --- | --- | --- | --- | --- | --- | --- | --- | --- | --- | --- |
|     |     |     | 195 |     |     |     | 200 |     |     |     | 205 |     |
| Ala | Asp | Tyr | Glu | Lys | His | Lys | Val | Tyr | Ala | Cys | Glu | Val | Thr | His | Gln |
|     | 210 |     |     |     |     | 215 |     |     |     |     | 220 |     |
| Gly | Leu | Ser | Ser | Pro | Val | Thr | Lys | Ser | Phe | Asn | Arg | Gly | Glu | Cys |
| 225 |     |     |     |     | 230 |     |     |     |     | 235 |

<210> SEQ ID NO 33
<211> LENGTH: 1413
<212> TYPE: DNA
<213> ORGANISM: Artificial Sequence
<220> FEATURE:
<223> OTHER INFORMATION: Nucleotide sequence coding hB273_H1
<220> FEATURE:
<221> NAME/KEY: CDS
<222> LOCATION: (1)..(1413)

<400> SEQUENCE: 33

| atg | aaa | cac | ctg | tgg | ttc | ttc | ctc | ctg | ctg | gtg | gca | gct | ccc | aga | tgg | 48 |
| --- | --- | --- | --- | --- | --- | --- | --- | --- | --- | --- | --- | --- | --- | --- | --- | --- |
| Met | Lys | His | Leu | Trp | Phe | Phe | Leu | Leu | Leu | Val | Ala | Ala | Pro | Arg | Trp |
| 1   |     |     |     | 5   |     |     |     |     | 10  |     |     |     |     | 15  |

| gtg | ctg | agc | caa | gtt | cag | ctc | gtg | cag | tcc | ggc | gcg | gag | gtt | aag | aaa | 96 |
| --- | --- | --- | --- | --- | --- | --- | --- | --- | --- | --- | --- | --- | --- | --- | --- | --- |
| Val | Leu | Ser | Gln | Val | Gln | Leu | Val | Gln | Ser | Gly | Ala | Glu | Val | Lys | Lys |
|     |     |     | 20  |     |     |     |     | 25  |     |     |     |     | 30  |

| cca | ggc | gca | tcc | gtt | aaa | gtg | tca | tgt | aag | gcc | agc | ggg | tac | tcc | ttt | 144 |
| --- | --- | --- | --- | --- | --- | --- | --- | --- | --- | --- | --- | --- | --- | --- | --- | --- |
| Pro | Gly | Ala | Ser | Val | Lys | Val | Ser | Cys | Lys | Ala | Ser | Gly | Tyr | Ser | Phe |
|     | 35  |     |     |     |     | 40  |     |     |     |     | 45  |

| atc | ggc | tac | ttt | atg | aac | tgg | gtg | cgg | cag | gcc | cct | ggt | atg | ggc | ctg | 192 |
| --- | --- | --- | --- | --- | --- | --- | --- | --- | --- | --- | --- | --- | --- | --- | --- | --- |
| Ile | Gly | Tyr | Phe | Met | Asn | Trp | Val | Arg | Gln | Ala | Pro | Gly | Met | Gly | Leu |
| 50  |     |     |     |     | 55  |     |     |     |     | 60  |

| gag | tgg | atg | gga | cgg | ttt | aat | cca | tat | aat | ggc | gat | act | ttt | tac | aac | 240 |
| --- | --- | --- | --- | --- | --- | --- | --- | --- | --- | --- | --- | --- | --- | --- | --- | --- |
| Glu | Trp | Met | Gly | Arg | Phe | Asn | Pro | Tyr | Asn | Gly | Asp | Thr | Phe | Tyr | Asn |
| 65  |     |     |     | 70  |     |     |     |     | 75  |     |     |     |     | 80  |

| cag | aaa | ttt | aaa | gga | agg | gtc | act | ctc | aca | gtg | gat | aaa | agc | act | agt | 288 |
| --- | --- | --- | --- | --- | --- | --- | --- | --- | --- | --- | --- | --- | --- | --- | --- | --- |
| Gln | Lys | Phe | Lys | Gly | Arg | Val | Thr | Leu | Thr | Val | Asp | Lys | Ser | Thr | Ser |
|     |     |     |     | 85  |     |     |     |     | 90  |     |     |     |     | 95  |

| acg | gct | tac | atg | gaa | ctg | tcc | tcc | ctc | aga | tca | gaa | gat | act | gcc | gtc | 336 |
| --- | --- | --- | --- | --- | --- | --- | --- | --- | --- | --- | --- | --- | --- | --- | --- | --- |
| Thr | Ala | Tyr | Met | Glu | Leu | Ser | Ser | Leu | Arg | Ser | Glu | Asp | Thr | Ala | Val |
|     |     |     | 100 |     |     |     |     | 105 |     |     |     |     | 110 |

| tac | tac | tgc | gcc | cga | agt | gct | tac | tat | ttc | gac | agc | ggg | ggc | tac | ttt | 384 |
| --- | --- | --- | --- | --- | --- | --- | --- | --- | --- | --- | --- | --- | --- | --- | --- | --- |
| Tyr | Tyr | Cys | Ala | Arg | Ser | Ala | Tyr | Tyr | Phe | Asp | Ser | Gly | Gly | Tyr | Phe |
|     |     | 115 |     |     |     |     | 120 |     |     |     |     | 125 |

| gat | tat | tgg | ggc | cag | ggg | acc | ctg | gta | act | gtg | agc | tca | gcc | tcc | acc | 432 |
| --- | --- | --- | --- | --- | --- | --- | --- | --- | --- | --- | --- | --- | --- | --- | --- | --- |
| Asp | Tyr | Trp | Gly | Gln | Gly | Thr | Leu | Val | Thr | Val | Ser | Ser | Ala | Ser | Thr |
|     | 130 |     |     |     |     | 135 |     |     |     |     | 140 |

| aag | ggc | cca | agc | gtc | ttc | ccc | ctg | gca | ccc | tcc | tcc | aag | agc | acc | tct | 480 |
| --- | --- | --- | --- | --- | --- | --- | --- | --- | --- | --- | --- | --- | --- | --- | --- | --- |
| Lys | Gly | Pro | Ser | Val | Phe | Pro | Leu | Ala | Pro | Ser | Ser | Lys | Ser | Thr | Ser |
| 145 |     |     |     |     | 150 |     |     |     |     | 155 |     |     |     |     | 160 |

| ggc | ggc | aca | gcc | gcc | ctg | ggc | tgc | ctg | gtc | aag | gac | tac | ttc | ccc | gaa | 528 |
| --- | --- | --- | --- | --- | --- | --- | --- | --- | --- | --- | --- | --- | --- | --- | --- | --- |
| Gly | Gly | Thr | Ala | Ala | Leu | Gly | Cys | Leu | Val | Lys | Asp | Tyr | Phe | Pro | Glu |
|     |     |     |     | 165 |     |     |     |     | 170 |     |     |     |     | 175 |

| ccc | gtg | acc | gtg | agc | tgg | aac | tca | ggc | gcc | ctg | acc | agc | ggc | gtg | cac | 576 |
| --- | --- | --- | --- | --- | --- | --- | --- | --- | --- | --- | --- | --- | --- | --- | --- | --- |
| Pro | Val | Thr | Val | Ser | Trp | Asn | Ser | Gly | Ala | Leu | Thr | Ser | Gly | Val | His |
|     |     |     | 180 |     |     |     |     | 185 |     |     |     |     | 190 |

| acc | ttc | ccc | gct | gtc | ctg | cag | tcc | tca | gga | ctc | tac | tcc | ctc | agc | agc | 624 |
| --- | --- | --- | --- | --- | --- | --- | --- | --- | --- | --- | --- | --- | --- | --- | --- | --- |
| Thr | Phe | Pro | Ala | Val | Leu | Gln | Ser | Ser | Gly | Leu | Tyr | Ser | Leu | Ser | Ser |
|     |     | 195 |     |     |     |     | 200 |     |     |     |     | 205 |

| gtg | gtg | acc | gtg | ccc | tcc | agc | agc | ttg | ggc | acc | cag | acc | tac | atc | tgc | 672 |
| --- | --- | --- | --- | --- | --- | --- | --- | --- | --- | --- | --- | --- | --- | --- | --- | --- |
| Val | Val | Thr | Val | Pro | Ser | Ser | Ser | Leu | Gly | Thr | Gln | Thr | Tyr | Ile | Cys |
|     | 210 |     |     |     |     | 215 |     |     |     |     | 220 |

| aac | gtg | aat | cac | aag | ccc | agc | aac | acc | aag | gtg | gac | aag | aga | gtt | gag | 720 |
| --- | --- | --- | --- | --- | --- | --- | --- | --- | --- | --- | --- | --- | --- | --- | --- | --- |
| Asn | Val | Asn | His | Lys | Pro | Ser | Asn | Thr | Lys | Val | Asp | Lys | Arg | Val | Glu |

```
                225                 230                 235                 240
ccc aaa tct tgt gac aaa act cac aca tgc cca ccc tgc cca gca cct      768
Pro Lys Ser Cys Asp Lys Thr His Thr Cys Pro Pro Cys Pro Ala Pro
                    245                 250                 255 gaa ctc ctg ggg gga ccc tca gtc ttc ctc ttc ccc cca aaa ccc aag      816
Glu Leu Leu Gly Gly Pro Ser Val Phe Leu Phe Pro Pro Lys Pro Lys
                260                 265                 270 gac acc ctc atg atc tcc cgg acc cct gag gtc aca tgc gtg gtg gtg      864
Asp Thr Leu Met Ile Ser Arg Thr Pro Glu Val Thr Cys Val Val Val
            275                 280                 285 gac gtg agc cac gaa gac cct gag gtc aag ttc aac tgg tac gtg gac      912
Asp Val Ser His Glu Asp Pro Glu Val Lys Phe Asn Trp Tyr Val Asp
        290                 295                 300 ggc gtg gag gtg cat aat gcc aag aca aag ccc cgg gag gag cag tac      960
Gly Val Glu Val His Asn Ala Lys Thr Lys Pro Arg Glu Glu Gln Tyr
305                 310                 315                 320 aac agc acg tac cgg gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc     1056
Trp Leu Asn Gly Lys Glu Tyr Lys Cys Lys Val Ser Asn Lys Ala Leu
                340                 345                 350 cca gcc ccc atc gag aaa acc atc tcc aaa gcc aaa ggc cag ccc cgg     1104
Pro Ala Pro Ile Glu Lys Thr Ile Ser Lys Ala Lys Gly Gln Pro Arg
            355                 360                 365 gaa cca cag gtg tac acc ctg ccc cca tcc cgg gag gag atg acc aag     1152
Glu Pro Gln Val Tyr Thr Leu Pro Pro Ser Arg Glu Glu Met Thr Lys
        370                 375                 380 aac cag gtc agc ctg acc tgc ctg gtc aaa ggc ttc tat ccc agc gac     1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag     1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc     1296
Thr Thr Pro Pro Val Leu Asp Ser Asp Gly Ser Phe Phe Leu Tyr Ser
                420                 425                 430 aag ctc acc gtg gac aag agc agg tgg cag cag ggc aac gtc ttc tca     1344
Lys Leu Thr Val Asp Lys Ser Arg Trp Gln Gln Gly Asn Val Phe Ser
            435                 440                 445 tgc tcc gtg atg cat gag gct ctg cac aac cac tac acc cag aag agc     1392
Cys Ser Val Met His Glu Ala Leu His Asn His Tyr Thr Gln Lys Ser
        450                 455                 460 ctc tcc ctg tct ccc ggc aaa                                         1413
Leu Ser Leu Ser Pro Gly Lys
465                 470

<210> SEQ ID NO 34
<211> LENGTH: 471
<212> TYPE: PRT
<213> ORGANISM: Artificial Sequence
<220> FEATURE:
<223> OTHER INFORMATION: Synthetic Construct

<400> SEQUENCE: 34

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
```

-continued

```
                35                  40                  45
Ile Gly Tyr Phe Met Asn Trp Val Arg Gln Ala Pro Gly Met Gly Leu
 50                  55                  60
Glu Trp Met Gly Arg Phe Asn Pro Tyr Asn Gly Asp Thr Phe Tyr Asn
 65                  70                  75                  80
Gln Lys Phe Lys Gly Arg Val Thr Leu Thr Val Asp Lys Ser Thr Ser
                 85                  90                  95
Thr Ala Tyr Met Glu Leu Ser Ser Leu Arg Ser Glu Asp Thr Ala Val
             100                 105                 110
Tyr Tyr Cys Ala Arg Ser Ala Tyr Tyr Phe Asp Ser Gly Gly Tyr Phe
         115                 120                 125
Asp Tyr Trp Gly Gln Gly Thr Leu Val Thr Val Ser Ser Ala Ser Thr
     130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
```

Leu Ser Leu Ser Pro Gly Lys
465                 470

<210> SEQ ID NO 35
<211> LENGTH: 1413
<212> TYPE: DNA
<213> ORGANISM: Artificial Sequence
<220> FEATURE:
<223> OTHER INFORMATION: Nucleotide sequence coding hB273_H2
<220> FEATURE:
<221> NAME/KEY: CDS
<222> LOCATION: (1)..(1413)

<400> SEQUENCE: 35

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |
| gtg | ctg | agc | cag | gtc | cag | ctg | gtg | cag | agt | gga | gcc | gag | gta | aaa | aaa | 96 |
| Val | Leu | Ser | Gln | Val | Gln | Leu | Val | Gln | Ser | Gly | Ala | Glu | Val | Lys | Lys | |
| | | | 20 | | | | | 25 | | | | | 30 | | | |
| cca | ggg | gct | agt | gtc | aag | gtc | tcc | tgt | aag | gca | tct | ggt | tac | tct | ttt | 144 |
| Pro | Gly | Ala | Ser | Val | Lys | Val | Ser | Cys | Lys | Ala | Ser | Gly | Tyr | Ser | Phe | |
| | | 35 | | | | | 40 | | | | | 45 | | | | |
| ata | gga | tac | ttc | atg | aac | tgg | atg | aag | cag | tct | ccc | ggt | atg | tct | ctg | 192 |
| Ile | Gly | Tyr | Phe | Met | Asn | Trp | Met | Lys | Gln | Ser | Pro | Gly | Met | Ser | Leu | |
| | 50 | | | | | 55 | | | | | 60 | | | | | |
| gag | tgg | att | ggc | aga | ttc | aac | ccc | tac | aac | ggg | gac | act | ttt | tat | aat | 240 |
| Glu | Trp | Ile | Gly | Arg | Phe | Asn | Pro | Tyr | Asn | Gly | Asp | Thr | Phe | Tyr | Asn | |
| 65 | | | | | 70 | | | | | 75 | | | | | 80 | |
| cag | aag | ttc | aaa | ggg | aaa | gcc | act | ctg | acc | gtg | gac | aag | tca | act | tcc | 288 |
| Gln | Lys | Phe | Lys | Gly | Lys | Ala | Thr | Leu | Thr | Val | Asp | Lys | Ser | Thr | Ser | |
| | | | | 85 | | | | | 90 | | | | | 95 | | |
| aca | gca | tac | atg | gaa | ttg | tcc | tca | ctg | agg | tcc | gaa | gat | acc | gcc | gtg | 336 |
| Thr | Ala | Tyr | Met | Glu | Leu | Ser | Ser | Leu | Arg | Ser | Glu | Asp | Thr | Ala | Val | |
| | | | 100 | | | | | 105 | | | | | 110 | | | |
| tac | ttc | tgc | gct | cgg | agt | gct | tat | tat | ttc | gat | agc | gga | ggg | tat | ttt | 384 |
| Tyr | Phe | Cys | Ala | Arg | Ser | Ala | Tyr | Tyr | Phe | Asp | Ser | Gly | Gly | Tyr | Phe | |
| | | 115 | | | | | 120 | | | | | 125 | | | | |
| gac | tat | tgg | ggg | caa | ggg | acc | ctt | gta | acc | gtg | agc | tca | gcc | tcc | acc | 432 |
| Asp | Tyr | Trp | Gly | Gln | Gly | Thr | Leu | Val | Thr | Val | Ser | Ser | Ala | Ser | Thr | |
| | 130 | | | | | 135 | | | | | 140 | | | | | |
| aag | ggc | cca | agc | gtc | ttc | ccc | ctg | gca | ccc | tcc | tcc | aag | agc | acc | tct | 480 |
| Lys | Gly | Pro | Ser | Val | Phe | Pro | Leu | Ala | Pro | Ser | Ser | Lys | Ser | Thr | Ser | |
| 145 | | | | | 150 | | | | | 155 | | | | | 160 | |
| ggc | ggc | aca | gcc | gcc | ctg | ggc | tgc | ctg | gtc | aag | gac | tac | ttc | ccc | gaa | 528 |
| Gly | Gly | Thr | Ala | Ala | Leu | Gly | Cys | Leu | Val | Lys | Asp | Tyr | Phe | Pro | Glu | |
| | | | | 165 | | | | | 170 | | | | | 175 | | |
| ccc | gtg | acc | gtg | agc | tgg | aac | tca | ggc | gcc | ctg | acc | agc | ggc | gtg | cac | 576 |
| Pro | Val | Thr | Val | Ser | Trp | Asn | Ser | Gly | Ala | Leu | Thr | Ser | Gly | Val | His | |
| | | | 180 | | | | | 185 | | | | | 190 | | | |
| acc | ttc | ccc | gct | gtc | ctg | cag | tcc | tca | gga | ctc | tac | tcc | ctc | agc | agc | 624 |
| Thr | Phe | Pro | Ala | Val | Leu | Gln | Ser | Ser | Gly | Leu | Tyr | Ser | Leu | Ser | Ser | |
| | | 195 | | | | | 200 | | | | | 205 | | | | |
| gtg | gtg | acc | gtg | ccc | tcc | agc | agc | ttg | ggc | acc | cag | acc | tac | atc | tgc | 672 |
| Val | Val | Thr | Val | Pro | Ser | Ser | Ser | Leu | Gly | Thr | Gln | Thr | Tyr | Ile | Cys | |
| | 210 | | | | | 215 | | | | | 220 | | | | | |
| aac | gtg | aat | cac | aag | ccc | agc | aac | acc | aag | gtg | gac | aag | aga | gtt | gag | 720 |
| Asn | Val | Asn | His | Lys | Pro | Ser | Asn | Thr | Lys | Val | Asp | Lys | Arg | Val | Glu | |
| 225 | | | | | 230 | | | | | 235 | | | | | 240 | |
| ccc | aaa | tct | tgt | gac | aaa | act | cac | aca | tgc | cca | ccc | tgc | cca | gca | cct | 768 |
| Pro | Lys | Ser | Cys | Asp | Lys | Thr | His | Thr | Cys | Pro | Pro | Cys | Pro | Ala | Pro | |

```
                        245                 250                 255
gaa ctc ctg ggg gga ccc tca gtc ttc ctc ttc ccc cca aaa ccc aag    816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg    864
Asp Thr Leu Met Ile Ser Arg Thr Pro Glu Val Thr Cys Val Val Val
        275                 280                 285 gac gtg agc cac gaa gac cct gag gtc aag ttc aac tgg tac gtg gac    912
Asp Val Ser His Glu Asp Pro Glu Val Lys Phe Asn Trp Tyr Val Asp
    290                 295                 300 ggc gtg gag gtg cat aat gcc aag aca aag ccc cgg gag gag cag tac    960
Gly Val Glu Val His Asn Ala Lys Thr Lys Pro Arg Glu Glu Gln Tyr
305                 310                 315                 320 aac agc acg tac cgg gtg gtc agc gtc ctc acc gtc ctg cac cag gac   1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc   1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg   1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag   1152
Glu Pro Gln Val Tyr Thr Leu Pro Pro Ser Arg Glu Glu Met Thr Lys
    370                 375                 380 aac cag gtc agc ctg acc tgc ctg gtc aaa ggc ttc tat ccc agc gac   1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag   1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc   1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca   1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc   1392
Cys Ser Val Met His Glu Ala Leu His Asn His Tyr Thr Gln Lys Ser
    450                 455                 460 ctc tcc ctg tct ccc ggc aaa                                       1413
Leu Ser Leu Ser Pro Gly Lys
465                 470

<210> SEQ ID NO 36
<211> LENGTH: 471
<212> TYPE: PRT
<213> ORGANISM: Artificial Sequence
<220> FEATURE:
<223> OTHER INFORMATION: Synthetic Construct

<400> SEQUENCE: 36

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Lys Gln Ser Pro Gly Met Ser Leu
    50                  55                  60
```

```
Glu Trp Ile Gly Arg Phe Asn Pro Tyr Asn Gly Asp Thr Phe Tyr Asn
 65                  70                  75                  80

Gln Lys Phe Lys Gly Lys Ala Thr Leu Thr Val Asp Lys Ser Thr Ser
             85                  90                  95

Thr Ala Tyr Met Glu Leu Ser Ser Leu Arg Ser Glu Asp Thr Ala Val
            100                 105                 110

Tyr Phe Cys Ala Arg Ser Ala Tyr Tyr Phe Asp Ser Gly Gly Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

```
<210> SEQ ID NO 37
<211> LENGTH: 1413
<212> TYPE: DNA
<213> ORGANISM: Artificial Sequence
<220> FEATURE:
<223> OTHER INFORMATION: Nucleotide sequence coding hB273_H3
<220> FEATURE:
<221> NAME/KEY: CDS
<222> LOCATION: (1)..(1413)

<400> SEQUENCE: 37 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gaa gtg cag ctc gtg caa agc ggc gct gaa gtg aaa aaa      96
Val Leu Ser Glu Val Gln Leu Val Gln Ser Gly Ala Glu Val Lys Lys
            20                  25                  30 cca gga gcc tca gtc aaa gtg tcc tgt aag gcc tcc ggg tat agc ttc     144
Pro Gly Ala Ser Val Lys Val Ser Cys Lys Ala Ser Gly Tyr Ser Phe
        35                  40                  45 atc ggc tat ttt atg aac tgg atg aag cag agc ccg ggc aaa agc ctc     192
Ile Gly Tyr Phe Met Asn Trp Met Lys Gln Ser Pro Gly Lys Ser Leu
    50                  55                  60 gaa tgg atc ggg aga ttc aat cca tac aat ggt gac acc ttt tac aat     240
Glu Trp Ile Gly Arg Phe Asn Pro Tyr Asn Gly Asp Thr Phe Tyr Asn
65                  70                  75                  80 cag aaa ttc aaa ggc aag gcc acg ctg act gta gac aaa tcc acc agc     288
Gln Lys Phe Lys Gly Lys Ala Thr Leu Thr Val Asp Lys Ser Thr Ser
                85                  90                  95 aca gcc cac atg gaa ttg tct tcc ctg agg tct gag gat acc gcg gtg     336
Thr Ala His Met Glu Leu Ser Ser Leu Arg Ser Glu Asp Thr Ala Val
            100                 105                 110 tac ttt tgt ggc cga agt gcg tat tat ttc gat tca ggc ggg tac ttc     384
Tyr Phe Cys Gly Arg Ser Ala Tyr Tyr Phe Asp Ser Gly Gly Tyr Phe
        115                 120                 125 gat tac tgg ggt cag ggg acg ctc gtc acc gta agc tca gcc tcc acc     432
Asp Tyr Trp Gly Gln Gly Thr Leu Val Thr Val Ser Ser Ala Ser Thr
    130                 135                 140 aag ggc cca agc gtc ttc ccc ctg gca ccc tcc tcc aag agc acc tct     480
Lys Gly Pro Ser Val Phe Pro Leu Ala Pro Ser Ser Lys Ser Thr Ser
145                 150                 155                 160 ggc ggc aca gcc gcc ctg ggc tgc ctg gtc aag gac tac ttc ccc gaa     528
Gly Gly Thr Ala Ala Leu Gly Cys Leu Val Lys Asp Tyr Phe Pro Glu
                165                 170                 175 ccc gtg acc gtg agc tgg aac tca ggc gcc ctg acc agc ggc gtg cac     576
Pro Val Thr Val Ser Trp Asn Ser Gly Ala Leu Thr Ser Gly Val His
            180                 185                 190 acc ttc ccc gct gtc ctg cag tcc tca gga ctc tac tcc ctc agc agc     624
Thr Phe Pro Ala Val Leu Gln Ser Ser Gly Leu Tyr Ser Leu Ser Ser
        195                 200                 205 gtg gtg acc gtg ccc tcc agc agc ttg ggc acc cag acc tac atc tgc     672
Val Val Thr Val Pro Ser Ser Ser Leu Gly Thr Gln Thr Tyr Ile Cys
    210                 215                 220 aac gtg aat cac aag ccc agc aac acc aag gtg gac aag aga gtt gag     720
Asn Val Asn His Lys Pro Ser Asn Thr Lys Val Asp Lys Arg Val Glu
225                 230                 235                 240 ccc aaa tct tgt gac aaa act cac aca tgc cca ccg tgc cca gca cct     768
Pro Lys Ser Cys Asp Lys Thr His Thr Cys Pro Pro Cys Pro Ala Pro
                245                 250                 255 gaa ctc ctg ggg gga ccc tca gtc ttc ctc ttc ccc cca aaa ccc aag     816
Glu Leu Leu Gly Gly Pro Ser Val Phe Leu Phe Pro Pro Lys Pro Lys
```

```
gac acc ctc atg atc tcc cgg acc cct gag gtc aca tgc gtg gtg gtg      864
Asp Thr Leu Met Ile Ser Arg Thr Pro Glu Val Thr Cys Val Val Val
            275                 280                 285 gac gtg agc cac gaa gac cct gag gtc aag ttc aac tgg tac gtg gac      912
Asp Val Ser His Glu Asp Pro Glu Val Lys Phe Asn Trp Tyr Val Asp
    290                 295                 300 ggc gtg gag gtg cat aat gcc aag aca aag ccc cgg gag gag cag tac      960
Gly Val Glu Val His Asn Ala Lys Thr Lys Pro Arg Glu Glu Gln Tyr
305                 310                 315                 320 aac agc acg tac cgg gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc     1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg     1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag     1152
Glu Pro Gln Val Tyr Thr Leu Pro Pro Ser Arg Glu Glu Met Thr Lys
370                 375                 380 aac cag gtc agc ctg acc tgc ctg gtc aaa ggc ttc tat ccc agc gac     1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag     1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc     1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca     1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc     1392
Cys Ser Val Met His Glu Ala Leu His Asn His Tyr Thr Gln Lys Ser
450                 455                 460 ctc tcc ctg tct ccc ggc aaa                                         1413
Leu Ser Leu Ser Pro Gly Lys
465                 470
```

<210> SEQ ID NO 38
<211> LENGTH: 471
<212> TYPE: PRT
<213> ORGANISM: Artificial Sequence
<220> FEATURE:
<223> OTHER INFORMATION: Synthetic Construct

<400> SEQUENCE: 38

```
Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Lys Gln Ser Pro Gly Lys Ser Leu
    50                  55                  60

Glu Trp Ile Gly Arg Phe Asn Pro Tyr Asn Gly Asp Thr Phe Tyr Asn
65                  70                  75                  80
```

```
Gln Lys Phe Lys Gly Lys Ala Thr Leu Thr Val Asp Lys Ser Thr Ser
                85                  90                  95

Thr Ala His Met Glu Leu Ser Ser Leu Arg Ser Glu Asp Thr Ala Val
            100                 105                 110

Tyr Phe Cys Gly Arg Ser Ala Tyr Tyr Phe Asp Ser Gly Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 39
<211> LENGTH: 1413
<212> TYPE: DNA
```

```
<213> ORGANISM: Artificial Sequence
<220> FEATURE:
<223> OTHER INFORMATION: Nucleotide sequence coding hB273_H1-1
<220> FEATURE:
<221> NAME/KEY: CDS
<222> LOCATION: (1)..(1413)

<400> SEQUENCE: 39 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
                20                  25                  30 cct ggc gct tct gtg aag gtg tcc tgc aag gcc agc ggc tac agc ttc     144
Pro Gly Ala Ser Val Lys Val Ser Cys Lys Ala Ser Gly Tyr Ser Phe
            35                  40                  45 atc ggc tac ttc atg aac tgg atg cgg cag gcc cct ggc atg gga ctg     192
Ile Gly Tyr Phe Met Asn Trp Met Arg Gln Ala Pro Gly Met Gly Leu
        50                  55                  60 gaa tgg atg ggc cgg ttc aac ccc tac aac ggc gac acc ttc tac aac     240
Glu Trp Met Gly Arg Phe Asn Pro Tyr Asn Gly Asp Thr Phe Tyr Asn
65                  70                  75                  80 cag aaa ttc aag ggc aga gtg acc ctg acc gtg gac aag agc acc agc     288
Gln Lys Phe Lys Gly Arg Val Thr Leu Thr Val Asp Lys Ser Thr Ser
                85                  90                  95 acc gcc tac atg gaa ctg agc agc ctg cgg agc gag gat acc gcc gtg     336
Thr Ala Tyr Met Glu Leu Ser Ser Leu Arg Ser Glu Asp Thr Ala Val
            100                 105                 110 tat ttc tgc ggc aga agc gcc tac tac ttc gac agc ggc ggc tac ttc     384
Tyr Phe Cys Gly Arg Ser Ala Tyr Tyr Phe Asp Ser Gly Gly Tyr Phe
        115                 120                 125 gac tac tgg ggc cag ggc acc ctg gtg aca gtg agc tca gcc tcc acc     432
Asp Tyr Trp Gly Gln Gly Thr Leu Val Thr Val Ser Ser Ala Ser Thr
    130                 135                 140 aag ggc cca agc gtc ttc ccc ctg gca ccc tcc tcc aag agc acc tct     480
Lys Gly Pro Ser Val Phe Pro Leu Ala Pro Ser Ser Lys Ser Thr Ser
145                 150                 155                 160 ggc ggc aca gcc gcc ctg ggc tgc ctg gtc aag gac tac ttc ccc gaa     528
Gly Gly Thr Ala Ala Leu Gly Cys Leu Val Lys Asp Tyr Phe Pro Glu
                165                 170                 175 ccc gtg acc gtg agc tgg aac tca ggc gcc ctg acc agc ggc gtg cac     576
Pro Val Thr Val Ser Trp Asn Ser Gly Ala Leu Thr Ser Gly Val His
            180                 185                 190 acc ttc ccc gct gtc ctg cag tcc tca gga ctc tac tcc ctc agc agc     624
Thr Phe Pro Ala Val Leu Gln Ser Ser Gly Leu Tyr Ser Leu Ser Ser
        195                 200                 205 gtg gtg acc gtg ccc tcc agc agc ttg ggc acc cag acc tac atc tgc     672
Val Val Thr Val Pro Ser Ser Ser Leu Gly Thr Gln Thr Tyr Ile Cys
    210                 215                 220 aac gtg aat cac aag ccc agc aac acc aag gtg gac aag aga gtt gag     720
Asn Val Asn His Lys Pro Ser Asn Thr Lys Val Asp Lys Arg Val Glu
225                 230                 235                 240 ccc aaa tct tgt gac aaa act cac aca tgc cca ccc tgc cca gca cct     768
Pro Lys Ser Cys Asp Lys Thr His Thr Cys Pro Pro Cys Pro Ala Pro
                245                 250                 255 gaa ctc ctg ggg gga ccc tca gtc ttc ctc ttc ccc cca aaa ccc aag     816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg     864
Asp Thr Leu Met Ile Ser Arg Thr Pro Glu Val Thr Cys Val Val Val
```

```
                275                 280                 285
gac gtg agc cac gaa gac cct gag gtc aag ttc aac tgg tac gtg gac      912
Asp Val Ser His Glu Asp Pro Glu Val Lys Phe Asn Trp Tyr Val Asp
    290                 295                 300 ggc gtg gag gtg cat aat gcc aag aca aag ccc cgg gag gag cag tac      960
Gly Val Glu Val His Asn Ala Lys Thr Lys Pro Arg Glu Glu Gln Tyr
305                 310                 315                 320 aac agc acg tac cgg gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc     1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg     1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag     1152
Glu Pro Gln Val Tyr Thr Leu Pro Pro Ser Arg Glu Glu Met Thr Lys
    370                 375                 380 aac cag gtc agc ctg acc tgc ctg gtc aaa ggc ttc tat ccc agc gac     1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag     1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc     1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca     1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc     1392
Cys Ser Val Met His Glu Ala Leu His Asn His Tyr Thr Gln Lys Ser
    450                 455                 460 ctc tcc ctg tct ccc ggc aaa                                         1413
Leu Ser Leu Ser Pro Gly Lys
465                 470

<210> SEQ ID NO 40
<211> LENGTH: 471
<212> TYPE: PRT
<213> ORGANISM: Artificial Sequence
<220> FEATURE:
<223> OTHER INFORMATION: Synthetic Construct

<400> SEQUENCE: 40

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Arg Gln Ala Pro Gly Met Gly Leu
    50                  55                  60

Glu Trp Met Gly Arg Phe Asn Pro Tyr Asn Gly Asp Thr Phe Tyr Asn
65                  70                  75                  80

Gln Lys Phe Lys Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
```

```
                100             105             110
Tyr Phe Cys Gly Arg Ser Ala Tyr Tyr Phe Asp Ser Gly Gly Tyr Phe
            115             120             125

Asp Tyr Trp Gly Gln Gly Thr Leu Val Thr Val Ser Ser Ala Ser Thr
            130             135             140

Lys Gly Pro Ser Val Phe Pro Leu Ala Pro Ser Ser Lys Ser Thr Ser
145             150             155             160

Gly Gly Thr Ala Ala Leu Gly Cys Leu Val Lys Asp Tyr Phe Pro Glu
            165             170             175

Pro Val Thr Val Ser Trp Asn Ser Gly Ala Leu Thr Ser Gly Val His
            180             185             190

Thr Phe Pro Ala Val Leu Gln Ser Ser Gly Leu Tyr Ser Leu Ser Ser
            195             200             205

Val Val Thr Val Pro Ser Ser Leu Gly Thr Gln Thr Tyr Ile Cys
            210             215             220

Asn Val Asn His Lys Pro Ser Asn Thr Lys Val Asp Lys Arg Val Glu
225             230             235             240

Pro Lys Ser Cys Asp Lys Thr His Thr Cys Pro Pro Cys Pro Ala Pro
            245             250             255

Glu Leu Leu Gly Gly Pro Ser Val Phe Leu Phe Pro Pro Lys Pro Lys
            260             265             270

Asp Thr Leu Met Ile Ser Arg Thr Pro Glu Val Thr Cys Val Val Val
            275             280             285

Asp Val Ser His Glu Asp Pro Glu Val Lys Phe Asn Trp Tyr Val Asp
            290             295             300

Gly Val Glu Val His Asn Ala Lys Thr Lys Pro Arg Glu Glu Gln Tyr
305             310             315             320

Asn Ser Thr Tyr Arg Val Val Ser Val Leu Thr Val Leu His Gln Asp
            325             330             335

Trp Leu Asn Gly Lys Glu Tyr Lys Cys Lys Val Ser Asn Lys Ala Leu
            340             345             350

Pro Ala Pro Ile Glu Lys Thr Ile Ser Lys Ala Lys Gly Gln Pro Arg
            355             360             365

Glu Pro Gln Val Tyr Thr Leu Pro Pro Ser Arg Glu Glu Met Thr Lys
            370             375             380

Asn Gln Val Ser Leu Thr Cys Leu Val Lys Gly Phe Tyr Pro Ser Asp
385             390             395             400

Ile Ala Val Glu Trp Glu Ser Asn Gly Gln Pro Glu Asn Asn Tyr Lys
            405             410             415

Thr Thr Pro Pro Val Leu Asp Ser Asp Gly Ser Phe Phe Leu Tyr Ser
            420             425             430

Lys Leu Thr Val Asp Lys Ser Arg Trp Gln Gln Gly Asn Val Phe Ser
            435             440             445

Cys Ser Val Met His Glu Ala Leu His Asn His Tyr Thr Gln Lys Ser
            450             455             460

Leu Ser Leu Ser Pro Gly Lys
465             470

<210> SEQ ID NO 41
<211> LENGTH: 1413
<212> TYPE: DNA
<213> ORGANISM: Artificial Sequence
<220> FEATURE:
<223> OTHER INFORMATION: Nucleotide sequence coding hB273_H2-1
<220> FEATURE:
```

```
<221> NAME/KEY: CDS
<222> LOCATION: (1)..(1413)

<400> SEQUENCE: 41 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gag gtg cag ctg gtg cag tct ggc gcc gaa gtg aag aaa      96
Val Leu Ser Glu Val Gln Leu Val Gln Ser Gly Ala Glu Val Lys Lys
            20                  25                  30 cct gga gcc agc gtg aag gtg tcc tgc aag gcc agc ggc tac agc ttc     144
Pro Gly Ala Ser Val Lys Val Ser Cys Lys Ala Ser Gly Tyr Ser Phe
        35                  40                  45 atc ggc tac ttc atg aac tgg atg aag cag agc ccc ggc atg agc ctg     192
Ile Gly Tyr Phe Met Asn Trp Met Lys Gln Ser Pro Gly Met Ser Leu
    50                  55                  60 gaa tgg atc ggc cgg ttc aac ccc tac aac ggc gac acc ttc tac aac     240
Glu Trp Ile Gly Arg Phe Asn Pro Tyr Asn Gly Asp Thr Phe Tyr Asn
65                  70                  75                  80 cag aag ttc aag gga aag gcc acc ctg aca gtg gac aag agc acc agc     288
Gln Lys Phe Lys Gly Lys Ala Thr Leu Thr Val Asp Lys Ser Thr Ser
                85                  90                  95 acc gcc tac atg gaa ctg agc agc ctg cgg agc gag gat acc gcc gtg     336
Thr Ala Tyr Met Glu Leu Ser Ser Leu Arg Ser Glu Asp Thr Ala Val
            100                 105                 110 tac ttc tgc gcc aga agc gcc tac tac ttc gac agc ggc ggc tac ttc     384
Tyr Phe Cys Ala Arg Ser Ala Tyr Tyr Phe Asp Ser Gly Gly Tyr Phe
        115                 120                 125 gac tac tgg ggc cag ggc acc ctg gtg aca gtg agc tca gcc tcc acc     432
Asp Tyr Trp Gly Gln Gly Thr Leu Val Thr Val Ser Ser Ala Ser Thr
    130                 135                 140 aag ggc cca agc gtc ttc ccc ctg gca ccc tcc tcc aag agc acc tct     480
Lys Gly Pro Ser Val Phe Pro Leu Ala Pro Ser Ser Lys Ser Thr Ser
145                 150                 155                 160 ggc ggc aca gcc gcc ctg ggc tgc ctg gtc aag gac tac ttc ccc gaa     528
Gly Gly Thr Ala Ala Leu Gly Cys Leu Val Lys Asp Tyr Phe Pro Glu
                165                 170                 175 ccc gtg acc gtg agc tgg aac tca ggc gcc ctg acc agc ggc gtg cac     576
Pro Val Thr Val Ser Trp Asn Ser Gly Ala Leu Thr Ser Gly Val His
            180                 185                 190 acc ttc ccc gct gtc ctg cag tcc tca gga ctc tac tcc ctc agc agc     624
Thr Phe Pro Ala Val Leu Gln Ser Ser Gly Leu Tyr Ser Leu Ser Ser
        195                 200                 205 gtg gtg acc gtg ccc tcc agc agc ttg ggc acc cag acc tac atc tgc     672
Val Val Thr Val Pro Ser Ser Ser Leu Gly Thr Gln Thr Tyr Ile Cys
    210                 215                 220 aac gtg aat cac aag ccc agc aac acc aag gtg gac aag aga gtt gag     720
Asn Val Asn His Lys Pro Ser Asn Thr Lys Val Asp Lys Arg Val Glu
225                 230                 235                 240 ccc aaa tct tgt gac aaa act cac aca tgc cca ccc tgc cca gca cct     768
Pro Lys Ser Cys Asp Lys Thr His Thr Cys Pro Pro Cys Pro Ala Pro
                245                 250                 255 gaa ctc ctg ggg gga ccc tca gtc ttc ctc ttc ccc cca aaa ccc aag     816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg     864
Asp Thr Leu Met Ile Ser Arg Thr Pro Glu Val Thr Cys Val Val Val
        275                 280                 285 gac gtg agc cac gaa gac cct gag gtc aag ttc aac tgg tac gtg gac     912
Asp Val Ser His Glu Asp Pro Glu Val Lys Phe Asn Trp Tyr Val Asp
```

-continued

```
                        290                 295                 300
ggc gtg gag gtg cat aat gcc aag aca aag ccc cgg gag gag cag tac      960
Gly Val Glu Val His Asn Ala Lys Thr Lys Pro Arg Glu Glu Gln Tyr
305                 310                 315                 320 aac agc acg tac cgg gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc     1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg     1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag     1152
Glu Pro Gln Val Tyr Thr Leu Pro Pro Ser Arg Glu Glu Met Thr Lys
    370                 375                 380 aac cag gtc agc ctg acc tgc ctg gtc aaa ggc ttc tat ccc agc gac     1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag     1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc     1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca     1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc     1392
Cys Ser Val Met His Glu Ala Leu His Asn His Tyr Thr Gln Lys Ser
    450                 455                 460 ctc tcc ctg tct ccc ggc aaa                                          1413
Leu Ser Leu Ser Pro Gly Lys
465                 470

<210> SEQ ID NO 42
<211> LENGTH: 471
<212> TYPE: PRT
<213> ORGANISM: Artificial Sequence
<220> FEATURE:
<223> OTHER INFORMATION: Synthetic Construct

<400> SEQUENCE: 42

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Lys Gln Ser Pro Gly Met Ser Leu
    50                  55                  60

Glu Trp Ile Gly Arg Phe Asn Pro Tyr Asn Gly Asp Thr Phe Tyr Asn
65                  70                  75                  80

Gln Lys Phe Lys Gly Lys Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Phe Cys Ala Arg Ser Ala Tyr Tyr Phe Asp Ser Gly Gly Tyr Phe
        115                 120                 125
```

```
Asp Tyr Trp Gly Gln Gly Thr Leu Val Thr Val Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 43
<211> LENGTH: 1413
<212> TYPE: DNA
<213> ORGANISM: Artificial Sequence
<220> FEATURE:
<223> OTHER INFORMATION: Nucleotide sequence coding hB273_H2-2
<220> FEATURE:
<221> NAME/KEY: CDS
<222> LOCATION: (1)..(1413)

<400> SEQUENCE: 43
```

```
atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa    96
Val Leu Ser Gln Val Gln Leu Val Gln Ser Gly Ala Glu Val Lys Lys
            20                  25                  30 cct gga gcc agc gtg aag gtg tcc tgc aag gcc agc ggc tac agc ttc   144
Pro Gly Ala Ser Val Lys Val Ser Cys Lys Ala Ser Gly Tyr Ser Phe
        35                  40                  45 atc ggc tac ttc atg aac tgg atg aag cag agc ccc ggc atg agc ctg   192
Ile Gly Tyr Phe Met Asn Trp Met Lys Gln Ser Pro Gly Met Ser Leu
50                  55                  60 gaa tgg atc ggc cgg ttc aac ccc tac aac ggc gac acc ttc tac aac   240
Glu Trp Ile Gly Arg Phe Asn Pro Tyr Asn Gly Asp Thr Phe Tyr Asn
65                  70                  75                  80 cag aag ttc aag gga aag gcc acc ctg aca gtg gac aag agc acc agc   288
Gln Lys Phe Lys Gly Lys Ala Thr Leu Thr Val Asp Lys Ser Thr Ser
                85                  90                  95 acc gcc cac atg gaa ctg agc agc ctg cgg agc gag gat acc gcc gtg   336
Thr Ala His Met Glu Leu Ser Ser Leu Arg Ser Glu Asp Thr Ala Val
            100                 105                 110 tac ttc tgc gcc aga agc gcc tac tac ttc gac agc ggc ggc tac ttc   384
Tyr Phe Cys Ala Arg Ser Ala Tyr Tyr Phe Asp Ser Gly Gly Tyr Phe
        115                 120                 125 gac tac tgg ggc cag ggc acc ctg gtg aca gtg agc tca gcc tcc acc   432
Asp Tyr Trp Gly Gln Gly Thr Leu Val Thr Val Ser Ser Ala Ser Thr
130                 135                 140 aag ggc cca agc gtc ttc ccc ctg gca ccc tcc tcc aag agc acc tct   480
Lys Gly Pro Ser Val Phe Pro Leu Ala Pro Ser Ser Lys Ser Thr Ser
145                 150                 155                 160 ggc ggc aca gcc gcc ctg ggc tgc ctg gtc aag gac tac ttc ccc gaa   528
Gly Gly Thr Ala Ala Leu Gly Cys Leu Val Lys Asp Tyr Phe Pro Glu
                165                 170                 175 ccc gtg acc gtg agc tgg aac tca ggc gcc ctg acc agc ggc gtg cac   576
Pro Val Thr Val Ser Trp Asn Ser Gly Ala Leu Thr Ser Gly Val His
            180                 185                 190 acc ttc ccc gct gtc ctg cag tcc tca gga ctc tac tcc ctc agc agc   624
Thr Phe Pro Ala Val Leu Gln Ser Ser Gly Leu Tyr Ser Leu Ser Ser
        195                 200                 205 gtg gtg acc gtg ccc tcc agc agc ttg ggc acc cag acc tac atc tgc   672
Val Val Thr Val Pro Ser Ser Ser Leu Gly Thr Gln Thr Tyr Ile Cys
210                 215                 220 aac gtg aat cac aag ccc agc aac acc aag gtg gac aag aga gtt gag   720
Asn Val Asn His Lys Pro Ser Asn Thr Lys Val Asp Lys Arg Val Glu
225                 230                 235                 240 ccc aaa tct tgt gac aaa act cac aca tgc cca ccc tgc cca gca cct   768
Pro Lys Ser Cys Asp Lys Thr His Thr Cys Pro Pro Cys Pro Ala Pro
                245                 250                 255 gaa ctc ctg ggg gga ccc tca gtc ttc ctc ttc ccc cca aaa ccc aag   816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg   864
Asp Thr Leu Met Ile Ser Arg Thr Pro Glu Val Thr Cys Val Val Val
        275                 280                 285 gac gtg agc cac gaa gac cct gag gtc aag ttc aac tgg tac gtg gac   912
Asp Val Ser His Glu Asp Pro Glu Val Lys Phe Asn Trp Tyr Val Asp
290                 295                 300 ggc gtg gag gtg cat aat gcc aag aca aag ccc cgg gag gag cag tac   960
Gly Val Glu Val His Asn Ala Lys Thr Lys Pro Arg Glu Glu Gln Tyr
```

```
                     305                 310                 315                 320
aac agc acg tac cgg gtg gtc agc gtc ctc acc gtc ctg cac cag gac              1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc              1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg              1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag              1152
Glu Pro Gln Val Tyr Thr Leu Pro Pro Ser Arg Glu Glu Met Thr Lys
    370                 375                 380 aac cag gtc agc ctg acc tgc ctg gtc aaa ggc ttc tat ccc agc gac              1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag              1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc              1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca              1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc              1392
Cys Ser Val Met His Glu Ala Leu His Asn His Tyr Thr Gln Lys Ser
    450                 455                 460 ctc tcc ctg tct ccc ggc aaa                                                  1413
Leu Ser Leu Ser Pro Gly Lys
465                 470

<210> SEQ ID NO 44
<211> LENGTH: 471
<212> TYPE: PRT
<213> ORGANISM: Artificial Sequence
<220> FEATURE:
<223> OTHER INFORMATION: Synthetic Construct

<400> SEQUENCE: 44

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Lys Gln Ser Pro Gly Met Ser Leu
    50                  55                  60

Glu Trp Ile Gly Arg Phe Asn Pro Tyr Asn Gly Asp Thr Phe Tyr Asn
65                  70                  75                  80

Gln Lys Phe Lys Gly Lys Ala Thr Leu Thr Val Asp Lys Ser Thr Ser
                85                  90                  95

Thr Ala His Met Glu Leu Ser Ser Leu Arg Ser Glu Asp Thr Ala Val
            100                 105                 110

Tyr Phe Cys Ala Arg Ser Ala Tyr Tyr Phe Asp Ser Gly Gly Tyr Phe
        115                 120                 125

Asp Tyr Trp Gly Gln Gly Thr Leu Val Thr Val Ser Ser Ala Ser Thr
    130                 135                 140
```

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 45
<211> LENGTH: 1413
<212> TYPE: DNA
<213> ORGANISM: Artificial Sequence
<220> FEATURE:
<223> OTHER INFORMATION: Nucleotide sequence coding hB273_H2-3
<220> FEATURE:
<221> NAME/KEY: CDS
<222> LOCATION: (1)..(1413)

<400> SEQUENCE: 45 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15

| | | |
|---|---|---|
| gtg ctg agc gag gtg cag ctg gtg cag tct ggc gcc gaa gtg aag aaa<br>Val Leu Ser Glu Val Gln Leu Val Gln Ser Gly Ala Glu Val Lys Lys<br>20                         25                    30 | | 96 |
| cct gga gcc agc gtg aag gtg tcc tgc aag gcc agc ggc tac agc ttc<br>Pro Gly Ala Ser Val Lys Val Ser Cys Lys Ala Ser Gly Tyr Ser Phe<br>        35                    40                    45 | | 144 |
| atc ggc tac ttc atg aac tgg atg aag cag agc ccc ggc atg agc ctg<br>Ile Gly Tyr Phe Met Asn Trp Met Lys Gln Ser Pro Gly Met Ser Leu<br>50                          55                    60 | | 192 |
| gaa tgg atc ggc cgg ttc aac ccc tac aac ggc gac acc ttc tac aac<br>Glu Trp Ile Gly Arg Phe Asn Pro Tyr Asn Gly Asp Thr Phe Tyr Asn<br>65                    70                    75                    80 | | 240 |
| cag aag ttc aag gga aag gcc acc ctg aca gtg gac aag agc acc agc<br>Gln Lys Phe Lys Gly Lys Ala Thr Leu Thr Val Asp Lys Ser Thr Ser<br>                        85                    90                    95 | | 288 |
| acc gcc cac atg gaa ctg agc agc ctg cgg agc gag gat acc gcc gtg<br>Thr Ala His Met Glu Leu Ser Ser Leu Arg Ser Glu Asp Thr Ala Val<br>        100                    105                    110 | | 336 |
| tac ttc tgc gcc aga agc gcc tac tac ttc gac agc ggc ggc tac ttc<br>Tyr Phe Cys Ala Arg Ser Ala Tyr Tyr Phe Asp Ser Gly Gly Tyr Phe<br>        115                    120                    125 | | 384 |
| gac tac tgg ggc cag ggc acc ctg gtg aca gtg agc tca gcc tcc acc<br>Asp Tyr Trp Gly Gln Gly Thr Leu Val Thr Val Ser Ser Ala Ser Thr<br>130                        135                    140 | | 432 |
| aag ggc cca agc gtc ttc ccc ctg gca ccc tcc tcc aag agc acc tct<br>Lys Gly Pro Ser Val Phe Pro Leu Ala Pro Ser Ser Lys Ser Thr Ser<br>145                        150                    155                    160 | | 480 |
| ggc ggc aca gcc gcc ctg ggc tgc ctg gtc aag gac tac ttc ccc gaa<br>Gly Gly Thr Ala Ala Leu Gly Cys Leu Val Lys Asp Tyr Phe Pro Glu<br>                        165                    170                    175 | | 528 |
| ccc gtg acc gtg agc tgg aac tca ggc gcc ctg acc agc ggc gtg cac<br>Pro Val Thr Val Ser Trp Asn Ser Gly Ala Leu Thr Ser Gly Val His<br>        180                    185                    190 | | 576 |
| acc ttc ccc gct gtc ctg cag tcc tca gga ctc tac tcc ctc agc agc<br>Thr Phe Pro Ala Val Leu Gln Ser Ser Gly Leu Tyr Ser Leu Ser Ser<br>        195                    200                    205 | | 624 |
| gtg gtg acc gtg ccc tcc agc agc ttg ggc acc cag acc tac atc tgc<br>Val Val Thr Val Pro Ser Ser Ser Leu Gly Thr Gln Thr Tyr Ile Cys<br>210                        215                    220 | | 672 |
| aac gtg aat cac aag ccc agc aac acc aag gtg gac aag aga gtt gag<br>Asn Val Asn His Lys Pro Ser Asn Thr Lys Val Asp Lys Arg Val Glu<br>225                        230                    235                    240 | | 720 |
| ccc aaa tct tgt gac aaa act cac aca tgc cca ccc tgc cca gca cct<br>Pro Lys Ser Cys Asp Lys Thr His Thr Cys Pro Pro Cys Pro Ala Pro<br>                        245                    250                    255 | | 768 |
| gaa ctc ctg ggg gga ccc tca gtc ttc ctc ttc ccc cca aaa ccc aag<br>Glu Leu Leu Gly Gly Pro Ser Val Phe Leu Phe Pro Pro Lys Pro Lys<br>260                        265                    270 | | 816 |
| gac acc ctc atg atc tcc cgg acc cct gag gtc aca tgc gtg gtg gtg<br>Asp Thr Leu Met Ile Ser Arg Thr Pro Glu Val Thr Cys Val Val Val<br>        275                    280                    285 | | 864 |
| gac gtg agc cac gaa gac cct gag gtc aag ttc aac tgg tac gtg gac<br>Asp Val Ser His Glu Asp Pro Glu Val Lys Phe Asn Trp Tyr Val Asp<br>290                        295                    300 | | 912 |
| ggc gtg gag gtg cat aat gcc aag aca aag ccc cgg gag gag cag tac<br>Gly Val Glu Val His Asn Ala Lys Thr Lys Pro Arg Glu Glu Gln Tyr<br>305                        310                    315                    320 | | 960 |
| aac agc acg tac cgg gtg gtc agc gtc ctc acc gtc ctg cac cag gac<br>Asn Ser Thr Tyr Arg Val Val Ser Val Leu Thr Val Leu His Gln Asp | | 1008 |

```
                    325                 330                 335
tgg ctg aat ggc aag gag tac aag tgc aag gtc tcc aac aaa gcc ctc   1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg   1104
Pro Ala Pro Ile Glu Lys Thr Ile Ser Lys Ala Lys Gly Gln Pro Arg
                355                 360                 365 gaa cca cag gtg tac acc ctg ccc cca tcc cgg gag gag atg acc aag   1152
Glu Pro Gln Val Tyr Thr Leu Pro Pro Ser Arg Glu Glu Met Thr Lys
370                 375                 380 aac cag gtc agc ctg acc tgc ctg gtc aaa ggc ttc tat ccc agc gac   1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag   1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc   1296
Thr Thr Pro Pro Val Leu Asp Ser Asp Gly Ser Phe Phe Leu Tyr Ser
                420                 425                 430 aag ctc acc gtg gac aag agc agg tgg cag cag ggc aac gtc ttc tca   1344
Lys Leu Thr Val Asp Lys Ser Arg Trp Gln Gln Gly Asn Val Phe Ser
            435                 440                 445 tgc tcc gtg atg cat gag gct ctg cac aac cac tac acc cag aag agc   1392
Cys Ser Val Met His Glu Ala Leu His Asn His Tyr Thr Gln Lys Ser
450                 455                 460 ctc tcc ctg tct ccc ggc aaa                                       1413
Leu Ser Leu Ser Pro Gly Lys
465                 470

<210> SEQ ID NO 46
<211> LENGTH: 471
<212> TYPE: PRT
<213> ORGANISM: Artificial Sequence
<220> FEATURE:
<223> OTHER INFORMATION: Synthetic Construct

<400> SEQUENCE: 46

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Lys Gln Ser Pro Gly Met Ser Leu
    50                  55                  60

Glu Trp Ile Gly Arg Phe Asn Pro Tyr Asn Gly Asp Thr Phe Tyr Asn
65                  70                  75                  80

Gln Lys Phe Lys Gly Lys Ala Thr Leu Thr Val Asp Lys Ser Thr Ser
                85                  90                  95

Thr Ala His Met Glu Leu Ser Ser Leu Arg Ser Glu Asp Thr Ala Val
            100                 105                 110

Tyr Phe Cys Ala Arg Ser Ala Tyr Tyr Phe Asp Ser Gly Gly Tyr Phe
        115                 120                 125

Asp Tyr Trp Gly Gln Gly Thr Leu Val Thr Val Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
```

```
                165                 170                 175
Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Gln Thr Tyr Ile Cys
                210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
                290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Glu Glu Met Thr Lys
                370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly Lys
465                 470

<210> SEQ ID NO 47
<211> LENGTH: 1413
<212> TYPE: DNA
<213> ORGANISM: Artificial Sequence
<220> FEATURE:
<223> OTHER INFORMATION: Nucleotide sequence coding hB273_H2-4
<220> FEATURE:
<221> NAME/KEY: CDS
<222> LOCATION: (1)..(1413)

<400> SEQUENCE: 47 atg aaa cac ctg tgg ttc ttc ctc ctg ctg gtg gca gct ccc aga tgg     48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa     96
Val Leu Ser Gln Val Gln Leu Val Gln Ser Gly Ala Glu Val Lys Lys
            20                  25                  30
```

| | | |
|---|---|---|
| cct gga gcc agc gtg aag gtg tcc tgc aag gcc agc ggc tac agc ttc<br>Pro Gly Ala Ser Val Lys Val Ser Cys Lys Ala Ser Gly Tyr Ser Phe<br>35                          40                       45 | 144 |
| atc ggc tac ttc atg aac tgg atg aag cag agc ccc ggc atg agc ctg<br>Ile Gly Tyr Phe Met Asn Trp Met Lys Gln Ser Pro Gly Met Ser Leu<br>     50                    55                    60 | 192 |
| gaa tgg atc ggc cgg ttc aac ccc tac aac ggc gac acc ttc tac aac<br>Glu Trp Ile Gly Arg Phe Asn Pro Tyr Asn Gly Asp Thr Phe Tyr Asn<br>65                       70                     75                    80 | 240 |
| cag aag ttc aag gga aag gcc acc ctg aca gtg gac aag agc acc agc<br>Gln Lys Phe Lys Gly Lys Ala Thr Leu Thr Val Asp Lys Ser Thr Ser<br>                  85                    90                    95 | 288 |
| acc gcc tac atg gaa ctg agc agc ctg cgg agc gag gat acc gcc gtg<br>Thr Ala Tyr Met Glu Leu Ser Ser Leu Arg Ser Glu Asp Thr Ala Val<br>                100                   105                  110 | 336 |
| tac ttc tgc ggc aga agc gcc tac tac ttc gac agc ggc ggc tac ttc<br>Tyr Phe Cys Gly Arg Ser Ala Tyr Tyr Phe Asp Ser Gly Gly Tyr Phe<br>           115                   120                   125 | 384 |
| gac tac tgg ggc cag ggc acc ctg gtg aca gtg agc tca gcc tcc acc<br>Asp Tyr Trp Gly Gln Gly Thr Leu Val Thr Val Ser Ser Ala Ser Thr<br>130                      135                   140 | 432 |
| aag ggc cca agc gtc ttc ccc ctg gca ccc tcc tcc aag agc acc tct<br>Lys Gly Pro Ser Val Phe Pro Leu Ala Pro Ser Ser Lys Ser Thr Ser<br>145                      150                   155                   160 | 480 |
| ggc ggc aca gcc gcc ctg ggc tgc ctg gtc aag gac tac ttc ccc gaa<br>Gly Gly Thr Ala Ala Leu Gly Cys Leu Val Lys Asp Tyr Phe Pro Glu<br>                  165                   170                   175 | 528 |
| ccc gtg acc gtg agc tgg aac tca ggc gcc ctg acc agc ggc gtg cac<br>Pro Val Thr Val Ser Trp Asn Ser Gly Ala Leu Thr Ser Gly Val His<br>                180                    185                   190 | 576 |
| acc ttc ccc gct gtc ctg cag tcc tca gga ctc tac tcc ctc agc agc<br>Thr Phe Pro Ala Val Leu Gln Ser Ser Gly Leu Tyr Ser Leu Ser Ser<br>          195                   200                   205 | 624 |
| gtg gtg acc gtg ccc tcc agc agc ttg ggc acc cag acc tac atc tgc<br>Val Val Thr Val Pro Ser Ser Ser Leu Gly Thr Gln Thr Tyr Ile Cys<br>210                      215                   220 | 672 |
| aac gtg aat cac aag ccc agc aac acc aag gtg gac aag aga gtt gag<br>Asn Val Asn His Lys Pro Ser Asn Thr Lys Val Asp Lys Arg Val Glu<br>225                      230                   235                   240 | 720 |
| ccc aaa tct tgt gac aaa act cac aca tgc cca ccc tgc cca gca cct<br>Pro Lys Ser Cys Asp Lys Thr His Thr Cys Pro Pro Cys Pro Ala Pro<br>                  245                   250                   255 | 768 |
| gaa ctc ctg ggg gga ccc tca gtc ttc ctc ttc ccc cca aaa ccc aag<br>Glu Leu Leu Gly Gly Pro Ser Val Phe Leu Phe Pro Pro Lys Pro Lys<br>                  260                   265                   270 | 816 |
| gac acc ctc atg atc tcc cgg acc cct gag gtc aca tgc gtg gtg gtg<br>Asp Thr Leu Met Ile Ser Arg Thr Pro Glu Val Thr Cys Val Val Val<br>          275                   280                   285 | 864 |
| gac gtg agc cac gaa gac cct gag gtc aag ttc aac tgg tac gtg gac<br>Asp Val Ser His Glu Asp Pro Glu Val Lys Phe Asn Trp Tyr Val Asp<br>290                      295                   300 | 912 |
| ggc gtg gag gtg cat aat gcc aag aca aag ccc cgg gag gag cag tac<br>Gly Val Glu Val His Asn Ala Lys Thr Lys Pro Arg Glu Glu Gln Tyr<br>305                      310                   315                   320 | 960 |
| aac agc acg tac cgg gtg gtc agc gtc ctc acc gtc ctg cac cag gac<br>Asn Ser Thr Tyr Arg Val Val Ser Val Leu Thr Val Leu His Gln Asp<br>                  325                   330                   335 | 1008 |
| tgg ctg aat ggc aag gag tac aag tgc aag gtc tcc aac aaa gcc ctc<br>Trp Leu Asn Gly Lys Glu Tyr Lys Cys Lys Val Ser Asn Lys Ala Leu | 1056 |

```
               340                 345                 350
cca gcc ccc atc gag aaa acc atc tcc aaa gcc aaa ggc cag ccc cgg      1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag      1152
Glu Pro Gln Val Tyr Thr Leu Pro Pro Ser Arg Glu Glu Met Thr Lys
370                 375                 380 aac cag gtc agc ctg acc tgc ctg gtc aaa ggc ttc tat ccc agc gac      1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag      1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc      1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca      1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc      1392
Cys Ser Val Met His Glu Ala Leu His Asn His Tyr Thr Gln Lys Ser
450                 455                 460 ctc tcc ctg tct ccc ggc aaa                                          1413
Leu Ser Leu Ser Pro Gly Lys
465                 470

<210> SEQ ID NO 48
<211> LENGTH: 471
<212> TYPE: PRT
<213> ORGANISM: Artificial Sequence
<220> FEATURE:
<223> OTHER INFORMATION: Synthetic Construct

<400> SEQUENCE: 48

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Lys Gln Ser Pro Gly Met Ser Leu
    50                  55                  60

Glu Trp Ile Gly Arg Phe Asn Pro Tyr Asn Gly Asp Thr Phe Tyr Asn
65                  70                  75                  80

Gln Lys Phe Lys Gly Lys Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Phe Cys Gly Arg Ser Ala Tyr Tyr Phe Asp Ser Gly Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190
```

```
Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Glu Glu Met Thr Lys
                370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly Lys
465                 470

<210> SEQ ID NO 49
<211> LENGTH: 1413
<212> TYPE: DNA
<213> ORGANISM: Artificial Sequence
<220> FEATURE:
<223> OTHER INFORMATION: Nucleotide sequence coding hB273_H2-5
<220> FEATURE:
<221> NAME/KEY: CDS
<222> LOCATION: (1)..(1413)

<400> SEQUENCE: 49 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cct gga gcc agc gtg aag gtg tcc tgc aag gcc agc ggc tac agc ttc     144
Pro Gly Ala Ser Val Lys Val Ser Cys Lys Ala Ser Gly Tyr Ser Phe
        35                  40                  45
```

| | | |
|---|---|---|
| atc ggc tac ttc atg aac tgg atg aag cag agc ccc ggc aag agc ctg<br>Ile Gly Tyr Phe Met Asn Trp Met Lys Gln Ser Pro Gly Lys Ser Leu<br>50 55 60 | | 192 |
| gaa tgg atc ggc cgg ttc aac ccc tac aac ggc gac acc ttc tac aac<br>Glu Trp Ile Gly Arg Phe Asn Pro Tyr Asn Gly Asp Thr Phe Tyr Asn<br>65 70 75 80 | | 240 |
| cag aag ttc aag gga aag gcc acc ctg aca gtg gac aag agc acc agc<br>Gln Lys Phe Lys Gly Lys Ala Thr Leu Thr Val Asp Lys Ser Thr Ser<br>85 90 95 | | 288 |
| acc gcc tac atg gaa ctg agc agc ctg cgg agc gag gat acc gcc gtg<br>Thr Ala Tyr Met Glu Leu Ser Ser Leu Arg Ser Glu Asp Thr Ala Val<br>100 105 110 | | 336 |
| tac ttc tgc ggc aga agc gcc tac tac ttc gac agc ggc ggc tac ttc<br>Tyr Phe Cys Gly Arg Ser Ala Tyr Tyr Phe Asp Ser Gly Gly Tyr Phe<br>115 120 125 | | 384 |
| gac tac tgg ggc cag ggc acc ctg gtg aca gtg agc tca gcc tcc acc<br>Asp Tyr Trp Gly Gln Gly Thr Leu Val Thr Val Ser Ser Ala Ser Thr<br>130 135 140 | | 432 |
| aag ggc cca agc gtc ttc ccc ctg gca ccc tcc tcc aag agc acc tct<br>Lys Gly Pro Ser Val Phe Pro Leu Ala Pro Ser Ser Lys Ser Thr Ser<br>145 150 155 160 | | 480 |
| ggc ggc aca gcc gcc ctg ggc tgc ctg gtc aag gac tac ttc ccc gaa<br>Gly Gly Thr Ala Ala Leu Gly Cys Leu Val Lys Asp Tyr Phe Pro Glu<br>165 170 175 | | 528 |
| ccc gtg acc gtg agc tgg aac tca ggc gcc ctg acc agc ggc gtg cac<br>Pro Val Thr Val Ser Trp Asn Ser Gly Ala Leu Thr Ser Gly Val His<br>180 185 190 | | 576 |
| acc ttc ccc gct gtc ctg cag tcc tca gga ctc tac tcc ctc agc agc<br>Thr Phe Pro Ala Val Leu Gln Ser Ser Gly Leu Tyr Ser Leu Ser Ser<br>195 200 205 | | 624 |
| gtg gtg acc gtg ccc tcc agc agc ttg ggc acc cag acc tac atc tgc<br>Val Val Thr Val Pro Ser Ser Ser Leu Gly Thr Gln Thr Tyr Ile Cys<br>210 215 220 | | 672 |
| aac gtg aat cac aag ccc agc aac acc aag gtg gac aag aga gtt gag<br>Asn Val Asn His Lys Pro Ser Asn Thr Lys Val Asp Lys Arg Val Glu<br>225 230 235 240 | | 720 |
| ccc aaa tct tgt gac aaa act cac aca tgc cca ccc tgc cca gca cct<br>Pro Lys Ser Cys Asp Lys Thr His Thr Cys Pro Pro Cys Pro Ala Pro<br>245 250 255 | | 768 |
| gaa ctc ctg ggg gga ccc tca gtc ttc ctc ttc ccc cca aaa ccc aag<br>Glu Leu Leu Gly Gly Pro Ser Val Phe Leu Phe Pro Pro Lys Pro Lys<br>260 265 270 | | 816 |
| gac acc ctc atg atc tcc cgg acc cct gag gtc aca tgc gtg gtg gtg<br>Asp Thr Leu Met Ile Ser Arg Thr Pro Glu Val Thr Cys Val Val Val<br>275 280 285 | | 864 |
| gac gtg agc cac gaa gac cct gag gtc aag ttc aac tgg tac gtg gac<br>Asp Val Ser His Glu Asp Pro Glu Val Lys Phe Asn Trp Tyr Val Asp<br>290 295 300 | | 912 |
| ggc gtg gag gtg cat aat gcc aag aca aag ccc cgg gag gag cag tac<br>Gly Val Glu Val His Asn Ala Lys Thr Lys Pro Arg Glu Glu Gln Tyr<br>305 310 315 320 | | 960 |
| aac agc acg tac cgg gtg gtc agc gtc ctc acc gtc ctg cac cag gac<br>Asn Ser Thr Tyr Arg Val Val Ser Val Leu Thr Val Leu His Gln Asp<br>325 330 335 | | 1008 |
| tgg ctg aat ggc aag gag tac aag tgc aag gtc tcc aac aaa gcc ctc<br>Trp Leu Asn Gly Lys Glu Tyr Lys Cys Lys Val Ser Asn Lys Ala Leu<br>340 345 350 | | 1056 |
| cca gcc ccc atc gag aaa acc atc tcc aaa gcc aaa ggc cag ccc cgg<br>Pro Ala Pro Ile Glu Lys Thr Ile Ser Lys Ala Lys Gly Gln Pro Arg | | 1104 |

```
                    355                 360                 365
gaa cca cag gtg tac acc ctg ccc cca tcc cgg gag gag atg acc aag       1152
Glu Pro Gln Val Tyr Thr Leu Pro Pro Ser Arg Glu Glu Met Thr Lys
    370                 375                 380 aac cag gtc agc ctg acc tgc ctg gtc aaa ggc ttc tat ccc agc gac       1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag       1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc       1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca       1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc       1392
Cys Ser Val Met His Glu Ala Leu His Asn His Tyr Thr Gln Lys Ser
    450                 455                 460 ctc tcc ctg tct ccc ggc aaa                                           1413
Leu Ser Leu Ser Pro Gly Lys
465                 470

<210> SEQ ID NO 50
<211> LENGTH: 471
<212> TYPE: PRT
<213> ORGANISM: Artificial Sequence
<220> FEATURE:
<223> OTHER INFORMATION: Synthetic Construct

<400> SEQUENCE: 50

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Lys Gln Ser Pro Gly Lys Ser Leu
    50                  55                  60

Glu Trp Ile Gly Arg Phe Asn Pro Tyr Asn Gly Asp Thr Phe Tyr Asn
65                  70                  75                  80

Gln Lys Phe Lys Gly Lys Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Phe Cys Gly Arg Ser Ala Tyr Tyr Phe Asp Ser Gly Gly Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205
```

```
Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 51
<211> LENGTH: 717
<212> TYPE: DNA
<213> ORGANISM: Artificial Sequence
<220> FEATURE:
<223> OTHER INFORMATION: Nucleotide sequence coding hB273_L1-NE
<220> FEATURE:
<221> NAME/KEY: CDS
<222> LOCATION: (1)..(717)

<400> SEQUENCE: 51 atg gtg ctg cag acc cag gtg ttc atc tcc ctg ctg ctg tgg atc tcc        48
Met Val Leu Gln Thr Gln Val Phe Ile Ser Leu Leu Leu Trp Ile Ser
1               5                   10                  15 ggc gca tat ggc gac atc gta atg acc cag tct ccg ctg agt ctt cct        96
Gly Ala Tyr Gly Asp Ile Val Met Thr Gln Ser Pro Leu Ser Leu Pro
            20                  25                  30 gtg act cca ggg gag ccc gca agc atc tct tgt cgc agc agt cag tca       144
Val Thr Pro Gly Glu Pro Ala Ser Ile Ser Cys Arg Ser Ser Gln Ser
        35                  40                  45 ctg gtc cat agc aat gag aac act tac ctg cat tgg tac ctc caa aaa       192
Leu Val His Ser Asn Glu Asn Thr Tyr Leu His Trp Tyr Leu Gln Lys
    50                  55                  60
```

```
cca ggg cag tcc cca cag ctc ttg atc tac aag gtg tcc aat cgg ttc        240
Pro Gly Gln Ser Pro Gln Leu Leu Ile Tyr Lys Val Ser Asn Arg Phe
 65                  70                  75                  80 agt ggt gtg cct gac cgc ttc tcc gga agt ggc tcc ggg aca gat ttc        288
Ser Gly Val Pro Asp Arg Phe Ser Gly Ser Gly Ser Gly Thr Asp Phe
                 85                  90                  95 act ctt aag att tca aga gtg gag gca gaa gac gtt gga gtc tat tat        336
Thr Leu Lys Ile Ser Arg Val Glu Ala Glu Asp Val Gly Val Tyr Tyr
            100                 105                 110 tgc tca cag agc aca cat gtc ccc tgg act ttc ggt ccc ggc aca aaa        384
Cys Ser Gln Ser Thr His Val Pro Trp Thr Phe Gly Pro Gly Thr Lys
        115                 120                 125 gtc gag atc aag cgt acg gtg gcc gcc ccc tcc gtg ttc atc ttc ccc        432
Val Glu Ile Lys Arg Thr Val Ala Ala Pro Ser Val Phe Ile Phe Pro
130                 135                 140 ccc tcc gac gag cag ctg aag tcc ggc acc gcc tcc gtg gtg tgc ctg        480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac        528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac        576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa        624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag        672
Ala Asp Tyr Glu Lys His Lys Val Tyr Ala Cys Glu Val Thr His Gln
210                 215                 220 ggc ctg agc tcc ccc gtc acc aag agc ttc aac agg ggg gag tgt            717
Gly Leu Ser Ser Pro Val Thr Lys Ser Phe Asn Arg Gly Glu Cys
225                 230                 235

<210> SEQ ID NO 52
<211> LENGTH: 239
<212> TYPE: PRT
<213> ORGANISM: Artificial Sequence
<220> FEATURE:
<223> OTHER INFORMATION: Synthetic Construct

<400> SEQUENCE: 52

Met Val Leu Gln Thr Gln Val Phe Ile Ser Leu Leu Leu Trp Ile Ser
  1               5                  10                  15

Gly Ala Tyr Gly Asp Ile Val Met Thr Gln Ser Pro Leu Ser Leu Pro
                 20                  25                  30

Val Thr Pro Gly Glu Pro Ala Ser Ile Ser Cys Arg Ser Ser Gln Ser
             35                  40                  45

Leu Val His Ser Asn Glu Asn Thr Tyr Leu His Trp Tyr Leu Gln Lys
         50                  55                  60

Pro Gly Gln Ser Pro Gln Leu Leu Ile Tyr Lys Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Pro Gly Thr Lys
        115                 120                 125
```

```
Val Glu Ile Lys Arg Thr Val Ala Ala Pro Ser Val Phe Ile Phe Pro
130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
        195                 200                 205
Ala Asp Tyr Glu Lys His Lys Val Tyr Ala Cys Glu Val Thr His Gln
210                 215                 220
Gly Leu Ser Ser Pro Val Thr Lys Ser Phe Asn Arg Gly Glu Cys
225                 230                 235
```

<210> SEQ ID NO 53
<211> LENGTH: 32
<212> TYPE: DNA
<213> ORGANISM: Artificial Sequence
<220> FEATURE:
<223> OTHER INFORMATION: Primer L-F1

<400> SEQUENCE: 53
aggtaagctt gctagcgcca ccatggtgct gc     32

<210> SEQ ID NO 54
<211> LENGTH: 42
<212> TYPE: DNA
<213> ORGANISM: Artificial Sequence
<220> FEATURE:
<223> OTHER INFORMATION: Primer L-NE-R2

<400> SEQUENCE: 54
ccaatgcagg taagtgttct cattgctatg gaccagtgac tg     42

<210> SEQ ID NO 55
<211> LENGTH: 42
<212> TYPE: DNA
<213> ORGANISM: Artificial Sequence
<220> FEATURE:
<223> OTHER INFORMATION: Primer L-NE-F2

<400> SEQUENCE: 55
cagtcactgg tccatagcaa tgagaacact tacctgcatt gg     42

<210> SEQ ID NO 56
<211> LENGTH: 32
<212> TYPE: DNA
<213> ORGANISM: Artificial Sequence
<220> FEATURE:
<223> OTHER INFORMATION: Primer L-R1

<400> SEQUENCE: 56
ggatgccacc cgtttaaacg ggcccctaac ac     32

<210> SEQ ID NO 57
<211> LENGTH: 717
<212> TYPE: DNA
<213> ORGANISM: Artificial Sequence
<220> FEATURE:
<223> OTHER INFORMATION: Nucleotide sequence coding hB273_L1-NF
<220> FEATURE:
<221> NAME/KEY: CDS
<222> LOCATION: (1)..(717)

<400> SEQUENCE: 57

```
atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
1               5                   10                  15 ggc gca tat ggc gac atc gta atg acc cag tct ccg ctg agt ctt cct    96
Gly Ala Tyr Gly Asp Ile Val Met Thr Gln Ser Pro Leu Ser Leu Pro
            20                  25                  30 gtg act cca ggg gag ccc gca agc atc tct tgt cgc agc agt cag tca   144
Val Thr Pro Gly Glu Pro Ala Ser Ile Ser Cys Arg Ser Ser Gln Ser
        35                  40                  45 ctg gtc cat agc aat ttc aac act tac ctg cat tgg tac ctc caa aaa   192
Leu Val His Ser Asn Phe Asn Thr Tyr Leu His Trp Tyr Leu Gln Lys
    50                  55                  60 cca ggg cag tcc cca cag ctc ttg atc tac aag gtg tcc aat cgg ttc   240
Pro Gly Gln Ser Pro Gln Leu Leu Ile Tyr Lys Val Ser Asn Arg Phe
65                  70                  75                  80 agt ggt gtg cct gac cgc ttc tcc gga agt ggc tcc ggg aca gat ttc   288
Ser Gly Val Pro Asp Arg Phe Ser Gly Ser Gly Ser Gly Thr Asp Phe
                85                  90                  95 act ctt aag att tca aga gtg gag gca gaa gac gtt gga gtc tat tat   336
Thr Leu Lys Ile Ser Arg Val Glu Ala Glu Asp Val Gly Val Tyr Tyr
            100                 105                 110 tgc tca cag agc aca cat gtc ccc tgg act ttc ggt ccc ggc aca aaa   384
Cys Ser Gln Ser Thr His Val Pro Trp Thr Phe Gly Pro Gly Thr Lys
        115                 120                 125 gtc gag atc aag cgt acg gtg gcc gcc ccc tcc gtg ttc atc ttc ccc   432
Val Glu Ile Lys Arg Thr Val Ala Ala Pro Ser Val Phe Ile Phe Pro
    130                 135                 140 ccc tcc gac gag cag ctg aag tcc ggc acc gcc tcc gtg gtg tgc ctg   480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac   528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac   576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa   624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag   672
Ala Asp Tyr Glu Lys His Lys Val Tyr Ala Cys Glu Val Thr His Gln
    210                 215                 220 ggc ctg agc tcc ccc gtc acc aag agc ttc aac agg ggg gag tgt       717
Gly Leu Ser Ser Pro Val Thr Lys Ser Phe Asn Arg Gly Glu Cys
225                 230                 235
```

<210> SEQ ID NO 58
<211> LENGTH: 239
<212> TYPE: PRT
<213> ORGANISM: Artificial Sequence
<220> FEATURE:
<223> OTHER INFORMATION: Synthetic Construct

<400> SEQUENCE: 58

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Leu Ser Leu Pro
            20                  25                  30
```

Val Thr Pro Gly Glu Pro Ala Ser Ile Ser Cys Arg Ser Gln Ser
         35                  40                  45

Leu Val His Ser Asn Phe Asn Thr Tyr Leu His Trp Tyr Leu Gln Lys
 50                  55                  60

Pro Gly Gln Ser Pro Gln Leu Leu Ile Tyr Lys Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
             100                 105                 110

Cys Ser Gln Ser Thr His Val Pro Trp Thr Phe Gly Pro Gly Thr Lys
         115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 59
<211> LENGTH: 42
<212> TYPE: DNA
<213> ORGANISM: Artificial Sequence
<220> FEATURE:
<223> OTHER INFORMATION: Primer L-NF-R2

<400> SEQUENCE: 59
ccaatgcagg taagtgttga aattgctatg gaccagtgac tg                    42

<210> SEQ ID NO 60
<211> LENGTH: 42
<212> TYPE: DNA
<213> ORGANISM: Artificial Sequence
<220> FEATURE:
<223> OTHER INFORMATION: Primer L-NF-F2

<400> SEQUENCE: 60
cagtcactgg tccatagcaa tttcaacact tacctgcatt gg                    42

<210> SEQ ID NO 61
<211> LENGTH: 717
<212> TYPE: DNA
<213> ORGANISM: Artificial Sequence
<220> FEATURE:
<223> OTHER INFORMATION: Nucleotide sequence coding hB273_L1-NK
<220> FEATURE:
<221> NAME/KEY: CDS
<222> LOCATION: (1)..(717)

<400> SEQUENCE: 61 atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
 1               5                  10                  15

```
ggc gca tat ggc gac atc gta atg acc cag tct ccg ctg agt ctt cct      96
Gly Ala Tyr Gly Asp Ile Val Met Thr Gln Ser Pro Leu Ser Leu Pro
            20                  25                  30 gtg act cca ggg gag ccc gca agc atc tct tgt cgc agc agt cag tca     144
Val Thr Pro Gly Glu Pro Ala Ser Ile Ser Cys Arg Ser Ser Gln Ser
        35                  40                  45 ctg gtc cat agc aat aag aac act tac ctg cat tgg tac ctc caa aaa     192
Leu Val His Ser Asn Lys Asn Thr Tyr Leu His Trp Tyr Leu Gln Lys
    50                  55                  60 cca ggg cag tcc cca cag ctc ttg atc tac aag gtg tcc aat cgg ttc     240
Pro Gly Gln Ser Pro Gln Leu Leu Ile Tyr Lys Val Ser Asn Arg Phe
65                  70                  75                  80 agt ggt gtg cct gac cgc ttc tcc gga agt ggc tcc ggg aca gat ttc     288
Ser Gly Val Pro Asp Arg Phe Ser Gly Ser Gly Ser Gly Thr Asp Phe
                85                  90                  95 act ctt aag att tca aga gtg gag gca gaa gac gtt gga gtc tat tat     336
Thr Leu Lys Ile Ser Arg Val Glu Ala Glu Asp Val Gly Val Tyr Tyr
            100                 105                 110 tgc tca cag agc aca cat gtc ccc tgg act ttc ggt ccc ggc aca aaa     384
Cys Ser Gln Ser Thr His Val Pro Trp Thr Phe Gly Pro Gly Thr Lys
        115                 120                 125 gtc gag atc aag cgt acg gtg gcc gcc ccc tcc gtg ttc atc ttc ccc     432
Val Glu Ile Lys Arg Thr Val Ala Ala Pro Ser Val Phe Ile Phe Pro
    130                 135                 140 ccc tcc gac gag cag ctg aag tcc ggc acc gcc tcc gtg gtg tgc ctg     480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac     528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac     576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa     624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag     672
Ala Asp Tyr Glu Lys His Lys Val Tyr Ala Cys Glu Val Thr His Gln
    210                 215                 220 ggc ctg agc tcc ccc gtc acc aag agc ttc aac agg ggg gag tgt         717
Gly Leu Ser Ser Pro Val Thr Lys Ser Phe Asn Arg Gly Glu Cys
225                 230                 235

<210> SEQ ID NO 62
<211> LENGTH: 239
<212> TYPE: PRT
<213> ORGANISM: Artificial Sequence
<220> FEATURE:
<223> OTHER INFORMATION: Synthetic Construct

<400> SEQUENCE: 62

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Val His Ser Asn Lys Asn Thr Tyr Leu His Trp Tyr Leu Gln Lys
    50                  55                  60
```

Pro Gly Gln Ser Pro Gln Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Pro Gly Thr Lys
        115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 63
<211> LENGTH: 42
<212> TYPE: DNA
<213> ORGANISM: Artificial Sequence
<220> FEATURE:
<223> OTHER INFORMATION: Primer L-NK-R2

<400> SEQUENCE: 63
ccaatgcagg taagtgttct tattgctatg gaccagtgac tg         42

<210> SEQ ID NO 64
<211> LENGTH: 42
<212> TYPE: DNA
<213> ORGANISM: Artificial Sequence
<220> FEATURE:
<223> OTHER INFORMATION: Primer L-NK-F2

<400> SEQUENCE: 64
cagtcactgg tccatagcaa taagaacact tacctgcatt gg         42

<210> SEQ ID NO 65
<211> LENGTH: 717
<212> TYPE: DNA
<213> ORGANISM: Artificial Sequence
<220> FEATURE:
<223> OTHER INFORMATION: Nucleotide sequence coding hB273_L1-NL
<220> FEATURE:
<221> NAME/KEY: CDS
<222> LOCATION: (1)..(717)

<400> SEQUENCE: 65 atg gtg ctg cag acc cag gtg ttc atc tcc ctg ctg ctg tgg atc tcc     48
Met Val Leu Gln Thr Gln Val Phe Ile Ser Leu Leu Leu Trp Ile Ser
1               5                   10                  15 ggc gca tat ggc gac atc gta atg acc cag tct ccg ctg agt ctt cct     96
Gly Ala Tyr Gly Asp Ile Val Met Thr Gln Ser Pro Leu Ser Leu Pro
            20                  25                  30 gtg act cca ggg gag ccc gca agc atc tct tgt cgc agc agt cag tca    144

```
                Val Thr Pro Gly Glu Pro Ala Ser Ile Ser Cys Arg Ser Gln Ser
                         35                  40                  45 ctg gtc cat agc aat ctg aac act tac ctg cat tgg tac ctc caa aaa    192
Leu Val His Ser Asn Leu Asn Thr Tyr Leu His Trp Tyr Leu Gln Lys
 50                  55                  60 cca ggg cag tcc cca cag ctc ttg atc tac aag gtg tcc aat cgg ttc    240
Pro Gly Gln Ser Pro Gln Leu Leu Ile Tyr Lys Val Ser Asn Arg Phe
 65                  70                  75                  80 agt ggt gtg cct gac cgc ttc tcc gga agt ggc tcc ggg aca gat ttc    288
Ser Gly Val Pro Asp Arg Phe Ser Gly Ser Gly Ser Gly Thr Asp Phe
                     85                  90                  95 act ctt aag att tca aga gtg gag gca gaa gac gtt gga gtc tat tat    336
Thr Leu Lys Ile Ser Arg Val Glu Ala Glu Asp Val Gly Val Tyr Tyr
                100                 105                 110 tgc tca cag agc aca cat gtc ccc tgg act ttc ggt ccc ggc aca aaa    384
Cys Ser Gln Ser Thr His Val Pro Trp Thr Phe Gly Pro Gly Thr Lys
                115                 120                 125 gtc gag atc aag cgt acg gtg gcc gcc ccc tcc gtg ttc atc ttc ccc    432
Val Glu Ile Lys Arg Thr Val Ala Ala Pro Ser Val Phe Ile Phe Pro
130                 135                 140 ccc tcc gac gag cag ctg aag tcc ggc acc gcc tcc gtg gtg tgc ctg    480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac    528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac    576
Asn Ala Leu Gln Ser Gly Asn Ser Gln Glu Ser Val Thr Glu Gln Asp
                180                 185                 190 agc aag gac agc acc tac agc ctg agc agc acc ctg acc ctg agc aaa    624
Ser Lys Asp Ser Thr Tyr Ser Leu Ser Ser Thr Leu Thr Leu Ser Lys
                195                 200                 205 gcc gac tac gag aag cac aag gtg tac gcc tgc gag gtg acc cac cag    672
Ala Asp Tyr Glu Lys His Lys Val Tyr Ala Cys Glu Val Thr His Gln
210                 215                 220 ggc ctg agc tcc ccc gtc acc aag agc ttc aac agg ggg gag tgt        717
Gly Leu Ser Ser Pro Val Thr Lys Ser Phe Asn Arg Gly Glu Cys
225                 230                 235

<210> SEQ ID NO 66
<211> LENGTH: 239
<212> TYPE: PRT
<213> ORGANISM: Artificial Sequence
<220> FEATURE:
<223> OTHER INFORMATION: Synthetic Construct

<400> SEQUENCE: 66

Met Val Leu Gln Thr Gln Val Phe Ile Ser Leu Leu Trp Ile Ser
 1               5                  10                  15

Gly Ala Tyr Gly Asp Ile Val Met Thr Gln Ser Pro Leu Ser Leu Pro
                 20                  25                  30

Val Thr Pro Gly Glu Pro Ala Ser Ile Ser Cys Arg Ser Gln Ser
                 35                  40                  45

Leu Val His Ser Asn Leu Asn Thr Tyr Leu His Trp Tyr Leu Gln Lys
 50                  55                  60

Pro Gly Gln Ser Pro Gln Leu Leu Ile Tyr Lys Val Ser Asn Arg Phe
 65                  70                  75                  80

Ser Gly Val Pro Asp Arg Phe Ser Gly Ser Gly Ser Gly Thr Asp Phe
                     85                  90                  95
```

```
Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Pro Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 67
<211> LENGTH: 42
<212> TYPE: DNA
<213> ORGANISM: Artificial Sequence
<220> FEATURE:
<223> OTHER INFORMATION: Primer L-NL-R2

<400> SEQUENCE: 67
ccaatgcagg taagtgttca gattgctatg gaccagtgac tg                          42

<210> SEQ ID NO 68
<211> LENGTH: 42
<212> TYPE: DNA
<213> ORGANISM: Artificial Sequence
<220> FEATURE:
<223> OTHER INFORMATION: Primer L-NL-F2

<400> SEQUENCE: 68
cagtcactgg tccatagcaa tctgaacact tacctgcatt gg                          42

<210> SEQ ID NO 69
<211> LENGTH: 1413
<212> TYPE: DNA
<213> ORGANISM: Artificial Sequence
<220> FEATURE:
<223> OTHER INFORMATION: Nucleotide sequence coding hB273_H2-1-NE
<220> FEATURE:
<221> NAME/KEY: CDS
<222> LOCATION: (1)..(1413)

<400> SEQUENCE: 69 atg aaa cac ctg tgg ttc ttc ctc ctg ctg gtg gca gct ccc aga tgg       48
Met Lys His Leu Trp Phe Phe Leu Leu Leu Val Ala Ala Pro Arg Trp
1               5                   10                  15 gtg ctg agc gag gtg cag ctg gtg cag tct ggc gcc gaa gtg aag aaa       96
Val Leu Ser Glu Val Gln Leu Val Gln Ser Gly Ala Glu Val Lys Lys
            20                  25                  30 cct gga gcc agc gtg aag gtg tcc tgc aag gcc agc ggc tac agc ttc      144
Pro Gly Ala Ser Val Lys Val Ser Cys Lys Ala Ser Gly Tyr Ser Phe
        35                  40                  45 atc ggc tac ttc atg aac tgg atg aag cag agc ccc ggc atg agc ctg      192
Ile Gly Tyr Phe Met Asn Trp Met Lys Gln Ser Pro Gly Met Ser Leu
    50                  55                  60
```

```
gaa tgg atc ggc cgg ttc aac ccc tac aac gag gac acc ttc tac aac      240
Glu Trp Ile Gly Arg Phe Asn Pro Tyr Asn Glu Asp Thr Phe Tyr Asn
65              70                  75                  80 cag aag ttc aag gga aag gcc acc ctg aca gtg gac aag agc acc agc      288
Gln Lys Phe Lys Gly Lys Ala Thr Leu Thr Val Asp Lys Ser Thr Ser
                85                  90                  95 acc gcc tac atg gaa ctg agc agc ctg cgg agc gag gat acc gcc gtg      336
Thr Ala Tyr Met Glu Leu Ser Ser Leu Arg Ser Glu Asp Thr Ala Val
            100                 105                 110 tac ttc tgc gcc aga agc gcc tac tac ttc gac agc ggc ggc tac ttc      384
Tyr Phe Cys Ala Arg Ser Ala Tyr Tyr Phe Asp Ser Gly Gly Tyr Phe
        115                 120                 125 gac tac tgg ggc cag ggc acc ctg gtg aca gtg agc tca gcc tcc acc      432
Asp Tyr Trp Gly Gln Gly Thr Leu Val Thr Val Ser Ser Ala Ser Thr
130                 135                 140 aag ggc cca agc gtc ttc ccc ctg gca ccc tcc tcc aag agc acc tct      480
Lys Gly Pro Ser Val Phe Pro Leu Ala Pro Ser Ser Lys Ser Thr Ser
145                 150                 155                 160 ggc ggc aca gcc gcc ctg ggc tgc ctg gtc aag gac tac ttc ccc gaa      528
Gly Gly Thr Ala Ala Leu Gly Cys Leu Val Lys Asp Tyr Phe Pro Glu
                165                 170                 175 ccc gtg acc gtg agc tgg aac tca ggc gcc ctg acc agc ggc gtg cac      576
Pro Val Thr Val Ser Trp Asn Ser Gly Ala Leu Thr Ser Gly Val His
            180                 185                 190 acc ttc ccc gct gtc ctg cag tcc tca gga ctc tac tcc ctc agc agc      624
Thr Phe Pro Ala Val Leu Gln Ser Ser Gly Leu Tyr Ser Leu Ser Ser
        195                 200                 205 gtg gtg acc gtg ccc tcc agc agc ttg ggc acc cag acc tac atc tgc      672
Val Val Thr Val Pro Ser Ser Ser Leu Gly Thr Gln Thr Tyr Ile Cys
210                 215                 220 aac gtg aat cac aag ccc agc aac acc aag gtg gac aag aga gtt gag      720
Asn Val Asn His Lys Pro Ser Asn Thr Lys Val Asp Lys Arg Val Glu
225                 230                 235                 240 ccc aaa tct tgt gac aaa act cac aca tgc cca ccc tgc cca gca cct      768
Pro Lys Ser Cys Asp Lys Thr His Thr Cys Pro Pro Cys Pro Ala Pro
                245                 250                 255 gaa ctc ctg ggg gga ccc tca gtc ttc ctc ttc ccc cca aaa ccc aag      816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg      864
Asp Thr Leu Met Ile Ser Arg Thr Pro Glu Val Thr Cys Val Val Val
        275                 280                 285 gac gtg agc cac gaa gac cct gag gtc aag ttc aac tgg tac gtg gac      912
Asp Val Ser His Glu Asp Pro Glu Val Lys Phe Asn Trp Tyr Val Asp
290                 295                 300 ggc gtg gag gtg cat aat gcc aag aca aag ccc cgg gag gag cag tac      960
Gly Val Glu Val His Asn Ala Lys Thr Lys Pro Arg Glu Glu Gln Tyr
305                 310                 315                 320 aac agc acg tac cgg gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc     1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggc cag ccc cgg     1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gag gag atg acc aag     1152
Glu Pro Gln Val Tyr Thr Leu Pro Pro Ser Arg Glu Glu Met Thr Lys
```

```
                370                 375                 380
aac cag gtc agc ctg acc tgc ctg gtc aaa ggc ttc tat ccc agc gac       1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag       1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc       1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca       1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc       1392
Cys Ser Val Met His Glu Ala Leu His Asn His Tyr Thr Gln Lys Ser
450                 455                 460 ctc tcc ctg tct ccc ggc aaa                                           1413
Leu Ser Leu Ser Pro Gly Lys
465                 470

<210> SEQ ID NO 70
<211> LENGTH: 471
<212> TYPE: PRT
<213> ORGANISM: Artificial Sequence
<220> FEATURE:
<223> OTHER INFORMATION: Synthetic Construct

<400> SEQUENCE: 70

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Ile Gly Tyr Phe Met Asn Trp Met Lys Gln Ser Pro Gly Met Ser Leu
    50                  55                  60

Glu Trp Ile Gly Arg Phe Asn Pro Tyr Asn Glu Asp Thr Phe Tyr Asn
65                  70                  75                  80

Gln Lys Phe Lys Gly Lys Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Phe Cys Ala Arg Ser Ala Tyr Tyr Phe Asp Ser Gly Gly Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
```

```
                    225                 230                 235                 240
Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 71
<211> LENGTH: 32
<212> TYPE: DNA
<213> ORGANISM: Artificial Sequence
<220> FEATURE:
<223> OTHER INFORMATION: Primer H-F1

<400> SEQUENCE: 71
aggtaagctt gctagcgcca ccatgaaaca cc                                    32

<210> SEQ ID NO 72
<211> LENGTH: 42
<212> TYPE: DNA
<213> ORGANISM: Artificial Sequence
<220> FEATURE:
<223> OTHER INFORMATION: Primer H-NE-R2

<400> SEQUENCE: 72
ctggttgtag aaggtgtcct cgttgtaggg gttgaaccgg cc                         42

<210> SEQ ID NO 73
<211> LENGTH: 42
<212> TYPE: DNA
<213> ORGANISM: Artificial Sequence
<220> FEATURE:
<223> OTHER INFORMATION: Primer H-NE-F2
```

```
<400> SEQUENCE: 73
ggccggttca acccctacaa cgaggacacc ttctacaacc ag                              42

<210> SEQ ID NO 74
<211> LENGTH: 33
<212> TYPE: DNA
<213> ORGANISM: Artificial Sequence
<220> FEATURE:
<223> OTHER INFORMATION: Primer H-R1

<400> SEQUENCE: 74
ggatgccacc cgtttaaacg ggcccgatat ctc                                        33

<210> SEQ ID NO 75
<211> LENGTH: 705
<212> TYPE: DNA
<213> ORGANISM: Artificial Sequence
<220> FEATURE:
<223> OTHER INFORMATION: Nucleotide sequence coding the light chain of
      conatumumab
<220> FEATURE:
<221> NAME/KEY: CDS
<222> LOCATION: (1)..(705)

<400> SEQUENCE: 75 atg gtg ctg cag acc cag gtg ttc atc tcc ctg ctg ctg tgg atc tcc            48
Met Val Leu Gln Thr Gln Val Phe Ile Ser Leu Leu Leu Trp Ile Ser
1               5                   10                  15 ggc gca tat ggc gaa atc gtg ttg aca cag agt ccc ggc act ctt agc            96
Gly Ala Tyr Gly Glu Ile Val Leu Thr Gln Ser Pro Gly Thr Leu Ser
                20                  25                  30 ctt agc ccg ggt gaa cgc gcc acc ctg tcc tgc cgc gcc tct cag gga           144
Leu Ser Pro Gly Glu Arg Ala Thr Leu Ser Cys Arg Ala Ser Gln Gly
            35                  40                  45 atc tct cgc tct tac ctc gcg tgg tac cag cag aaa ccc ggc cag gcc           192
Ile Ser Arg Ser Tyr Leu Ala Trp Tyr Gln Gln Lys Pro Gly Gln Ala
        50                  55                  60 ccc agt ttg ctg ata tac ggt gcc tct agc cga gca act ggc atc cca           240
Pro Ser Leu Leu Ile Tyr Gly Ala Ser Ser Arg Ala Thr Gly Ile Pro
65                  70                  75                  80 gac cgg ttc tca gga tct ggc tcc ggg act gac ttc act ctg acc atc           288
Asp Arg Phe Ser Gly Ser Gly Ser Gly Thr Asp Phe Thr Leu Thr Ile
                85                  90                  95 tcc aga ctg gag ccc gag gat ttc gcg gta tat tac tgc cag cag ttc           336
Ser Arg Leu Glu Pro Glu Asp Phe Ala Val Tyr Tyr Cys Gln Gln Phe
                100                 105                 110 ggc agc agt cct tgg acc ttc gga cag ggt act aag gtg gag att aaa           384
Gly Ser Ser Pro Trp Thr Phe Gly Gln Gly Thr Lys Val Glu Ile Lys
            115                 120                 125 cgt acg gtg gcc gcc ccc tcc gtg ttc atc ttc ccc ccc tcc gac gag           432
Arg Thr Val Ala Ala Pro Ser Val Phe Ile Phe Pro Pro Ser Asp Glu
        130                 135                 140 cag ctg aag tcc ggc acc gcc tcc gtg gtg tgc ctg ctg aat aac ttc           480
Gln Leu Lys Ser Gly Thr Ala Ser Val Val Cys Leu Leu Asn Asn Phe
145                 150                 155                 160 tac ccc aga gag gcc aag gtg cag tgg aag gtg gac aac gcc ctg cag           528
Tyr Pro Arg Glu Ala Lys Val Gln Trp Lys Val Asp Asn Ala Leu Gln
                165                 170                 175 tcc ggg aac tcc cag gag agc gtg acc gag cag gac agc aag gac agc           576
Ser Gly Asn Ser Gln Glu Ser Val Thr Glu Gln Asp Ser Lys Asp Ser
            180                 185                 190 acc tac agc ctg agc agc acc ctg acc ctg agc aaa gcc gac tac gag           624
```

```
Thr Tyr Ser Leu Ser Ser Thr Leu Thr Leu Ser Lys Ala Asp Tyr Glu
            195                 200                 205 aag cac aag gtg tac gcc tgc gag gtg acc cac cag ggc ctg agc tcc    672
Lys His Lys Val Tyr Ala Cys Glu Val Thr His Gln Gly Leu Ser Ser
    210                 215                 220 ccc gtc acc aag agc ttc aac agg ggg gag tgt                        705
Pro Val Thr Lys Ser Phe Asn Arg Gly Glu Cys
225                 230                 235

<210> SEQ ID NO 76
<211> LENGTH: 235
<212> TYPE: PRT
<213> ORGANISM: Artificial Sequence
<220> FEATURE:
<223> OTHER INFORMATION: Synthetic Construct

<400> SEQUENCE: 76

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Gly
        35                  40                  45

Ile Ser Arg Ser Tyr Leu Ala Trp Tyr Gln Gln Lys Pro Gly Gln Ala
    50                  55                  60

Pro Ser Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
            100                 105                 110

Gly Ser Ser Pro Trp Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 77
<211> LENGTH: 1413
<212> TYPE: DNA
<213> ORGANISM: Artificial Sequence
<220> FEATURE:
<223> OTHER INFORMATION: Nucleotide sequence coding the heavy chain of
      conatumumab
<220> FEATURE:
<221> NAME/KEY: CDS
<222> LOCATION: (1)..(1413)

<400> SEQUENCE: 77
```

```
atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctt cag gaa agc ggg ccc ggc ctc gtg aag      96
Val Leu Ser Gln Val Gln Leu Gln Glu Ser Gly Pro Gly Leu Val Lys
            20                  25                  30 ccc tcc cag acc ctg tct ctt act tgt aca gtg agc ggt ggc agc att     144
Pro Ser Gln Thr Leu Ser Leu Thr Cys Thr Val Ser Gly Gly Ser Ile
        35                  40                  45 tct tca ggc gat tac ttc tgg agt tgg att cgc caa ctg cct ggt aaa     192
Ser Ser Gly Asp Tyr Phe Trp Ser Trp Ile Arg Gln Leu Pro Gly Lys
    50                  55                  60 ggg ctg gaa tgg atc ggg cat att cac aat tca gga acc aca tat tat     240
Gly Leu Glu Trp Ile Gly His Ile His Asn Ser Gly Thr Thr Tyr Tyr
65              70                  75                  80 aac cct tca ctg aag agc cgg gta act atc tcc gtt gac act agc aag     288
Asn Pro Ser Leu Lys Ser Arg Val Thr Ile Ser Val Asp Thr Ser Lys
                85                  90                  95 aaa cag ttc tcc ctc cgg ctg tct tct gtc aca gcc gct gac acc gct     336
Lys Gln Phe Ser Leu Arg Leu Ser Ser Val Thr Ala Ala Asp Thr Ala
            100                 105                 110 gtt tac tac tgt gca aga gat cgg ggt ggc gac tac tat tac ggc atg     384
Val Tyr Tyr Cys Ala Arg Asp Arg Gly Gly Asp Tyr Tyr Tyr Gly Met
        115                 120                 125 gat gtt tgg gga cag gga acc acc gta aca gtg agc tca gcc tcc acc     432
Asp Val Trp Gly Gln Gly Thr Thr Val Thr Val Ser Ser Ala Ser Thr
    130                 135                 140 aag ggc cca agc gtc ttc ccc ctg gca ccc tcc tcc aag agc acc tct     480
Lys Gly Pro Ser Val Phe Pro Leu Ala Pro Ser Ser Lys Ser Thr Ser
145                 150                 155                 160 ggc ggc aca gcc gcc ctg ggc tgc ctg gtc aag gac tac ttc ccc gaa     528
Gly Gly Thr Ala Ala Leu Gly Cys Leu Val Lys Asp Tyr Phe Pro Glu
                165                 170                 175 ccc gtg acc gtg agc tgg aac tca ggc gcc ctg acc agc ggc gtg cac     576
Pro Val Thr Val Ser Trp Asn Ser Gly Ala Leu Thr Ser Gly Val His
            180                 185                 190 acc ttc ccc gct gtc ctg cag tcc tca gga ctc tac tcc ctc agc agc     624
Thr Phe Pro Ala Val Leu Gln Ser Ser Gly Leu Tyr Ser Leu Ser Ser
        195                 200                 205 gtg gtg acc gtg ccc tcc agc agc ttg ggc acc cag acc tac atc tgc     672
Val Val Thr Val Pro Ser Ser Ser Leu Gly Thr Gln Thr Tyr Ile Cys
    210                 215                 220 aac gtg aat cac aag ccc agc aac acc aag gtg gac aag aga gtt gag     720
Asn Val Asn His Lys Pro Ser Asn Thr Lys Val Asp Lys Arg Val Glu
225                 230                 235                 240 ccc aaa tct tgt gac aaa act cac aca tgc cca ccc tgc cca gca cct     768
Pro Lys Ser Cys Asp Lys Thr His Thr Cys Pro Pro Cys Pro Ala Pro
                245                 250                 255 gaa ctc ctg ggg gga ccc tca gtc ttc ctc ttc ccc cca aaa ccc aag     816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg     864
Asp Thr Leu Met Ile Ser Arg Thr Pro Glu Val Thr Cys Val Val Val
        275                 280                 285 gac gtg agc cac gaa gac cct gag gtc aag ttc aac tgg tac gtg gac     912
Asp Val Ser His Glu Asp Pro Glu Val Lys Phe Asn Trp Tyr Val Asp
    290                 295                 300 ggc gtg gag gtg cat aat gcc aag aca aag ccc cgg gag gag cag tac     960
Gly Val Glu Val His Asn Ala Lys Thr Lys Pro Arg Glu Glu Gln Tyr
```

```
                305                 310                 315                 320
aac agc acg tac cgg gtg gtc agc gtc ctc acc gtc ctg cac cag gac         1008
Asn Ser Thr Tyr Arg Val Val Ser Val Leu Thr Val Leu His Gln Asp
                    325                 330                 335 tgg ctg aat ggc aag gag tac aag tgc aag gtc tcc aac aaa gcc ctc         1056
Trp Leu Asn Gly Lys Glu Tyr Lys Cys Lys Val Ser Asn Lys Ala Leu
                340                 345                 350 cca gcc ccc atc gag aaa acc atc tcc aaa gcc aaa ggc cag ccc cgg         1104
Pro Ala Pro Ile Glu Lys Thr Ile Ser Lys Ala Lys Gly Gln Pro Arg
            355                 360                 365 gaa cca cag gtg tac acc ctg ccc cca tcc cgg gag gag atg acc aag         1152
Glu Pro Gln Val Tyr Thr Leu Pro Pro Ser Arg Glu Glu Met Thr Lys
        370                 375                 380 aac cag gtc agc ctg acc tgc ctg gtc aaa ggc ttc tat ccc agc gac         1200
Asn Gln Val Ser Leu Thr Cys Leu Val Lys Gly Phe Tyr Pro Ser Asp
385                 390                 395                 400 atc gcc gtg gag tgg gag agc aat ggc cag ccc gag aac aac tac aag         1248
Ile Ala Val Glu Trp Glu Ser Asn Gly Gln Pro Glu Asn Asn Tyr Lys
                405                 410                 415 acc acc cct ccc gtg ctg gac tcc gac ggc tcc ttc ttc ctc tac agc         1296
Thr Thr Pro Pro Val Leu Asp Ser Asp Gly Ser Phe Phe Leu Tyr Ser
            420                 425                 430 aag ctc acc gtg gac aag agc agg tgg cag cag ggc aac gtc ttc tca         1344
Lys Leu Thr Val Asp Lys Ser Arg Trp Gln Gln Gly Asn Val Phe Ser
        435                 440                 445 tgc tcc gtg atg cat gag gct ctg cac aac cac tac acc cag aag agc         1392
Cys Ser Val Met His Glu Ala Leu His Asn His Tyr Thr Gln Lys Ser
450                 455                 460 ctc tcc ctg tct ccc ggc aaa                                              1413
Leu Ser Leu Ser Pro Gly Lys
465                 470

<210> SEQ ID NO 78
<211> LENGTH: 471
<212> TYPE: PRT
<213> ORGANISM: Artificial Sequence
<220> FEATURE:
<223> OTHER INFORMATION: Synthetic Construct

<400> SEQUENCE: 78

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Ser Gly Asp Tyr Phe Trp Ser Trp Ile Arg Gln Leu Pro Gly Lys
    50                  55                  60

Gly Leu Glu Trp Ile Gly His Ile His Asn Ser Gly Thr Thr Tyr Tyr
65                  70                  75                  80

Asn Pro Ser Leu Lys Ser Arg Val Thr Ile Ser Val Asp Thr Ser Lys
                85                  90                  95

Lys Gln Phe Ser Leu Arg Leu Ser Ser Val Thr Ala Ala Asp Thr Ala
            100                 105                 110

Val Tyr Tyr Cys Ala Arg Asp Arg Gly Gly Asp Tyr Tyr Gly Met
        115                 120                 125

Asp Val Trp Gly Gln Gly Thr Thr Val Thr Val Ser Ser Ala Ser Thr
    130                 135                 140
```

```
Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 79
<211> LENGTH: 16
<212> TYPE: PRT
<213> ORGANISM: Mus musculus

<400> SEQUENCE: 79

Arg Ser Ser Gln Ser Leu Val His Ser Asn Gly Asn Thr Tyr Leu His
1               5                   10                  15

<210> SEQ ID NO 80
<211> LENGTH: 7
<212> TYPE: PRT
<213> ORGANISM: Mus musculus
```

<400> SEQUENCE: 80

Lys Val Ser Asn Arg Phe Ser
1               5

<210> SEQ ID NO 81
<211> LENGTH: 9
<212> TYPE: PRT
<213> ORGANISM: Mus musculus

<400> SEQUENCE: 81

Ser Gln Ser Thr His Val Pro Trp Thr
1               5

<210> SEQ ID NO 82
<211> LENGTH: 5
<212> TYPE: PRT
<213> ORGANISM: Mus musculus

<400> SEQUENCE: 82

Gly Tyr Phe Met Asn
1               5

<210> SEQ ID NO 83
<211> LENGTH: 17
<212> TYPE: PRT
<213> ORGANISM: Mus musculus

<400> SEQUENCE: 83

Arg Phe Asn Pro Tyr Asn Gly Asp Thr Phe Tyr Asn Gln Lys Phe Lys
1               5                   10                  15

Gly

<210> SEQ ID NO 84
<211> LENGTH: 13
<212> TYPE: PRT
<213> ORGANISM: Mus musculus

<400> SEQUENCE: 84

Ser Ala Tyr Tyr Phe Asp Ser Gly Gly Tyr Phe Asp Tyr
1               5                   10

<210> SEQ ID NO 85
<211> LENGTH: 16
<212> TYPE: PRT
<213> ORGANISM: Artificial Sequence
<220> FEATURE:
<223> OTHER INFORMATION: CDRL1 of hB273_L1-NE

<400> SEQUENCE: 85

Arg Ser Ser Gln Ser Leu Val His Ser Asn Glu Asn Thr Tyr Leu His
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: CDRL1 of hB273_L1-NF

<400> SEQUENCE: 86

Arg Ser Ser Gln Ser Leu Val His Ser Asn Phe Asn Thr Tyr Leu His
1               5                   10                  15

```
<210> SEQ ID NO 87
<211> LENGTH: 16
<212> TYPE: PRT
<213> ORGANISM: Artificial Sequence
<220> FEATURE:
<223> OTHER INFORMATION: CDRL1 of hB273_L1-NK

<400> SEQUENCE: 87

Arg Ser Ser Gln Ser Leu Val His Ser Asn Lys Asn Thr Tyr Leu His
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: CDRL1 of hB273_L1-NL

<400> SEQUENCE: 88

Arg Ser Ser Gln Ser Leu Val His Ser Asn Leu Asn Thr Tyr Leu His
1               5                   10                  15

<210> SEQ ID NO 89
<211> LENGTH: 17
<212> TYPE: PRT
<213> ORGANISM: Artificial Sequence
<220> FEATURE:
<223> OTHER INFORMATION: CDRH2 of hB273_H2-1-NE

<400> SEQUENCE: 89

Arg Phe Asn Pro Tyr Asn Glu Asp Thr Phe Tyr Asn Gln Lys Phe Lys
1               5                   10                  15

Gly
```